(12) United States Patent
Honma et al.

(10) Patent No.: US 7,169,598 B2
(45) Date of Patent: Jan. 30, 2007

(54) POLYHYDROXYALKANOATE, METHOD FOR PRODUCTION THEREOF AND MICROORGANISMS FOR USE IN THE SAME

(75) Inventors: Tsutomu Honma, Atsugi (JP); Toyoko Kobayashi, Yokohama (JP); Tetsuya Yano, Atsugi (JP); Shin Kobayashi, Kawasaki (JP); Takeshi Imamura, Chigasaki (JP); Sakae Suda, Ushiku (JP); Takashi Kenmoku, Fujisawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 505 days.

(21) Appl. No.: 10/649,646

(22) Filed: Aug. 28, 2003

(65) Prior Publication Data

US 2004/0067576 A1    Apr. 8, 2004

Related U.S. Application Data

(62) Division of application No. 10/411,319, filed on Apr. 11, 2003, now Pat. No. 6,649,381, which is a division of application No. 09/748,205, filed on Dec. 27, 2000, now Pat. No. 6,586,562.

(30) Foreign Application Priority Data

| Dec. 27, 1999 | (JP) | ................... | 11-371863 |
| Jan. 31, 2000 | (JP) | ................... | 2000-023078 |
| Jan. 31, 2000 | (JP) | ................... | 2000-023080 |
| Jan. 31, 2000 | (JP) | ................... | 2000-023083 |
| Mar. 30, 2000 | (JP) | ................... | 2000-095011 |
| Mar. 30, 2000 | (JP) | ................... | 2000-095012 |
| Mar. 30, 2000 | (JP) | ................... | 2000-095013 |
| Jul. 7, 2000 | (JP) | ................... | 2000-207089 |
| Jul. 7, 2000 | (JP) | ................... | 2000-207091 |
| Nov. 27, 2000 | (JP) | ................... | 2000-359789 |

(51) Int. Cl.
*C12N 1/20* (2006.01)

(52) U.S. Cl. .................. 435/253.3

(58) Field of Classification Search ............. None
See application file for complete search history.

(56) References Cited

U.S. PATENT DOCUMENTS

| 4,393,167 | A | 7/1983 | Holmes et al. ............ 525/64 |
| 4,876,331 | A | 10/1989 | Doi ..................... 528/361 |
| 5,292,860 | A | 3/1994 | Shiotani et al. ........... 528/361 |
| 5,334,698 | A | 8/1994 | Witholt et al. ............ 528/354 |
| 5,387,513 | A | 2/1995 | Anderson et al. .......... 435/195 |
| 5,661,026 | A | 8/1997 | Peoples et al. ........... 435/252.3 |
| 5,665,597 | A | 9/1997 | Imamura et al. .......... 435/253.3 |
| 5,952,460 | A | 9/1999 | Liddell et al. ............ 528/503 |
| 5,977,291 | A | 11/1999 | Cox et al. ............... 528/272 |

FOREIGN PATENT DOCUMENTS

| EP | 0288908 | 11/1988 |
| EP | 0392687 | 10/1990 |
| EP | 0520405 | 12/1992 |
| JP | 5-159 | 1/1993 |
| JP | 5-49487 | 3/1993 |
| JP | 5-64591 | 3/1993 |
| JP | 5-74492 | 3/1993 |
| JP | 5-214081 | 8/1993 |
| JP | 6-15604 | 3/1994 |
| JP | 6-145311 | 5/1994 |
| JP | 6-169988 | 6/1994 |
| JP | 6-225921 | 8/1994 |
| JP | 6-284892 | 10/1994 |
| JP | 7-14352 | 2/1995 |
| JP | 7-48438 | 2/1995 |
| JP | 7-265065 | 10/1995 |
| JP | 8-19227 | 2/1996 |
| JP | 8-89264 | 4/1996 |
| JP | 2642937 | 5/1997 |
| JP | 9-191893 | 7/1997 |
| JP | 11-32789 | 2/1999 |
| JP | 2989175 | 10/1999 |
| WO | WO 97/24387 | 7/1997 |
| WO | WO 99/61624 | 12/1999 |
| WO | WO 99/64617 | 12/1999 |

OTHER PUBLICATIONS

Henderson, et al., "Enzyme-Catalyzed Polymerizations of ε-Caprolactone: Effects of Initiator on Product Structure, Propagation Kinetics, and Mechanism"; Macromolecules, 1996, vol. 29, pp. 7759-7766.

Aróstegui, et al., "Bacterial Polyesters Produced by *Pseudomonas oleovorans* Containing Nitrophenyl Groups"; Macromolecules, 1999, vol. 32, pp. 2889-2895.

Andújar et al., "Polyesters Produced by *Pseudomonas oleovorans* Containing Cyclohexyl Groups"; Macromolecules, 1997, vol. 30, pp. 1611-1615.

Kim, et al., "Preparation and Characterization of Poly (β-hydroxyalkanoates) Obtained from *Pseudomonas olevorans* Grown with Mixtures of 5-Phenylvaleric Acid and n-Alkanoic Acids"; Macromolecules, 1991, vol. 24, pp. 5256-5260.

Kim, et al., "Poly-3-hydroxyalkanoates Produced from *Pseudomonas oleovorans* Grown with w-Phenoxyalkanoates"; Macromolecules, 1996, vol. 29, pp. 3432-3235.

Ritter, et al., "Bacterial production of polyesters bearing phenoxy groups in the side chains, 1"; Macromol. Chem. Phys., 1994, vol. 195, pp. 1665-1672.

Vogel, et al.; "Acetylornithinase of *Escherichia coli*: Partial Purification and Some Properties"; J. Biol. Chem., 1956, vol. 215, pp. 97-105.

Abe, et al., Int. J. Biol. Micromol., vol. 16, No. 3, "Biosynthesis . . . sp 61-3", 115-119 (1994).

Ramsay, et al., Appl. & Environ. Microb. vol. 58, No. 2, "Effect of . . . resinovorans"; 744-746 (1992).

Hulsman, et al., "Metabolism of . . . oleovorans", J. Biol. Chem., vol. 266, No. 4, 2191-2198 (1992).

Matsusaki, et al., "Cloning . . . Strain 61-3", J. Bact., vol. 180, No. 24, 6459-6467 (1988).

Garcia, et al., "Novel . . . Source", J. Biol. Chem., vol. 274, No. 41, 29228-29241 (1999).

Database WPI, Week 9431, Derwent, XP 002209643 of JP 6-181784 (1994).

Database WPI, Derwent, XP 002209644 of JP4-325094 (1992).

Database WPI, Week 0023, Derwent, XP 002209645 for JP 2-989175 (2000).

EMBL: AB014758, XP-002176216 (1998) submitted to EMBL/Gen Bank/DDBJ database, Pseudomonas Sp 61-3 genes.

Kim, et al.: "Bioengineering of poly(β-hydroxyalkanoates) . . . Substituents"; Can. J. Microbiol., 41, (Suppl. 1): 32-43 (1995).

Curley, et al.: "Production of Poly(3-hydroxyalkanoates) . . . *oleovorans*"; J.A.C.S., 1996, 29, 1762-1766.
Kim, et al.; "Microbial Synthesis . . . Substituents"; Macromolecules 29, 13, (1996) 4572-4581.
A. Steinbüchel, et al., "Diversity of bacterial polyhydroxyalkanoic acids", FEMS Microbiology Letters 128 (1995), pp. 219-228.

*Primary Examiner*—Irene Marx
(74) *Attorney, Agent, or Firm*—Fitzpatrick, Cella, Harper & Scinto

(57) ABSTRACT

A polyhydroxyalkanoate having a monomer unit composition represented by General Formula (1):

$$A_m B_{(1-m)} \quad (1)$$

wherein A is represented by General Formula (2), B is at least one selected from the group consisting of monomer units represented by General Formula (3) or (4), and m has a value of 0.01 or larger and smaller than 1:

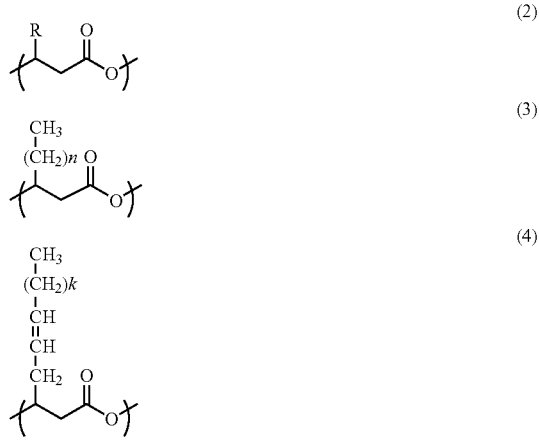

wherein
n has a value of 0 to 10, k has a value of 3 or 5, and R is at least one group selected from the group consisting of groups represented by General Formulae (5) to (7):

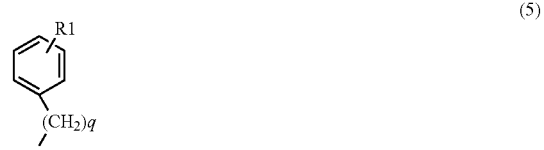

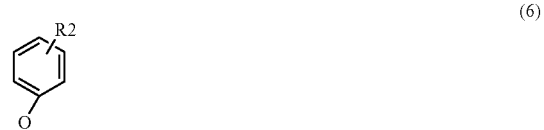

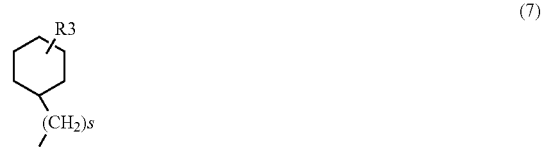

in Formula (5)
R1 is a group selected from the group consisting of a hydrogen atom (H), halogen atoms, —CN, —NO$_2$, —CF$_3$, —C$_2$F$_5$. and —C$_3$F$_7$; and q is an integer selected from 1 to 8;
in Formula (6)
R2 is a group selected from the group consisting of a hydrogen atom (H), halogen atoms, —CN, —NO$_2$, —CF$_3$, —C$_2$F$_5$ and —C$_3$F$_7$; and r is an integer selected from 1 to 8;
in Formula (7)
R3 is a group selected from the group consisting of a hydrogen atom (H), halogen atoms, —CN, —NO$_2$, —CF$_3$, —C$_2$F$_5$ and —C$_3$F$_7$; and s is an integer selected from 1 to 8.

The efficient production methods are also provided.

4 Claims, 56 Drawing Sheets

5-(4-Fluorophenyl) valeric acid
1999/06/14

(4-fluoro)-5-phenoxyvaleric acid (FPxVA)

p-CNPxBA, YN2, seed (Glu3day)/Glu2day)/Glu2day 4-(p-fluoro-phenoxy)-n-buttric acid 4-(m-fluorophenoxy)butyric acid

POLYHYDROXYALKANOATE, METHOD FOR PRODUCTION THEREOF AND MICROORGANISMS FOR USE IN THE SAME

This application is a division of application Ser. No. 10/411,319, filed Apr. 11, 2003, now U.S. Pat. No. 6,649,381, which was a division of application Ser. No. 09/748,205, filed Dec. 27, 2000, now U.S. Pat. No. 6,586,562.

BACKGROUND OF THE INVENTION

1. Field of the Invention

The present invention relates to a novel polyhydroxyalkanoate (PHA), a method for production of such PHA and microorganisms for use in the same.

2. Related Background Art

Synthetic polymers derived from petroleum have been used as plastics etc. for a long time. Recently, the treatment of the used plastics has become one of serious social problems. These synthetic polymers have advantages of hard-to-decompose have been used in the place of metal or glass materials. On mass consumption and mass disposal, however, this feature of hard-to-decompose makes them accumulated in waste-disposal facilities, or when they are burned, it causes increased carbon dioxide exhaust, and harmful substances such as dioxin and endocrine-disruptors may be generated to cause environmental pollution. On the other hand, polyhydroxyalkanoates (PHAs) produced by microorganisms (hereinafter referred to as "microbial polyester") represented by poly-3-hydroxy butyric acid (PHB) can be used as the conventional plastics to make various kinds of products with melting processes etd., and can be decomposed by organisms unlike oil-derived synthetic polymers. Therefore, the microbial polyester is bio-decomposed and thus incorporated in the natural material cycle when discarded, and would not remain in the natural environment to cause pollution unlike many conventional synthetic polymer compounds. Furthermore, since the microbial polyesters do not require incineration processes, they are also effective in terms of prevention of air pollution and global warming. Thus, they can be used as a plastic enabling environmental integrity. In addition, the application of the microbial polyesters to medical soft members is under consideration (Japanese Patent Application Laid-Open No. 5-159, Japanese Patent Application Laid-Open No. 6-169980, Japanese Patent Application Laid-Open No. 6-169988, Japanese Patent Application Laid-Open No. 6-225921 and the like).

Heretofore, various bacteria have been reported to produce and accumulate PHB or copolymers of other hydroxyalkanoic acids in the cells ("Biodegradable Plastics Handbook", edited by Biodegradable Plastics Society, issued by NTS Co. Ltd., P178–197, (1995)). It is known that such microbial PHAs may have a variety of compositions and structures depending on types of the producing microorganisms, the composition of culture media, culture conditions and the like, and up to now, studies regarding the control of these compositions and structures have been carried out to improve the properties of PHA.

For example, *Alcaligenes eutropus* H16 (ATCC No. 17699) and its mutant strains reportedly produce copolymers of 3-hydroxy butyric acid (3HB) and 3-hydroxy valeric acid (3HV) at a variety of composition ratios according to the carbon source in culture (Japanese Patent Publication No. 6-15604, Japanese Patent Publication No. 7-14352, Japanese Patent Publication No. 8-19227 and the like).

Japanese Patent Application Laid-Open No. 5-74492 discloses a method in which the copolymer of 3HB and 3HV is produced by bringing *Methylobacterium* sp., *Paracoccus* sp., *Alcalugenes* sp. or *Pseudomonas* sp. into contact primary alcohol having 3 to 7 carbons.

Japanese Patent Application Laid-Open No. 5-93049 and Japanese Patent Application Laid-Open No. 7-265065 disclose that two-component copolymers of 3HB and 3-hydroxy hexanoic acid (3HHx) are produced by culturing *Aeromonas caviae* using oleic acid or olive oil as a carbon source.

Japanese Patent Application Laid-Open No. 9-191893 discloses that *Comamonas acidovorans* IFO 13852 produces polyester having 3HB and 4-hydroxy butyric acid as monomer units in culture with gluconic acid and 1,4-butandiol as a carbon source.

Also, in recent years, active researches about PHA composed of 3-hydroxyalkanoate (3HA) of medium-chain-length (abbreviated to mcl) having up to about 12 carbons. Synthetic routes can be classified broadly into two types, and their specific examples will be shown in (1) and (2) below.

(1) Synthesis Using β-Oxidation

Japanese Patent No. 2642937 discloses that PHA having monomer units of 3-hydroxyalkanoate having 6 to 12 carbons is produced by providing as a carbon source aliphatic hydrocarbon to *Pseudomonas oleovorans* ATCC 29347. Furthermore, it is reported in Appl. Environ. Microbiol, 58(2), 746 (1992) that *Pseudomonas resinovorans* produces polyester having 3-hydroxybutyric acid, 3-hydroxyhexanoic acid, 3-hydroxyoctanoic acid and 3-hydroxydecanoic acid at a ratio of 1:15:75:9 as monomer units, using octanoic acid as a single carbon source, and also produces polyester having 3-hydroxybutyric acid, 3-hydroxyhexanoic acid, 3-hydroxyoctanoic acid and 3-hydroxydecanoic acid (quantitative ratio of 8:62:23:7) as units, using hexanoic acid as a single carbon source. Herein, it is assumed that 3HA monomer units having longer chain length than that of the starting fatty acid are made by way of fatty acid synthetic route that will be described next in (2).

(2) Synthesis Using Fatty Acid Synthetic Route

It is reported in Int. J. Biol. Macromol., 16(3), 119 (1994) that *Pseudomonas* sp. 61–3 strain produces polyester made of 3-hydroxyalkanoic acids such as 3-hydroxybutyric acid, 3-hydroxyhexanoic acid, 3-hydroxyoctanoic acid, 3-hydroxydecanoic acid and 3-hydroxydodecanoic acid and 3-hydroxyalkenoic acids such as 3-hydroxy-5-cis-decenoic acid, 3-hydroxy-5-cis-dodecenoic acid, using sodium gluconate as a single carbon source.

By the way, the biosynthesis of PHA is usually carried out by a PHA synthase using as a substrate "D-3-hydroxyacyl-CoA" occurring as an intermediate of a variety of metabolic pathways in the cell.

Herein, "CoA" means a "coenzyme A". And, as described in the prior art of the above (1), the biosynthesis of PHA is carried out with "D-3-hydroxyacyl-CoA" occurring in the "β oxidation cycle" being a starting substance in the case where fatty acids such as octanoic acid and nonanoic acid are used as carbon sources.

Reactions through which PHA is synthesized by way of the "β oxidation cycle" will be shown below.

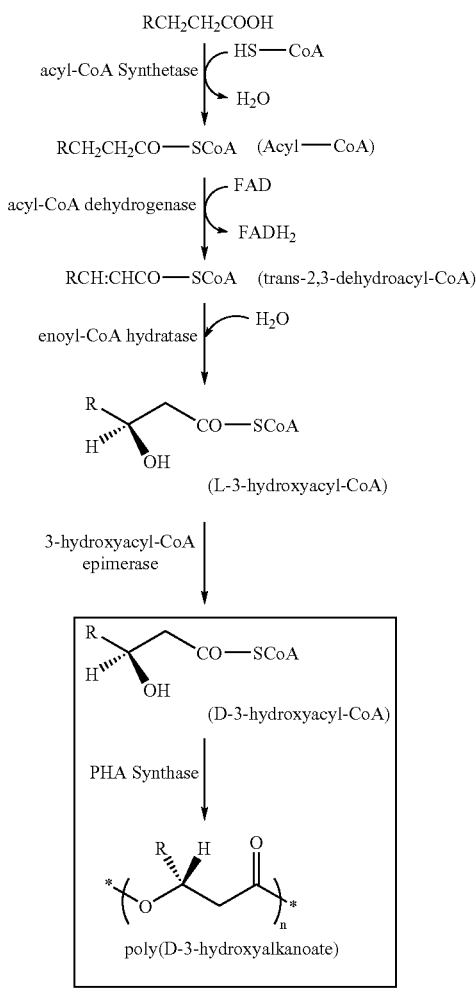

On the other hand, as described in the prior art of the above (2), in the case where the PHA is biosynthesized using saccharides such as glucose and the like, the biosynthesis is carried out with "D-3-hydroxyacyl-CoA" converted from "D-3-hydroxyacyl-ACP" occurring in the "fatty acid synthesis pathway" being a starting substance.

Herein, "ACP" means a "acyl carrier protein".

By the way, as described previously, the PHA synthesized in both (1) and (2) described above is PHA constituted by monomer units having alkyl groups in side chains. However, if a wider range of application of the microbial PHA like this, for example an application as a functional polymer is considered, it is expected that PHA having various substituents (for example phenyl groups) introduced in the side chain is significantly useful. With respect to the synthesis of such PHA, for the synthesis using β oxidation, a report regarding PHA having the aryl group and the like in the side chain can be found in, for example, Macromolecules, 24, p 5256–5260 (1991). Specifically, it is reported that *Pseudomonas oleovorans* produces polyester having 3-hydroxy valeric acid, 3-hydroxyheptanoic acid, 3-hydroxynonanoic acid, 3-hydroxyundecanoic acid and 3-hydroxy-5-phenyl valeric acid (quantitative ratio of 0.6:16.0:41.1:1.7:40.6) as units in the amount of 160 mg for 1 L of culture solution (ratio in dry weight to the cell mass is 31.6%), using 5-phenylvaleric acid and nonanoic acid (mole ratio of 2:1, total concentration of 10 mmol/L) as a medium, and also produces polyester having 3-hydroxyhexanoic acid, 3-hydroxyoctanoic acid, 3-hydroxydecanoic acid and 3-hydroxy-5-phenyl valeric acid (quantitative ratio of 7.3:64.5:3.9:24.3) as units in the amount of 200 mg for 1 L of culture solution (ratio in dry weight to the cell mass is 39.2%), using 5-phenyl valeric acid and octanoic acid (mole ratio of 1:1, total concentration of 10 mmol/L). It is conceivable that the PHA in this report is principally synthesized by way of the β oxidation pathway due to that fact that nonanoic acid and octanoic acid are used.

As described above, in the microbial PHA, those with various kinds of compositions/structures are obtained by changing the type of microorganisms for use in its production, culture medium compositions, culture conditions, but if considering the application of the microbial PHA as plastics, they could not be sufficient yet in terms of properties. In order to further expand the range of the microbial PHA utility, it is important that the improvement of its properties are more widely considered, and for this purpose, the development and the search of the PHA containing monomer units of further diverse structures, its manufacturing processes and microorganisms enabling desired PHA to be produced efficiently are essential.

On the other hand, the PHA of a type having substituents introduced in the side chain as described previously is selected in accordance with the property for which the introduced substituent is desired, thereby making it possible to expect its development as a "functional polymer" having very useful functions and properties resulting from the property and the like of the introduced substituent, and the development and the search of excellent PHA allowing such functionality and the biodegradability to be compatible with each other, its manufacturing processes and microorganisms enabling desired PHA to be produced efficiently are also important challenges.

Another example of such PHA having substituents introduced in the side chain includes PHA having the above described phenyl groups, and further phenoxy groups in the side chain.

For another example of phenyl group, it is reported in Macromolecules, 29, 1762–1766 (1996) that *Pseudomonas oleovorans* produces PHA including 3-hydroxy-5-(4-toryl) valeric acid as a monomer unit through the culture in a culture medium including 5-(4-toryl) valeric acid (5-(4-methylphenyl) valeric acid) as a substrate.

Furthermore, it is reported in Macromolecules, 32, 2889–2895 (1999) that *Pseudomonas oleovorans* produces PHA including 3-hydroxy-5-(2,4-dinitrophenyl) valeric acid and 3-hydroxy-5-(4-nitrophenyl) valeric acid as monomer units through the culture in a culture medium including 5-(2,4-dinitrophenyl) valeric acid and nonanoic acid as a substrate.

Also, for an example of the phenoxy group, it is reported in Macromol. Chem. Phys., 195, 1665–1672 (1994) that *Pseudomonas oleovorans* produces PHA including 3-hydroxy-5-phenoxy valeric acid and 3-hydroxy-9-phenoxynonanoic acid as units from 11-phenoxyundecanoic acid.

Also, it is reported in Macromolecules, 29, 3432–3435 (1996) that *Pseudomonas oleovorans* is used to produce PHA including 3-hydroxy-4-phenoxybutyric acid and 3-hydroxy-6-phenoxyhexanoic acid as units from 6-phenoxyhexanoic acid, PHA including 3-hydroxy-4-phenoxybutyric acid, 3-hydroxy-6-phenoxyhexanoic acid and 3-hydroxy-8-phenoxyoctanoic acid as units from 8-phenoxyoctanoic acid, and PHA including 3-hydroxy-5-phenoxyvaleric acid and 3-hydroxy-7-phenoxyheptanoic acid as units from 11-phenoxyundecanoic acid. Excerpts of yields of polymers from this report are shown in Table 1.

Furthermore, in Can. J. Microbiol., 41, 32–43 (1995), PHA including 3-hydroxy-p-cyanophenoxyhexanoic acid or 3-hydroxy-p-nitrophenoxyhexanoic acid as a monomer unit is successfully produced with octanoic acid and p-cyanophenoxyhexanoic acid or p-nitrophenoxyhexanoic acid being a substrate, using *Pseudomonas oleovorans* ATCC 29347 and *Pseudomonas putida* KT 2442.

In Japanese Patent No. 2989175, a homopolymer constituted by 3-hydroxy-5-(monofluorophenoxy)pentanoate(3H5 (MFP)P) units or 3-hydroxy-5-(difluorophenoxy)pentanoate (3H5(DFP)P) units and a copolymer containing at least 3H5(MFP)P units or 3H5(DFP)P units; *Pseudomonas putida* for synthesizing these polymers; and a method of producing the aforesaid polymers using *Pseudomonas* species are described.

These productions are carried out through "two-stage culture" as described below.

Time of Culture: First Stage, 24 Hours; Second Stage, 96 Hours

A substrate and a resulting polymer at each stage will be shown below.

(1) Resulting polymer: 3H5 (MFP) P homopolymer
  Substrate at the first stage: Citric acid, Yeast extract
  Substrate at the second stage: Monofluorophenoxyundecanoic acid
(2) Resulting polymer: 3H5 (DFP) P homopolymer
  Substrate at the first stage: Citric acid, Yeast extract
  Substrate at the second stage: Difluorophenoxyundecanoic acid
(3) Resulting polymer: 3H5 (MFP) P copolymer
  Substrate at the first stage: Octanoic acid or Nonanoic acid, Yeast extract
  Substrate at the second stage: Monofluorophenoxyundecanoic acid
(4) Resulting polymer: 3H5 (DFP) P copolymer
  Substrate at the first stage: Octanoic acid or Nonanoic acid, Yeast extract
  Substrate at the second stage: Difluorophenoxyundecanoic acid As its effect, a medium-chain-length fatty acid having substituents may be materialized to synthesize a polymer having phenoxy groups with ends of the side chain replaced by one to two fluorine atoms, and stereoregularity and water repellency can be provided while maintaining a high melting point and good processability.

Also, PHA including cyclohexyl groups in monomer units is expected to show polymeric properties different from those of PHA including normal aliphatic hydroxyalkanoic acid as a unit, and an example of production using *Pseudomonas oleovorans* has been reported (Macromolecules, 30, 1611–1615 (1997)).

According to this report, when *Pseudomonas oleovorans* was cultured in a culture medium where nonanoic acid (hereinafter described as NA) and cyclohexylbutyric acid (hereinafter described as CHBA) or cyclohexyl valeric acid (hereinafter described as CHVA) coexisted, PHA including units containing cyclohexyl groups and units originating from nonanoic acid were obtained (each ratio unknown)

About the yields, it is reported that quantitative ratios of CHBA and NA are varied with substrate concentration total of 20 mmol/L and results as shown in Table 2 were obtained.

However, in this example, the yield of polymers per culture solution is not sufficient, and the obtained PHA itself has aliphatic hydroxyalkanoic acid coexist in its monomer unit.

In this way, in the case where PHA with a variety of substituents introduced in the side chain is produced, as seen in the reported example of *Pseudomonas oleovorans* described previously and the like, a method is used in which alkanoate having a substituent to be introduced is used not only as a stock for the polymer but also as a carbon source for growth.

However, for the method in which alkanoate having a substituent to be introduced is used not only as a stock for the polymer but also as a carbon source for growth, the supply of an energy source based on the production of the acetyl-CoA by β oxidation from such alkanoate is expected, and in this method, only a substrate having a certain degree of chain length is capable of producing acetyl-CoA by β oxidation, thus limiting alkanoate that can be used as a substrate of PHA, which is a major problem. Also, generally, since substrates with the chain length decreased by two methylene chains an after another are newly produced by the β oxidation, and these are captured as monomer units of PHA, the PHA that is synthesized is often a copolymer constituted by monomer units that are different in the chain length by two methylene chains one after another. In the reported example described above, a copolymer constituted by three types of monomer units, that is 3-hydroxy-8-phenoxyoctanoic acid originating from 8-phenoxyoctanoic acid which is a substrate, 3-hydroxy-6-phenoxyhexanoic acid and 3-hydroxy-4-phenoxybutyric acid which are by-products originating from metabolites is produced. In this respect, if PHA constituted by single monomer units is to be obtained, it is quite difficult to use this method. Furthermore, for a method premised on the supply of an energy source based on the production of acetyl-CoA by the β oxidation, the growth of microorganisms is slow and the synthesis of PHA requires lots of time, and the yield of the synthesized PHA is often low, which is also a major problem.

For this reason, a method in which, in addition to the alkanoate having substituents to be introduced, microorganisms are cultured in the culture medium in which fatty acids of medium-chain-length and the like such as octanoic acid and nonanoic acid as the carbon source for growth, followed by extracting PHA is considered to be effective and is generally used.

However, according to the study by the inventors, the PHA synthesized by way of the β oxidation pathway using fatty acids of medium-chain-length such as octanoic acid and nonanoic acid as the carbon source for growth has poor purity, and 50% or more of the polymers are made of mcl-3HA monomer units originating from the carbon source (for example, 3-hydroxyoctanoic acid, 3-hydroxynonanoic acid and the like). These mcl-3HA units make polymers adhesive at room temperature when they are sole components, and if they coexist in the PHA of the present invention in large quantity, the glass transition temperature (Tg) of the polymer is significantly lowered. Thus, to obtain hard polymers at room temperature, the coexistence of mcl-3HA monomer units is not desired. Also, it is known that such a hetero-side chain structure interferes intra-molecular or inter-molecular interaction originating from the side chain structure, and has significant influence on crystallinity and orientation. For achieving the improvement of polymer properties and the addition of functionality, the coexistence of these mcl-3HA monomer units raises a major problem. Means for solving this problem includes providing a refinement process to separate/remove "undesired" monomer units such as mcl-3HA monomer units originating from the carbon source for growth, in order to acquire PHA constituted by monomer units having only specified substituents. However, the problem is that operations are complicated and a significant decrease in the yield can not be avoided. A more serious problem is that if desired monomer units and undesired monomer units form a copolymer, it is quite difficult to remove only undesired monomer units. Particularly, in the case where the purpose is to synthesize PHA including monomer units having groups obtained from unsaturated hydrocarbons, ester groups, aryl groups, cyan groups, nitro groups, groups obtained from halogenated hydrocarbons, groups having epoxide and the like introduced therein as side chain structures, the mcl-3HA monomer unit often forms a copolymer with a desired monomer unit, and it is extremely difficult to remove the mcl-3HA monomer unit after PHA is synthesized.

SUMMARY OF THE INVENTION

The present invention solves the above described problems, and provides PHA including monomer units of diverse structures having substituents in the side chain, which is useful as device materials, medical materials and the like, and a method of producing such PHA using microorganisms, and particularly a production method in which the coexistence of undesired monomer units is reduced, desired PHA can be obtained in high purity and also in high yields. The present invention is also intended to provide strains enabling such PHA to be synthesized in high purity and with efficiency.

According to one aspect of the present invention, there is provided a polyhydroxyalkanoate having a monomer unit composition represented by a general formula (1):

$$A_m B_{(1-m)} \quad (1)$$

wherein A is represented by General Formula (2), B is at least one selected from the group consisting of monomer units represented by General Formula (3) or (4), and m has a value of 0.01 or larger and smaller than 1:

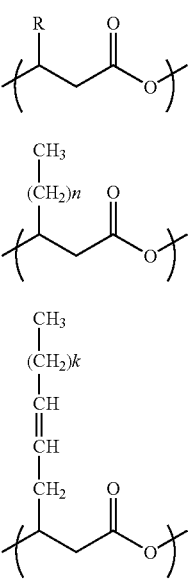

wherein
n has a value of 0 to 10, k has a value of 3 or 5, and
R is at least one group selected from the group consisting of groups represented by General Formulae (5) to (7):

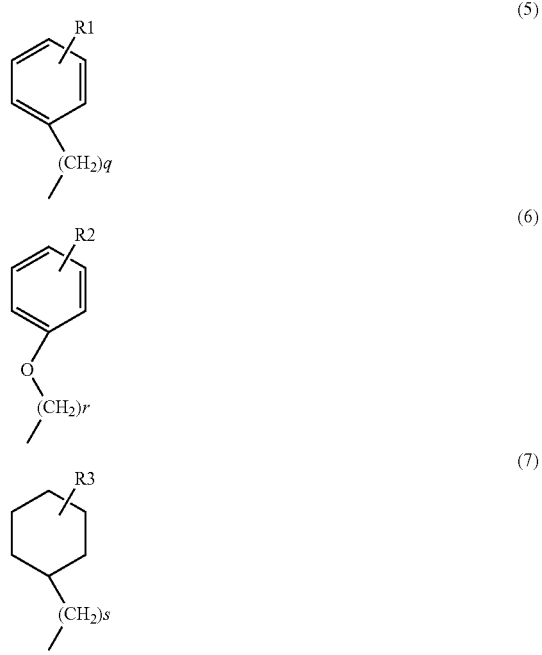

in Formula (5)
R1 is a group selected from the group consisting of a hydrogen atom (H), halogen atoms, —CN, —NO$_2$, —CF$_3$, —C$_2$F$_5$ and —C$_3$F$_7$; and q is an integer selected from 1 to 8;

in Formula (6)
R2 is a group selected from the group consisting of a hydrogen atom (H), halogen atoms, —CN, —NO$_2$, —CF$_3$, —C$_2$F$_5$ and —C$_3$F$_7$; and r is an integer selected from 1 to 8;

in Formula (7)
R3 is a group selected from the group consisting of a hydrogen atom (H), halogen atoms, —CN, —NO$_2$, —CF$_3$, —C$_2$F$_5$ and —C$_3$F$_7$; and s is an integer selected from 1 to 8;
provided that following R are excluded from the choice:
when selecting one type of group as R in the general formula (2):
groups of Formula (5) in which R1 is H and q=2, R1 is H and q=3, and R1 is —NO$_2$ and q=2;
groups of Formula (6) in which R2 is a halogen atom and r=2, provided that two components are selected as B from General Formula (3) or (4), R2 is —CN and r=3, and R2 is —NO$_2$ and r=3; and the groups of Formula (7) in which R3 is H and s=1, and R3 is H and s=2; and
when selecting two types of groups as R in General Formula (2), the combinations of two types of groups of Formula (6) in which R2 is a halogen atom and r=2, and R2 is a halogen atom and r=4, provided that one component is selected as B from General Formula (3) or (4).

According to one aspect of the present invention, there is provided 5-(4-trifluoromethylphenyl)valeric acid of Formula (21).

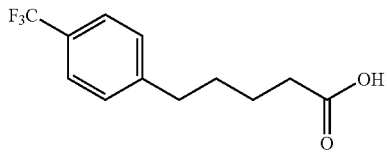
(21)

According to another aspect of the present invention, there is provided a method of producing a polyhydroxyalkanoate, comprising a step of culturing a microorganism capable of synthesizing a polyhydroxyalkanoate of which monomer unit is represented by Formula (1) from an alkanoate in a medium containing the alkanoate:

$$A_m B_{(1-m)} \qquad (1)$$

wherein A is represented by General Formula (2), B is at least one selected from the group consisting of monomer units represented by General Formula (3) or (4), and m is 0.01 or larger and smaller than 1,

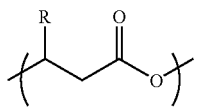
(2)

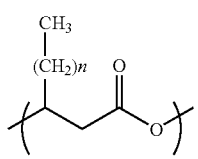
(3)

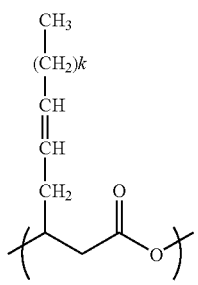
(4)

wherein n is an integer selected from 0 to 10, k is 3 or 5, and

R is at least one group selected from the group consisting of the groups represented by General Formulae (5) to (7):

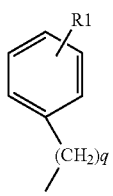
(5)

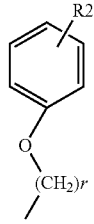
(6)

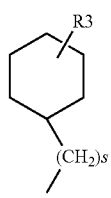
(7)

in Formula (5)

R1 is a group selected from the group consisting of a hydrogen atom (H), halogen atoms, —CN, —NO$_2$, —CF$_3$, —C$_2$F$_5$ and —C$_3$F$_7$; and q is an integer selected from 1 to 8;

in Formula (6)

R2 is a group selected from the group consisting of a hydrogen atom (H), halogen atoms, —CN, —NO$_2$, —CF$_3$, —C$_2$F$_5$ and —C$_3$F$_7$; and r is an integer selected from 1 to 8;

in Formula (7)

R3 is a group selected from the group consisting of a hydrogen atom (H), halogen atoms, —CN, —NO$_2$, —CF$_3$, —C$_2$F$_5$ and —C$_3$F$_7$; and s is an integer selected from 1 to 8;

provided that following R are excluded from the choice:

when selecting one type of group as R in General Formula (2):

groups of Formula (5) in which R1 is H and q=2, R1 is H and q=3, and R1 is —NO$_2$ and q=2;

the groups of Formula (6) in which R2 is a halogen atom and r=2, R2 is —CN and r=3, and R2 is —NO$_2$ and r=3; and groups of Formula (7) in which R3 is H and s=1, and R3 is H and s=2; and when selecting two types of groups as R in General Formula (2), groups of Formula (6) in which R2 is a halogen atom and r=2.

According to a further aspect of the present invention, there is provided a process of producing polyhydroxyalkanoate, comprising a step of culturing a microorganism capable of producing the polyhydroxyalkanoate utilizing alkanoate in a medium containing the alkanoate and a saccharide.

According to a further aspect of the present invention, there is provided a process of producing polyhydroxyalkanoate, comprising a step of culturing a microorganism capable of producing a polyhydroxyalkanoate utilizing an alkanoate in a medium containing the alkanoate and a polypeptone.

According to a further aspect of the present invention, there is provided a process of producing polyhydroxyalkanoate comprising a step of culturing a microorganism capable of producing a polyhydroxyalkanoate utilizing an alkanoate in a medium containing the alkanoate and an organic acid participating in TCA cycle.

According to a further aspect of the present invention, there is provided a process of producing polyhydroxyalkanoate, wherein the a microorganism is cultured in at least two steps: one is in a medium containing an alkanoate and a polypeptone and the subsequent one is in a medium containing the alkanoate and pyruvic acid or salt thereof with nitrogen source limitation.

According to a further aspect of the present invention, there is provided *Pseudomonas cichorii* H45, FERM BP-7374.

According to a further aspect of the present invention, there is provided a novel bacterial strain *Pseudomonas cichorii* YN2, FERM BP-7375.

According to a further aspect of the present invention, there is provided a novel bacterial strain *Pseudomonas putida* P91, FERM BP-7373.

According to a further aspect of the present invention, there is provided a novel bacterial strain *Pseudomonas jessenii* P161, FERM BP-7376.

As already stated above, the present invention provides novel polyhydroxyalkanoates and novel substituted alkanoic acids to be a raw material therefor and novel microorganisms which have ability to produce and accumulate in the cell the novel polyhydroxyalkanoates, and provides methods for producing the polyhydroxyalkanoates using such microorganism. According to them, the polyhydroxyalkanoates useful as functional polymers in which different functional groups are introduced can be manufactured very efficiently and in high purity, therefore it may be expected to be applied to each field such as device and medical materials.

BRIEF DESCRIPTION OF THE DRAWINGS

FIG. 12A is the Total Ion Chromatography (TIC) of the methylated compounds of PHA copolymers and FIG. 12B is the mass spectrum for the peak (around 36.5 min.) containing 3-hydroxy-5-(4-trifluoromethylphenyl)valeric acid which is an objective unit on the TIC;

FIG. 13A is the Total Ion Chromatography (TIC) of the methylated compounds of PHA copolymers and FIG. 13B is the mass spectrum for the peak (around 36.5 min.) containing 3-hydroxy-5-(4-trifluoromethylphenyl)valeric acid which is an objective unit on the TIC;

FIG. 120 is a chart which shows the mass spectrum of methyl 3-hydroxy-5-phenoxyvalerate (3HPxV) obtained from the GC-MS measurement in Example 70;

FIG. 121 is a chart which shows the mass spectrum of methyl 3-hydroxyoctanoate obtained from the GC-MS measurement in Example 71;

FIG. 122 is a chart which shows the mass spectrum of methyl 3-hydroxydecanoate obtained from the GC-MS measurement in Example 71;

FIG. 123 is a chart which shows the mass spectrum of methyl 3-hydroxy-5-phenylvalerate (3HPV) obtained from the GC-MS measurement in Example 71;

FIG. 124 is a chart which shows the mass spectrum of methyl 3-hydroxy-octanoate obtained from the GC-MS measurement in Example 72;

FIG. 125 is a chart which shows the mass spectrum of methyl 3-hydroxy-5-phenylvalerate (3HPV) obtained from the GC-MS measurement in Example 72;

FIG. 126 is a chart which shows the mass spectrum of methyl 3-hydroxybutyrate obtained from the GC-MS measurement in Example 73;

FIG. 127 is a chart which shows the mass spectrum of methyl 3-hydroxyoctanoate obtained from the GC-MS measurement in Example 73;

FIG. 128 is a chart which shows the mass spectrum of methyl 3-hydroxydecanoate obtained from the GC-MS measurement in Example 73; and FIG. 129 is a chart which shows the mass spectrum of methyl 3-hydroxy-5-phenylvalerate (3HPV) obtained from the GC-MS measurement in Example 73.

DETAILED DESCRIPTION OF THE PREFERRED EMBODIMENTS

Figure 1:
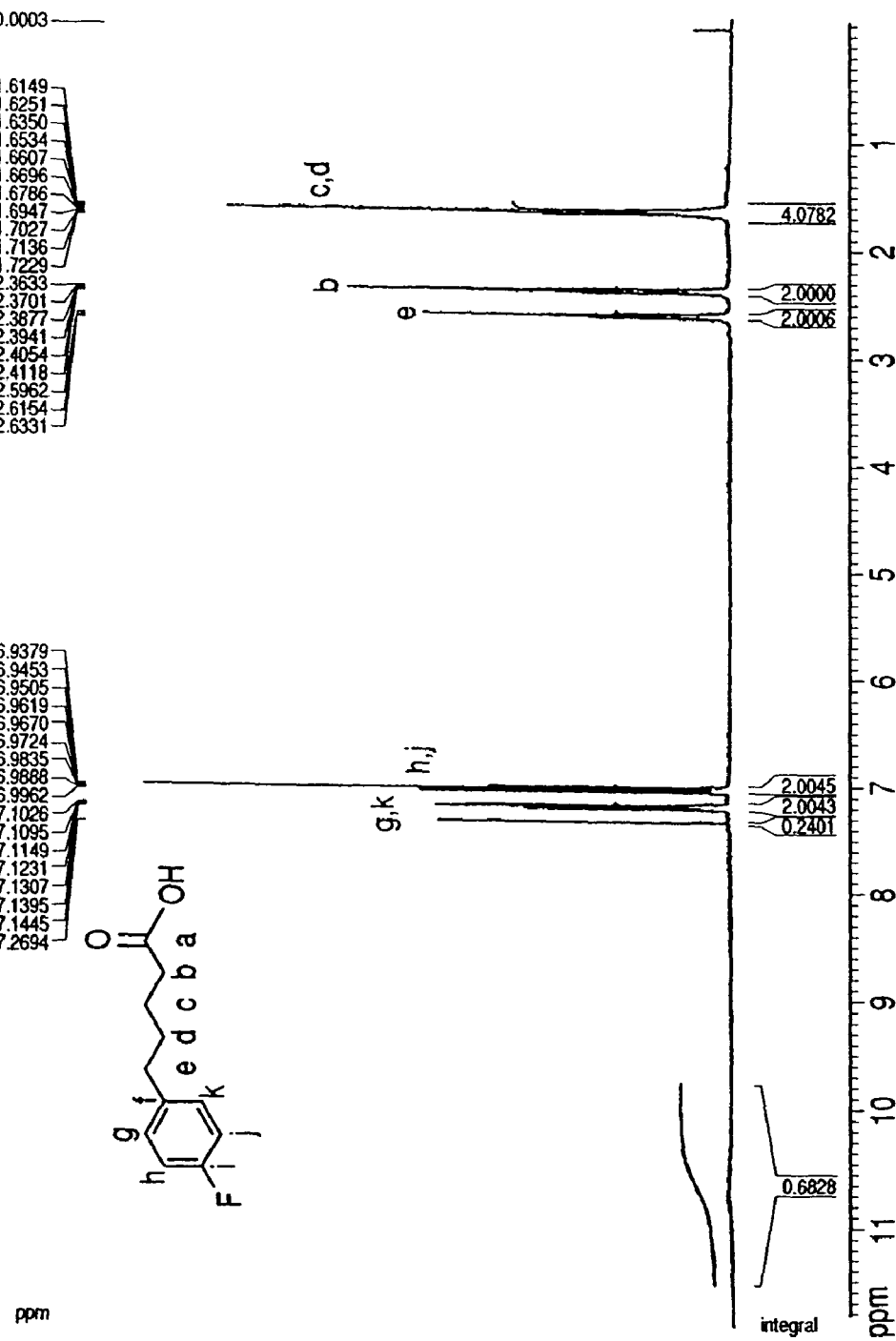
FIG. 1 is a chart which shows the measurement of nuclear magnetic resonance spectrum of 3HFPV synthesized in Example 1.

For solving the above described problems, the inventor et al. strenuously carried out researches for search of innovative microorganisms capable of producing PHA and accumulating the same in the cells and a method of manufacturing desired PHA using the innovative microorganism, particularly with the aim of developing PHA having substituted or unsubstituted phenoxy groups, phenyl groups and cyclohexyl groups on the side chain, which is useful as device materials and medical materials, and completed the invention.

The polyhydroxyalkanoate of the present invention is characterized by having a monomer unit composition represented by formula (1).

$$A_m B_{(1-m)} \quad (1)$$

(wherein A is represented by formula (2), B is at least one or more selected from monomer units represented by formula (3) or (4), and m is 0.01 or more and less than 1).

$$\left(\begin{array}{c} R \\ | \\ CH \\ | \\ CH_2 \\ | \\ C=O \\ | \\ O \end{array}\right) \quad (2)$$

$$\left(\begin{array}{c} CH_3 \\ | \\ (CH_2)_n \\ | \\ CH \\ | \\ CH_2 \\ | \\ C=O \\ | \\ O \end{array}\right) \quad (3)$$

$$\left(\begin{array}{c} CH_3 \\ | \\ (CH_2)_k \\ | \\ CH \\ \| \\ CH \\ | \\ CH_2 \\ | \\ C=O \\ | \\ O \end{array}\right) \quad (4)$$

(In formulae, n is 0 to 10, k is 3 or 5, and R is at least one or more groups selected from groups represented by formulae (5) to (7)).

$$\begin{array}{c} R1 \\ \phantom{xx}\bigcirc \\ (CH_2)_q \end{array} \quad (5)$$

$$\begin{array}{c} R2 \\ \phantom{xx}\bigcirc \\ O \\ (CH_2)_r \end{array} \quad (6)$$

$$\begin{array}{c} R3 \\ \phantom{xx}\bigcirc \\ (CH_2)_s \end{array} \quad (7)$$

(In formula (5), R1 is a group selected from hydrogen atom (H), halogen atom, —CN, —NO$_2$, —CF$_3$, —C$_2$F$_5$ and —C$_3$F$_7$, and q is selected from integers of 1 to 8;

In formula (6), R2 is a group selected from hydrogen atom (H), halogen atom, —CN, —NO$_2$, —CF$_3$, —C$_2$F$_5$ and —C$_3$F$_7$, and r is selected from integers of 1 to 8;

In formula (7), R3 is a group selected from hydrogen atom (H), halogen atom, —CN, —NO$_2$, —CF$_3$, —C$_2$F$_5$ and —C$_3$F$_7$, and s is selected from integers of 1 to 8;

wherein, when one kind of group is selected, as R in formula (2), the group of R1=H and q=2, the group of R1=H and q=3, and the group of R1=—NO$_2$ and q=2 in formula (5), the group of R2=halogen atom and r=2 [however, only when two components are selected from formula (3) or (4) as the above described B], the group of R2=—CN and r=3, and the group of R2=—NO$_2$ and r=3 in formula (6), and the group of R3=H and s=1 and the group of R3=H and s=2 in formula (7)

are excluded from alternatives, and when two kinds of groups are selected, in formula (6), a combination of two kinds of groups of R2=halogen atom and r=2 and 4 [however, only when one component is selected from formula (3) or (4) as the above described B]

are excluded from alternatives).

Herein, the polyhydroxyalkanoate of the present invention may include more than two kinds of monomer units represented by formula (2), but it is preferably designed so that the appropriate number of monomer units are included, considering the needed polymer's functionality and properties. Generally, when alkanoates up to about five kinds are used as a raw material of desired monomer units, "secondary" substrates with the chain length sequentially decreased by two methylene units are newly produced by β oxidation from part of the alkanoates, as described previously, and captured as monomer units of the PHA. Thus, about ten kinds or less of monomer units represented by formula (2) are included in PHA and it is expected that the object of the present invention be sufficiently achieved. Furthermore, if fine control of the functionality and the property is desired, configuration with more species of monomer units is also possible.

Also, with respect to substituted positions of R1, R2 and R3, for any of a ortho, meta or para position, and for a first position in the case of the cyclohexyl group of R3, polyhydroxyalkanoate containing corresponding monomer units can be configured, but if there is no significant differences in functionality and properties for any isomer, it is advantageously configured with constituents at the meta or para position in terms of yields or ease with which it is captured in the polymer.

Also, the method of manufacturing polyhydroxyalkanoate of the present invention is a method of manufacturing polyhydroxyalkanoate having monomer unit composition represented by formula (1) using microorganisms, characterized in that microorganisms are cultured together with the alkanoate and the polyhydroxyalkanoate is extracted from the cells of organisms to obtain the polyhydroxyalkanoate having monomer unit composition represented by formula (1).

  (1)

(wherein A is represented by formula (2), B is at least one or more selected from monomer units represented by formula (3) or (4), and m is 0.01 or more and less than 1).

  (2)

  (3)

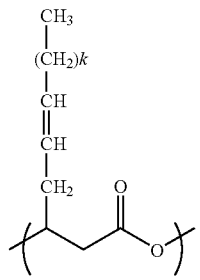  (4)

(In formulae, n is 0 to 10, k is 3 or 5, and R is at least one or more groups selected from groups represented by formulae (5) to (7)).

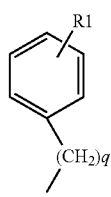  (5)

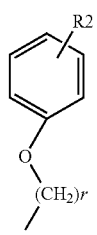  (6)

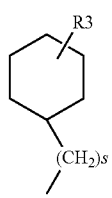  (7)

(In formula (5), R1 is a group selected from hydrogen atom (H), halogen atom, —CN, —NO$_2$, —CF$_3$, —C$_2$F$_5$ and —C$_3$F$_7$, and q is selected from integers of 1 to 8;

In formula (6), R2 is a group selected from hydrogen atom (H), halogen atom, —CN, —NO$_2$, —CF$_3$, —C$_2$F$_5$ and —C$_3$F$_7$, and r is selected from integers of 1 to 8;

In formula (7), R3 is a group selected from hydrogen atom (H), halogen atom, —CN, —NO$_2$, —CF$_3$, —C$_2$F$_5$ and —C$_3$F$_7$, and s is selected from integers of 1 to 8;

wherein, when one kind of group is selected, as R in formula (2), the group of R1=H and q=2, the group of R1=H and q=3, and the group of R1=—NO$_2$ and q=2 in formula (5), the group of R2=halogen atom and r=2, the group of R2=—CN and r=3, and the group of R2=—NO$_2$ and r=3 in formula (6), and the group of R3=H and s=1 and the group of R3=H and s=2 in formula (7)

are excluded from alternatives, and when two kinds of groups are selected, in formula (6), a combination of two kinds of groups of R2=halogen atom and r=2 are excluded from alternatives).

Herein, the polyhydroxyalkanoate of the present invention may more than two kinds of monomer units represented by formula (2), but it is preferably synthesized so that the appropriate number of monomer units are included, considering the needed polymer's functionality and properties. Generally, when alkanoates of up to about five kinds are used as a raw material for desired substrates, "secondary" substrates with the chain length shortened by two methylene units are newly produced by β oxidation from the alkanoates as described previously, and captured as monomer units in PHA. Thus, monomer units of up to ten kinds represented by formula (2) are included in PHA, and it is expected that the object of the present invention is sufficiently achieved. Furthermore, if fine control of the functionality and the property is desired, culture may be performed to include more species of monomer units.

Also, with respect to substituted positions of R1, R2 and R3, for any of a ortho, meta or para position, and for a first position in the case of the cyclohexyl group of R3, polyhydroxyalkanoate containing corresponding monomer units can be configured, but if there is no significant differences in functionality and properties for any isomer, it is advantageously configured with constituents at the meta or para position in terms of yields or ease with which it is captured in the polymer.

Furthermore, the inventors did strenuous research to develop a method for obtaining desired PHA having little or no undesired monomer units coexisting therein, and as a result, found that when the microorganism is cultured in a culture medium containing as the sole carbon source the alkanoate to be the raw material for PHA and a saccharide, it is possible to produce PHA having little or no undesired monomer units coexisting therein, leading to the completion of the invention.

That is, the method of manufacturing polyhydroxyalkanoate (PHA) of the present invention is a method of manufacturing polyhydroxyalkanoate containing monomer units represented by formula (23) using microorganisms, characterized by having a process in which a microorganism capable of synthesizing polyhydroxyalkanoate containing monomer units represented by formula (23) from the alkanoate represented by general formula (22) are cultured in a culture medium containing as the sole carbon source the alkanoate of formula (22) and a saccharide.

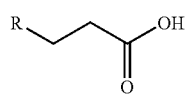
(22)

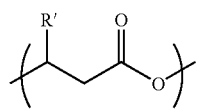
(23)

(In above formulae, R is at least one or more groups represented by formula (24), and R' is one or more groups selected from the groups selected in formula (22), the group of t-2 in the selected groups, the group of t-4 in the selected groups and the group of t-6 in the selected groups. Herein, t-2, t-4 and t-6 can be only integers of 1 or more.)

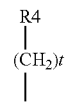
(24)

(In the above formula, R4 represents a saturated or unsaturated phenyl group, a saturated or unsaturated phenoxy group, and a saturated or unsaturated cyclohexyl group, and t represents an integer in the range of 1 to 8 independently.)

Herein, more than one kinds of alkanoate represented by formula (22) may be used when culture is carried out, but the appropriate number thereof are preferably used, considering the needed polymer's functionality and properties. Generally, when alkanoates of up to five kinds represented by formula (22) are used as raw materials for the desired monomer units, "secondary" substrates with the chain length shortened by two methylene units are newly produced by β oxidation from part of the alkanoates as described previously, and captured as monomer units of PHA. Thus, monomer units of up to ten kinds represented by formula (2), for example, are included in PHA, and it is expected that the above described object be sufficiently achieved. Furthermore, if fine control of the functionality and the property is desired, more kinds of alkanoates can be used.

Substituents at the group of R4 described above include halogen atom, —CN, —NO$_2$, —CF$_3$, —C$_2$F$_5$, —C$_3$F$_7$ and the like. With respect to substituted positions of R4, in any of a ortho, meta or para position, and in a first position in the case of the cyclohexyl group, polyhydroxyalkanoate constituted by corresponding monomer units can be obtained, but if there is no significant differences in functionality and properties for any isomer, constituents at the meta or para position can be suitably used in terms of yields or ease with which it is captured in the polymer.

Also, for saccharides, for example, glucose, fructose, mannose and the like may be suitably used.

Furthermore, the inventors did strenuous research to develop a method for producing desired PHA having little or no undesired monomer units coexisting therein, and as a result, found that when the microorganism is cultured in a culture medium containing as the sole carbon source an alkanoate to be the raw material for PHA and polypeptone only, it is possible to produce PHA having little or no undesired monomer units coexisting therein, leading to the completion of the invention.

That is, the method of manufacturing polyhydroxyalkanoate (PHA) of the present invention is a method of manufacturing polyhydroxyalkanoate containing monomer units represented by formula (23) using microorganisms, characterized by having a process in which microorganisms capable of synthesizing polyhydroxyalkanoate containing monomer units represented by formula (23) from the alkanoate represented by formula (22) are cultured in a culture medium containing the alkanoate and polypeptone as the only carbon source.

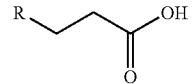
(22)

-continued

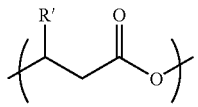
(23)

(In the above described formulae, R is at least one or more groups represented by formula (24), and R' is one or more groups selected from the groups selected in formula (22), the group of t-2 in the selected groups, the group of t-4 in the selected groups and the group of t-6 in the selected groups. Herein, t-2, t-4 and t-6 can be only integers of 1 or more.)

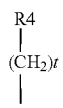
(24)

(In the above described formula, R4 represents a saturated or unsaturated phenyl group, a saturated or unsaturated phenoxy group, and a saturated or unsaturated cyclohexyl group, and t represents an integer in the range of 1 to 8 independently.)

Herein, more than one kinds of alkanoate represented by formula (22) may be used when culture is carried out, but the appropriate number thereof are preferably used, considering the needed polymer's functionality and properties. Generally, when up to five kinds of alkanoates represented by formula (22) are used as raw materials for the desired monomer units, secondary" substrates with the chain length shortened by two methylene units are newly produced by β oxidation from a part of the alkanoates as described previously, and captured as the monomer units in PHA. Thus, up to about ten kinds of monomer units represented by formula (2), for example, are included in PHA, and it is expected that the above described object be sufficiently achieved. Furthermore, if fine control of the functionality and the property is desired, more kinds of alkanoate can be used.

Substituents at the group of R4 described above include halogen atom, —CN, —NO$_2$, —CF$_3$, —C$_2$F$_5$, —C$_3$F$_7$ and the like. With respect to substituted positions of R4, in any of a ortho, meta or para position, and in a first position in the case of the cyclohexyl group, polyhydroxyalkanoate constituted by corresponding monomer units can be obtained, but if there is no significant differences in functionality and properties for any isomer, constituents at the meta or para position can be suitably used in terms of yields or ease with which it is captured in the polymer.

Furthermore, the inventors did strenuous research to develop a method for efficiently producing desired PHA having little or no undesired monomer units coexisting therein, and as a result, found that when the microorganism are cultured in a culture medium containing as the sole carbon source an alkanoate to be the raw material for PHA and an organic acid associated with the TCA cycle, it is possible to produce PHA having little or no undesired monomer units coexisting therein, leading to the completion of the invention.

That is, the method of producing polyhydroxyalkanoate (PHA) of the present invention is a method of producing polyhydroxyalkanoate containing monomer units represented by formula (23) using microorganisms, characterized by having a process in which microorganisms capable of synthesizing polyhydroxyalkanoate containing monomer units represented by formula (23) from the alkanoate represented by the following general formula (22) are cultured in a culture medium including the alkanoate and only an organic acid associated with the TCA cycle as a carbon source other than the alkanoate represented by the following formula (22).

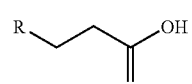
(22)

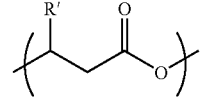
(23)

(In the above described formulae, R is at least one or more groups represented by formula (24), and R' is one or more groups selected from the groups selected in formula (22), the group of t-2 in the selected groups, the group of t-4 in the selected groups and the group of t-6 in the selected groups. Herein, t-2, t-4 and t-6 can be only integers of 1 or more.)

(24)

(In the above described formula, R4 represents a saturated or unsaturated phenyl group, a saturated or unsaturated phenoxy group, and a saturated or unsaturated cyclohexyl group, and t represents an integer in the range of 1 to 8 independently.)

Herein, more than one kinds of alkanoate represented by formula (22) may be used when culture is carried out, but the appropriate number thereof are preferably used, considering the needed polymer's functionality and properties. Generally, when up to about five kinds of alkanoates represented by formula (22) are used as the raw materials, "secondary" substrates with the chain length shortened by two methylene units are newly produced by β oxidation from a part of the alkanoates as described previously, and captured as the monomer units of PHA. Thus, up to about ten kinds of monomer units, for example, as represented by formula (2), are included in PHA, and it is expected that the above described object be sufficiently achieved. Furthermore, if fine control of the functionality and the property is desired, more kinds of alkanoates can be used.

Substituents at the group of R4 described above include halogen atom, —CN, —NO$_2$, —CF$_3$, —C$_2$F$_5$, —C$_3$F$_7$ and the like. With respect to substituted positions of R4, in any of a ortho, meta or para position, and in a first position in the case of the cyclohexyl group, polyhydroxyalkanoate constituted by corresponding monomer units can be obtained, but if there is no significant differences in functionality and properties for any isomer, constituents at the meta or para position can be suitably used in terms of yields or ease with which it is captured in the polymer.

Also, for organic acids associated with the TCA cycle, organic acids existing in the TCA cycle itself, for example citric acid, succinic acid, fumaric acid, malic acid and salts thereof, and organic acids existing on the main flux to the TCA cycle, for example lactic acid, pyruvic acid and salts thereof may be suitably used.

Furthermore, the inventors did strenuous research to develop a method for obtaining desired PHA having little or no undesired monomer units coexisting therein efficiently, and as a result, found that when microorganisms are cultured in at least two steps: first in a medium containing as the sole carbon source an alkanoate to be a raw material for PHA and polypeptone, and then in a medium containing the alkanoate and pyruvic acid or salts thereof as the sole carbon source with nitrogen limitation, it is possible to produce PHA having little or no undesired monomer units coexisting therein.

That is, the method of producing polyhydroxyalkanoate (PHA) of the present invention is a method of manufacturing polyhydroxyalkanoate containing monomer units represented by formula (23) using microorganisms, characterized by having a process in which microorganisms capable of synthesizing polyhydroxyalkanoate containing monomer units represented by formula (23) from the alkanoate represented by the following general formula (22) are cultured in at least two steps: first in a culture medium containing as the sole carbon source the alkanoate represented by formula (22) and polypeptone, and then in a culture medium containing as the sole carbon source the alkanoate represented by formula (22) and pyruvic acid or salts thereof under nitrogen limitation.

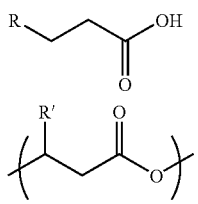

(In the above described formulae, R is at least one or more groups represented by formula (24), and R' is one or more groups selected from the groups selected in the above described formula (22), the group of t-2 in the selected groups, the group of t-4 in the selected groups and the group of t-6 in the selected groups. Herein, t-2, t-4 and t-6 can be only integers of 1 or more.)

(In the above described formula, R4 represents a saturated or unsaturated phenyl group, a saturated or unsaturated phenoxy group, and a saturated or unsaturated cyclohexyl group, and t represents an integer in the range of 1 to 8 independently.)

Herein, more than one kinds of alkanoate represented by formula (22) may be used when culture is carried out, but the appropriate number thereof are preferably used, considering the needed polymer's functionality and properties. Generally, when up to about five kinds of alkanoates represented by formula (22) are used as the raw materials, "secondary" substrates shortened by two methylene units are newly produced by β oxidation from part of the alkanoates as described previously, and captured as the monomer units in PHA, up to about ten kinds of monomer units, for example, those represented by formula (2), are included in PHA, and it is expected that the above described object be sufficiently achieved. Furthermore, if fine control of the functionality and the property is desired, more kinds of alkanoate can be used.

Substituents at the group of R4 described above include halogen atom, —CN, —NO$_2$, —CF$_3$, —C$_2$F$_5$, —C$_3$F$_7$ and the like. With respect to substituted positions of R4, in any of a ortho, meta or para position, and in a first position in the case of the cyclohexyl group, polyhydroxyalkanoate constituted by corresponding monomer units can be obtained, but if there is no significant differences in functionality and properties for any isomer, constituents at the meta or para position can be suitably used in terms of yields or ease with which it is captured in the polymer.

Also, new strains related to the present invention are characterized by having synthetic systems of polyhydroxyalkanoate including alkanoate represented by formula (22) to monomer units represented by formula (23).

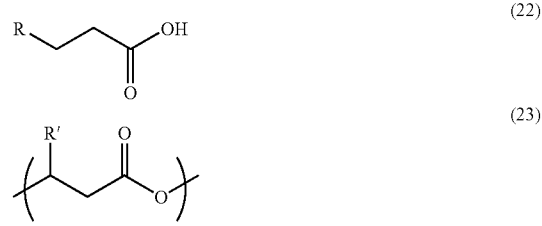

(In the above described formulae, R is at least one or more groups represented by formula (24), and R' is one or more groups selected from the groups selected in the above described formula (22), the group of t-2 in the selected groups, the group of t-4 in the selected groups and the group of t-6 in the selected groups. Herein, t-2, t-4 and t-6 can be only integers of 1 or more.)

(wherein R4 is a substituted or unsubstituted phenyl group, a substituted or unsubstituted phenoxy group, or a substituted or unsubstituted cyclohexyl group; and t is independently an integer of 1–8).

A substituent in the above described R4 group includes a halogen atom, —CN, —NO$_2$, —CF$_3$, —C$_2$F$_5$, —C$_3$F$_7$ or the like.

Hereinafter, a new polyhydroxyalkanoate of the present invention will be illustrated.

A new polyhydroxyalkanoate of the present invention is the one of formula (8):

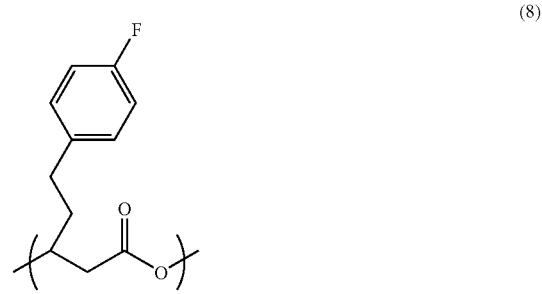

which contains 3-hydroxy-5-(4-fluorophenyl)valeric acid as a monomer unit.

Further, the polyhydroxyalkanoate is of formula (9):

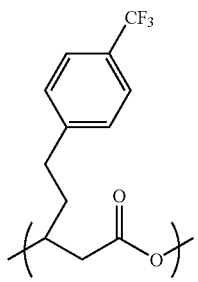
(9)

which contains 3-hydroxy-5-(4-trifluoromethylphenyl)valeric acid as a monomer unit.

In addition, a material substrate when producing new PHA of the present invention using microorganisms is 5-(4-trifluoromethylphenyl) valeric acid of the following chemical formula (21):

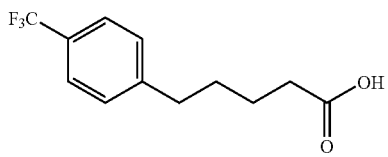
(21)

and the material substrate itself is a new compound.

Further, the polyhydroxyalkanoate is of formula (10):

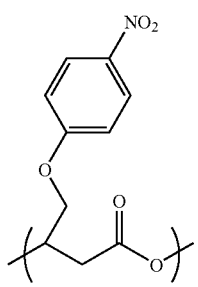
(10)

which contains 3-hydroxy-4-(4-nitrophenoxy)butyric acid as a monomer unit.

Further, the polyhydroxyalkanoate is of formula (11)

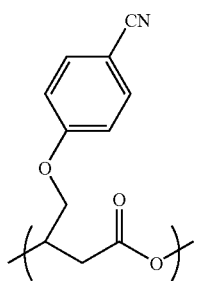
(11)

which contains 3-hydroxy-4-(4-cyanophenoxy)butyric acid as a monomer unit.

Further, the polyhydroxyalkanoate is of formula (12):

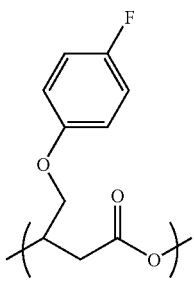
(12)

which contains 3-hydroxy-4-(4-fluorophenoxy)butyric acid as a monomer unit.

Further, the polyhydroxyalkanoate is of formula (13):

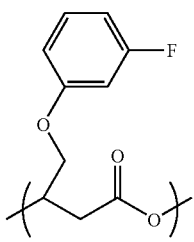
(13)

which contains 3-hydroxy-4-(3-fluorophenoxy)butyric acid as a monomer unit.

Further, the polyhydroxyalkanoate is of formula (14):

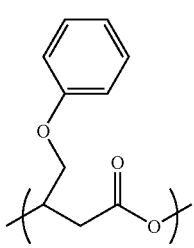
(14)

which contains 3-hydroxy-4-phenoxybutyric acid as a monomer unit. Herein, as the monomer unit except 3-hydroxy-4-phenoxybutyric acid of formula (14), at least one or more of the monomer units of formula (3) or (4) are contained.

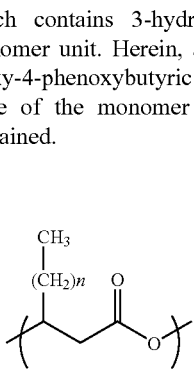
(3)

-continued

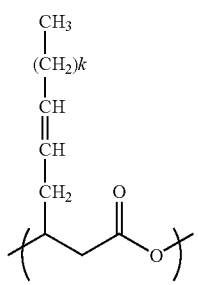
(4)

(wherein n is 0–10) (wherein k is 3 or 5)

Further, the polyhydroxyalkanoate is of formula (15):

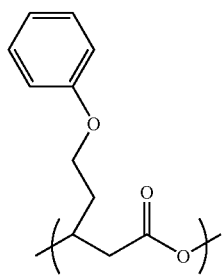
(15)

which contains 3-hydroxy-5-phenoxyvaleric acid as a monomer unit. Herein, as the monomer unit except 3-hydroxy-5-phenoxyvaleric acid of formula (15), at least one or more of the monomer units of formula (3) or (4) are contained.

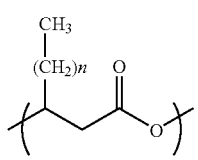
(3)

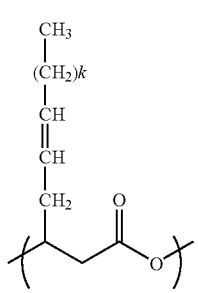
(4)

(wherein n is 0–10) (wherein k is 3 or 5)

Further, the polyhydroxyalkanoate is of formula (16):

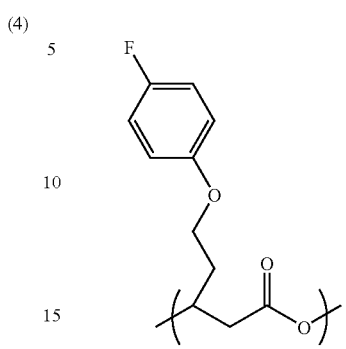
(16)

which contains 3-hydroxy-5-(4-fluorophenoxy)valeric acid as a monomer unit. Herein, as the monomer unit except 3-hydroxy-5-(4-fluorophenoxy)valeric acid of formula (16), the polyhydroxyalkanoate contains at least one or more of the monomer units of formula (3) or (4) and excludes the monomer unit of three component system.

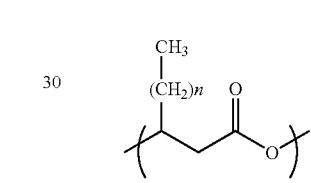
(3)

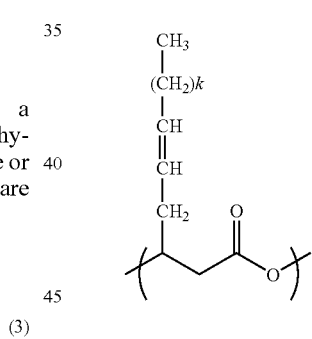
(4)

(wherein n is 0–10) (wherein k is 3 or 5)

Further, the polyhydroxyalkanoates are of formulas (8) and (16):

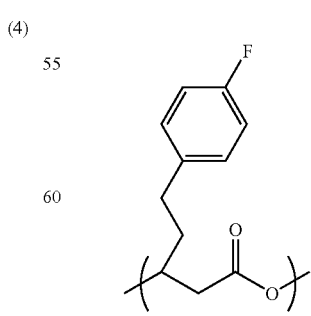
(8)

(16)

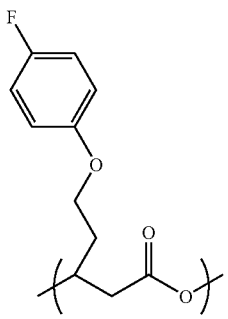

which contain 3-hydroxy-5-(4-fluorophenyl)valeric acid and 3-hydroxy-5-(4-fluorophenoxy)valeric acid as monomer units.

Further, the polyhydroxyalkanoates are of formulas (15) and (17):

(15)

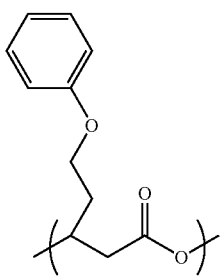

(17)

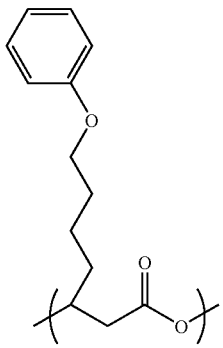

which contain 3-hydroxy-5-phenoxyvaleric acid and 3-hydroxy-7-phenoxyheptanoic acid as monomer units. Herein, as the monomer unit except 3-hydroxy-5-phenoxyvaleric acid and 3-hydroxy-7-phenoxyheptanoic acid of formulas (15) and (17), at least one or more of the monomer units of formula (3) or (4) are contained.

(3)

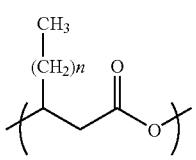

(4)

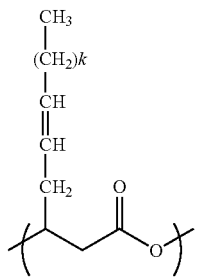

(wherein n is 0–10) (wherein k is 3 or 5)

Further, the polyhydroxyalkanoates are of formulas (14), (18) and (19):

(14)

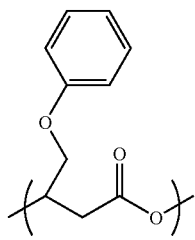

(18)

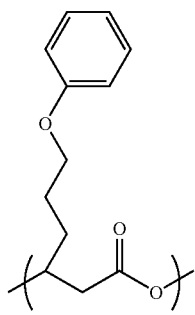

(19)

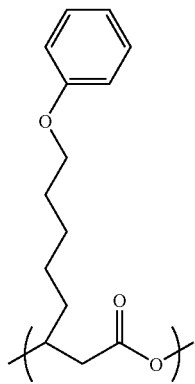

which contain 3-hydroxy-4-phenoxybutyric acid, 3-hydroxy-6-phenoxyhexanoic acid and 3-hydroxy-8-phenoxyoctanoic acid as monomer units. Herein, as the monomer unit except 3-hydroxy-4-phenoxybutyric acid, 3-hydroxy-6-phenoxyhexanoic acid and 3-hydroxy-8-phenoxyoctanoic acid of formulas (14), (18) and (19), at least one or more of the monomer units of formula (3) or (4) are contained.

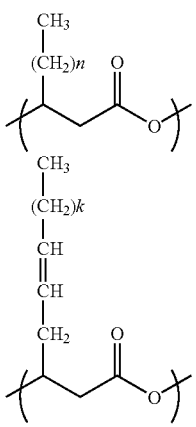

(wherein n is 0–10) (wherein k is 3 or 5)

Further, the polyhydroxyalkanoates are of formulas (15), (17) and (20):

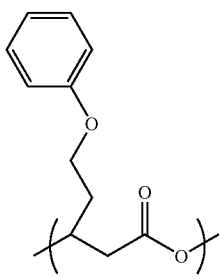

(15)

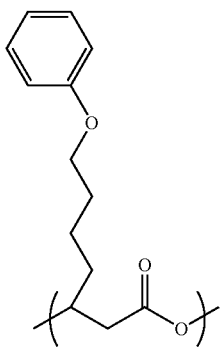

(17)

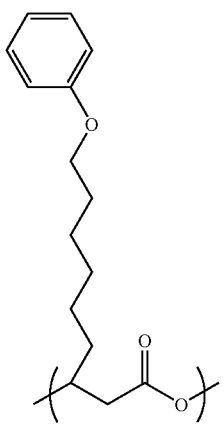

(20)

which contain 3-hydroxy-5-phenoxyvaleric acid, 3-hydroxy-7-phenoxyheptanoic acid and 3-hydroxy-9-phenoxynonanoic acid as monomer units. Herein, as the monomer unit except 3-hydroxy-5-phenoxyvaleric acid, 3-hydroxy-7-phenoxyheptanoic acid and 3-hydroxy-9-phenoxynonanoic acid of formulas (15), (17) and (20), at least one or more of the monomer units of formula (3) or (4) are contained.

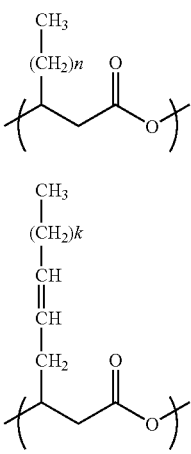

(3)

(4)

(wherein n is 0–10) (wherein k is 3 or 5)

Hereinafter, a manufacturing method for polyhydroxyalkanoates will be illustrated.

The present inventors have succeeded in obtaining microorganisms which can produce polyhydroxyalkanoates containing a monomer unit of 3-hydroxy-5-(4-fluorophenyl)valeric acid (3HFPV) of formula (8) by being cultivated in a culture medium containing 5-(4-fluorophenyl)valeric acid (FPVA) of formula (25).

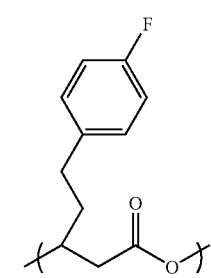

(8)

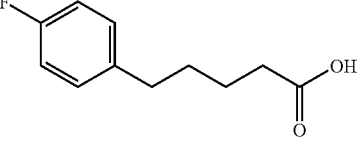

(25)

A manufacturing method for polyhydroxyalkanoates of the present invention is characterized by having a step of cultivating microorganisms which produce polyhydroxyalkanoates containing the monomer unit of 3HFPV of formula (8) using FPVA in a culture medium containing FPVA of formula (25).

In addition, another manufacturing method is characterized in that cultivation of the microorganisms is performed in a culture medium containing FPVA of formula (25) and saccharides.

Further, another manufacturing method is characterized in that cultivation of the microorganisms is performed in a culture medium containing FPVA of formula (25) and polypeptone.

Further, another manufacturing method is characterized in that cultivation of the microorganisms is performed in a culture medium containing FPVA of formula (25) and organic acids associated with the TCA cycle.

Furthermore, another manufacturing method is characterized in that cultivation of the microorganisms is performed by at least 2 step culturing: first in a culture medium containing FPVA of formula (25) and polypeptone, and then in a culture medium containing FPVA of formula (25) and pyruvic acid or its salt with nitrogen limitation.

The present inventors have succeeded in obtaining microorganisms which can produce polyhydroxyalkanoates containing a monomer unit of 3-hydroxy-5-(4-trifluoromethylphenyl)valeric acid (3HCF$_3$PV) of formula (9) by being cultured in a culture medium containing 5-(4-trifluoromethylphenyl)valeric acid (CF$_3$PVA) of formula (21).

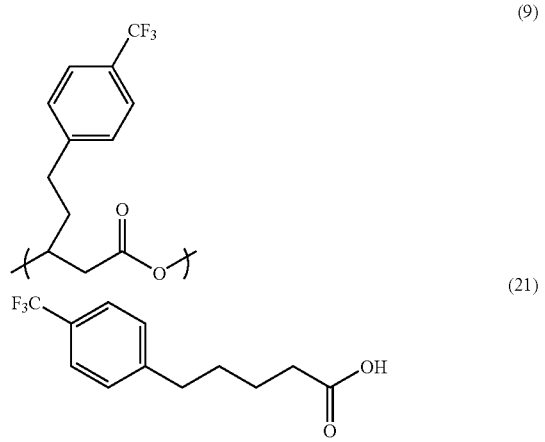

A manufacturing method for polyhydroxyalkanoates of the present invention comprise is characterized by culturing the microorganism which can produce polyhydroxyalkanoates containing the monomer unit of 3HCF$_3$PV of formula (9) from CF$_3$PVA of formula (21) in a culture medium containing CF$_3$PVA.

In addition, another manufacturing method is characterized in that cultivation of the microorganisms is performed in a culture medium containing CF$_3$PVA of formula (21) and a saccharide.

Further, another manufacturing method is characterized in that cultivation of the microorganisms is performed in a culture medium containing CF$_3$PVA of formula (21) and polypeptone.

Further, another manufacturing method is characterized in that cultivation of the microorganisms is performed in a culture medium containing CF$_3$PVA of formula (21) and an organic acid associated with the TCA cycle.

Furthermore, another manufacturing method is characterized in that cultivation of the microorganisms is performed by at least two step culturing: first in a culture medium containing CF$_3$PVA of formula (21) and polypeptone, and then in a culture medium containing CF$_3$PVA of formula (21) and pyruvic acid or its salt with nitrogen limitation.

The present inventors have succeeded in obtaining microorganisms which can produce polyhydroxyalkanoates containing a monomer unit of 3-hydroxy-4-(4-nitrophenoxy) butyric acid (3HNO$_2$PxB) formula (10) by being cultured in a culture medium containing 4-(4-nitrophenoxy)butyric acid (NO$_2$PxBA) of formula (26).

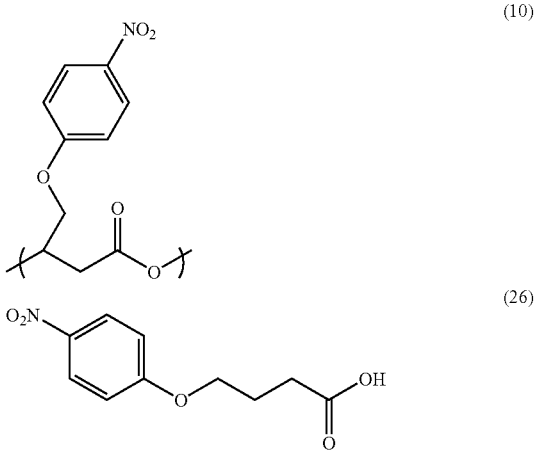

A manufacturing method for polyhydroxyalkanoates of the present invention is characterized by culturing a microorganism which can produce polyhydroxyalkanoates containing the monomer unit of 3HNO$_2$PxB represented by formula (10) using NO$_2$PxBA in a culture medium containing NO$_2$PxBA of formula (26).

In addition, another manufacturing method is characterized in that cultivation of the microorganism is performed in a culture medium containing NO$_2$PxBA of formula (26) and a saccharide.

Further, another manufacturing method is characterized in that cultivation of the microorganisms is performed in a culture medium containing NO$_2$PxBA of formula (26) and polypeptone.

Further, another manufacturing method is characterized in that cultivation of the microorganisms is performed in a culture medium containing NO$_2$PxBA of formula (26) and an organic acid associated with the TCA cycle.

Furthermore, another manufacturing method is characterized in that cultivation of the microorganism is performed by at least 2 steps of culturing, first in a culture medium containing NO$_2$PxBA of formula (26) and polypeptone, and then in a culture medium containing NO$_2$PxBA and pyruvic acid or its salt with nitrogen limitation.

The present inventors have succeeded in obtaining microorganisms which can produce polyhydroxyalkanoates containing a monomer unit of 3-hydroxy-4-(4-cyanophenoxy) butyric acid (3HCNPxB) of formula (11) by being cultivated in a culture medium containing 4-(4-cyanophenoxy)butyric acid (CNPxBA) of formula (27).

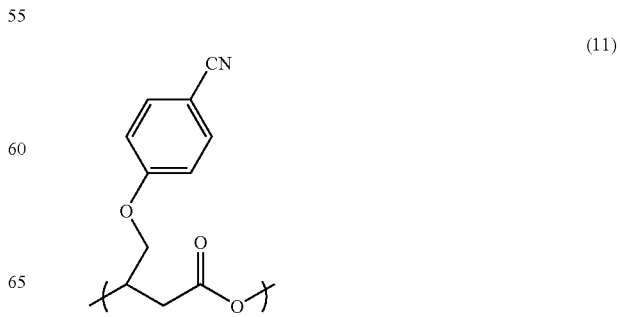

-continued

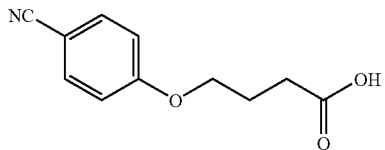
(27)

A manufacturing method for polyhydroxyalkanoates of the present invention is characterized by having steps of cultivating the microorganism which can produce polyhydroxyalkanoates containing the monomer unit of 3HCNPxB represented by formula (11) from CNPxBA of formula (27) in a culture medium containing CNPxBA.

In addition, another manufacturing method is characterized in that cultivation of the microorganism is performed in a culture medium containing CNPxBA of formula (27) and a saccharide.

Further, another manufacturing method is characterized in that cultivation of the microorganism is performed in a culture medium containing CNPxBA of formula (27) and polypeptone.

Further, another manufacturing method is characterized in that cultivation of the microorganism is performed in a culture medium containing CNPxBA of formula (27) and an organic acid associated with the TCA cycle.

Furthermore, another manufacturing method is characterized in that cultivation of the microorganism is performed by at least 2 steps of culturing: first in a culture medium containing CNPxBA of formula (27) and polypeptone, and then in a culture medium containing CNPxBA of formula (27) and pyruvic acid or its salt with nitrogen limitation.

The present inventors have succeeded in obtaining microorganisms which can produce polyhydroxyalkanoates containing a monomer unit of 3-hydroxy-4-(4-fluorophenoxy) butyric acid (3HFPxB) of formula (12) by being cultivated in a culture medium containing 4-(4-fluorophenoxy)butyric acid (FPxBA) of formula (28).

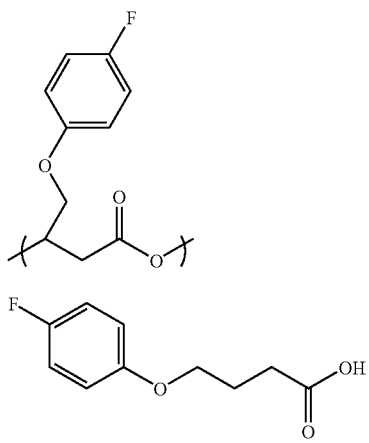

(12)

(28)

A manufacturing method for polyhydroxyalkanoates of the present invention is characterized by having the step of cultivating a microorganism which can produce polyhydroxyalkanoates containing the monomer unit of 3HFPxB of formula (12) using FPxBA in a culture medium containing FPxBA of formula (28).

In addition, another manufacturing method is characterized in that cultivation of the microorganism is performed in a culture medium containing FPxBA of formula (28) and a saccharide.

Further, another manufacturing method is characterized in that cultivation of the microorganisms is performed in a culture medium containing FPxBA of formula (28) and polypeptone.

Further, another manufacturing method is characterized in that cultivation of the microorganisms is performed in a culture medium containing FPxBA of formula (28) and an organic acid associated with the TCA cycle.

Furthermore, another manufacturing method is characterized in that cultivation of the microorganisms is performed by at least 2 steps of culturing: first in a culture medium containing FPxBA of formula (28) and polypeptone, and then in a culture medium containing FPxBA of formula (28) and pyruvic acid or its salt with nitrogen limitation.

The present inventors have succeeded in obtaining microorganisms which can produce polyhydroxyalkanoates containing a monomer unit of 3-hydroxy-4-(3-fluorophenoxy) butyric acid (3HmFPxB) of formula (13) by being cultivated in a culture medium containing 4-(3-fluorophenoxy)butyric acid (mFPxBA) of formula (29).

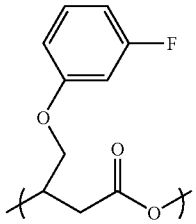
(13)

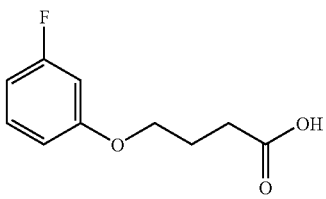
(29)

A manufacturing method for polyhydroxyalkanoates of the present invention is characterized by having steps of cultivating microorganisms which produce polyhydroxyalkanoates containing the monomer unit of 3HmFPxB of formula (13) using mFPxBA in a culture medium containing mFPxBA of formula (29).

In addition, another manufacturing method is characterized in that cultivation of the microorganisms is performed in a culture medium containing mFPxBA of formula (29) and saccharides.

Further, another manufacturing method is characterized in that cultivation of the microorganisms is performed in a culture medium containing mFPxBA of formula (29) and polypeptone.

Further, another manufacturing method is characterized in that cultivation of the microorganisms is performed in a culture medium containing mFPxBA of formula (29) and organic acids associated with the TCA cycle.

Furthermore, another manufacturing method is characterized in that cultivation of the microorganisms is performed by at least 2 steps of culturing: first in a culture medium containing mFPxBA of formula (29) and polypeptone, and then in a culture medium containing mFPxBA of formula (29) and pyruvic acid or its salt with nitrogen limitation.

The present inventors have succeeded in obtaining microorganisms which can produce polyhydroxyalkanoates containing a monomer unit of 3-hydroxy-5-phenylvaleric acid (3HPV) of formula (30) by being cultivated in a culture medium containing 5-phenylvaleric acid (PVA) of formula (31).

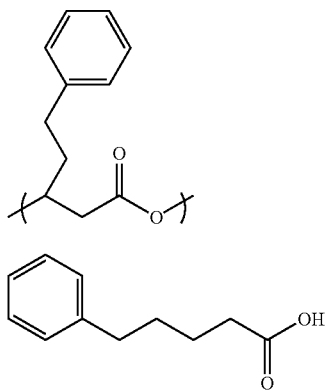

(30)

(31)

A manufacturing method for polyhydroxyalkanoates of the present invention is characterized by having the step of cultivating microorganisms which can produce polyhydroxyalkanoates containing the monomer unit of 3HPV of formula (30) using PVA in a culture medium containing PVA of formula (31) and a saccharide.

Further, another manufacturing method is characterized in that cultivation of the microorganisms is performed in a culture medium containing PVA of formula (31) and polypeptone.

Further, another manufacturing method is characterized in that cultivation of the microorganisms is performed in a culture medium containing PVA of formula (31) and an organic acid associated with the TCA cycle.

Furthermore, another manufacturing method is characterized in that cultivation of the microorganism is performed by at least 2 steps of culturing: first in a culture medium containing PVA of formula (31) and polypeptone, and then in a culture medium containing PVA of formula (31) and pyruvic acid or its salt with nitrogen limitation.

The present inventors have succeeded in obtaining microorganisms which can produce polyhydroxyalkanoates containing a monomer unit of 3-hydroxy-6-phenylhexanoic acid (3HPHx) of formula (32) by being cultivated in a culture medium containing 6-phenylhexanoic acid (PHxA) of formula (33).

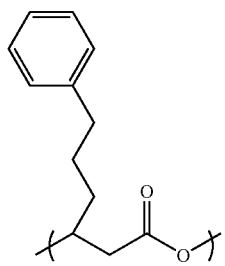

(32)

-continued

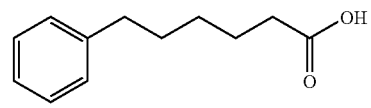

(33)

A manufacturing method for polyhydroxyalkanoates of the present invention is characterized by having the step of cultivating microorganisms which can produce polyhydroxyalkanoates containing the monomer unit of 3HPHx of formula (32) using PHxA in a culture medium containing PHxA of formula (33) and a saccharide.

Further, another manufacturing method is characterized in that cultivation of the microorganism is performed in a culture medium containing PHxA of formula (33) and polypeptone.

Further, another manufacturing method is characterized in that cultivation of the microorganism is performed in a culture medium containing PHxA of formula (33) and an organic acid associated with the TCA cycle.

Furthermore, another manufacturing method is characterized in that cultivation of the microorganism is performed by at least 2 steps of culturing: first in a culture medium containing PHxA of formula (33) and polypeptone, and then in a culture medium containing PHxA of formula (33) and pyruvic acid or its salt with nitrogen limitation.

The present inventors have succeeded in obtaining microorganisms which can produce polyhydroxyalkanoates containing a monomer unit of 3-hydroxy-4-phenoxybutyric acid (3HPxB) of formula (14) by being cultivated in a culture medium containing 4-phenoxybutyric acid (PxBA) of formula (34).

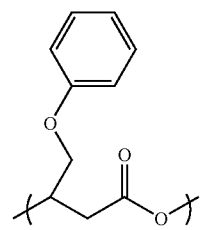

(14)

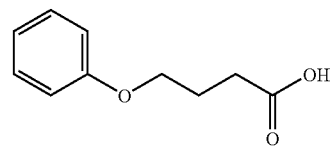

(34)

A manufacturing method for polyhydroxyalkanoates of the present invention is characterized by having the step of cultivating microorganisms which can produce polyhydroxyalkanoates containing the monomer unit of 3HPxB of formula (14) using PxBA in a culture medium containing PxBA of formula (34).

In addition, another manufacturing method is characterized in that cultivation of the microorganism is performed in a culture medium containing PxBA of formula (34) and a saccharide.

Further, another manufacturing method is characterized in that cultivation of the microorganism is performed in a culture medium containing PxBA of formula (34) and polypeptone.

Further, another manufacturing method is characterized in that cultivation of the microorganism is performed in a culture medium containing PxBA of formula (34) and an organic acid associated with the TCA cycle.

Furthermore, another manufacturing method is characterized in that cultivation of the microorganisms is performed by at least 2 steps of culturing: first in a culture medium containing PxBA of formula (34) and polypeptone, and then in a culture medium containing PxBA of formula (34) and pyruvic acid or its salt with nitrogen limitation.

The present inventors have succeeded in obtaining microorganisms which can produce polyhydroxyalkanoates containing a monomer unit of 3-hydroxy-5-phenoxyvaleric acid (3HPxV) of formula (15) by being cultivated in a culture medium containing 5-phenoxyvaleric acid (PxVA) of formula (35).

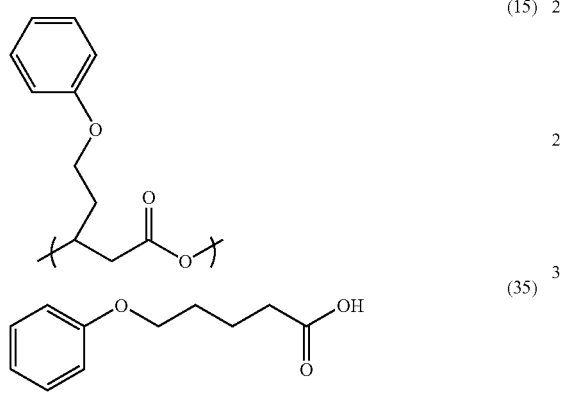

A manufacturing method for polyhydroxyalkanoates of the present invention is characterized by having the step of cultivating microorganisms which can produce polyhydroxyalkanoates containing the monomer unit of 3HPxV of formula (15) using PxVA in a culture medium containing PxVA of formula (35).

In addition, another manufacturing method is characterized in that cultivation of the microorganism is performed in a culture medium containing PxVA of formula (35) and a saccharide.

Further, another manufacturing method is characterized in that cultivation of the microorganism is performed in a culture medium containing PxVA of formula (35) and polypeptone.

Further, another manufacturing method is characterized in that cultivation of the microorganism is performed in a culture medium containing PxVA of formula (35) and an organic acid associated with the TCA cycle.

Furthermore, another manufacturing method is characterized in that cultivation of the microorganism is performed by at least 2 steps of culturing: first in a culture medium containing PxVA of formula (35) and polypeptone, and then in a culture medium containing PxVA of formula (35) and pyruvic acid or its salt with nitrogen limitation.

The present inventors have succeeded in obtaining microorganisms which can produce polyhydroxyalkanoates containing a monomer unit of 3-hydroxy-5-(4-fluorophenoxy) valeric acid (3HFPxV) of formula (16) by being cultivated in a culture medium containing 5-(4-fluorophenoxy)valeric acid (FPxVA) of formula (36).

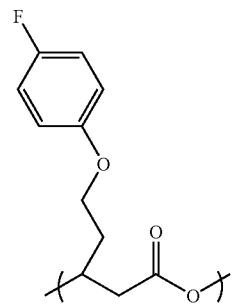

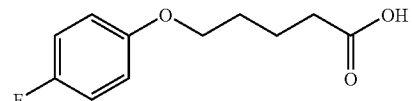

A manufacturing method for polyhydroxyalkanoates of the present invention is characterized by having the step of cultivating microorganisms which can produce polyhydroxyalkanoates containing the monomer unit of 3HFPxV of formula (16) using FPxVA in a culture medium containing FPxVA of formula (36) and a saccharide.

Further, another manufacturing method is characterized in that cultivation of the microorganism is performed in a culture medium containing FPxVA of formula (36) and polypeptone.

Further, another manufacturing method is characterized in that cultivation of the microorganism is performed in a culture medium containing FPxVA of formula (36) and an organic acid associated with the TCA cycle.

Furthermore, another manufacturing method is characterized in that cultivation of the microorganisms is performed by at least 2 steps of culturing, first in a culture medium containing FPxVA of formula (36) and polypeptone, and then in a culture medium containing FPxVA of formula (36) and pyruvic acid or its salt with nitrogen limitation.

The present inventors have succeeded in obtaining microorganisms which can produce polyhydroxyalkanoates containing a monomer unit of 3-hydroxy-4-cyclohexylbutyric acid (3HCHB) of formula (37) by being cultivated in a culture medium containing 4-cyclohexylbutyric acid (CHBA) of formula (38).

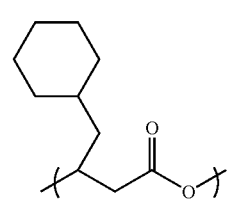

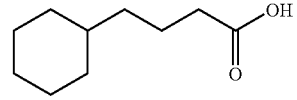

A manufacturing method for polyhydroxyalkanoates of the present invention is characterized by having the step of cultivating microorganisms which can produce polyhydroxyalkanoates containing the monomer unit of 3HCHB of formula (37) using CHBA in a culture medium containing CHBA of formula (38) and a saccharide.

Further, another manufacturing method is characterized in that cultivation of the microorganism is performed in a culture medium containing CHBA of formula (38) and polypeptone.

Further, another manufacturing method is characterized in that cultivation of the microorganism is performed in a culture medium containing CHBA of formula (38) and an organic acid associated with the TCA cycle.

Furthermore, another manufacturing method is characterized in that cultivation of the microorganism is performed by at least 2 steps in a culture medium containing CHBA of formula (38) and polypeptone followed by in a culture medium containing CHBA of formula (38) and pyruvic acid or its salt with nitrogen limitation.

The present inventors have succeeded in obtaining microorganisms which can produce polyhydroxyalkanoates containing monomer units of 3-hydroxy-5-(4-fluorophenyl)valeric acid (3HFPV) and 3-hydroxy-5-(4-fluorophenoxy) valeric acid (3HFPxV) of formulas (8) and (16), respectively, by being cultivated in a culture medium containing 5-(4-fluorophenyl)valeric acid (FPVA) and 5-(4-fluorophenoxy)valeric acid (FPxVA) of formulas (25) and (36), respectively.

and 3HFPxV of formulas (8) and (16), respectively, using FPVA and FPxVA in a culture medium containing FPVA and FPxVA of formulas (25) and (36), respectively, and a saccharide.

Further, another manufacturing method is characterized in that cultivation of the microorganism is performed in a culture medium containing FPVA and FPxVA of formulas (25) and (36), respectively, and polypeptone.

Further, another manufacturing method is characterized in that cultivation of the microorganism is performed in a culture medium containing FPVA and FPxVA of formulas (25) and (36), respectively, and an organic acid associated with the TCA cycle.

Furthermore, another manufacturing method is characterized in that cultivation of the microorganisms is performed by at least 2 steps of culturing; first in a culture medium containing FPVA and FPxVA of formulas (25) and (36), respectively, and polypeptone, and then in a culture medium containing FPVA and FPxVA of formulas (25) and (36), respectively, and pyruvic acid or its salt with nitrogen limitation.

The present inventors have succeeded in obtaining microorganisms which can produce polyhydroxyalkanoates containing monomer units of 3-hydroxy-5-phenoxyvaleric acid (3HPxV) and 3-hydroxy-7-phenoxyheptanoic acid (3HPxHp) of formulas (15) and (17), respectively, by being cultivated in a culture medium containing 7-phenoxyheptanoic acid (PxHpA) of formulas (39).

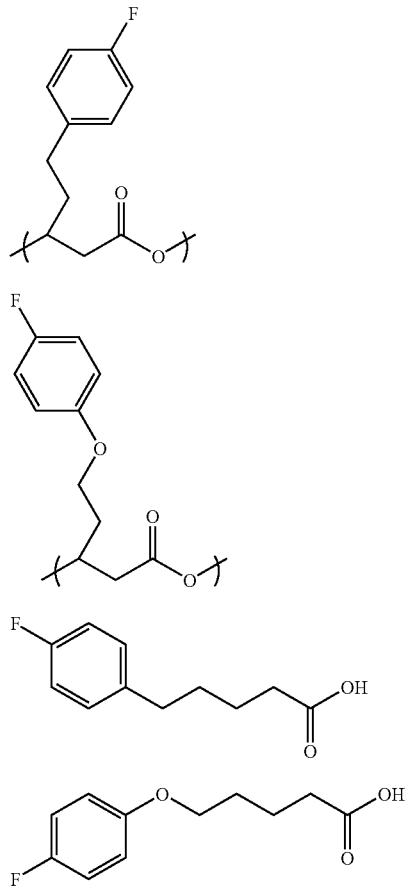
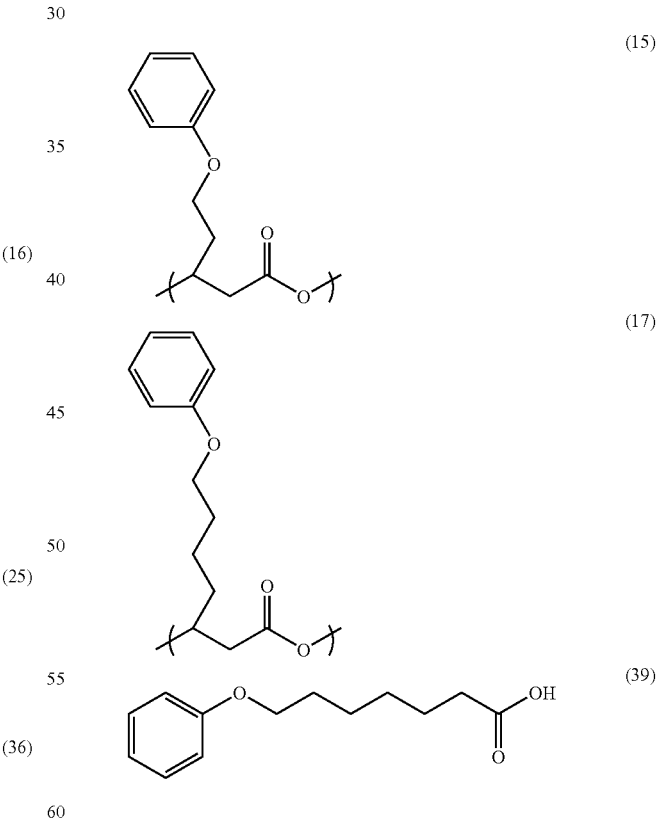

A manufacturing method for polyhydroxyalkanoates of the present invention is characterized by having the step of cultivating microorganisms which can produce polyhydroxyalkanoates containing the monomer units of 3HFPV A manufacturing method for polyhydroxyalkanoates of the present invention is characterized by having the step of cultivating microorganisms which can produce polyhydroxyalkanoates containing the monomer units of 3HPxV and 3HPxHp of formulas (15) and (17), respectively, using PxHpA in a culture medium containing PxHpA of formula (39) and a saccharide.

In addition, another manufacturing method is characterized in that cultivation of the microorganism is performed in a culture medium containing PxHpA of formula (39) and polypeptone.

Further, another manufacturing method is characterized in that cultivation of the microorganism is performed in a culture medium containing PxHpA of formula (39) and an organic acid associated with the TCA cycle.

Furthermore, another manufacturing method is characterized in that cultivation of the microorganisms is performed by at least 2 steps of culturing; first in a culture medium containing PxHpA of formula (39) and polypeptone, and then in a culture medium containing PxHpA of formula (39) and pyruvic acid or its salt with nitrogen limitation.

The present inventors have succeeded in obtaining microorganisms which can produce polyhydroxyalkanoates containing monomer units of 3-hydroxy-4-phenoxybutyric acid (3HPxB), 3-hydroxy-6-phenoxyhexanoic acid (3HPxHx) and 3-hydroxy-8-phenoxyoctanoic acid (3HPxO) of formulas (14), (18) and (19), respectively, by being cultivated in a culture medium containing 8-phenoxyoctanoic acid (PxOA) of formula (40).

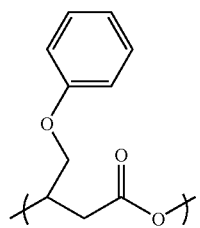

(14)

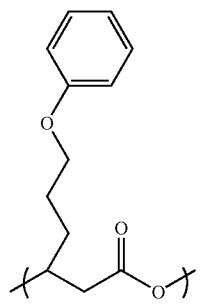

(18)

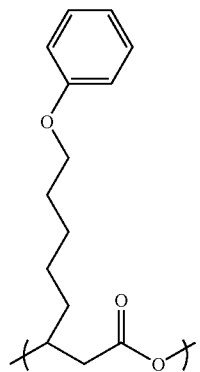

(19)

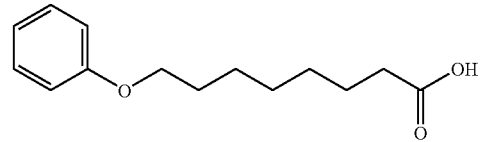

(40)

A manufacturing method for polyhydroxyalkanoates of the present invention is characterized by having the step of cultivating microorganisms which can produce polyhydroxyalkanoates containing the monomer units of 3HPxB, 3HPxHx and 3HPxO of formulas (14), (18) and (19), respectively, using PxOA in a culture medium containing PxOA of formula (40) and a saccharide.

In addition, another manufacturing method is characterized in that cultivation of the microorganism is performed in a culture medium containing PxOA of formula (40) and polypeptone.

Further, another manufacturing method is characterized in that cultivation of the microorganism is cultivated in a culture medium containing PxOA of formula (40) and an organic acid associated with the TCA cycle.

Furthermore, another manufacturing method is characterized in that cultivation of the microorganisms is performed by at least 2 steps of culturing first in a culture medium containing PxOA of formula (40) and polypeptone, and then in a culture medium containing PxOA of formula (40) and pyruvic acid or its salt with nitrogen limitation.

The present inventors have succeeded in obtaining microorganisms which can produce polyhydroxyalkanoates containing monomer units of 3-hydroxy-5-phenoxyvaleric acid (3HPxV), 3-hydroxy-7-phenoxyheptanoic acid (3HPxHp) and 3-hydroxy-9-phenoxynonanoic acid (3HPxN) of formulas (15), (17) and (20), respectively, by being cultivated in a culture medium containing 11-phenoxyundecanoic acid (PxUDA) of formula (41).

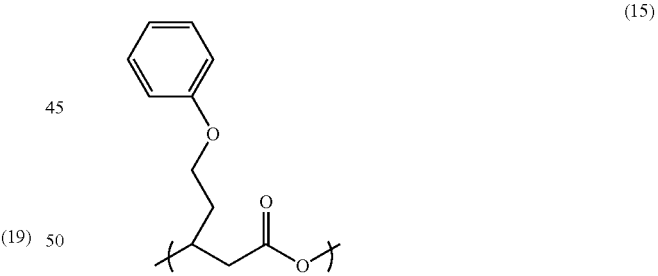

(15)

(17)

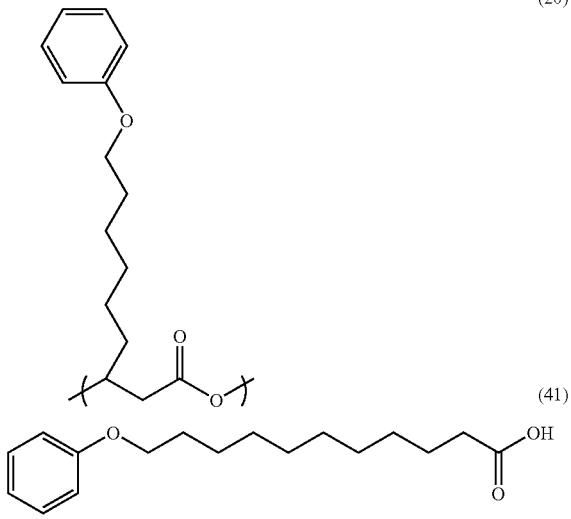

A manufacturing method for polyhydroxyalkanoates of the present invention is characterized by having the step of cultivating microorganisms which can produce polyhydroxyalkanoates containing the monomer units of 3HPxV, 3HPxHp and 3HPxN of formulas (15), (17) and (20), respectively, using PxUDA in a culture medium containing PxUDA of formula (41) and a saccharide.

In addition, another manufacturing method is characterized in that cultivation of the microorganism is performed in a culture medium containing PxUDA of formula (41) and polypeptone.

Further, another manufacturing method is characterized in that cultivation of the microorganism is performed in a culture medium containing PxUDA of formula (41) and an organic acid associated with the TCA cycle.

Furthermore, another manufacturing method is characterized in that cultivation of the microorganisms is performed by at least 2 steps of culturing; first in a culture medium containing PxUDA of formula (41) and polypeptone, and then in a culture medium containing PxUDA of formula (41) and pyruvic acid or its salt with nitrogen limitation.

Further, four new strains suitably usable for production of the above described polyhydroxyalkanoates of the present invention include *Pseudomonas cichorii* YN2, FERM BP-7375, *Pseudomonas cichorii* H45, FERM BP-7374, *Pseudomonas putida* P91, FERM BP-7373 and *Pseudomonas jessenii* P161, FERM BP-7376.

The PHAs according to the present invention are those PHAs which contain monomer units with a variety of structures having substituents useful as device and medical materials and others on the side chain, and more specifically, those which have the above-mentioned substituted or non-substituted phenoxy, phenyl and cyclohexyl groups on the side chain. In addition, the method according to the present invention enables the production of desired PHAs at a high purity and a high yield by using the microorganisms. Furthermore, the present invention can provide strains capable of efficient synthesis of the PHAs at a high purity. In general, the PHAs according to the present invention are of only the R form, and are isotactic polymers.

<Saccharides and Organic Acids Involved in the TCA Cycle: Differences from Conventional Technology>

One method for producing PHA according to the present invention is characterized in that when a microorganism is cultured, in addition to alkanoate for introducing the desired monomer unit, only saccharide(s) or organic acid(s) involved in the TCA cycle as the carbon source other than the alkanoate are added into the medium, so that the PHA produced by and accumulated in the microorganism has a significantly high content of the monomer unit of interest or alternatively only the monomer unit of interest. The effect of facilitating the preference of this particular monomer unit is achieved by adding into the medium only saccharide(s) or organic acid(s) involved in the TCA cycle as the carbon source other than the alkanoate.

That is, the inventors have found that when culture is carried out using saccharide(s) or organic acid(s) involved in the TCA cycle as the co-existing substrate and together with alkanoate for introducing the desired monomer unit, the PHA of interest is produced at a particularly superior yield and purity, compared to conventional methods employing mcl-alkanoate, such as nonanoate or octanoate, as the co-existing substrate, and that this effect is achieved by culture methods allowing acetyl-CoA that is a carbon source as well as an energy source of the microorganism to be produced by processes independent on the β-oxidation, and have reached the present invention.

In the methods according to the invention, saccharide compounds, for example, glucose, fructose, mannose, and the like, are utilized as growth substrates for microorganisms, and the produced PHA is of alkanoate for introducing the desired monomer unit which is existing with saccharide(s), so that there is contained none of or an extremely small amount of monomer units derived from the saccharides such as glucose and others. In this point, the methods according to the present invention is essentially different in structures and effects from conventional methods for microbial production of PHA in which saccharides themselves, such as glucose and others, are employed as the raw substrate of the monomer unit to be introduced into the PHA.

<Polypeptone: Differences from Conventional Technology>

One method for producing PHA according to the present invention is characterized in that when a microorganism is cultured, in addition to alkanoate, a raw material, for introducing the desired monomer unit, only polypeptone as the carbon source other than the alkanoate is added into the medium, so that the PHA produced by and accumulated in the microorganism has a significantly high content of the monomer unit of interest or alternatively only the monomer unit of interest. The effect of facilitating the preference of this particular monomer unit is achieved by adding into the medium only polypeptone as the carbon source other than the alkanoate.

As examples of utilizing polypeptone in microbial production of PHA, Japanese Patent Application Laid-Open Nos. 5-49487, 5-64591, 5-214081, 6-145311, 6-284892, 7-48438, 8-89264, 9-191893, and 11-32789 disclose that when PHA is produced by microorganisms, polypeptone is allowed to be contained in the media. However, all of these utilize polypeptone during pre-culture, that is, at the stage of simply growing cells, and there are not contained substrates resulting in the monomer unit of PHA during pre-culture. Furthermore, there are no examples utilizing polypeptone at the stage of allowing cells to produce PHA. In contrast, the present invention is intended to produce and accumulate PHA, as well as to grow cells, with alkanoate for introducing the desired monomer unit and by co-existing only polypeptone as the carbon sources other than the alkanoate. The production method according to the present invention employing polypeptone, therefore, has quite different structures and effects from conventional examples employing polypeptone. Moreover, there is no mention of the preference of the particular monomer units which is the effect of the present invention, and no indication of the effect of the preference of the particular monomer units having as substituents phenoxy, phenyl and cyclohexyl groups in the composition of PHAs produced by the microorganisms, as in the present invention.

The PHAs, production methods, and microorganisms of the present invention will be explained in more detail below.

<Supplying Pathways of PHA Monomer Units>

At first will be detailed the "fatty acid synthesis pathway," one of pathways supplying mcl-3HA monomer units to be mixed into the PHA of interest.

In the case where saccharides such as glucose and the like are substrates, alkanoates necessary for cellular components are biosynthesized form the "fatty acid synthesis pathway" in which acetyl-CoA produced from saccharides through the "glycolytic pathway" is a starting substance. The fatty acid synthesis involves the de novo synthesis pathway and the carbon-chain elongation pathway, as explained below.

1) De novo Synthesis Pathway

This pathway is catalyzed by two enzymes, acetyl-CoA carboxylase (EC 6.4.1.2) and fatty acid synthase (E.C. 2.3.1.85). Acetyl-CoA carboxylase is an enzyme interposing biotin, and ultimately catalyzing the following reaction to produce malonyl-CoA from acetyl-CoA. This reaction is of follows:

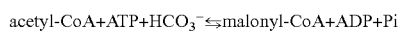

Also, fatty acid synthase is an enzyme catalyzing a cycles of reactions of transfer—decarbonation—reduction—dehydration—reduction. The entire reactions are represented as follows:

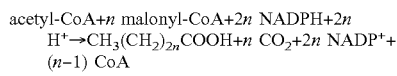

Reaction products may be free acids, CoA-derivatives, or ACP-derivatives, depending on the type of enzymes.

Now, acetyl-CoA and malonyl-CoA are represented by the following chemical formulae (42) and (43), respectively.

(42)

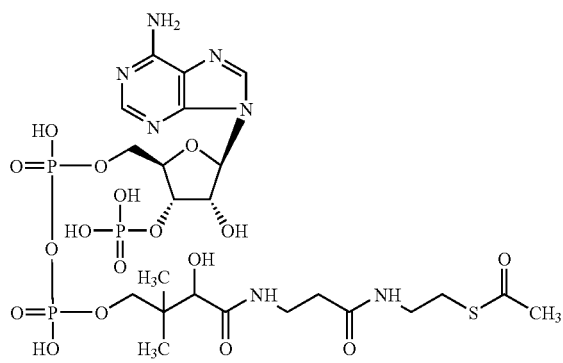

(43)

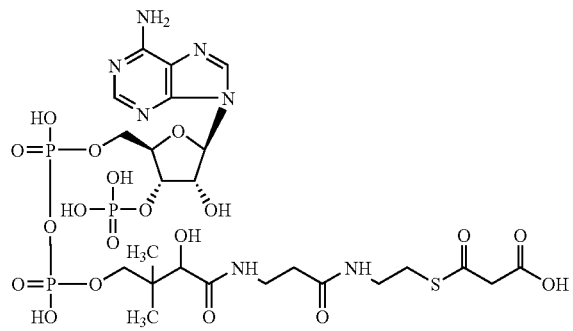

In addition, Co-A stands for co-enzyme A, and is represented by the following chemical formula (44).

(44)

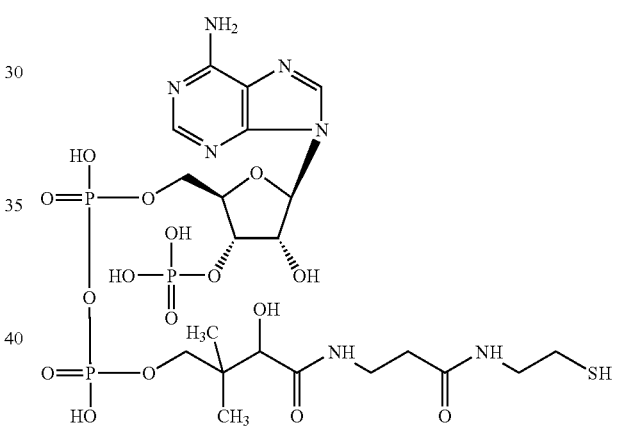

Within this reaction pathway, the route described below gives "D-3-hydroxyacyl-ACP," an intermediate to be the monomer substrate for the PHA biosynthesis. Additionally, as shown in the following reaction formulae, this route extends finally to palmitate with repeated addition of two carbons. Therefore, as the monomer substrate for the PHA biosynthesis are provided seven "D-3-hydroxyacyl-ACPs" having even numbers of the carbons, from "D-3-hydroxybutyryl-ACP" to "D-3-hydroxypalmityl-ACP."

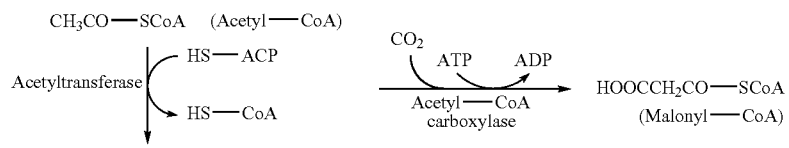

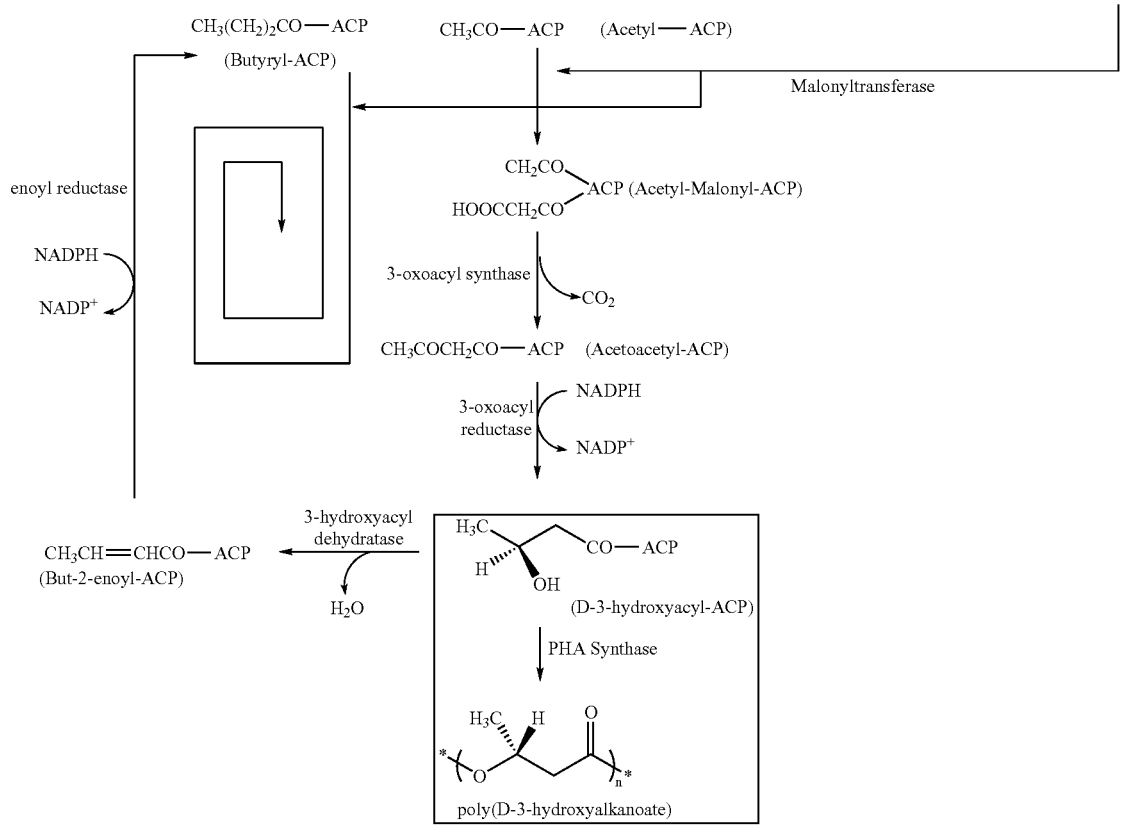

2) Carbon-Chain Elongation Pathway

This pathway is broadly divided into two pathways: a pathway in which malonyl-CoA is added to acyl-ACP, which is finally converted to acyl-ACP having the carbon chain extended with two carbons (and $CO_2$) (referred to as Pathway A) and a pathway in which acetyl-CoA is added to acyl-CoA, which is finally converted to acyl-CoA having the carbon chain extended with two carbons (referred to as Pathway B). Each pathway will be explained below.

Pathway A

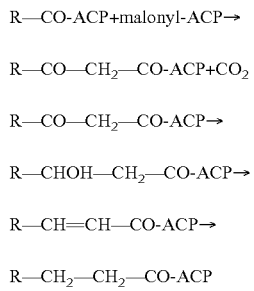

Pathway B

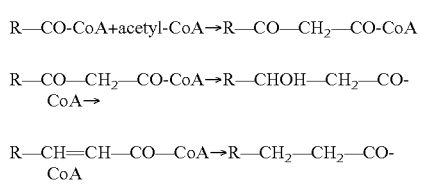

In either Pathway A or B, it is thought that "D-3-hydroxyacyl-CoA" or "D-3-hydroxyacyl-ACP" is yielded as an intermediate, and "D-3-hydroxyacyl-CoA" is utilized as the monomer substrate for the PHA synthesis as it is, while "D-3-hydroxyacyl-ACP" is utilized as the monomer substrate for the PHA synthesis after converting to "D-3-hydroxyacyl-CoA" by ACP-CoA transferase.

In the case where saccharides such as glucose and the like are used as a substrate, it is thought that an mcl-3HA monomer unit is generated within microbial cells via the "glycolytic pathway" and the "fatty acid synthesis pathway" as described above. In the case where organic acids involved in the TCA cycle are used as a substrate, acetyl-CoA is yielded directly from pyruvic acid by pyruvate dehydrogenase. Organic acids in the TCA cycle, for example, malic acid yields pyruvic acid by malate dehydrogenase, followed by acetyl-CoA by the above-mentioned reaction. Oxaloacetic acid yields phosphoenolpyruvic acid by phosphoenolpyruvate carboxykinase, which, in turn, is catalyzed to produce pyruvic acid by pyruvate kinase, followed by acetyl-CoA by the above-mentioned reaction. It is thought that acetyl-CoA produced by these reactions goes through the "fatty acid synthesis pathway" to produce an mcl-3HA monomer unit.

In these cases, it is thought that mcl-alkanoates, for example, octanoate, nonanoate, and the like, or alkanoates having functional groups other than straight aliphatic alkyl added at the end, for example, such as 5-phenylvalerate, 5-(4-fluorophenyl)valerate, 6-phenylhexanoate, 4-phenoxybutyrate, and 4-cyclohexylbutyrate are converted to their CoA-derivatives by CoA-ligases (EC 6.2.1.3, etc), followed by "D-3-hydroxyacyl-CoA" to be the monomer substrate for the PHA biosynthesis directly by a series of enzymes responsible for the β-oxidation pathway.

In short, the mcl-3HA monomer units generated from saccharides or organic acids involved in the TCA cycle is produced via quite a lot of enzymatic reaction steps (i.e., indirectly), but the mcl-alkanoates should yield the mcl-3HA monomer units quite directly.

There will now be described the generation of acetyl-CoA responsible for microbial growth. In the method in which mcl-alkanoate is co-existed in addition to alkanoate for introducing the monomer unit of interest, these alkanoates go through the β-oxidation pathway to produce acetyl-CoA. Generally, mcl-alkanoates are believed to have a superior substrate-affinity for a series of enzymes in the β-oxidation pathway, as compared with alkanoates having a bulky substituent (alkanoates having substituents such as phenyl, phenoxy, cyclohexyl group, or the like), and thus acetyl-CoA is effectively produced by co-existence with mcl-alkanoates. For this reason, it is advantageous to microbial growth utilizing acetyl-CoA as the energy and carbon source.

However, since mcl-alkanoates pathway are directly converted to the monomer unit for PHA via the β-oxidation, it is a significant problem that the produced PHAs also contains the mcl-3HA monomer unit a lot, in addition to the monomer unit of interest.

To solve this problem, methods are desirable in which rather than mcl-alkanoate, such substrates that can provide acetyl-CoA or the energy and carbon source effectively are selected and allowed to co-exist with the alkanoate of interest. As mentioned above, acetyl-CoA can be the monomer unit of PHA by going into the fatty acid synthesis pathway, but this process is an indirect process of many steps compared with mcl-alkanoate in β-oxidation. Therefore, it is possible to achieve a production method not to incorporate or decrease mcl-3HA in PHA by selecting culture conditions such as the substrate concentration to generate acetyl-CoA.

Alternatively, there are commonly used production methods by which culture is carried out at the first step only for the purpose of microbial growth and at the second step is added to the medium only the alkanoate of interest as the carbon source. In this case, ATP is required by acyl-CoA ligase which is an initial enzyme of the beta-oxidation pathway converting the alkanoate to acyl-CoA. Consequently, the inventors' investigation has provided the result that the production methods are more effective by which substrates capable of being utilized as the energy source by microorganisms are also co-existed at the second step, and accomplished the present invention.

As substrates which can effectively provide acyl-CoA or the energy and carbon source in method according to the present invention, as long as compounds can yield acyl-CoA or the energy and carbon source without going through the beta-oxidation pathway, for example, aldoses including glyceraldehyde, erythrose, arabinose, xylose, glucose, galactose, mannose, and fructose, alditols such as glycerol, erythritol, and xylitol, aldonic acids such as gluconic acid, uronic acids such as glucuronic acid and galacturonic acid, saccharides such as disaccharides including maltose, sucrose, and lactose, and in addition, organic acids involved in the TCA cycle such as lactic, pyruvic, malic, citric, succinic, fumaric acids and their salts, and further, medium components derived from natural products such as polypeptone, beef extract, and casamino acid, and the like, any compounds can be used, or selected as appropriate, based on usefulness as a substrate for the strains employed. Furthermore, if their combinations result in a small degree of mixture with mcl-3HA, two or more compounds also can be selected for use.

<Microorganisms>

As mentioned in Background of the Invention, there are reports of microorganisms that produce and accumulate within the cell PHA containing the monomer unit of, for example, 3-hydroxy-4-phenoxybutyrate, 3-hydroxy-5-fluorophenoxyvalerate, 3-hydroxy-6-cyanophenoxyhexanoate, 3-hydroxy-6-nitrophenoxyhexanoate, 3-hydroxy-7-fluorophenoxyheptanoate, such as *Pseudomonas oleovorance* and *Pseudomonas putida* as described in Macromolecules, 29, 3432–3435 (1996), Can. J. Microbiol., 41, 32–43 (1995), Japanese Patent No. 2989175, and others. However, there are no report of microorganisms that produce and accumulate within the cell PHA containing the monomer unit of 3-hydroxy-4-phenoxybutyrates having substituents such as fluorine, cyano, nitro groups. Macromolecules, 32, 2889–2895 (1999) reported that *Pseudomonas oleovorance* produces PHA containing the monomer units of 3-hydroxy-5-(2,4-dinitrophenyl)valerate and 3-hydroxy-5-(4-nitrophenyl)valerate by culturing it in a medium containing 5-(2,4-dinitrophenyl)valerate and nonanoate as substrates. However, there are no reports on microorganisms that produce and accumulate within the cell PHA containing as the monomer unit 3-hydroxy-phenylalkanoates having a substituent such as fluorine, trifluoromethyl group. Therefore, the present invention has been achieved by screening microorganisms capable of incorporating these new monomer units into PHA.

Novel microorganisms of the present invention have a previously unknown capability of producing and accumulating within the cell PHA containing a new monomer unit derived from an alkanoate using the alkanoate as a substrate. Microorganisms displaying such a novel enzymatic reaction have been found by the inventors by screening. The novel microorganisms of the present invention are *Pseudomonas cichorii* strain YN2 (FERM BP-7375), *Pseudomonas cichorii* strain H45 (FERM BP-7374), *Pseudomonas putida* strain P91 (FERM BP-7373), and *Pseudomonas jessenii* strain P161 (FERM BP-7376). Other than these microorganisms, microorganisms to be utilized in the production method of PHA according to the present invention can be obtained by culturing a bacterial strain, for example, of genus *Pseudomonas*, employing the alkanoates as the substrate, for example.

There will be given details concerning strains YN2, H45, P91, and P161.

<Bacteriological Properties of Strain YN2>
(1) Morphological Properties
Shape and size of cells: rod, 0.8 μm×1.5 to 2.0 μm
Polymorphism of cells: negative
Mobility: motile
Sporulation: negative
Gram staining: negative
Colony shape: circular; entire, smooth margin; low convex; smooth surface; glossy; translucent (2) Physiological Properties
Catalase: positive
Oxidase: positive
O/F test: oxidative (non-fermentative)
Nitrate reduction: negative
Indole production: positive
Acid production from glucose: negative
Arginine dihydrolase: negative Urease: negative
Esculin hydrolysis: negative
Gelatin hydrolysis: negative
β-Galactosidase: negative
Fluorescent pigment production on King's B agar: positive
Growth under 4% NaCl: positive (weak growth)
Poly-β-hydroxybutyrate accumulation: negative (*)
Tween 80 hydrolysis: positive
(*) Colonies cultured on nutrient agar were stained with Sudan Black for determination.

(3) Substrate Assimilation
Glucose: positive
L-Arabinose: positive
D-Mannose: negative
D-Mannitol: negative
N-Acetyl-D-glucosamine: negative
Maltose: negative
Potassium gluconate: positive
n-Caprate: positive
Adipate: negative
dl-Malate: positive
Sodium citrate: positive
Phenyl acetate: positive <Bacteriological Properties of Strain H45>

(1) Morphological Properties
Shape and size of cells: rod, 0.8 μm×1.0 to 1.2 μm
Polymorphism of cells: negative
Mobility: motile
Sporulation: negative
Gram staining: negative
Colony shape: circular; entire, smooth margin; low convex; smooth surface; glossy; cream-colored (2) Physiological Properties
Catalase: positive
Oxidase: positive
O/F test: oxidative
Nitrate reduction: negative
Indole production: negative
Acid production from glucose: negative
Arginine dihydrolase: negative
Urease: negative
Esculin hydrolysis: negative
Gelatin hydrolysis: negative
β-Galactosidase: negative
Fluorescent pigment production on the King's B agar: positive
Growth under 4% NaCl: negative
Poly-β-hydroxybutyrate accumulation: negative (3) Ability to Assimilate Substrates
Glucose: positive
L-Arabinose: negative
D-Mannose: positive
D-Mannitol: positive
N-Acetyl-D-glucosamine: positive
Maltose: negative
Potassium gluconate: positive
n-Caprate: positive
Adipate: negative
dl-Malate: positive
Sodium citrate: positive
Phenyl acetate: positive <Bacteriological Properties of Strain P91>

(1) Morphological Properties
Shape and size of cells: rod, 0.6 μm×1.5 μm
Polymorphism of cells: negative
Mobility: motile
Sporulation: negative
Gram staining: negative
Colony shape: circle; entire, smooth margin; low convex; smooth surface; glossy; cream-colored (2) Physiological Properties
Catalase: positive
Oxidase: positive
O/F test: oxidative
Nitrate reduction: negative
Indole production: negative
Acid production from glucose: negative
Arginine dihydrolase: positive
Urease: negative
Esculin hydrolysis: negative
Gelatin hydrolysis: negative
β-Galactosidase: negative
Fluorescent pigment production on the King's B agar: positive (3) Substrate Assimilation
Glucose: positive
L-Arabinose: negative
D-Mannose: negative
D-Mannitol: negative
N-Acetyl-D-glucosamine: negative
Maltose: negative
Potassium gluconate: positive
n-Caprate: positive
Adipate: negative
dl-Malate: positive
Sodium citrate: positive
Phenyl acetate: positive <Bacteriological Properties of the Strain P161>

(1) Morphological Properties
Shape and size of cells: spheres, φ0.6 μm rods, 0.6 μm×1.5 to 2.0 μm
Polymorphism of cells: elongated form
Mobility: motile
Sporulation: negative
Gram staining: negative
Colony shape: circle; entire, smooth margin; low convex; smooth surface; pale yellow (2) Physiological Properties
Catalase: positive
Oxidase: positive
O/F test: oxidative
Nitrate reduction: positive
Indole production: negative
Acid production from glucose: negative
Arginine dihydrolase: positive
Urease: negative
Esculin hydrolysis: negative
Gelatin hydrolysis: negative
β-Galactosidase: negative
Fluorescent pigment production on the King's B agar: positive (3) Substrate Assimilation
Glucose: positive
L-Arabinose: positive D-Mannose: positive
D-Mannitol: positive
N-Acetyl-D-glucosamine: positive
Maltose: negative
Potassium gluconate: positive
n-Caprate: positive
Adipate: negative
dl-Malate: positive
Sodium citrate: positive
Phenyl acetate: positive Based on these bacteriological properties, and referring to Bergey's Manual of Systematic Bacteriology, vol. 1 (1984) and Bergey's Manual of Determinative Bacteriology, 9th ed. (1994), strains YN2 and H45 were revealed to belong to *Pseudomonas cichorii*, and strain P91 was revealed to belong to *Pseudomonas putida*. Accordingly, these strains were designated *Pseudomonas cichorii* strain YN2, *Pseudomonas cichorii* strain H45, and *Pseudomonas putida* strain P91.

Strain P161, on the other hand, was revealed to belong to the genus *Pseudomonas* (*Pseudomonas* sp.), but its bacteriological properties could not identify its taxonomic position. Then, to do classification based on genetic properties, the DNA sequence of 16S rRNA coding region of strain P161 (SEQ ID NO: 1) has been determined to examine the homology with the DNA sequences of 16S RNA coding region of known microorganisms of genus *Pseudomonas*. The results have shown that there is a remarkably high homology of the DNA sequences between strain P161 and *Pseudomonas jessenii*. Furthermore, bacteriological properties of *Pseudomonas jessenii* described in System. Appl. Microbiol., 20, 137–149 (1997) and System. Appl. Microbiol., 22, 45–58 (1999) were found to have a high similarity to those of strain P161. From these results, strain P161 was designated *Pseudomonas jessenii* strain P161, since it was concluded that it is appropriate that strain P161 should be attributed to belong to *Pseudomonas jessenii*.

Strains YN2, H45, P91, and P161 have been deposited at the National Institute of Bioscience and Human-Technology (Patent Microorganism Depository Center), Agency of Industry Science and Technology, Ministry of International Trade and Industry, 1-3, Higashi 1-chome, Tsukuba-shi, Ibaraki-ken, 305 Japan, under the deposition numbers "FERM BP-7375," "FERM BP-7374," "FERM BP-7373," and "FERM BP-7376," respectively. These strains were deposited on Jun. 3, 1999 (date of the original deposit).

<Culture: General>

The PHAs of interest can be produced by culturing these microorganisms in a medium containing alkanoate for introducing the desired monomer unit and growth substrates according to the present invention. These PHAs are generally of only the R-form, and are isotactic polymers.

For usual culture of microorganisms to be employed in the production method of PHA according to the present invention, for example, for preparation of cell stocks, for maintaining of the number and activities of the cells, any type of media can be used, such as common natural media and synthetic media supplemented with nutrients, unless they have adverse effects on the growth or existence of the microorganisms. Culture conditions such as temperature, aeration, stirring, and the like are selected as appropriate, depending on the microorganism employed.

In the case where microorganisms are used to produce and accumulate PHA, inorganic media and others containing alkanoate for introducing the desired monomer unit can be employed as a medium for the PHA production.

For inorganic media employed in the above-mentioned culture method, any media can be used, as long as they contain components allowing microorganisms to grow, such as phosphorus sources (for example, phosphates), nitrogen sources (for example, ammonium salts, nitrates), and the like. Such inorganic media may include, for example, MSB medium, E medium (J. Biol. Chem. 218, 97–106 (1956)), M9 medium, and others.

The composition of M9 medium employed in Examples of the present invention is as follows:

$Na_2HPO_4$: 6.2 g
$KH_2PO_4$: 3.0 g
NaCl: 0.5 g
$NH_4Cl$: 1.0 g (per litter of medium, pH 7.0)

Culture conditions may include, for example, shaking culture and stirring culture under aerobic conditions at 15 to 40° C., and preferably 20 to 35° C.

The culture steps can utilize any processes employed for usual culture of microorganisms, such as batch, flow batch, semi-continuous, continuous, and reactor-type cultures, and may take multi-step processes connecting plural steps of these processes.

For respective growth substrates, specific culture steps will be described as follows:

<Culture: mcl-Alkanoates>

As a method of, for example, two-step culture, there is a method by which the first-step culture is carried out in an inorganic medium or the like containing a first alkanoate having 6 to 12 carbon atoms, such as octanoate and nonanoate, as the growth substrate at an amount of the order of 0.1% by weight to 0.2% by weight and a second alkanoate for introducing the desired monomer unit at an amount of the order of 0.01% by weight to 0.5% by weight until the time of the late logarithmic growth phase to the stationary phase, and at the second step, cells after the first-step culture is completed are collected by centrifugation or the like, followed by further culturing them in an inorganic medium containing the second alkanoate at an amount of the order of 0.01% by weight to 0.5% by weight and no nitrogen sources, and after the culture is completed, the cells are harvested to extract the desired PHA.

Alternatively, there is another method by which culture is carried out by supplying a first alkanoate having 6 to 12 carbon atoms, such as octanoate and nonanoate, at an amount of the order of 0.1% by weight to 0.2% by weight and a second alkanoate for introducing the desired monomer unit at an amount of the order of 0.01% by weight to 0.5% by weight, and cells are harvested at the time of the late logarithmic growth phase to the stationary phase to extract the desired PHA.

In the methods in which mcl-alkanoate as the growth substrate is added to the medium, the obtained PHAs are ones in which is mixed a large amount of the monomer unit derived from the mcl-alkanoate added as the growth substrate. Such PHAs are generally of only the R form, and are isotactic polymers.

<Culture: Saccharides>

As a method, for example, a two-step culture, there is a method by which the first-step culture is carried out in an inorganic medium or the like containing saccharide(s) (for example, glucose, mannose, fructose, etc.) as the growth substrate at an amount of the order of 0.1% by weight to 2.0% by weight and alkanoate for introducing the desired monomer unit at an amount of the order of 0.01% by weight to 0.5% by weight until the time of the late logarithmic growth phase to the stationary phase, and at the second step, cells after the first-step culture is completed are collected by centrifugation or the like, followed by further culturing them in an inorganic medium containing saccharide(s) (for example, glucose, mannose, fructose, etc.) as the growth substrate at an amount of the order of 0.1% by weight to 2.0% by weight, the alkanoate at an amount of the order of 0.01% by weight to 0.5% by weight, and no nitrogen sources, and after the culture is completed, the cells are harvested to extract the desired PHA.

Alternatively, there is another method by which culture is carried out by supplying saccharide(s) (for example, glucose, mannose, fructose, etc.) as the growth substrate at amounts of the order of 0.1% by weight to 2.0% by weight and alkanoate for introducing the desired monomer unit at an amount of the order of 0.01% by weight to 0.5% by weight, and cells are harvested at the time of the late logarithmic growth phase to the stationary phase to extract the desired PHA.

In these cases, the concentration of the saccharides (for example, glucose, mannose, fructose, etc.) to be added to the medium is selected as appropriate, depending on the type of alkanoate for introducing the desired monomer unit, the genus and species of the microorganism, the cell density, or the culture process, although addition can be selected such that the content in the medium is usually in the order of 0.1% by weight to 2.0% by weight. On the other hand, the concentration of the alkanoate to be raw material is also selected as appropriate, depending on the genus and species of the microorganism, the cell density, or the culture process, although addition can be selected such that the content in the medium is usually in the order of 0.01% by weight to 0.5% by weight. Thus, by culturing the microorganism in a medium containing saccharide(s) (for example, glucose, mannose, fructose, etc.) and the alkanoate, the desired PHAs can be produced and accumulated in which the monomer unit other than the intended one is incorporated at a small amount or not at all. These PHAs are generally of only the R form, and are isotactic polymers.

<Culture: Polypeptone>

As a method of, for example, a two-step culture, there is a method by which the first-step culture is carried out in an inorganic medium or the like containing polypeptone as the growth substrate at an amount of the order of 0.1% by weight to 2.0% by weight and alkanoate for introducing the desired monomer unit at an amount of the order of 0.01% by weight to 0.5% by weight until the time of the late logarithmic growth phase to the stationary phase, and at the second step, cells after the first-step culture is completed are collected by centrifugation or the like, followed by further culturing them in an inorganic medium containing the alkanoate at an amount of the order of 0.01% by weight to 0.5% by weight, and no nitrogen sources, and after the culture is completed, the cells are harvested to extract the desired PHA.

Alternatively, there is another method by which culture is carried out by supplying polypeptone at an amount of the order of 0.1% by weight to 2.0% by weight and alkanoate for introducing the desired monomer unit at an amount of the order of 0.01% by weight to 0.5% by weight, and cells are harvested at the time of the late logarithmic growth phase to the stationary phase to extract the desired PHA.

In these cases, the concentration of polypeptone to be added to the medium is selected as appropriate, depending on the type of alkanoate for introducing the desired monomer unit, the genus and species of the microorganism, the cell density, or the culture process, although addition can be selected such that the content in the medium is usually in the order of 0.1% by weight to 2.0% by weight. For polypeptone, it is also possible to use, as appropriate, any commercial available polypeptone that is commonly employed for culturing microorganisms and the like. On the other hand, the concentration of the alkanoate to be raw material is also selected as appropriate, depending on the genus and species of the microorganism, the cell density, or the culture process, although addition may be selected such that the content in the medium is usually in the order of 0.01% by weight to 0.5% by weight. Thus, by culturing the microorganism in a medium containing polypeptone and the alkanoate, the desired PHAs can be produced and accumulated in which the monomer unit other than the intended one is incorporated at a small amount or not at all. These PHAs are generally of only the R form, and are isotactic polymers.

<Culture: Organic Acids of TCA Cycle>

As a method of, for example, a two-step culture, there is a method by which the first-step culture is carried out in an inorganic medium or the like containing organic acid(s) involved in the TCA cycle (for example, lactic, pyruvic, citric, succinic, fumaric, malic acids and the like, and salts thereof) as the growth substrate at an amount of the order of 0.1% by weight to 2.0% by weight and alkanoate for introducing the desired monomer unit at an amount of the order of 0.01% by weight to 0.5% by weight until the time of the late logarithmic growth phase to the stationary phase, and at the second step, cells after the first-step culture is completed are collected by centrifugation or the like, followed by further culturing them in an inorganic medium containing organic acid(s) of the TCA cycle (for example, lactic, pyruvic, citric, succinic, fumaric, malic acids and the like, and salts thereof) as the growth substrate at an amount of the order of 0.1% by weight to 2.0% by weight, the alkanoate at an amount of the order of 0.01% by weight to 0.5% by weight, and no nitrogen sources, and after the culture is completed, the cells are harvested to extract the desired PHA.

Alternatively, there is another method by which culture is carried out by supplying organic acid(s) of the TCA cycle (for example, lactic, pyruvic, citric, succinic, fumaric, malic acids and the like, and salts thereof) at an amount of the order of 0.1% by weight to 2.0% by weight and alkanoate for introducing the desired monomer unit at an amount of the order of 0.01% by weight to 0.5% by weight, and cells are harvested at the time of the late logarithmic growth phase to the stationary phase to extract the desired PHA.

In these cases, the concentration of organic acids of the TCA cycle (for example, lactic, pyruvic, citric, succinic, fumaric, malic acids and the like, and salts thereof) to be added to the medium is selected as appropriate, depending on the type of alkanoate for introducing the desired monomer unit, the genus and species of the microorganism, the cell density, or the culture process, although addition can be selected such that the content in the medium is usually in the order of 0.1% by weight to 2.0% by weight. On the other hand, the concentration of the alkanoate to be raw material is also selected as appropriate, depending on the genus and species of the microorganism, the cell density, or the culture process, although addition can be selected such that the content in the medium is usually in the order of 0.01% by weight to 0.5% by weight. Thus, by culturing the microorganism in a medium containing organic acid(s) of the TCA cycle (for example, lactic, pyruvic, citric, succinic, fumaric, malic acids and the like, and salts thereof) and the alkanoate, the desired PHAs can be produced and accumulated in which the monomer unit other than the intended one is incorporated at a small amount or not at all. These PHAs are generally of only the R form, and are isotactic polymers.

<Culture: Polypeptone+Pyruvic Acid and Salts Thereof>

As a method of, for example, a two-step culture, there is a method by which the first-step culture is carried out in an inorganic medium or the like containing polypeptone as the growth substrate at an amount of the order of 0.1% by weight to 2.0% by weight and alkanoate for introducing the desired monomer unit at an amount of the order of 0.01% by weight to 0.5% by weight until the time of the late logarithmic growth phase to the stationary phase, and at the second step, cells after the first-step culture is completed are collected by centrifugation or the like, followed by further culturing them in an inorganic medium containing pyruvic acid or salt thereof as the growth substrate at an amount of the order of 0.1% by weight to 2.0% by weight, the alkanoate at an amount of the order of 0.01% by weight to 0.5% by weight, and no nitrogen sources, and after the culture is completed, the cells are harvested to extract the desired PHA.

In these cases, the concentration of polypeptone and pyruvic acid or salt thereof to be added to the medium is selected as appropriate, depending on the type of alkanoate for introducing the desired monomer unit, the genus and species of the microorganism, the cell density, or the culture process, although addition can be selected such that the content in the medium is usually in the order of 0.1% by weight to 2.0% by weight in each case. On the other hand, the concentration of the alkanoate to be raw material is also selected as appropriate, depending on the genus and species of the microorganism, the cell density, or the culture process, although addition can be selected such that the content in the medium is usually in the order of 0.01% by weight to 0.5% by weight. Thus, by culturing the microorganism in two steps utilizing a medium containing polypeptone and the alkanoate and a medium containing pyruvic acid or salt thereof and the alkanoate, the desired PHAs can be produced and accumulated in which the monomer unit other than the intended one is incorporated at a small amount or not at all. These PHAs are generally of only the R form, and are isotactic polymers.

<PHA Recovery>

For PHA recovery from cells in the method according to the present invention, usually-operating extraction with organic solvents such as chloroform is most convenient, but in the circumstances where it is difficult to use organic solvents, it is also possible to utilize methods of collecting PHA by removing cellular components other than PHA by means of treatment with detergents such as SDS and the like, treatment with enzymes such as lysozyme and the like, treatment with chemicals such as EDTA, sodium hypochlorite, ammonia, and the like.

<Molecular Weight>

The PHAs according to the present invention can be obtained by utilizing the above-mentioned methods. It is desirable that the PHAs have a number average molecular weight of more than at least 10,000 or so, in order to allow stable physical properties as polymer, for example, such as glass transition temperature, softening point, melting point, crystallinity, orientation defined by the monomer unit of which the polymer is composed, to be fixed. The PHAs according to the present invention have a number average molecular weight of about 20,000 or higher, and therefore can be sufficiently expected to display stable physical properties as polymer. From the viewpoint of convenience of treatments such as dissolving processes, the PHAs preferably have a number average molecular weight of up to 200,000 or so, and more preferably not more than 100,000. As mentioned above, these PHAs are generally composed of only the R form, and are isotactic polymers.

Culturing of the microorganisms, production and accumulation of PHAs within cells by the microorganisms, and recovery of PHAs from the cells are not limited to the methods described above. For example, in addition to four strains described above, microorganisms to be employed in the method of producing PHAs according to the present invention can utilize microorganisms having similar production capabilities of producing PHAs according to the present invention as those of these four strains.

It is likely that these PHAs are useful, for example, for device and medical materials and others, as well as applications in which common plastics are used. Those having fluorine atom(s), trifluoromethyl group, and the like introduced as a substituent group, in particular, are expected to have a superior biocompatibility, and therefore applications to medical uses. Furthermore, they are predicted to have a water-repellent effect due to containing fluorine atom(s), trifluoromethyl group, and the like, and thus applications to water-repellent treatments in various fields are also possible. Specifically, applications to temporary water-repellent treatments also can be contemplated utilizing biodegradability resulting from aliphatic polyesters.

EXAMPLES

Example 1

The substrate FPVA was first synthesized by the Grignard reaction according to the method described in "Macromolecules, 29, 1762–1766 (1996) and 27, 45–49 (1994)". 5-bromovaleric acid was dissolved in anhydrous tetrahydrofuran (THF), and 3 mol/L of a methyl magnesium chloride THF solution was added dropwise at −20° C. in an argon atmosphere. After stirring for about 15 min, a THF solution of 1-bromo-4-fluorobenzene and magnesium was further dropped and a THF solution of 0.1 mol/L $Li_2CuCl_4$ was added (temperature was maintained at −20° C.). The reaction solution was resumed to room temperature and further stirred overnight. Then the solution was poured into a 20% sulfuric acid solution cooled on ice, and stirred. The aqueous layer was recovered, saturated with salt, and extracted with ether. After the extract was further extracted with 100 mL of deionized water, to which 50 g of potassium hydroxide was added, the extract was acidified with a 20% sulfuric acid solution and the precipitate was recovered.

The precipitate was analyzed with nuclear magnetic resonance equipment (FT-NMR: Bruker DPX400) under the following conditions: nuclide: $^1H$ and $^{13}C$; solvent: heavy chloroform (containing TMS). The results are shown in FIG. 1 and Table 3.

Example 2

Cells of strain H45 was inoculated in 200 mL of M9 medium containing nonanoic acid 0.1% and FPVA 0.1%, and shake-cultured at 30° C. at 125 strokes/min. After 24 hours, the cells were collected by centrifugation, resuspended in 200 mL of M9 medium containing FPVA 0.2% but not a nitrogen source ($NH_4Cl$), and further shake-cultured at 30° C. at 125 strokes/min. After 24 hours, the cells were collected by centrifugation, washed once with cold methanol and lyophilized.

The lyophilized pellet was suspended in 100 mL of chloroform and stirred at 60° C. for 20 hours to extract PHA. After the extract was filtered with a membrane filter of 0.45 μm pore size, the filtrate was concentrated with a rotary evaporator and the concentrate was reprecipitated in cold methanol. Only the precipitate was then recovered and vacuum-dried to obtain PHA. After the PHA obtained was subjected to methanolysis according to the conventional method, it was analyzed with a gas chromatograph-mass spectrometer (GC-MS, Shimadzu QP-5050, EI method) and the methyl esters of the PHA monomer unit were identified. The results are shown in Table 4.

Example 3

Cells of strain YN2 was inoculated in 200 mL of M9 medium containing nonanoic acid 0.1% and FPVA 0.1%, and shake-cultured at 30° C. at 125 strokes/min. After 24 hours, the cells were collected by centrifugation, resuspended in 200 mL of M9 medium containing FVPA 0.2% but not a nitrogen source ($NH_4Cl$), and further shaken-cultured at 30° C. at 125 strokes/min. After 24 hours, the cells were collected by centrifugation, washed once with cold methanol and lyophilized.

The lyophilized pellet was suspended in 100 mL of chloroform, stirred at 60° C. for 20 hours to extract PHA. After the extract was filtered with a membrane filter of 0.45 μm in diameter, the filtrate was concentrated with a rotary evaporator and the concentrate was reprecipitated in cold methanol. The precipitate was then recovered and vacuum-dried to obtain PHA. After the PHA obtained was subjected to methanolysis according to the conventional method, it was analyzed with a gas chromatograph-mass spectrometer (GC-MS, Shimadzu QP-5050, EI method) and the methyl esters of the PHA monomer unit were identified. The results are shown in Table 5.

Example 4

Cells of strain P91 were inoculated in 200 mL of M9 medium containing nonanoic acid 0.1% and shaken-cultured at 30° C. at 125 strokes/min. After 24 hours, the cells were collected by centrifugation, resuspended in 200 mL of M9 medium containing nonanoic acid 0.1% and FPVA 0.1% but not a nitrogen source ($NH_4Cl$), and further shaken-cultured at 30° C. at 125 strokes/min. After 24 hours, the cells were collected by centrifugation, washed once with cold methanol and lyophilized.

The lyophilized pellet was suspended in 100 mL of chloroform and stirred at 60° C. for 20 hours to extract PHA. After the extract was filtered with a membrane filter of 0.45 μm in diameter, the filtrate was concentrated with a rotary evaporator and the concentrate was reprecipitated in cold methanol. Only the precipitate was then recovered and vacuum-dried to obtain PHA. After the PHA obtained was subjected to methanolysis according to the conventional method, it was analyzed with a gas chromatograph-mass spectrometer (GC-MS, Shimadzu QP-5050, EI method) and the methyl esters of the PHA monomer unit were identified. The results are shown in Table 6.

Example 5

Cells of strain P161 were inoculated in 200 mL of M9 medium containing nonanoic acid 0.1% and shaken-cultured at 30° C. at 125 strokes/min. After 24 hours, the cells were collected by centrifugation, resuspended in 200 mL of M9 medium containing nonanoic acid 0.1% and FPVA 0.1% but not a nitrogen source ($NH_4Cl$), and further shaken-cultured at 30° C. at 125 strokes/min. After 24 hours, the cells were collected by centrifugation, washed once with cold methanol and lyophilized.

The lyophilized pellet was suspended in 100 mL of chloroform and stirred at 60° C. for 20 hours to extract PHA. After the extract was filtered with a membrane filter of 0.45 μm in diameter, the filtrate was concentrated with a rotary evaporator and the concentrate was reprecipitated in cold methanol. Only the precipitate was then recovered and vacuum-dried to obtain PHA. After the PHA obtained was subjected to methanolysis according to the conventional method, it was analyzed with a gas chromatograph-mass spectrometer (GC-MS, Shimadzu QP-5050, EI method) and the methyl esters of the-PHA monomer unit were identified. The results are shown in Table 7.

Example 6

After 100 mg of PHA derived from strain H45 was dissolved in 1 mL of chloroform, n-hexane was added until it was clouded. This was centrifuged to recover and vacuum-dried the precipitate. This was again dissolved in 1 mL of chloroform, n-hexane was added, and the procedure of recovering the precipitate was repeated three times.

After the precipitate obtained was subjected to methanolysis according to the conventional method, it was analyzed with a gas chromatograph-mass spectrometer (GC-MS, Shimadzu QP-5050, EI method) and the methyl esters of the PHA monomer unit were identified. As a result, the precipitate was found to be PHA whose monomer unit consisted of 3HFPV monomer alone as shown in Table 8.

Figure 2:
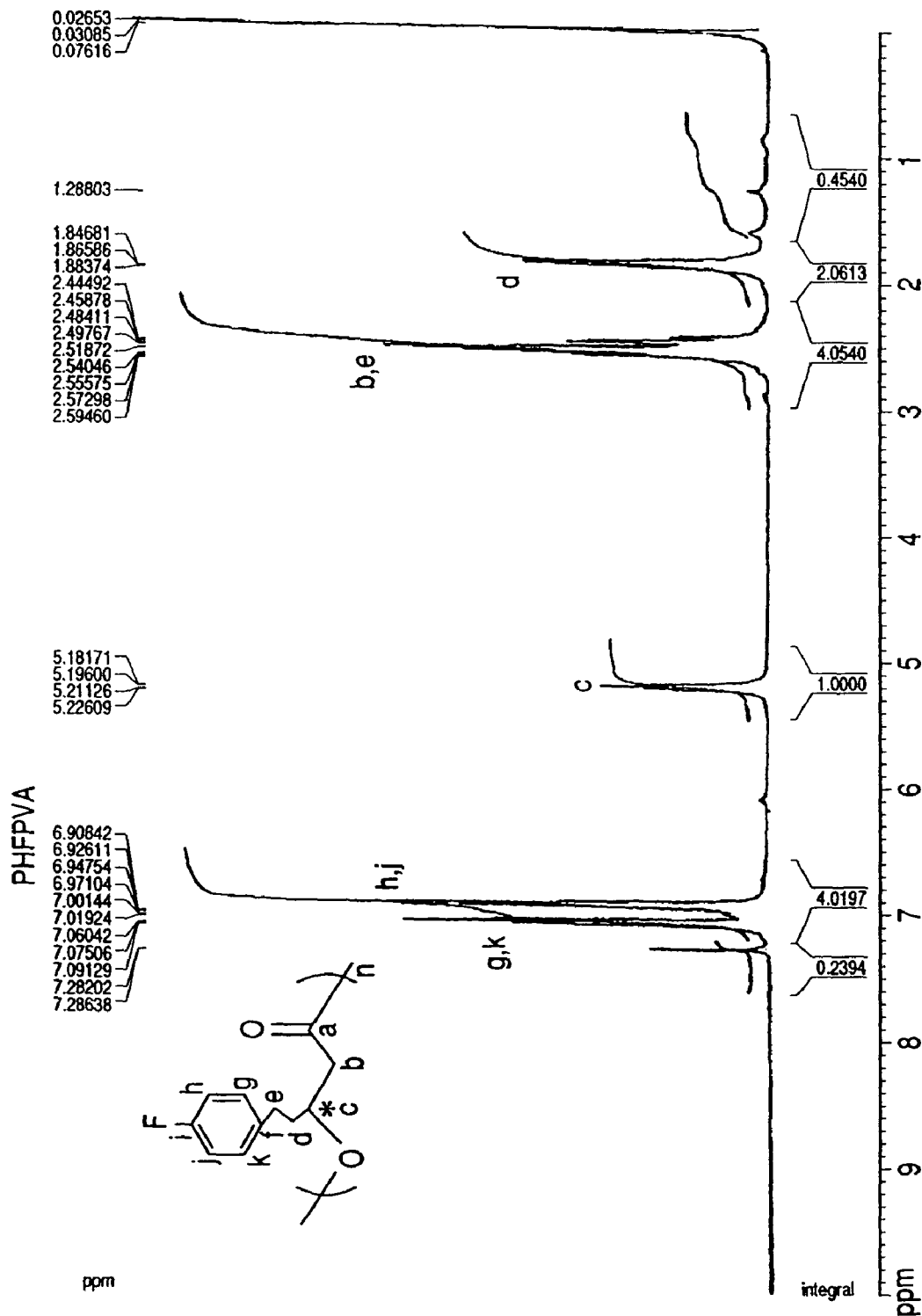
FIG. 2 is a chart which shows the measurement of $^1$H nuclear magnetic resonance spectrum of PHA obtained in Example 6.
Figure 3:
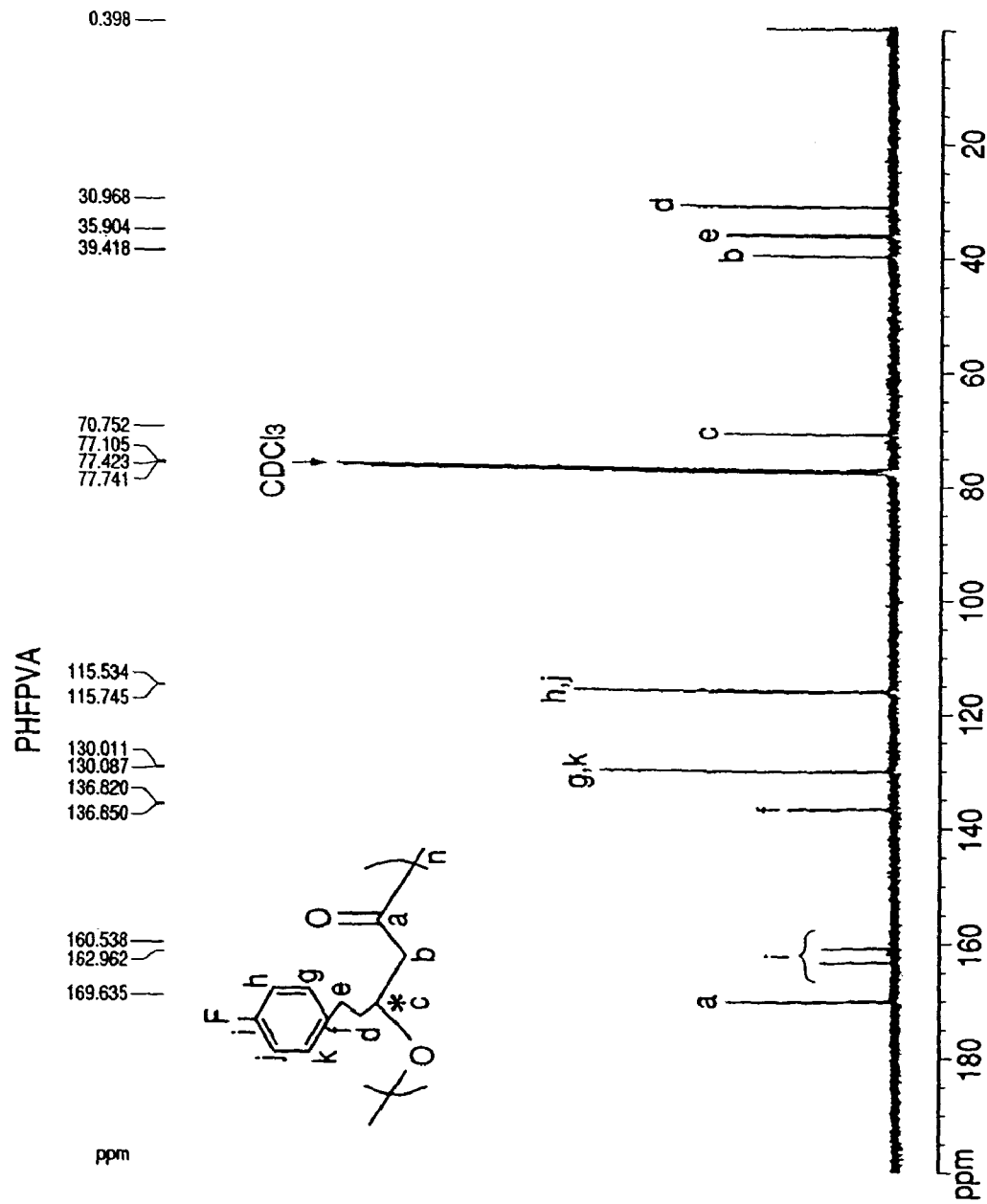
FIG. 3 is a chart which shows the measurement of $^{13}$C nuclear magnetic resonance spectrum of PHA obtained in Example 6.

In addition, nuclear magnetic resonance equipment (FT-NMR: Bruker DPX400) was used for analysis under the following condition: nuclide: $^1H$ and $^{13}C$; solvent: heavy chloroform (containing TMS). The results are shown in FIG. 2, Table 9, FIG. 3 and Table 10.

Example 7

Synthesis of FPxVA

After 240 mL of dehydrated acetone was put into a three-necked round-bottom flask, sodium iodide (0.06 mol), potassium carbonate (0.11 mol) and 4-fluorophenol (0.07 mol) were added and thoroughly stirred. 5-bromoethylvalerate (0.06 mol) was dropped into the solution in a nitrogen atmosphere, refluxed at 60±5° C. and allowed to react for 24 hours. After reaction, the reaction solution was concentrated to dryness with an evaporator and redissolved in methylene chloride. Water was added and the solution was separated. The organic layer was dehydrated with anhydrous magnesium sulfate and concentrated to dryness with an evaporator.

Hot methanol was added to the reactant, dissolved, slowly cooled and reprecipitated to obtain 5-(4-fluorophenoxy) ethylvalerate. At this time, the yield from 5-bromoethylvalerate was 68 mol %.

The reactant (ester) obtained was dissolved in ethanol-water (9.1 (v/v)) so as to be 5 weight %. Ten-fold molar quantity of potassium hydroxide was added and allowed to react at 0 to 4° C. for 4 hours to hydrolyze the ester.

The reaction solution was poured into 10 volumes of a 0.1 mol/L hydrochloric acid solution and the precipitate was recovered by filtration. The precipitate (reactant) recovered was vacuum-dried at room temperature for 36 hours. The dried substance obtained was dissolved in a small quantity of hot ethanol, and the solution was gradually cooled, reprecipitated, vacuum-dried at room temperature for 24 hours to obtain the target compound 5-(4-fluorophenoxy) valeric acid. The yield of this compound from 5-bromoethyl valerate was 49 mol %.

The compound obtained was analyzed by NMR under the following conditions:

<Equipment>
FT-NMR: Bruker DPX400
$^1$H resonance frequency: 400 MHZ

Figure 4:
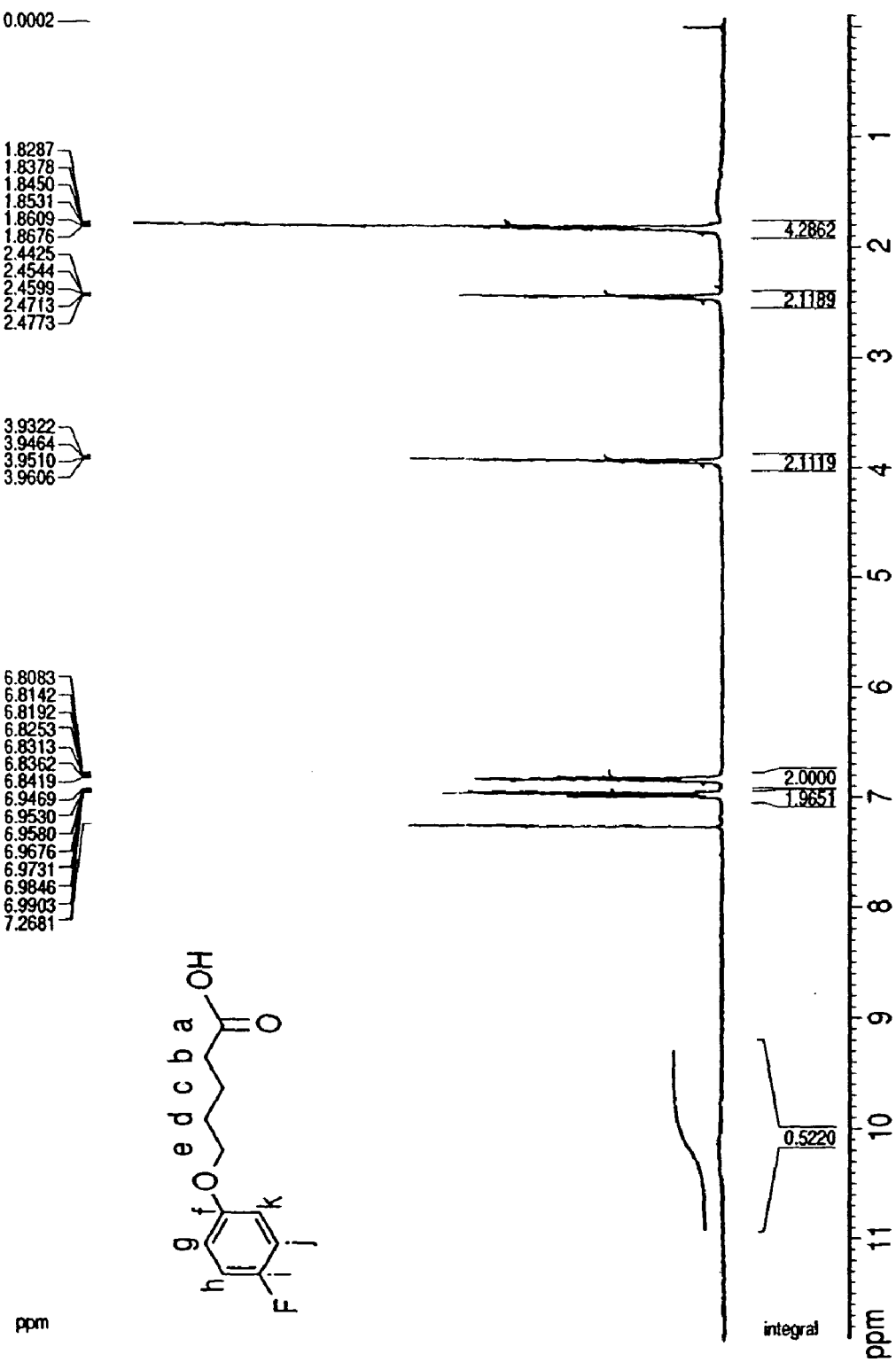
FIG. 4 is a chart which shows the measurement of nuclear magnetic resonance spectrum of 5-(4-fluorophenoxy)valeric acid obtained in Example 7.
Figure 5:
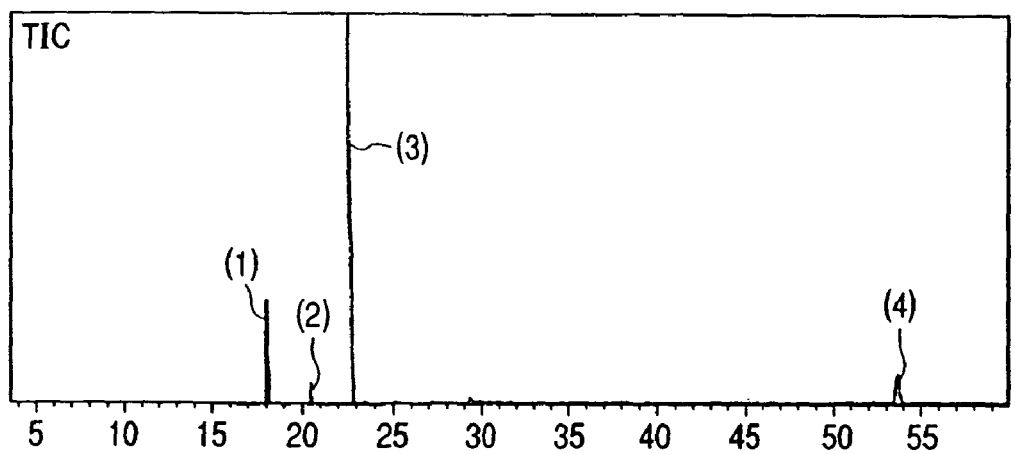
FIG. 5 is a chart which shows the Total Ion Chromatography (TIC) of GC-MS for a methyl esterification compound of a monomer unit constituting PHA obtained in Example 8.
Figure 6A:
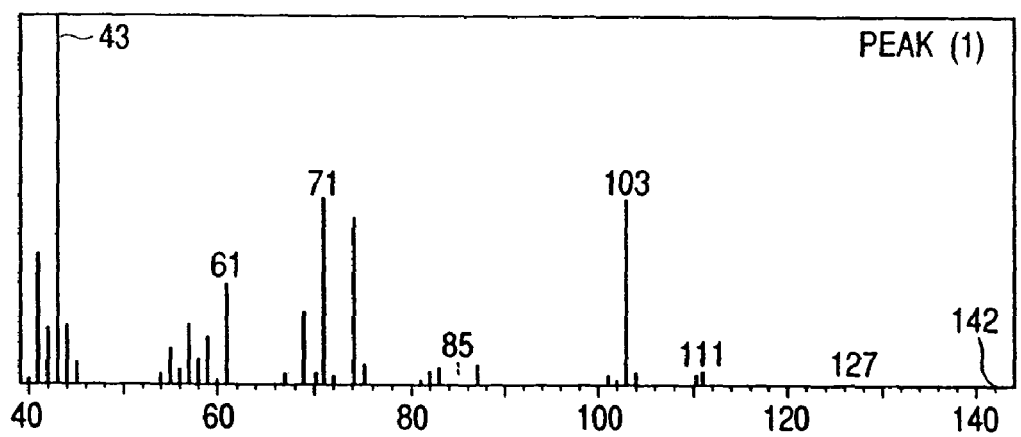
FIGS. 6A and 6B are charts which show the mass spectra of the peaks on TIC for a methyl esterification compound of a monomer unit constituting PHA obtained in Example 8.
Figure 6B:
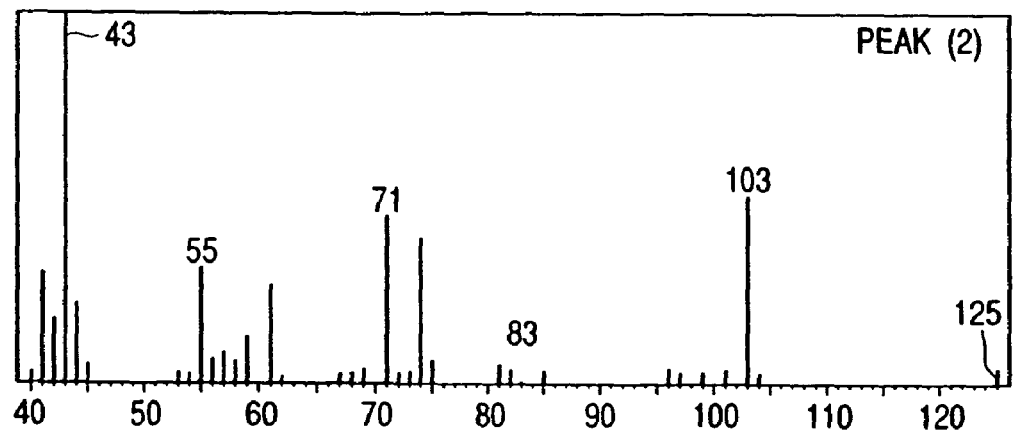
Figure 7A:
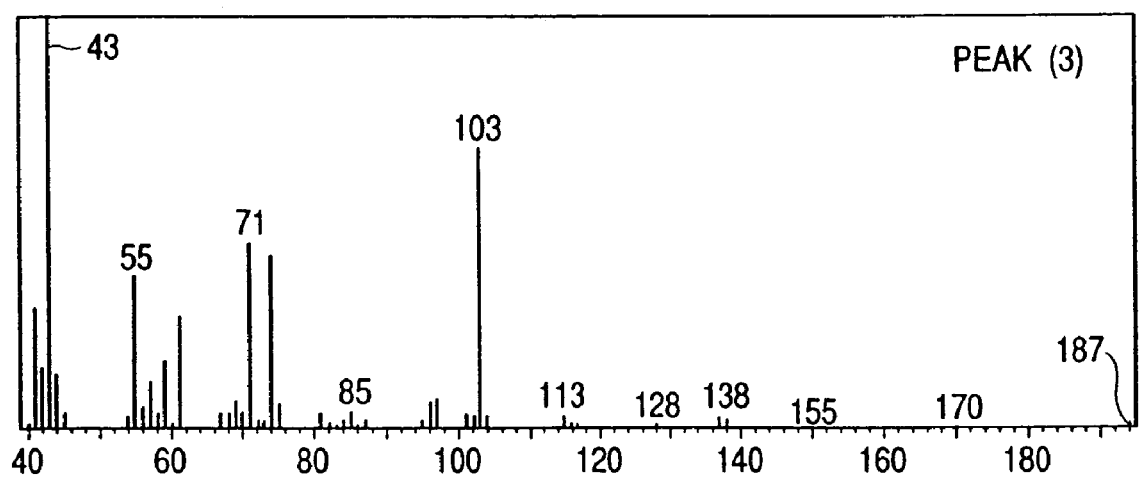
FIGS. 7A and 7B are charts which show the mass spectra of the peaks on TIC for a methyl esterification compound of a monomer unit constituting PHA obtained in Example 8.
Figure 7B:
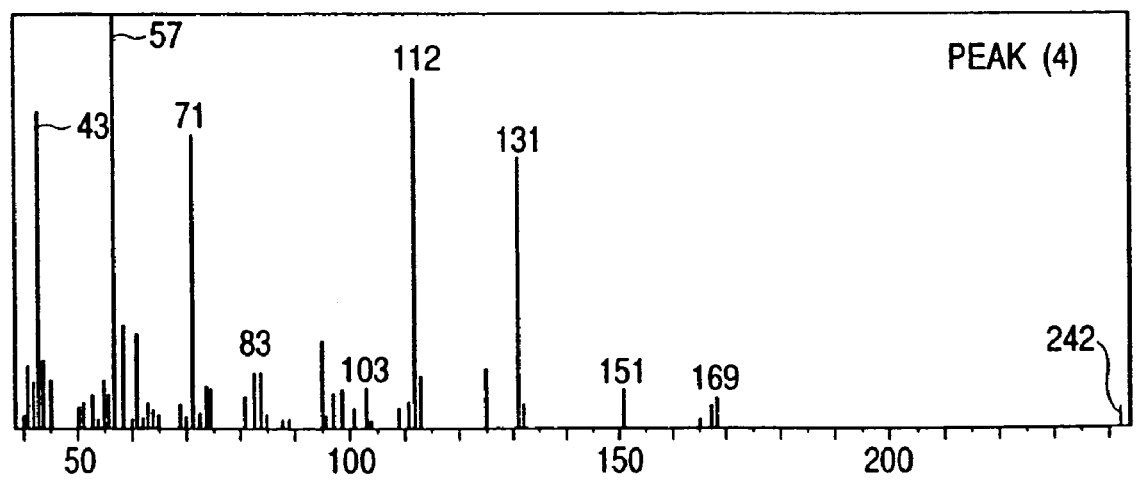

<Measurement Conditions>
nuclide: $^1$H
solvent: $CDCl_3$
reference: capillary-contained $TMS/CDCl_3$
temperature: room temperature The spectral chart is shown in FIG. 4 and the results of identification are shown in Table 11.

The above results confirmed that the desired FPxVA was certainly synthesized.

Example 8

Production of PHA by Strain P91

Cells of strain P91 were inoculated in 200 mL of M9 medium containing nonanoic acid 0.1 weight % and FPxVA 0.1 weight %, and shaken-cultured at 30° C. at 125 strokes/min. After 24 hours, the cells were collected by centrifugation, resuspended in 200 mL of M9 medium containing nonanoic acid 0.1 weight % and FPxVA 0.1 weight % but not a nitrogen source ($NH_4Cl$), and further shaken-cultured at 30° C. at 125 strokes/min. After 24 hours, the cells were collected by centrifugation, washed once with cold methanol and lyophilized.

After the lyophilized pellet was weighed, it was suspended in 100 mL of chloroform and stirred at 60° C. for 20 hours to extract PHA. After the extract was filtered with a membrane filter of 0.45 μm in pore size, the filtrate was concentrated with a rotary evaporator and the concentrate was reprecipitated in cold methanol. Only the precipitate was then recovered and vacuum-dried to obtain and weigh PHA. The yields are shown in Table 12.

The PHA obtained was measured for the molecular weight by gel permeation chromatography (GPC; Toso HCL-8020, column: Polymer Laboratory PLgel MIXED-C (5 μm), solvent: chloroform, converted on a polystyrene basis). The molecular weight is shown in Table 13.

In addition, after the PHA obtained was subjected to methanolysis according to the conventional method, it was analyzed by GC-MS and the methyl esters of the PHA monomer unit were identified. The TIC and the mass spectrum of each peak are shown in FIG. 5 to FIGS. 7A and 7B. Peak (1) was shown to represent 3-hydroxymethylheptanoate, Peak (2) 3-hydroxymethyloctanoate, Peak (3) 3-hydroxymethylnonanoate, and Peak (4) 3 hydroxy-4-(4-fluorophenoxy) methylvalerate.

The above results indicated that the polymer obtained was PHA containing the units of 3-hydroxyheptanoic acid, 3-hydroxyoctanoic acid, 3-hydroxynonanoic acid and 3-hydroxy-4-(4-fluorophenoxy)valeric acid.

Example 9

Production of PHA by Strain YN2 (1)

Figure 8:
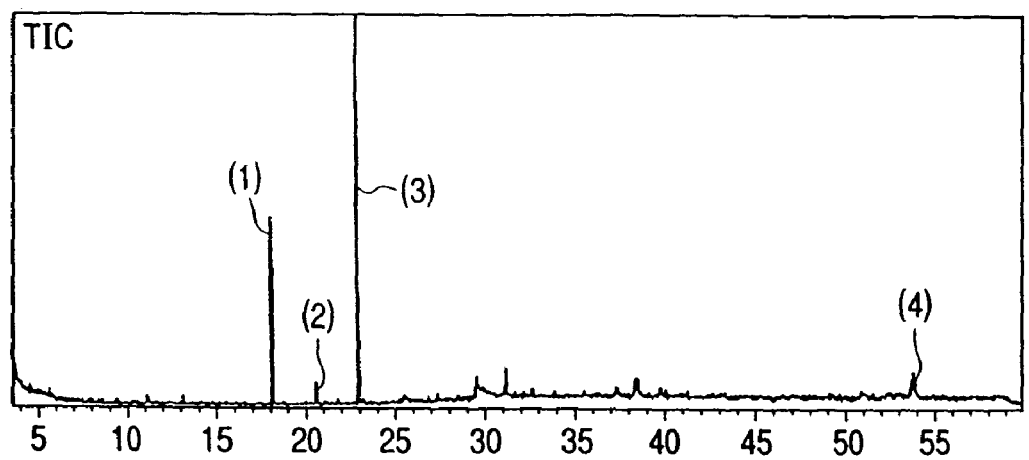
FIG. 8 is a chart which shows TIC for a methyl esterification compound of a monomer unit constituting PHA obtained in Example 9.

Except that strain P91 was replaced by strain YN2, the same procedures as described in Example 8 were used to produce PHA, and each analysis was performed. The yields are shown in Table 12, the molecular weight in Table 13, and the TIC of GC-MS in FIG. 8. Peak (1) was shown to represent 3-hydroxymethylheptanoate, Peak (2) 3-hydroxymethyloctanoate, Peak (3) 3-hydroxymethylnonanoate, and Peak (4) 3-hydroxy-4-(4-fluorophenoxy) methylvalerate.

The above results indicated that the polymer obtained was PHA containing the units of 3-hydroxyheptanoic acid, 3-hydroxyoctanoic acid, 3-hydroxynonanoic acid and 3-hydroxy-4-(4-fluorophenoxy)valeric acid.

Example 10

Production of PHA by Strain P161

Figure 9:
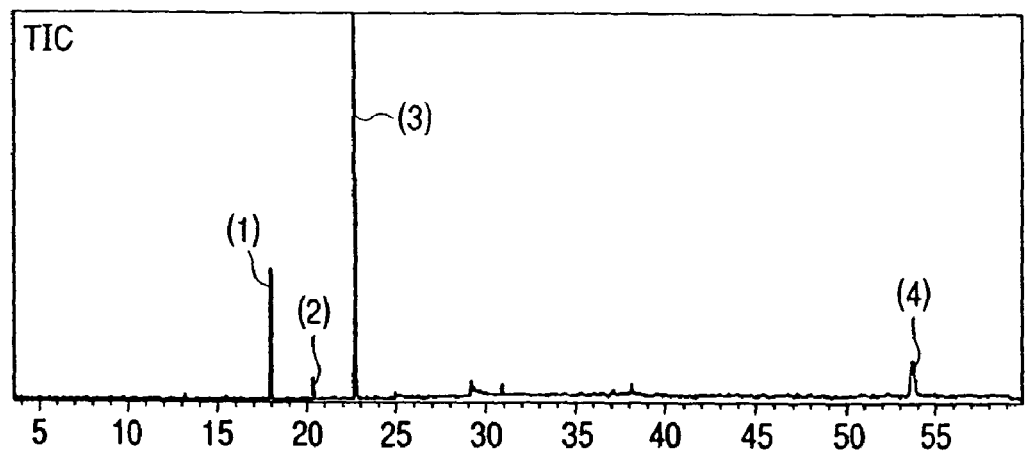
FIG. 9 is a chart which shows TIC for a methyl esterification compound of a monomer unit constituting PHA obtained in Example 10.

Except that strain P91 was replaced by strain P161, the same procedures as described in Example 8 were used to produce PHA, and each analysis was performed. The yields are shown in Table 12, the molecular weight in Table 13, and the TIC of GC-MS in FIG. 9. Peak (1) was shown to represent 3-hydroxymethylheptanoate, Peak (2) 3-hydroxymethyloctanoate, Peak (3) 3-hydroxymethylnonanoate, and Peak (4) 3 hydroxy-4-(4-fluorophenoxy) methylvalerate.

The above results indicated that the polymer obtained was PHA containing the units of 3-hydroxyheptanoic acid, 3-hydroxyoctanoic acid, 3-hydroxynonanoic acid and 3-hydroxy-4-(4-fluorophenoxy)valeric acid.

Example 11

Production of PHA by Strain H45

Figure 10:
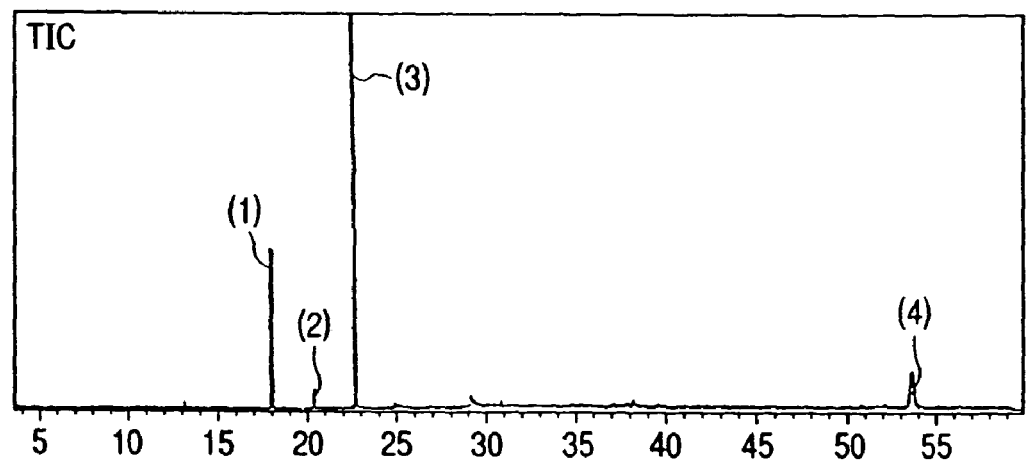
FIG. 10 is a chart which shows TIC for a methyl esterification compound of a monomer unit constituting PHA obtained in Example 11.

Except that strain P91 was replaced by H45 strain, the same procedures as described in Example 8 were used to produce PHA, and each analysis was performed. The yields are shown in Table 12, the molecular weight in Table 13, and the TIC of GC-MS in FIG. 10. Peak (1) was shown to represent 3-hydroxymethylheptanoate, Peak (2) 3-hydroxymethyloctanoate, Peak (3) 3-hydroxymethylnonanoate, and Peak (4) 3-hydroxy-4-(4-fluorophenoxy) methylvalerate.

The above results indicated that the polymer obtained was PHA containing the units of 3-hydroxyheptanoic acid, 3-hydroxyoctanoic acid, 3-hydroxynonanoic acid and 3-hydroxy-4-(4-fluorophenoxy)valeric acid.

Example 12

Production of PHA by Strain YN2 (2)

Cells of strain YN2 were inoculated in 200 mL of M9 medium containing hexanoic acid 0.1 weight % and FPxVA 0.1 weight %, and shaken-cultured at 30° C. at 125 strokes/min. After 72 hours, the cells were collected by centrifugation and resuspended in 200 mL of M9 medium containing hexanoic acid 0.1 weight % and FPxVA 0.1 weight % but not a nitrogen source (NH$_4$Cl), and further shaken-cultured at 30° C. at 125 strokes/min. After 30 hours, the cells were collected by centrifugation, washed once with cold methanol and lyophilized.

PHA was extracted with the same procedures as described in Example 8, and each analysis was performed The yields are shown in Table 12 and the molecular weight is shown in Table 13. The results of GC-MS analysis revealed that the PHA obtained by this method had the following composition:
3-hydroxybutyric acid: 8.1%
3-hydroxyhexanoic acid: 51.2%
3-hydroxyoctanoic acid: 1.3%
3-hydroxydecanoic acid: 7.0%
3-hydoxydodecanoic acid: 10.6%
unidentified substances: 9.9%
3 hydroxy-4-(4-fluorophenoxy)valeric acid: 11.9%

The above results indicated that the polymer obtained was PHA containing the units of 3-hydroxy-4-(4-fluorophenoxy) valeric acid.

Example 13

Synthesis of TFMPVA

The substrate TFMPVA was first synthesized by the Grignard reaction according to the method described in "Macromolecules, 29, 1762–1766 (1996) and 27, 45–49 (1994)." 5-bromovaleric acid was dissolved in anhydrous tetrahydrofuran (THF) and 3 mol/L of a methyl magnesium chloride THF solution was added dropwise at −20° C. in an argon atmosphere. After stirring for about 15 min, a THF solution of 1-bromo-4-trifluorobenzene and magnesium was further dropped and a THF solution of 0.1 mol/L Li$_2$CuCl$_2$ was added (temperature was maintained at −20° C.). The reaction solution was restored to room temperature and further stirred overnight. Then the solution was poured into a 20% sulfuric acid solution cooled on ice, and stirred. The aqueous layer was recovered, saturated with salt, and extracted with ether. After the extract was further extracted with 100 mL of deionized water, to which 50 g of potassium hydroxide was added, the extract was acidified with a 20% sulfuric acid solution and the precipitate was recovered.

Figure 11A:
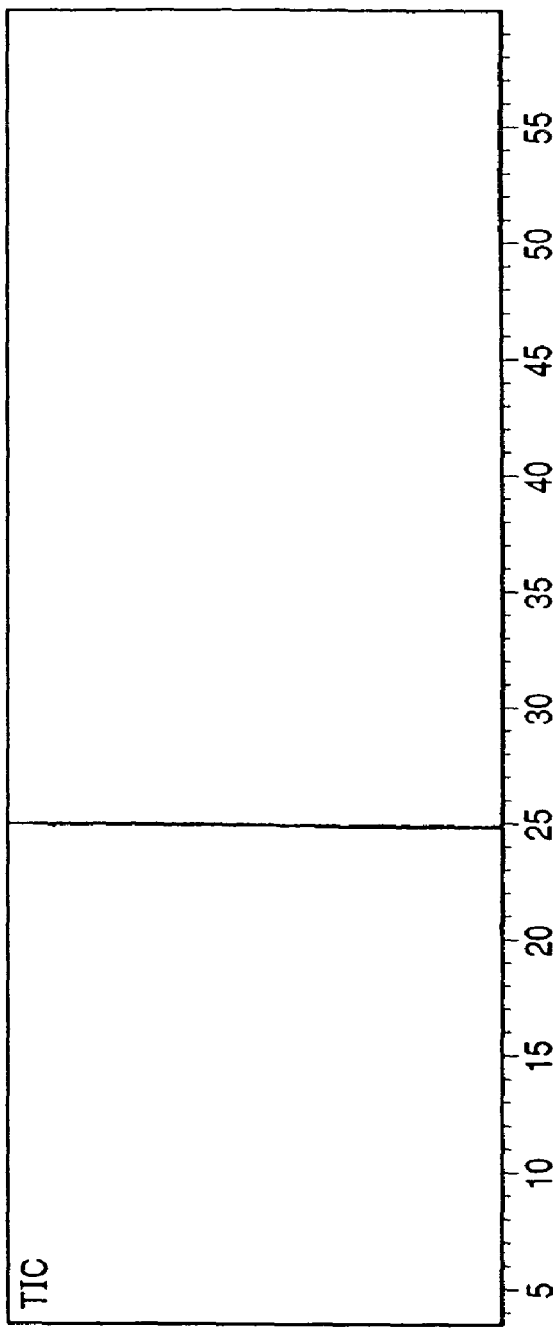
FIGS. 11A and 11B are charts which show the Total Ion Chromatography (TIC) of 5-(4-trifluoromethylphenyl)valeric acid (FIG. 11A) and its mass spectrum (FIG. 11B)
Figure 11B:
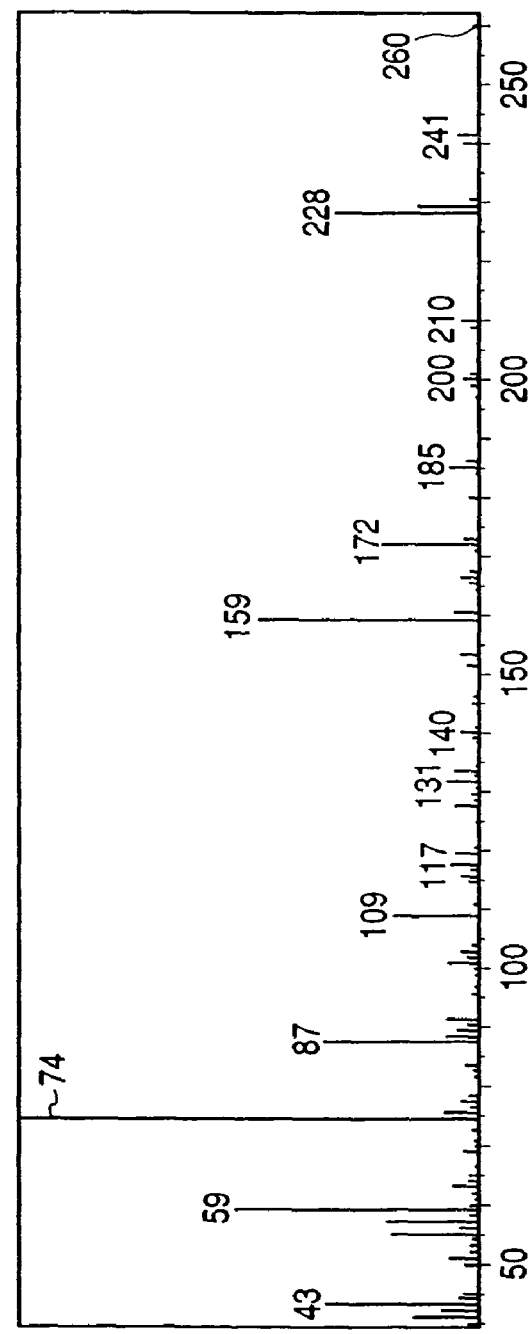

The compound recovered was methylesterified by the conventional method and analyzed with a gas chromatograph-mass spectrometer (GC-MS, Shimadzu GC-MS QP-5050, column: DB-WAXETR (30 m×0.32 mm×0.5 μm) (manufactured by J&W Inc.) The TIC (total ion chromatogram) and mass spectrum are shown in FIGS. 11A and 11B. These results revealed that the target TFMPVA was synthesized.

Example 14

Production of Polymer by Strain H45

Cells of strain H45 were inoculated in 200 mL of M9 medium containing nonanoic acid 0.1% and TFMPVA 0.1%, and shaken-cultured at 30° C. at 125 strokes/min. After 24 hours, the cells were collected by centrifugation, resuspended in 200 mL of M9 medium containing TFMPVA 0.2% but not a nitrogen source (NH$_4$Cl), and further shaken-cultured at 30° C. at 125 strokes/min. After 24 hours, the cells were collected by centrifugation, washed once with cold methanol, lyophilized and weighed.

The lyophilized pellet was suspended in 100 mL of chloroform and stirred at 60° C. for 20 hours to extract PHA. After the extract was filtered with a membrane filter of 0.45 μm in pore size, the filtrate was concentrated with a rotary evaporator and the concentrate was reprecipitated in cold methanol. Only the precipitate was then recovered and vacuum-dried to obtain and weigh PHA. The yields are shown in Table 14.

Evaluation of the molecular weight of the PHA by gel permeation chromatography (GPC: Toso HLC-8020, column: Polymer Laboratory PLgel MIXED-C (5 μm), solvent: chloroform, converted on a polystyrene basis) revealed Mn=64,000 and Mw=110,000.

Figures 12A, 12B:
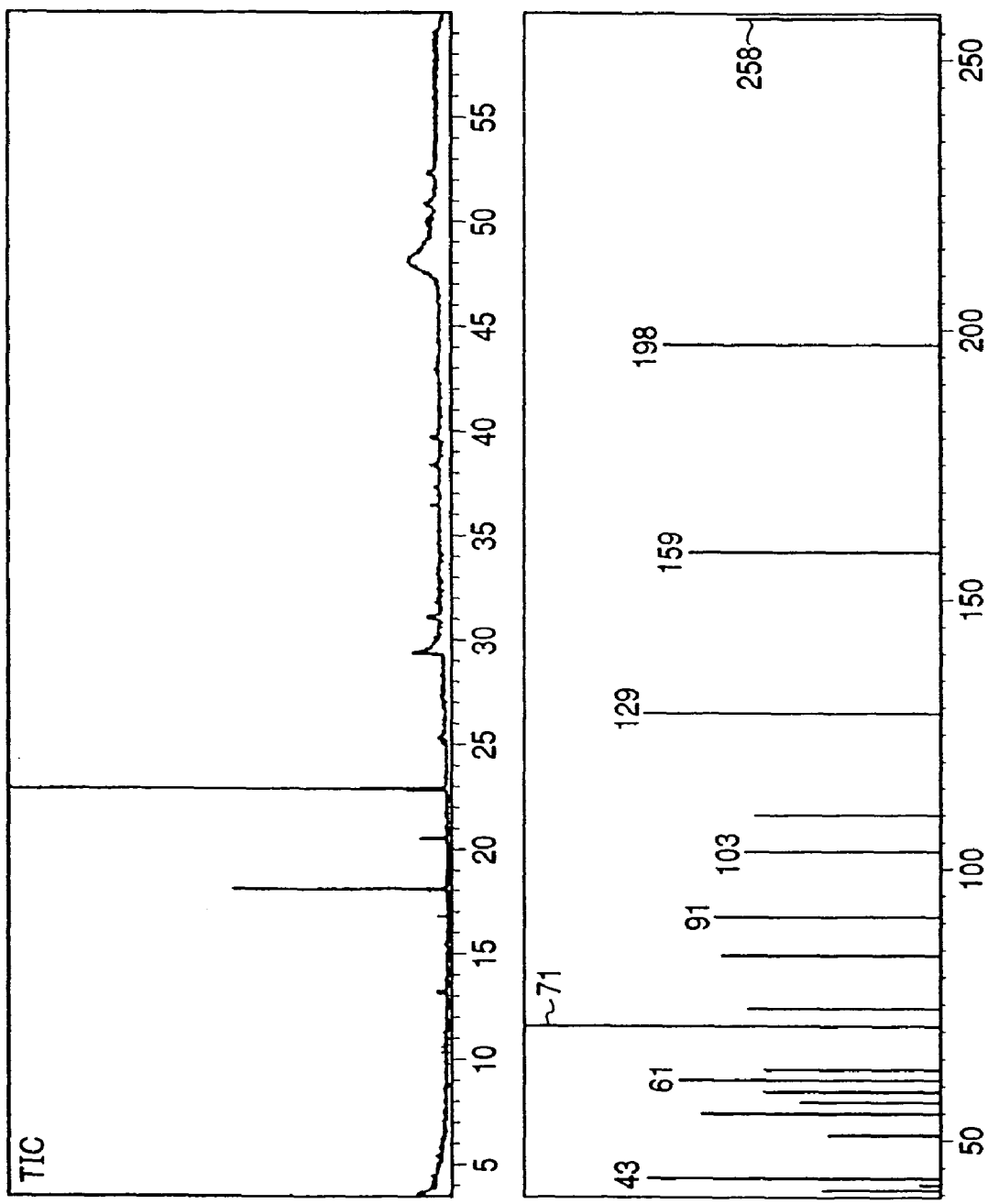
FIGS. 12A and 12B are charts which show the analytical results of the methylated compounds of PHA copolymers obtained in Example 14.

After the PHA obtained was subjected to methanolysis according to the conventional method, it was analyzed by gas chromatography-spectrometry (GC-MS, Shimadzu QP-5050, EI method, column: DB-WAXETR (30 m×0.32 mm×0.5 μm)) and the methyl esters of the PHA monomer unit were identified. The TIC (total ion chromatogram) and the mass spectrum of a peak (close to 36.5') representing the target unit 3-hydroxy-5-(4-trifluoromethylphenyl)valeric acid are shown in FIGS. 12A and 12B, respectively. The TIC area ratio of each unit of the PHA is shown in Table 15.

The above results indicated that one method of the present invention produced PHA containing 3-hydroxy-5-(4-trifluoromethylphenyl)valeric acid as a monomer unit.

Example 15

Production of Polymer by Strain P91

Cells of strain P91 were inoculated in 200 mL of M9 medium containing nonanoic acid 0.1% and TFMPVA 0.1%, and shaken-cultured at 30° C. at 125 strokes/min. After 30 hours, the cells were collected by centrifugation, resuspended in 200 mL of M9 medium containing TFMPVA 0.1% and nonanoic acid 0.05% but not a nitrogen source (NH$_4$Cl), and further shaken-cultured at 30° C. at 125 strokes/min. After 30 hours, the cells were collected by centrifugation, washed once with cold methanol, lyophilized and weighed.

The lyophilized pellet was suspended in 100 mL of chloroform and stirred at 60° C. for 20 hours to extract PHA. After the extract was filtered with a membrane filter of 0.45 μm in pore size, the filtrate was concentrated with a rotary evaporator and the concentrate reprecipitated in cold methanol. Only the precipitate was then recovered and vacuum-dried to obtain and weigh PHA.

The yield is shown in Table 16.

Evaluation of the molecular weight of the PHA by gel permeation chromatography (GPC; Toso HLC-8020, column: Polymer Laboratory PLgel MIXED-C (5 μm), solvent: chloroform, converted on a polystyrene basis) revealed Mn=69,000 and Mw=120,000.

Figure 13A:
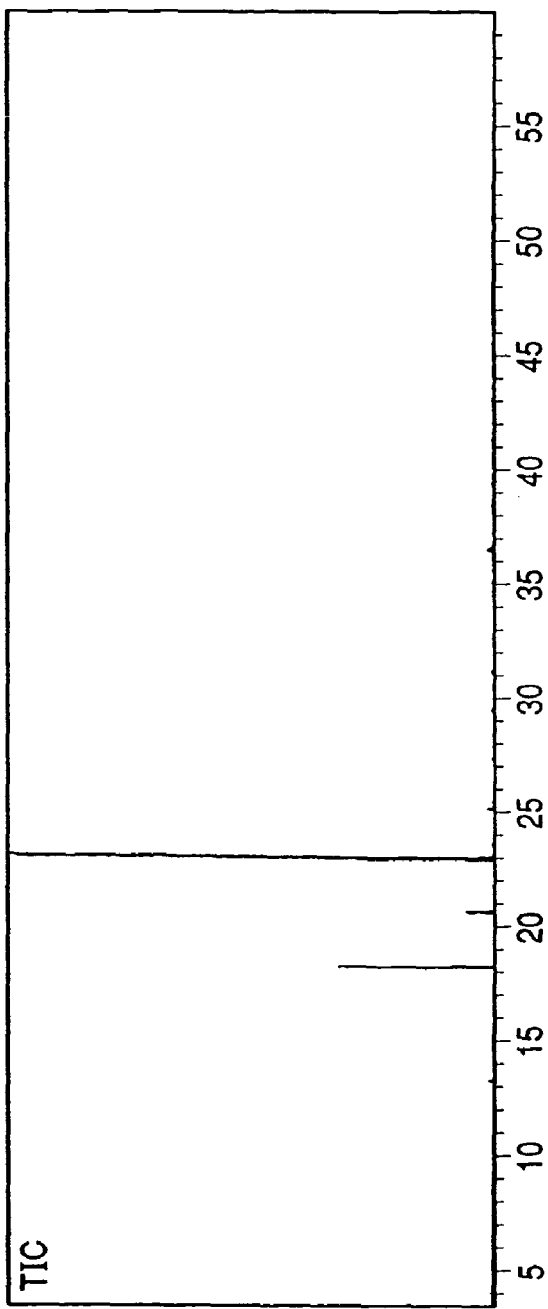
FIGS. 13A and 13B are charts which show the analytical results of the methylated compounds of PHA copolymers obtained in Example 15.
Figure 13B:
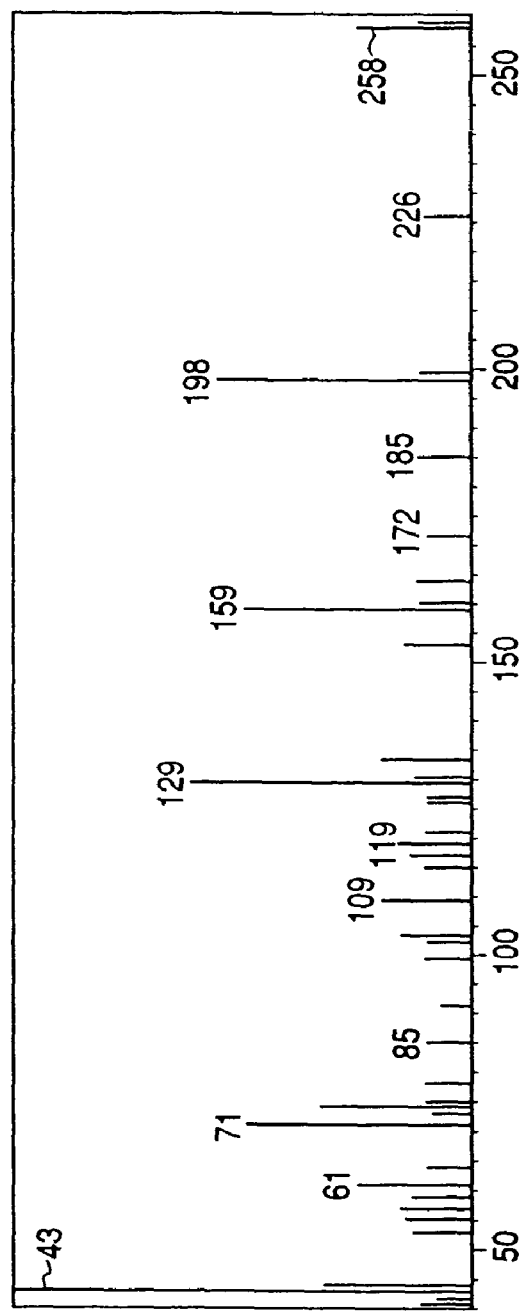

After the PHA obtained was subjected to methanolysis according to the conventional method, it was analyzed with a gas chromatograph-mass spectrometer (GC-MS, Shimadzu QP-5050, EI method, column: DB-WAXETR (30 m×0.32 mm×0.5 μm)) and the methyl esters of the PHA monomer unit were identified. The TIC (total ion chromatogram) and the mass spectrum of a peak (close to 36.5') representing the target unit 3-hydroxy-5-(4-trifluoromethylphenyl)valeric acid are shown in FIGS. 13A and 13B, respectively. The TIC area ratio of each unit of the PHA is shown in Table 17.

The above results indicated that one method of the present invention produced PHA containing 3-hydroxy-5-(4-trifluoromethylphenyl)valeric acid as a monomer unit.

Example 16

Cells of strain YN2 were inoculated in 200 mL of M9 medium containing D-glucose 0.5% or n-nonanoic acid 0.1% and PVA 0.1%, and shaken-cultured at 30° C. at 125 strokes/min. After 40 hours, the cells were collected by centrifugation, washed once with cold methanol and lyophilized to obtain a lyophilized pellet.

The lyophilized pellet was suspended in 20 mL of chloroform and stirred at 60° C. for 28 hours to extract PHA. After the extract was filtered with a membrane filter of 0.45 μm in pore size, the filtrate was concentrated with a rotary evaporator and the concentrate was resuspended in cold methanol. Only the precipitate was then recovered and vacuum-dried to obtain PHA. After the PHA obtained was subjected to methanolysis according to the conventional method, it was analyzed with a gas chromatograph-mass spectrometer (GC-MS, Shimadzu QP-5050, EI method) and the methyl esters of the PHA monomer unit were identified. As a result, PHA containing 3HPV being the desired PVA-derived monomer unit at a higher ratio was obtained in high yield by using D-glucose as a carbon source for growth as shown in Table 18.

Example 17

Cells of strain YN2 were inoculated in 200 mL of M9 medium containing D-glucose 0.5% or n-nonanoic acid 0.1% and PVA 0.1%, and shaken-cultured at 30° C. at 125 strokes/min. After 48 hours, the cells were collected by centrifugation, resuspended in 200 mL of M9 medium containing D-glucose 0.5% or n-nonanoic acid 0.1% and PVA 0.1% but not a nitrogen source ($NH_4Cl$), and further shaken-cultured at 30° C. at 125 strokes/min. After 40 hours, the cells were collected by centrifugation, washed once with cold methanol and lyophilized.

The lyophilized pellet was suspended in 20 mL of chloroform, stirred at 60° C. for 24 hours to extract PHA. After the extract was filtered with a membrane filter of 0.45 μm in pore size, the filtrate was concentrated with a rotary evaporator and the concentrate was reprecipitated in cold methanol. Only the precipitate was then recovered and vacuum-dried to obtain PHA. After the PHA obtained was subjected to methanolysis according to the conventional method, it was analyzed with a gas chromatograph-mass spectrometer (GC-MS, Shimadzu QP-5050, EI method) and the methyl esters of the PHA monomer unit were identified. As a result, PHA containing 3HPV being the desired PVA-derived monomer unit at a higher ratio was obtained in a high yield by using D-glucose as a carbon source for growth, as shown in Table 19.

Example 18

Cells of strain YN2 were inoculated in 200 mL of M9 medium containing D-mannose 0.5% or D-fructose 0.5% and PVA 0.1%, and cultured with shaking at 30° C. at 125 strokes/min. After 100 hours in the D-mannose system and 40 hours in the D-fructose system, the cells were collected by centrifugation, resuspended in 200 mL of M9 medium containing D-mannose 0.5% or D-fructose 0.5% and PVA 0.1% but not a nitrogen source ($NH_4Cl$), and further shaken-cultured at 30° C. at 125 strokes/min. After 48 hours, the cells were collected by centrifugation, washed once with cold methanol and lyophilized.

The lyophilized pellet was suspended in 20 mL of chloroform and stirred at 60° C. for 24 hours to extract PHA. After the extract was filtered with a membrane filter of 0.45 μm in pore size, the filtrate was concentrated with a rotary evaporator and the concentrate was reprecipitated in cold methanol. The precipitate was then recovered and vacuum-dried to obtain PHA. After the PHA obtained was subjected to methanolysis according to the conventional method, it was analyzed with a gas chromatograph-mass spectrometer (GC-MS, Shimadzu QP-5050, EI method) and the methyl esters of the PHA monomer unit were identified. As a result, as shown in Table 20, D-mannose and D-fructose were also as effective as D-glucose as the carbon source to obtain PHA having a high proportion of 3HPV being the desired PVA-derived monomer unit at a high PHA yield.

Example 19

Cells of strain P161 were inoculated in 200 mL of M9 medium containing D-glucose 0.5% or n-nonanoic acid 0.1% and PVA 0.1%, and cultured with shaking at 30° C. at 125 strokes/min. After 48 hours, the cells were collected by centrifugation, resuspended in 200 mL of M9 medium containing D-glucose 0.5% or n-nonanoic acid 0.1% and PVA 0.1% but not a nitrogen source ($NH_4Cl$), and further cultured at 30° C. at 125 strokes/min. After 40 hours, the cells were collected by centrifugation, washed once with cold methanol and lyophilized.

The lyophilized pellet was suspended in 20 mL of chloroform and stirred at 60° C. for 24 hours to extract PHA. After the extract was filtered with a membrane filter of 0.45 μm in pore size, the filtrate was concentrated with a rotary evaporator and the concentrate was reprecipitated in cold methanol. Only the precipitate was then recovered and vacuum-dried to obtain PHA. After the PHA obtained was subjected to methanolysis according to the conventional method, it was analyzed with a gas chromatograph-mass spectrometer (GC-MS, Shimadzu QP-5050, EI method) and the methyl esters of the PHA monomer unit were identified. As a result, PHA having a higher proportion of 3HPV as the desired PVA-derived monomer unit was obtained in high yield by using D-glucose as a carbon source, as shown in Table 21.

Example 20

The cells of strain YN2 were shake-cultured in 200 mL of M9 medium, containing 0.5% of D-glucose or 0.1% of n-nonanoic acid and 0.1% of FPVA under the conditions of 30° C. and 125 strokes/min for 48 hours. The cells were recovered by centrifugal separation, and resuspended in 200 mL of M9 medium, containing 0.5% of D-glucose or 0.1% of n-nonanoic acid and 0.1% of FPVA but no nitrogen source ($NH_4Cl$), where they were further shake-cultured under the conditions of 30° C. and 125 strokes/min for 40 hours. The cells were recovered by centrifugal separation, washed once with cold methanol, and lyophilized.

The lyophilized pellet was suspended in 20 mL of chloroform, and stirred at 60° C. for 24 hours, to extract the PHA. The extract solution was filtered through a membrane having a pore size of 0.45 μm and concentrated by a rotary evaporator. The concentrated solution was reprecipitated in cold methanol, and the precipitate only was recovered and dried under a vacuum, to obtain the PHA. The PHA thus prepared was subjected to methanolysis by the normal procedure, and analyzed by a gas chromatograph/mass spectrometer (GC-MS, Shimadzu QP-5050, based on the EI method), to identify the methyl-esterified product of the PHA monomer units. The results are given in Table 22. As shown, culturing with D-glucose as the carbon source for growth gives the PHA having a higher proportion of 3-hydroxy-5-(4-fluorophenyl)valeric acid as the desired FPVA-derived monomer unit in higher yield.

Example 21

Cells of strain P161 was shake-cultured in 200 mL of M9 medium, containing 0.5% of D-glucose or 0.1% of n-nonanoic acid and 0.1% of PHxA under the conditions of 30° C. and 125 strokes/min for 48 hours. The cells were recovered by centrifugation, and resuspended in 200 mL of M9 medium, containing 0.5% of D-glucose or 0.1% of n-nonanoic acid and 0.1% of PHxA but no nitrogen source (NH$_4$Cl), where they were further shake-cultured under the conditions of 30° C. and 125 strokes/min for 40 hours. The cells were recovered by centrifugation, washed once with cold methanol, and lyophilized.

The lyophilized pellet was suspended in 20 mL of chloroform, and stirred at 60° C. for 24 hours, to extract the PHA. The extract solution was filtered through a membrane having a pore size of 0.45 µm and concentrated by a rotary evaporator. The concentrated solution was reprecipitated in cold methanol, and the precipitate only was recovered and dried under a vacuum, to obtain the PHA. The PHA thus prepared was subjected to methanolysis by the normal procedure, and analyzed by a gas chromatograph/mass spectrometer (GC-MS, Shimadzu QP-5050, based on the EI method), to identify the methyl-esterified product of the PHA monomer units. The results are given in Table 23. As shown, culturing with D-glucose as the carbon source for growth gives the PHA having a higher proportion of 3-hydroxy-6-phenylhexanoic acid as the desired PHxA-derived monomer unit in higher yield.

Example 22

Cells of strain YN2 were shake-cultured in 200 mL of M9 medium, containing 0.5% of D-glucose or 0.1% of n-nonanoic acid and 0.1% of PxBA under the conditions of 30° C. and 125 strokes/min for 48 hours. The cells were recovered by centrifugation, and resuspended in 200 mL of M9 medium, containing 0.5% of D-glucose or 0.1% of n-nonanoic acid and 0.1% of PxBA but no nitrogen source (NH$_4$Cl), where they were further shake-cultured under the conditions of 30° C. and 125 strokes/min for 40 hours. The cells were recovered by centrifugation, washed once with cold methanol, and lyophilized.

The lyophilized pellet was suspended in 20 mL of chloroform, and stirred at 60° C. for 24 hours, to extract the PHA. The extract solution was filtered through a membrane having a pore size of 0.45 µm and concentrated by a rotary evaporator. The concentrated solution was reprecipitated in cold methanol, and the precipitate only was recovered and dried under a vacuum, to obtain the PHA. The PHA thus prepared was subjected to methanolysis by the normal procedure, and analyzed by a gas chromatograph/mass spectrometer (GC-MS, Shimadzu QP-5050, based on the EI method), to identify the methyl-esterified product of the PHA monomer units. The results are given in Table 24. As shown, culturing with D-glucose as the carbon source for growth gives the PHA having a higher proportion of 3-hydroxy-4-phenoxybutyric acid as the desired PxBA-derived monomer unit in higher yield.

Example 23

Cells of strain H45 was shake-cultured in 200 mL of M9 medium, containing 0.5% of D-glucose or 0.1% of n-nonanoic acid and 0.1% of PxBA under the conditions of 30° C. and 125 strokes/min for 48 hours. The cells were recovered by centrifugation, and resuspended in 200 mL of M9 medium, containing 0.5% of D-glucose or 0.1% of n-nonanoic acid and 0.1% of PxBA but no nitrogen source (NH$_4$Cl), where they were further shake-cultured under the conditions of 30° C. and 125 strokes/min for 40 hours. The cells were recovered by centrifugation, washed once with cold methanol, and lyophilized.

The lyophilized pellet was suspended in 20 mL of chloroform, and stirred at 60° C. for 24 hours, to extract the PHA. The extract solution was filtered through a membrane having a pore size of 0.45 µm and concentrated by a rotary evaporator. The concentrated solution was reprecipitated in cold methanol, and the precipitate only was recovered and dried under a vacuum, to obtain the PHA. The PHA thus prepared was subjected to methanolysis by the normal procedure, and analyzed by a gas chromatograph/mass spectrometer (GC-MS, Shimadzu QP-5050, based on the EI method), to identify the methyl-esterified product of the PHA monomer units. The results are given in Table 25. As shown, culturing with D-glucose as the carbon source for growth gives the PHA having a higher proportion of 3-hydroxy-4-phenoxybutyric acid as the desired PxBA-derived monomer unit in higher yield.

Example 24

Cells of strain P161 were shake-cultured in 200 mL of M9 medium, containing 0.5% of D-glucose or 0.1% of n-nonanoic acid and 0.1% of PxBA under the conditions of 30° C. and 125 strokes/min for 48 hours. The cells were recovered by centrifugation, and resuspended in 200 mL of M9 medium, containing 0.5% of D-glucose or 0.1% of n-nonanoic acid and 0.1% of PxBA but no nitrogen source (NH$_4$Cl), where they were further shake-cultured under the conditions of 30° C. and 125 strokes/min for 40 hours. The cells were recovered by centrifugation, washed once with cold methanol, and lyophilized.

The lyophilized pellet was suspended in 20 mL of chloroform, and stirred at 60° C. for 24 hours, to extract the PHA. The extract solution was filtered through a membrane having a pore size of 0.45 µm and concentrated by a rotary evaporator. The concentrated solution was reprecipitated in cold methanol, and the precipitate only was recovered and dried under a vacuum, to obtain the PHA. The PHA thus prepared was subjected to methanolysis by the normal procedure, and analyzed by a gas chromatograph/mass spectrometer (GC-MS, Shimadzu QP-5050, based on the EI method), to identify the methyl-esterified product of the PHA monomer units. The results are given in Table 26. As shown, culturing with D-glucose as the carbon source for growth gives the PHA having a higher proportion of 3-hydroxy-4-phenoxybutyric acid as the desired PxBA-derived monomer unit in higher yield.

Example 25

Cells of strain YN2 were shake-cultured in 200 mL of M9 medium, containing 0.5% of D-glucose or 0.1% of n-nonanoic acid and 0.1% of CHBA under the conditions of 30° C. and 125 strokes/min for 40 hours. The cells were recovered by centrifugation, washed once with cold methanol, and lyophilized.

The lyophilized pellet was suspended in 20 mL of chloroform, and stirred at 60° C. for 28 hours, to extract the PHA. The extract solution was filtered through a membrane having a pore size of 0.45 µm and concentrated by a rotary evaporator. The concentrated solution was reprecipitated in cold methanol, and the precipitate only was recovered and dried under a vacuum, to obtain the PHA. The PHA thus prepared was subjected to methanolysis by the normal procedure, and analyzed by a gas chromatograph/mass spectrometer (GC-MS, Shimadzu QP-5050, based on the EI method), to identify the methyl-esterified product of the PHA monomer units. The results are given in Table 27. As shown, culturing with D-glucose as the carbon source for growth gives the PHA having a higher proportion of 3HCHB as the desired CHBA-derived monomer unit in higher yield.

Example 26

Production of poly-3-hydroxy-5-phenylvaleric acid by strain YN2

A colony of strain YN2 on M9 agar medium containing 0.1% of nonanoic acid (hereinafter referred as to NA) was inoculated in a total of 4 types of media (each 200 mL), (1) M9 liquid medium containing 0.5% of a yeast extract (DIFCO, hereinafter referred to as YE) and 0.1% of 5-phenylvaleric acid, (2) M9 liquid medium containing 0.5% of a beef extract (DIFCO, hereinafter referred to as BE) and 0.1% of 5-phenylvaleric acid, (3) M9 liquid medium containing 0.5% of Casamino acid (DIFCO, hereinafter referred to as CA) and 0.1% of 5-phenylvaleric acid, and (4) M9 liquid medium containing 0.5% of polypeptone (Wako Junyaku, hereinafter referred to as PP) and 0.1% of 5-phenylvaleric acid, and cultured at 30° C. for 24 hours. The cells were recovered from each medium by centrifugation, washed once with cold methanol, and lyophilized.

The lyophilized pellets from each medium were weighed and suspended in 100 mL of chloroform, and stirred at 55° C. for 20 hours, to extract the PHA. Each extract solution was filtered through a membrane having a pore size of 0.45 µm and concentrated by a evaporator. The concentrated solution was reprecipitated in cold methanol, to obtain the polymer, which was dried under a vacuum at room temperature and weighed. The yield results are given in Table 28.

The PHA composition thus prepared was analyzed by the following procedure. Approximately 10 mg of the PHA was dissolved in 2 mL of chloroform in a 25 mL egg-plant type flask, to which 2 mL of a methanol solution containing 3% sulfuric acid was added. The mixture was heated at 100° C. with reflux for 3.5 hours for the reactions. On completion of the reactions, the effluent was incorporated with 10 mL of deionized water and vigorously shaken for 10 min. It was separated into two layers, and the lower chloroform layer was taken out, dehydrated with magnesium sulfate, and analyzed by a gas chromatograph/mass spectrometer (GC-MS, Shimadzu QP-5050, based on the EI method, with a 0.32 mm by 30 m column (J&W, DB-WAX)), to identify the methyl-esterified product of the PHA monomer units. The PHA monomer units were found to comprise 96% of 3-hydroxy-5-phenylvaleric acid unit and 4% of 3-hydroxybutyric acid unit.

The results indicate that one of the embodiments of the present invention gives the PHA containing a very high proportion of the 3-hydroxy-5-phenylvaleric acid unit in a high yield.

Example 27

Production of poly-3-hydroxy-4-cyclohexylbutyric acid by strain YN2

A colony of strain YN2 grown on M9 agar medium containing 0.1% of NA was inoculated into 2 types of media (each 200 mL), (1) M9 liquid medium containing 0.5% of YE and 0.1% of 4-cyclohexylbutyric acid, and (2) M9 liquid medium containing 0.5% of PP and 0.1% of 4-cyclohexylbutyric acid, and cultured at 30° C. for 24 hours. The cells were recovered from each medium by centrifugation, washed once with cold methanol, and lyophilized.

The lyophilized pellets from each medium were weighed and suspended in 100 mL of chloroform, and stirred at 55° C. for 20 hours, to extract the PHA. Each extract solution was filtered through a membrane having a pore size of 0.45 µm and concentrated by a evaporator. The concentrated solution was reprecipitated in cold methanol, to obtain the polymer, which was dried under a vacuum at room temperature and weighed. The yield results are given in Table 29.

The PHA composition thus prepared was analyzed in a manner similar to that for EXAMPLE 26. The PHA monomer units were found to comprise 97% of 3-hydroxy-4-cyclohexylbutyric acid unit and 3% of 3-hydroxybutyric acid unit.

The results indicate that one of the embodiments of the present invention gives the PHA containing a very high proportion of the 3-hydroxy-4-cyclohexylbutyric acid unit in a high yield.

Example 28

Production of poly-3-hydroxy-5-phenoxyvaleric acid by strain YN2

A colony of strain YN2 grown on M9 agar medium containing 0.1% of NA was inoculated in 2 types of media (each 200 mL), (1) M9 liquid medium containing 0.5% of YE and 0.1% of 5-phenoxyvaleric acid, and (2) M9 liquid medium containing 0.5% of PP and 0.1% of 5-phenoxyvaleric acid, and cultured at 30° C. for 26 hours. The cells were recovered from each medium by centrifugation, washed once with cold methanol, and lyophilized.

The lyophilized pellets from each medium were weighed and suspended in 100 mL of chloroform, and stirred at 55° C. for 20 hours, to extract the PHA. Each extract solution was filtered through a membrane having a pore size of 0.45 µm and concentrated by a evaporator. The concentrated solution was reprecipitated in cold methanol, to obtain the polymer, which was dried under a vacuum at room temperature and weighed. The yield results are given in Table 30.

The PHA composition thus prepared was analyzed in a manner similar to that in EXAMPLE 26. The PHA monomer units were found to comprise 95% of 3-hydroxy-5-phenoxyvaleric acid unit and 5% of 3-hydroxybutyric acid unit.

The results indicate that one of the embodiments of the present invention gives the PHA containing a very high proportion of the 3-hydroxy-5-phenoxyvaleric acid unit in a high yield.

Example 29

Production of poly-3-hydroxy-5-phenylvaleric acid by strain H45

A colony of strain H45 grown on M9 agar medium containing 0.1% of NA was inoculated in 4 types of media (each 200 mL), (1) M9 liquid medium containing 0.5% of YE and 0.1% of 5-phenylvaleric acid, (2) M9 liquid medium containing 0.5% of sodium glutamate (Kishida Kagaku, hereinafter referred to as SG) and 0.1% of 5-phenylvaleric acid, (3) M9 liquid medium containing 0.5% of CA and 0.1% of 5-phenylvaleric acid, and (4) M9 liquid medium containing 0.5% of PP and 0.1% of 5-phenylvaleric acid, and cultured at 30° C. for 28 hours. The cells were recovered from each medium by centrifugation, washed once with cold methanol, and lyophilized.

The lyophilized pellets from each medium were weighed and suspended in 100 mL of chloroform, and stirred at 55° C. for 20 hours, to extract the PHA. Each extract solution was filtered through a membrane having a pore size of 0.45 µm and concentrated by a evaporator. The concentrated solution was reprecipitated in cold methanol, to obtain the polymer, which was dried under a vacuum at room temperature and weighed. The yield results are given in Table 31.

The PHA composition thus prepared was analyzed in a manner similar to that in EXAMPLE 26. The PHA was found to be essentially the homopolymer of 3-hydroxy-5-phenylvaleric acid.

The results indicate that one of the embodiments of the present invention gives the PHA containing a very high proportion of the 3-hydroxy-5-phenylvaleric acid unit in a high yield.

Example 30

Production of poly-3-hydroxy-5-phenylvaleric acid by strain P161

A colony of strain P161 grown on M9 agar medium containing 0.1% of NA was inoculated in 4 types of media (each 200 mL), (1) M9 liquid medium containing 0.5% of YE and 0.1% of 5-phenylvaleric acid, (2) M9 liquid medium containing 0.5% of SG and 0.1% of 5-phenylvaleric acid, (3) M9 liquid medium containing 0.5% of BE and 0.1% of 5-phenylvaleric acid, and (4) M9 liquid medium containing 0.5% of PP and 0.1% of 5-phenylvaleric acid, and cultured at 30° C. for 24 hours. The cells were recovered from each medium by centrifugation, washed once with cold methanol, and lyophilized.

The lyophilized pellets from each medium were weighed and suspended in 100 mL of chloroform, and stirred at 55° C. for 20 hours, to extract the PHA. Each extract solution was filtered through a membrane having a pore size of 0.45 µm and concentrated by a evaporator. The concentrated solution was reprecipitated in cold methanol, to obtain the polymer, which was dried under a vacuum at room temperature and weighed. The yield results are given in Table 32.

The PHA composition thus prepared was analyzed in a manner similar to that in EXAMPLE 26. The PHA monomer units were found to comprise 97% of 3-hydroxy-5-phenylvaleric acid unit and 3% of 3-hydroxybutyric acid unit.

The results indicate that one of the embodiments of the present invention gives the PHA containing a very high proportion of the 3-hydroxy-5-phenylvaleric acid unit in a high yield.

Example 31

*Pseudomonas cichorii* strain YN2 was shake-cultured in 10 mL of M9 medium containing 0.5% of D-glucose under the conditions of 30° C. and 125 strokes/min for 72 hours, and 2 mL of the culture was transferred for further shake-culture in 200 mL of M9 medium containing 0.5% of D-glucose and 0.1% of $NO_2PxBA$ under the conditions of 30° C. and 125 strokes/min for another 72 hours. The cells were recovered by centrifugation, and resuspended in 200 mL of M9 medium, containing 0.5% of D-glucose and 0.1% of $NO_2PxBA$ but no nitrogen source ($NH_4Cl$), where they were further shake-cultured under the conditions of 30° C. and 125 strokes/min for 48 hours. The cells were recovered by centrifugation, washed once with cold methanol, and lyophilized.

The lyophilized pellets were suspended in 20 mL of chloroform, and stirred at 60° C. for 20 hours, to extract the PHA. The extract solution was filtered through a membrane having a pore size of 0.45 µm and concentrated by a rotary evaporator. The concentrated solution was reprecipitated in cold methanol, and the precipitate only was recovered and dried under a vacuum, to obtain the PHA.

The PHA thus prepared was analyzed by NMR under the following conditions:

<Analyzer>
FT-NMR: Bruker DPX400
Resonance frequency: $^1H=400$ MHz

Figure 14:
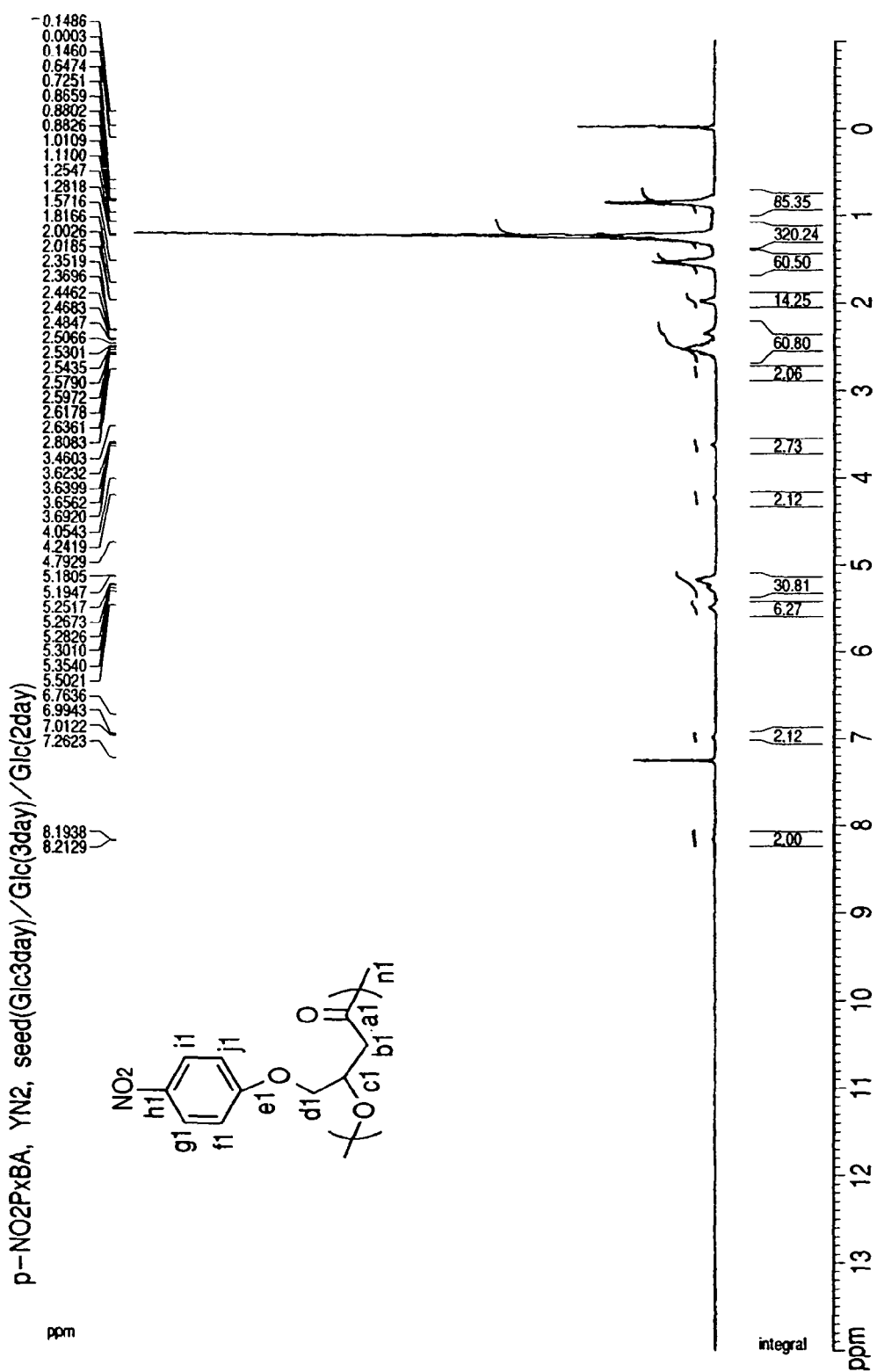
FIG. 14 is a chart which shows the $^1$H-NMR spectrum of PHA obtained in Example 30.

<Analysis Conditions>
Nuclide to be analyzed: $^1H$
Solvent: $CDCl_3$
Reference: $TMS/CDCl_3$ sealed in a capillary
Temperature: room temperature FIG. 14 shows the $^1H$-NMR spectral patterns, Table 33 the results of identification of the patterns, and Table 34 the composition of the monomer units of 3-hydroxy-4-(4-nitrophenoxy)butyric acid. As shown in Table 33, the PHA is the one represented by the chemical formula (45), containing 3-hydroxy-4-(4-nitrophenoxy)butyric acid as the monomer unit.

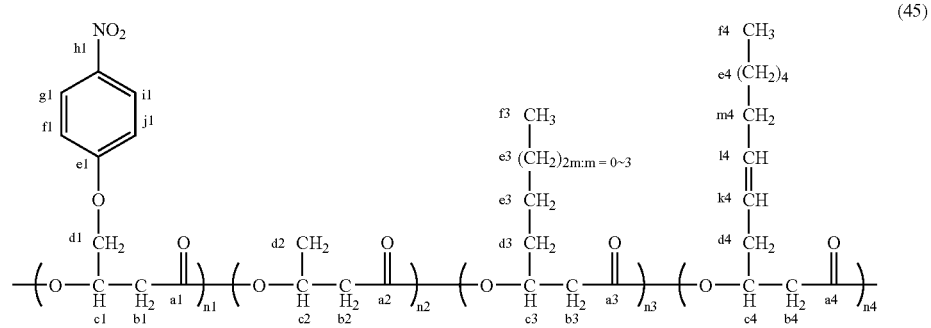

The PHA thus prepared was subjected to methanolysis by the normal procedure, and analyzed by a gas chromatograph/mass spectrometer (GC-MS, Shimadzu QP-5050, based on the EI method), to identify the methyl-esterified product of the PHA monomer units, other than 3-hydroxy-4-(4-nitrophenoxy)butyric acid. The results are given in Table 34.

The PHA had a number-average molecular weight (Mn) of 81,900 and weight-average molecular weight (Mw) of 226,200, as determined by a gel permeation chromatograph (GPC; Toso HLC-8020, column: Polymer Laboratory's PLgel MIXED-C(5 μm), solvent: chloroform, as polystyrene).

Example 32

Cells of *Pseudomonas cichorii* strain YN2 were inoculated into 200 mL of M9 culture medium containing 0.5% D-glucose and 0.1% NO$_2$PxBA, and shake cultured at 30° C. at 125 stroke/min. After 45 hours, the cells were recovered by centrifugation and re-suspended into 200 mL of M9 culture medium containing 0.5% D-glucose, 0.1% NO$_2$PxBA and nitrogen (NH$_4$Cl)-free, and further shake cultured at 30° C. at 125 stroke/min. After 48 hours, the cells were recovered by centrifugation, washed once with cold methanol and lyophilized.

This lyophilized pellet was suspended into 20 mL of chloroform, and stirred at 60° C. for 20 hours to extract PHA. After the extracts were filtrated through a membrane filter with a pore size of 0.45 μm, they were concentrated by a rotating evaporator, and the concentrates were re-precipitated with cold methanol, and further the precipitates alone were recovered and vacuum dried to provide PHA.

The resulting PHA was determined by NMR analysis under the condition shown in the Example 31. As a result, it was confirmed that the PHA was the PHA containing 3-hydroxy-4-(4-nitrophenoxy)butyric acid as a monomer unit, as shown in Table 35.

Further, the resulting PHA was done methanolysis according to conventional method, and then analyzed by gas chromatography-mass spectrometer (GC-MS, Shimadzu QP-5050, EI method) to identify methylesterified materials of PHA monomer unit and identify monomer unit other than 3-hydroxy-4-(4-nitrophenoxy)butyric acid. The result was shown in the Table 35.

Example 33

Cells of *Pseudomonas cichorii* strain YN2 were inoculated into 200 mL of M9 culture medium containing 0.5% Polypeptone and 0.1% NO$_2$PxBA, and shake cultured at 30° C. at 125 stroke/min. After 21 hours, the cells were recovered by centrifugation and re-suspended into 200 mL of M9 culture medium containing 0.5% sodium pyruvate, 0.1% NO$_2$PxBA and nitrogen (NH$_4$Cl)-free, and further shake cultured at 30° C. at 125 stroke/min. After 24 hours, the cells were recovered by centrifugation, washed once with cold methanol and lyophilized.

This lyophilized pellet was suspended into 20 mL of chloroform, and stirred at 60° C. for 20 hours to extract PHA. After the extracts were filtrated through a membrane filter with a pore size of 0.45 μm, they were concentrated by rotating evaporator, and the concentrates were re-precipitated with cold methanol, and further the precipitates alone were recovered and vacuum dried to provide PHA.

The resulting PHA was determined by NMR analysis under the condition shown in the Example 31. As a result, it was confirmed that the PHA was the PHA containing 3-hydroxy-4-(4-nitrophenoxy)butyric acid as a monomer unit, as shown in Table 36.

Further, the resulting PHA was done methanolysis according to the conventional method, and then analyzed by gas chromatography-mass spectrometer (GC-MS, Shimadzu QP-5050, EI method) to identify methylesterified materials of PHA monomer unit and identify monomer unit other than 3-hydroxy-4-(4-nitrophenoxy)butyric acid. The result was shown in the Table 36.

Example 34

First, cells of *Pseudomonas cichorii* strain YN2 were inoculated into 10 mL of M9 culture medium containing 0.5% D-glucose and shake-cultured at 30° C. at 125 stroke/min, and then 2 mL of the culture was added into 200 mL of M9 culture medium containing 0.5% D-glucose and 0.1% CNPxBA, and shake cultured at 30° C. at 125 stroke/min. 48 hours later, the cells were recovered by centrifugation and re-suspended into 200 mL of M9 culture medium containing 0.5% D-glucose, 0.1% CNPxBA and nitrogen (NH$_4$Cl)-free, and further shake cultured at 30° C. at 125 stroke/min. 47 hours later, the cells were recovered by centrifugation, washed once with cold methanol and lyophilized.

This lyophilized pellet was suspended into 20 mL of chloroform, and stirred at 60° C. for 20 hours to extract PHA. After the extracts were filtrated through a membrane filter with a pore size of 0.45 μm, they were concentrated by rotating evaporator, and the concentrates were re-precipitated with cold methanol, and further the precipitates alone were recovered and vacuum dried to provide PHA.

The resulting PHA was determined by NMR analysis on the following conditions.

<Measuring Apparatus>
FT-NMR: Bruker DPX 400

Resonance frequency: $^1$H=400 MHz

<Measuring Condition>
Measuring nuclide: $^1$H

Measuring solvent: CDCl$_3$

Reference: capillary inclusion TMS/CDCl$_3$

Measuring temperature: room temperature

Figure 15:
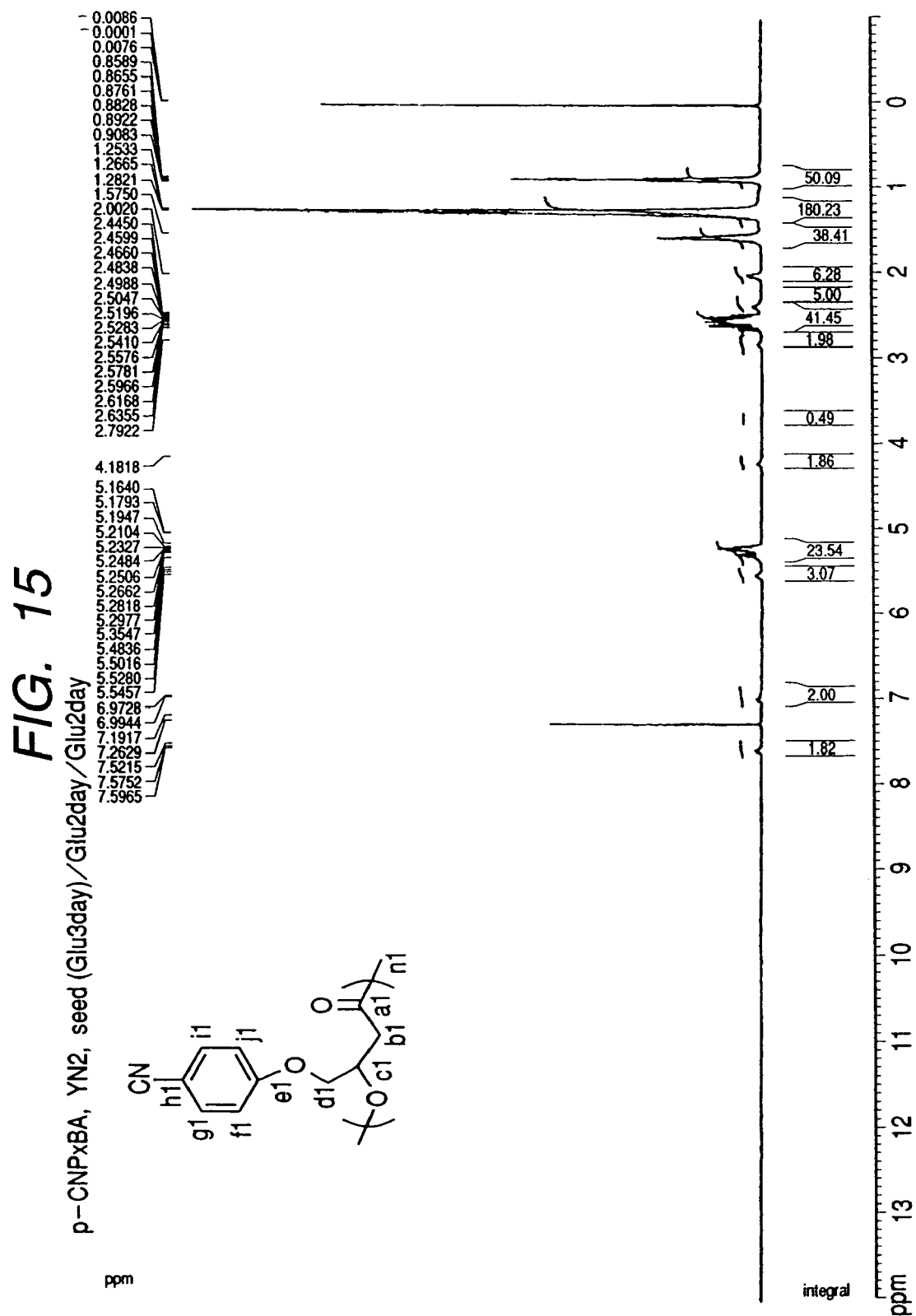
FIG. 15 is a chart which shows the $^1$H-NMR spectrum of PHA obtained in Example 34.

FIG. 15 illustrates $^1$H-NMR spectra, Table 37 shows their corresponding results, and Table 38 shows the ratio of 3-hydroxy-4-(4-cyanophenoxy)butyric acid monomer unit contained in PHA. As shown in the Table 37, it was confirmed that the PHA was the PHA expressed by the chemical formula (46) containing 3-hydroxy-4-(4-cyanophenoxy)butyric acid as a monomer unit.

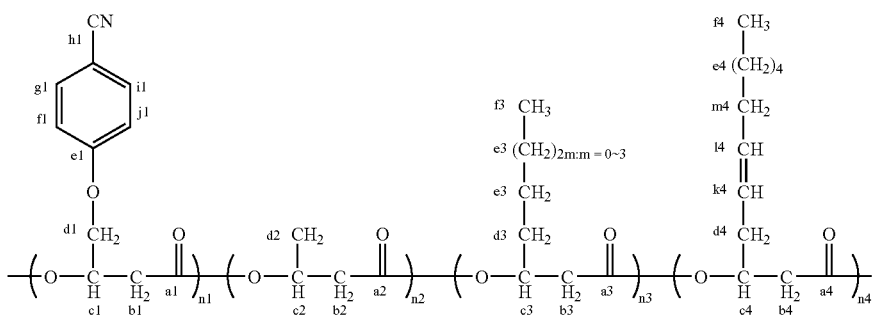

(46)

Further, the resulting PHA was done methanolysis according to the conventional method, and then analyzed by gas chromatography-mass spectrometer (GC-MS, Shimadzu QP-5050, EI method) to identify methylesterified materials of PHA monomer unit and identify monomer unit other than 3-hydroxy-4-(4-cyanophenoxy)butyric acid. The result was shown in the Table 38.

Moreover, the molecular weight of the PHA was evaluated by gel permeation chromatography (GPC; Toso HLC-8020, column; Polymer Laboratory PL gel MIXED-C (5 μm), solvent; (chloroform, polystyrene reduced) to obtain Mn=58200 and Mw=108100.

Example 35

First, cells of *Pseudomonas cichorii* strain H45 were inoculated into 10 mL of M9 culture medium containing 0.5% D-glucose and shake-cultured at 30° C. at 125 stroke/min, and then 2 mL of the culture were added into 200 mL of M9 culture medium containing 0.5% D-glucose and 0.1% CNPxBA, and shake cultured at 30° C. at 125 stroke/min. 48 hours later, the cells were recovered by centrifugation and re-suspended into 200 mL of M9 culture medium containing 0.5% D-glucose, 0.1% CNPxBA and nitrogen ($NH_4Cl$)-free, and further shake cultured at 30° C. at 125 stroke/min. 47 hours later, the cells were recovered by centrifugation, washed once with cold methanol and lyophilized.

This lyophilized pellet was suspended into 20 mL of chloroform, and stirred at 60° C. for 20 hours to extract PHA. After the extracts were filtrated through a membrane filter with a pore size of 0.45 μm, they were concentrated by rotating evaporator, and the concentrates were re-precipitated with cold methanol, and further the precipitates alone were recovered and vacuum dried to provide PHA.

The resulting PHA was determined by NMR analysis under the condition shown in the Example 34. As a result, it was confirmed that the PHA was the PHA containing 3-hydroxy-4-(4-cyanophenoxy)butyric acid as a monomer unit, as shown in Table 39.

Further, the resulting PHA was done methanolysis according to the conventional method, and then analyzed by gas chromatography-mass spectrometer (GC-MS, Shimadzu QP-5050, EI method) to identify methylesterified materials of PHA monomer unit and identify monomer unit other than 3-hydroxy-4-(4-cyanophenoxy)butyric acid. The result was shown in the Table 39.

Example 36

Cells of *Pseudomonas cichorii* strain YN2 were inoculated into 200 mL of M9 culture medium containing 0.5% D-glucose and 0.1% CNPxBA, and shake cultured at 30° C. at 125 stroke/min. After 48 hours, the cells were recovered by centrifugation and re-suspended into 200 mL of M9 culture medium containing 0.5% D-glucose, 0.1% CNPxBA and nitrogen ($NH_4Cl$)-free, and further shake cultured at 30° C. at 125 stroke/min. After 48 hours, the cells were recovered by centrifugation, washed once with cold methanol and lyophilized.

This lyophilized pellet was suspended into 20 mL of chloroform, and stirred at 60° C. for 20 hours to extract PHA. After the extracts were filtrated through a membrane filter with a pore size of 0.45 μm, they were concentrated by rotating evaporator, and the concentrates were re-precipitated with cold methanol, and further the precipitates alone were recovered and vacuum dried to provide PHA.

The resulting PHA was determined by NMR analysis under the condition shown in the Example 34. As a result, it was confirmed that the PHA was the PHA containing 3-hydroxy-4-(4-cyanophenoxy)butyric acid as a monomer unit, as shown in Table 40.

Further, the resulting PHA was done methanolysis according to the conventional method, and then analyzed by gas chromatography-mass spectrometer (GC-MS, Shimadzu QP-5050, EI method) to identify methylesterified materials of PHA monomer unit and identify monomer unit other than 3-hydroxy-4-(4-cyanophenoxy)butyric acid. The result was shown in the Table 40.

Example 37

Cells of *Pseudomonas cichorii* strain H45 were inoculated into 200 mL of M9 culture medium containing 0.5% D-glucose and 0.1% CNPxBA, and shake cultured at 30° C. at 125 stroke/min. After 48 hours, the cells were recovered by centrifugation and re-suspended into 200 mL of M9 culture medium containing 0.5% D-glucose, 0.1% CNPxBA and nitrogen ($NH_4Cl$)-free, and further shake cultured at 30° C. at 125 stroke/min. After 48 hours, the cells were recovered by centrifugation, washed once with cold methanol and lyophilized.

This lyophilized pellet was suspended into 20 mL of chloroform, and stirred at 60° C. for 20 hours to extract PHA. After the extracts were filtrated through a membrane filter with a pore size of 0.45 μm, they were concentrated by rotating evaporator, and the concentrates were re-precipitated with cold methanol, and further the precipitates alone were recovered and vacuum dried to provide PHA.

The resulting PHA was determined by NMR analysis under the condition shown in the Example 34. As a result, it was confirmed that the PHA was the PHA containing 3-hydroxy-4-(4-cyanophenoxy)butyric acid as a monomer unit, as shown in Table 41.

Further, the resulting PHA was done methanolysis according to the conventional method, and then analyzed by gas chromatography-mass spectrometer (GC-MS, Shimadzu QP-5050, EI method) to identify methylesterified materials of PHA monomer unit and identify monomer unit other than 3-hydroxy-4-(4-cyanophenoxy)butyric acid. The result was shown in the Table 41.

Example 38

Cells of *Pseudomonas Cichorii* strain YN2 were inoculated into 200 mL of M9 culture medium containing 0.5% polypeptone and 0.1% CNPxBA and cultured at 30° C. with shaking at 125 stroke/min. After 23 hours, the cells were recovered by centrifugation and re-suspended into 200 mL of M9 culture medium containing 0.5% sodium pyruvate, 0.1% CNPxBA but no nitrogen source ($NH_4Cl$), and further cultured at 30° C. at 125 stroke/min. After 24 hours, the cells were recovered by centrifugation, washed once with cold methanol and lyophilized.

The lyophilized pellet was suspended into 20 mL of chloroform, and stirred at 60° C. for 20 hours to extract PHA. After the extracts were filtrated through a membrane filter with a pore size of 0.45 μm, they were concentrated by rotating evaporator, and the concentrates were re-precipitated with cold methanol, and further the precipitates alone were recovered and vacuum dried to provide PHA.

The resulting PHA was determined by NMR analysis under the condition shown in the Example 34. As a result, it was confirmed that the PHA was the PHA containing 3-hydroxy-4-(4-cyanophenoxy)butyric acid as a monomer unit, as shown in Table 42.

Further, the resulting PHA was done methanolysis according to the conventional method, and then analyzed by gas chromatography-mass spectrometer (GC-MS, Shimadzu QP-5050, EI method) to identify methylesterified materials of PHA monomer unit and identify monomer unit other than 3-hydroxy-4-(4-cyanophenoxy)butyric acid. The result was shown in the Table 42.

Example 39

Cells of *Pseudomonas cichorii* strain H45 were inoculated into 200 mL of M9 culture medium containing 0.5% polypeptone and 0.1% CNPxBA, and cultured at 30° C. with shaking at 125 stroke/min. After 23 hours, the cells were recovered by centrifugation and re-suspended into 200 mL of M9 culture medium containing 0.5% Sodium pyruvate, 0.1% CNPxBA but no nitrogen source ($NH_4Cl$), and further shake cultured at 30° C. at 125 stroke/min. After 24 hours, the cells were recovered by centrifugation, washed once with cold methanol and lyophilized.

This lyophilized pellet was suspended into 20 mL of chloroform, and stirred at 60° C. for 20 hours to extract PHA. After the extracts were filtrated through a membrane filter with a pore size of 0.45 μm, they were concentrated by rotating evaporator, and the concentrates were re-precipitated with cold methanol, and further the precipitates alone were recovered and vacuum dried to provide PHA.

The resulting PHA was determined by NMR analysis under the condition shown in the Example 34. As a result, it was confirmed that the PHA was the PHA containing 3-hydroxy-4-(4-cyanophenoxy)butyric acid as a monomer unit, as shown in Table 43.

Further, the resulting PHA was done methanolysis according to the conventional method, and then analyzed by gas chromatography-mass spectrometer (GC-MS, Shimadzu QP-5050, EI method) to identify methylesterified materials of PHA monomer unit and identify monomer unit other than 3-hydroxy-4-(4-cyanophenoxy)butyric acid. The result was shown in the Table 43.

Example 40

Synthesis of 4-(4-fluorophenoxy)butyric acid

A new compound, 4-(4-fluorophenoxy)butyric acid was prepared by the synthetic method mentioned below.

Into a round-bottom flask with four opening was put 240 mL of dehydrated acetone, added 15.2 g (0.11 mol) of potassium carbonate, and stirred under nitrogen atmosphere. Into this solution were added 9.0 g (0.06 mol) of sodium iodide and 7.9 g (0.07 mol) of 4-fluorophenol, and thoroughly stirred at room temperature under nitrogen atmosphere. 11.7 g (0.06 mol) of 4-bromoethyl butyrate was then added, and heat refluxed at 65° C. for 24 hours.

After aforesaid reaction was completed, the solvent acetone was removed by rotating evaporator, and its residue was re-dissolved in chloroform. Water was added for phase separation, and the organic layer was collected. After the organic layer was dehydrated with anhydrous magnesium sulfate, chloroform was removed by rotating evaporator. Then, it was dried by a vacuum pump to provide 14.0 g of crude 4-(4-fluorophenoxy)ethyl butyrate (gas chromatograph-mass spectrometer: GC-MS Shimadzu QP-5050, GC-MS peak ratio purity: 65.2% with EI method). Without purifying the resulting crude 4-(4-fluorophenoxy)ethyl butyrate, it was used in the following ester hydrolytic reaction.

The resulting crude 4-(4-fluorophenoxy)ethyl butyrate was dissolved in 300 mL of ethanol-water (1:9 (V/V)) mixed solution, and approximately ten-fold molar equivalent weight of potassium hydroxide was added to react for four hours under ice cooling (at 0 to 4° C.). This cocktail was poured into 3 L of 0.1 mol/L hydrochloric acid to precipitate. Precipitates were filtrated, separated, and dried by vacuum pump to provide crude 4-(4-fluorophenoxy)butyric acid.

The resulting crude 4-(4-fluorophenoxy)butyric acid (precipitate) was dissolved in a small amount of hot methanol, and gradually cooled to recrystallize. Filtrated recrystallization materials were dried by vacuum pump to provide objective compound, 4-(4-fluorophenoxy)butyric acid. In this series of processes, the resulting 4-(4-fluorophenoxy) butyric acid was 52.7% in yield based on the raw material 4-bromoethylbutyrate.

In order to verify that the resulting compound was the objective 4-(4-fluorophenoxy)butyric acid, NMR analysis was carried out by the following measuring apparatus under measuring condition to identify the structure.

<Measuring Apparatus>
FT-NMR: Bruker DPX 400

<Measuring Condition>
Resonance frequency: $^1H$ 400 MHz
$^{13}C$ 100 MHz
Measuring nuclide: $^1H$, $^{13}C$ Used solvent: $CDCl_3$
Reference: capillary inclusion $TMS/CDCl_3$
Measuring temperature: room temperature
Determined $^1H$-NMR spectra chart and $^{13}C$-NMR spectra chart were illustrated in FIGS. 16 and 17, respectively. Table 44 and 45 show analytical (corresponding) result of each signal for NMR spectra illustrated in the FIGS. 16 and 17. This analytical (corresponding) result confirmed that the resulting compound was the objective 4-(4-fluorophenoxy) butyric acid.

Example 41

First, cells of *Pseudomonas cichorii* strain YN2 (FERM BP-7375) were inoculated into 10 mL of M9 culture medium containing 0.5% D-glucose, and shake cultured at 30° C. at 125 stroke/min for 72 hours. Then 2 mL of the culture was added into 200 mL of M9 culture medium (no inorganic nitrogen source, $NH_4Cl$) containing 0.5% D-glucose and 0.1% pFPxBA, and continuously shake cultured at 125 stroke/min. After 45 hours, the cells were recovered by centrifugation and re-suspended into 200 mL of M9 culture medium containing 0.5% D-glucose and 0.1% pFPxBA, and further shake cultured at 30° C. at 125 stroke/min. After 46 hours, the cells were recovered by centrifugation, washed once with cold methanol and lyophilized.

This lyophilized pellet was suspended into 20 mL of chloroform, and stirred at 60° C. for 20 hours to extract PHA. After the extracts were filtrated through a membrane filter with a pore size of 0.45 μm, they were concentrated by rotating evaporator, and the concentrates were re-precipitated with cold methanol, and further the precipitates alone were recovered and vacuum dried to provide PHA.

Figure 18:
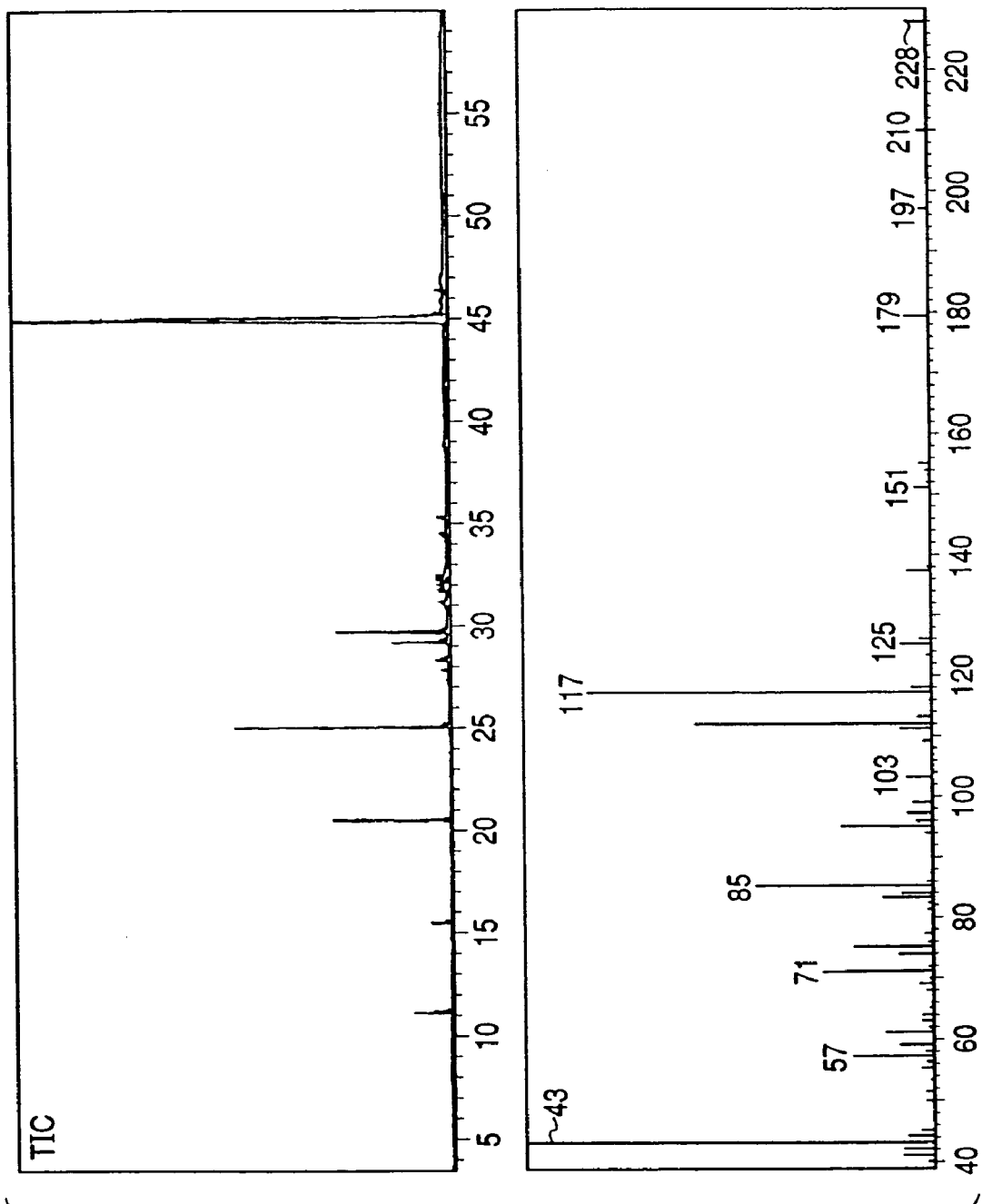
FIG. 18 are charts which show the GC-MS spectrum data measured after methanolysis of PHA recovered from the cultured cells of strain YN2 in Example 41.

The resulting PHA was done methanolysis according to the conventional method, and then analyzed by gas chromatography-mass spectrometer (GC-MS, Shimadzu QP-5050, EI method) to identify methylesterified materials of PHA monomer unit. FIG. 18 illustrates measured GC-MS spectra data, and the upper chart shows GC spectrum, and the lower chart shows an MS spectrum corresponding to the main peak on the GC spectrum. This result shows that the resulting PHA contains 3-hydroxy-4-(4-fluorophenoxy)butyric acid (3HpFPxB) as a main component of monomer unit, in addition it also contains a small amount of six kinds of monomer units, and can be represented by the following chemical formula (47).

Furthermore, the molecular weight of the PHA was determined by gel permeation chromatography (GPC; Toso•HLC-8020, column; Polymer laboratory•PL gel•MIX ED-C•5 μm, solvent; chloroform, polystyrene reduced molecular weight).

Identification result, average molecular weight, as well as yield of lyophilized pellet and recovered polymer are shown in Table 46. It shows that the resulting PHA is the PHA containing 3-hydroxy-4-(4-fluorophenoxy)butyric acid (3HpFPxB) as a monomer unit. Further, it is likely that the extracted PHA includes 3HpFPxB unit as a major component, however, it is the mixture containing more than one kind of component as a monomer unit selected from the group consisting of 3-hydroxybutyric acid, 3-hydroxyhexanoic acid, 3-hydroxyoctanoic acid, 3-hydroxydecanoic acid, 3-hydroxydodecanoic acid, 3-hydroxydodecenoic acid. Estimated average molecular weight was Mn=42400 for number-average molecular weight, on the other hand, Mw=90600 for weight-average molecular weight.

Figure 19:
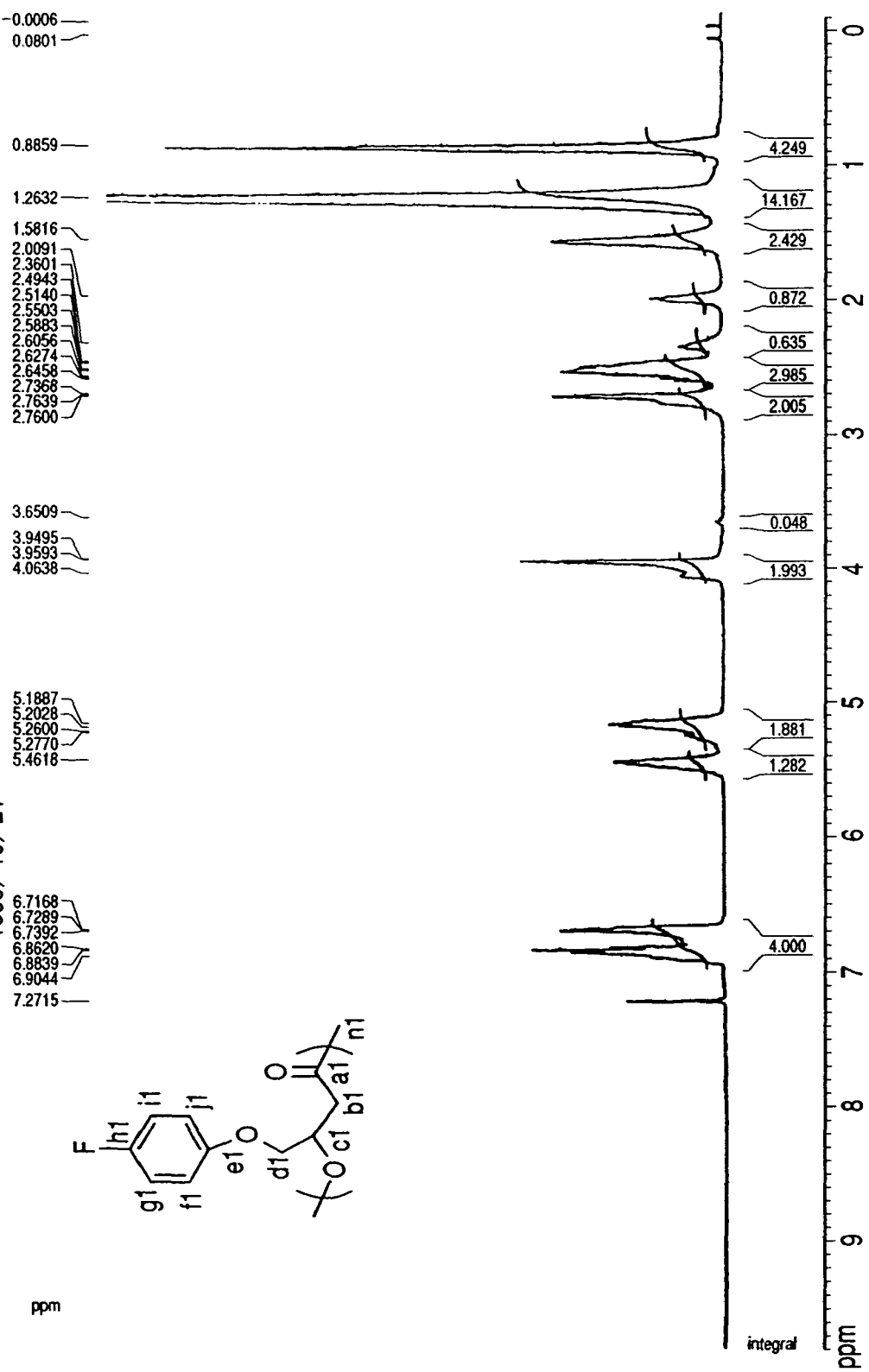
FIG. 19 is a chart which shows the $^1$H-NMR spectrum of PHA recovered from the cultured microbial cells of strain YN2 in Example 41.

This PHA was also determined by NMR analysis with the same measuring apparatus and same measuring condition as shown in the Example 40. The measured $^1H$-NMR spectra chart is shown in FIG. 19. Table 47 shows the analytical (corresponding) result of each signal for major peak for NMR spectra illustrated in the FIG. 19. This analytical (corresponding) result confirmed that the resulting PHA contained 3HpFPxB unit as a major component.

Example 42

Cells of *Pseudomonas cichorii* H45; FERM BP-7374 were inoculated in 10 mL of M9 medium containing D-glucose 0.5%, and was shake-cultured at 30° C. in 125 strokes/min. for 72 hours. Then 2 ml of the culture was transferred into 200 ml of M9 medium containing 0.5% D-glucose and 0.1% pFPxBA, and further shake cultured at 30° C. in 125 strokes/min. After 45 hours, cultured cells were recovered by centrifugation, and re-suspended in M9 medium containing D-glucose 0.5% and pFPxBA 0.1%, but not containing inorganic nitrogen source ($NH_4Cl$), and further cultured at 30° C. in 125 strokes/min. After 46 hours, cells were recovered by centrifugation, washed once with cold methanol and lyophilized.

The lyophilized pellet was suspended in chloroform 20 mL, and stirred at 60° C. for 20 hours to extract PHA. The extract was filtered using membrane filter, pore size 0.45 μm, concentrated using rotary evaporator, precipitated the con-

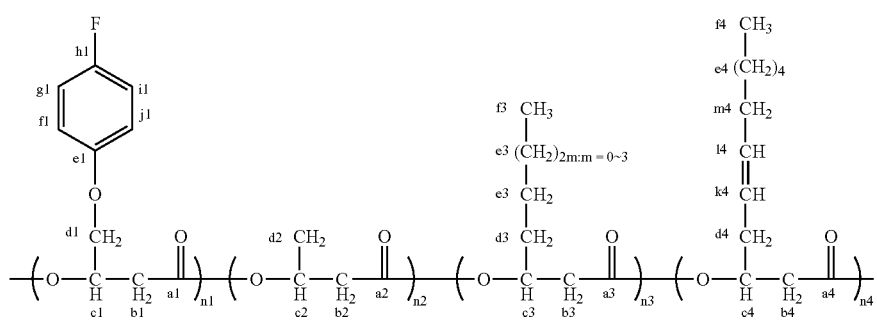
(47)

centrate with cold methanol, and recovered the precipitate to obtain PHA by vacuum drying.

The thus obtained PHA was subjected to methanolysis, and the product was analyzed using gas-chromatography mass spectrograph (GC-MS, Shimadzu QP-5050, EI method) to identify methyl esterified PHA monomer units. In Table 48, result of identification, and, weight obtained and yield of the lyophilized pellet and the recovered polymer are shown. The thus obtained PHA is the PHA with 3HpFPxB as a monomer unit. The extracted PHA mainly consists of 3HpFPxB as a main component, and is considered to be a mixture containing more than one of compounds selected from the group consisting of 3-hydroxybutyric acid, 3-hydroxyhexanoic acid, 3-hydroxyoctanoic acid, 3-hydroxydecanoic acid, 3-hydroxydodecanoic acid and 3-hydroxydodecenoic acid, as a monomer unit.

Example 43

Cells of *Pseudomonas cichorii* YN2 were inoculated in 200 ml M9 medium containing D-glucose 0.5% and pFPxBA 0.1% and was shake cultured at 30° C. in 125 strokes/min. After 96 hours, the cultured cells were recovered by centrifugation, and re-suspended in 200 ml of M9 medium containing D-glucose 0.5% and pFPxBA 0.1% but not containing an inorganic nitrogen source ($NH_4Cl$), and further shake cultured at 30° C. in 125 strokes/min. After 64 hours, cells were recovered by centrifugation, washed once with cold methanol and lyophilized.

The lyophilized pellet was suspended in chloroform 20 mL, and stirred at 60° C. for 20 hours to extract PHA. The extract was filtered using membrane filter, pore size 0.45 μm, concentrated using rotary evaporator, precipitated the concentrate with cold methanol, and recovered the precipitate to obtain PHA by vacuum drying.

The thus obtained PHA was subjected to methanolysis, and the product was analyzed using gas-chromatography mass spectrograph (GC-MS, Shimadzu QP-5050, EI method) to identify methyl esterified PHA monomer units. In Table 49, result of identification, and weight obtained and yield of the lyophilized pellet and the recovered polymer are shown. The thus obtained PHA is the PHA with 3HpFPxB as a major monomer unit.

Example 44

Cells of *Pseudomonas cichorii* H45 were inoculated in M9 medium 200 mL containing D-glucose 0.5% and pFPxBA 0.1% and was shake cultured at 30° C. in 125 strokes/min. After 96 hours, cultured cells were recovered by centrifugation, and re-suspended in M9 medium not containing inorganic nitrogen source $NH_4Cl$, containing D-glucose 0.5% and pFPxBA 0.1% (200 ml), then further shake cultured at 30° C. in 125 strokes/min. After 64 hours, cells were recovered by centrifugation, washed once with cold methanol and lyophilized.

The lyophilized pellet was suspended in chloroform 20 mL, and stirred at 60° C. for 20 hours to extract PHA. The extract was filtered using membrane filter of pore size 0.45 μm, concentrated using rotary evaporator, precipitated the concentrate with cold methanol, and recovered the precipitate to obtain PHA by vacuum drying.

The thus obtained PHA was subjected to methanolysis, and the product was analyzed using gas-chromatography mass spectrograph (GC-MS, Shimadzu QP-5050, EI method) to identify methyl esterified PHA monomer units. In Table 50, result of identification, and, weight obtained and yield of the lyophilized pellet and the recovered polymer are shown. The thus obtained PHA is the PHA with 3HpFPxB as a major monomer unit.

Example 45

Cells of *Pseudomonas cichorii* YN2 were inoculated in 200 ml of M9 medium containing polypeptone 0.5% and pFPxBA 0.1% and was shake cultured at 30° C. in 125 strokes/min. After 24 hours, cultured cells were recovered by centrifugation, and re-suspended in 200 ml of M9 medium containing sodium pyruvate 0.5% and pFPxBA 0.1%, but not containing inorganic nitrogen source $NH_4Cl$, and further shake cultured at 30° C. in 125 strokes/min. After 24 hours, cells were recovered by centrifugation, washed once with cold methanol and lyophilized.

The lyophilized pellet was suspended in chloroform 20 mL, and stirred at 60° C. for 20 hours to extract PHA. The extract was filtered using membrane filter (pore size 0.45 μm), concentrated by rotary evaporator, precipitated the concentrate with cold methanol, and recovered the precipitate to obtain PHA by vacuum drying.

The thus obtained PHA was subjected to methanolysis, and the product was analyzed using gas-chromatography mass spectrograph (GC-MS, Shimadzu QP-5050, EI method) to identify methyl esterified PHA monomer units. In Table 51, result of identification, weight obtained and yield of the lyophilized pellet and the recovered polymer are shown. The thus obtained PHA is the PHA with 3HpFPxB as a major monomer unit.

Example 46

Cells of *Pseudomonas cichorii* H45 were inoculated in 200 ml of M9 medium containing polypeptone 0.5% and pFPxBA 0.1% and was shake cultured at 30° C. in 125 strokes/min. After 24 hours, the cells were recovered by centrifugation, and re-suspended in 200 ml of M9 medium not containing inorganic nitrogen source $NH_4Cl$, and containing sodium pyruvate 0.5% and pFPxBA 0.1%, then further shake cultured at 30° C. in 125 strokes/min. After 24 hours, the cells were recovered by centrifugation, washed once with cold methanol and lyophilized.

The lyophilized pellet was suspended in chloroform 20 mL, and stirred at 60° C. for 20 hours to extract PHA. The extract was filtered using membrane filter, pore size 0.45 μm, concentrated using rotary evaporator, precipitated the concentrate with cold methanol, and recovered the precipitate to obtain PHA by vacuum drying.

The thus obtained PHA was subjected to methanolysis, and the product was analyzed using gas-chromatography mass spectrograph (GC-MS, Shimadzu QP-5050, EI method) to identify methyl esterified PHA monomer units. In Table 52, result of identification, and, weight obtained and yield of the lyophilized pellet and the recovered polymer are shown. The thus obtained PHA is the PHA with 3HpFPxB as a major monomer unit.

Example 47

Synthesis of 4-(3-fluorophenoxy)butyric acid

Novel compound 4-(3-fluorophenoxy)butyric acid was prepared by the following synthetic method.

Dehydrated acetone 240 mL was poured in a four-neck round-bottom flask, and potassium carbonate 15.2 g (0.11 mol) was added thereto, then stirred under nitrogen atmosphere. Sodium iodide 9.0 g (0.06 mol) and 3-fluorophenol 7.9 g (0.07 mol) were added to the solution, and the mixture was stirred sufficiently at room temperature under nitrogen atmosphere. Then ethyl 4-bromobutyrate 11.7 g (0.06 mol) and refluxed at 65° C. for 24 hours.

After completed the above reaction, solvent acetone was distilled off using rotary evaporator, and the residue was dissolved in chloroform. Water was added therein for separation and the organic layer was collected. The organic layer was dehydrated by adding anhydrous magnesium sulfate and the chloroform was distilled off by using rotary evaporator. Further, the residue was dried in vacuo using vacuum pump to obtain crude ethyl 4-(3-fluorophenoxy) butyrate 14 g (purification 87.9%, GC-MS peak ratio, determined by EI method using gas chromatography-mass spectrograph: GC-MS Shimadzu QP-5050). The thus obtained crude ethyl 4-(3-fluorophenoxy) butyrate was used subsequent ester hydrolysis without purification.

The thus obtained crude ester 3.0 g was dissolved in a mixture of ethanol-water [1:9 (V/V)] 100 mL, to which about 10-fold excess molar equivalent of potassium hydroxide was added, and the mixture was reacted at room temperature for 4 hours. The reaction mixture was poured into about 200 mL of 0.1 mol/l aqueous hydrochloric acid to precipitate. The precipitate was filtered, separated and dried in vacuo under the vacuum pump to obtain crude 4-(3-fluorophenoxy) butyric acid.

The thus obtained crude 4-(3-fluorophenoxy) butyric acid (precipitate) was dissolved in a small amount of hot methanol and gradually cooled for recrystallization. Filtered recrystallized product was dried using vacuum pump to obtain 4-(3-fluorophenoxy) butyric acid.

The yield of 4-(3-fluorophenoxy) butyric acid obtained from crude ester 3.0 g was 2.4 g. Consequently, total yield in the whole process based on the raw material ethyl 4-bromobutyrate is 93.2%.

For verification of the objective compound. 4-(3-fluorophenoxy) butyric acid, structure of the obtained compound was identified by NMR using following measuring apparatus and conditions.

Figure 20:
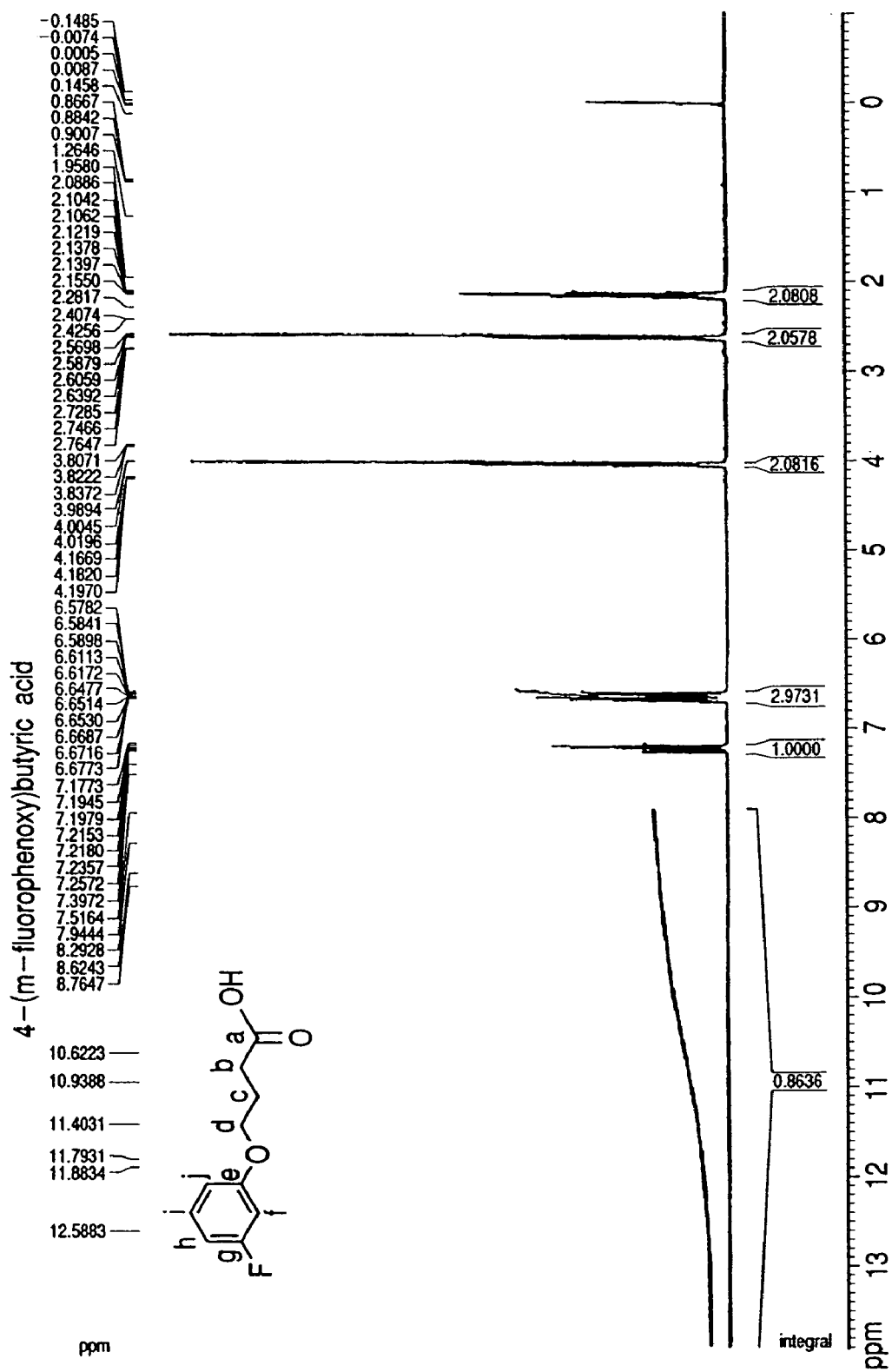
FIG. 20 is a chart which shows the $^1$H-NMR spectrum of 4-(3-fluorophenoxy)butyric acid.
Figure 21:
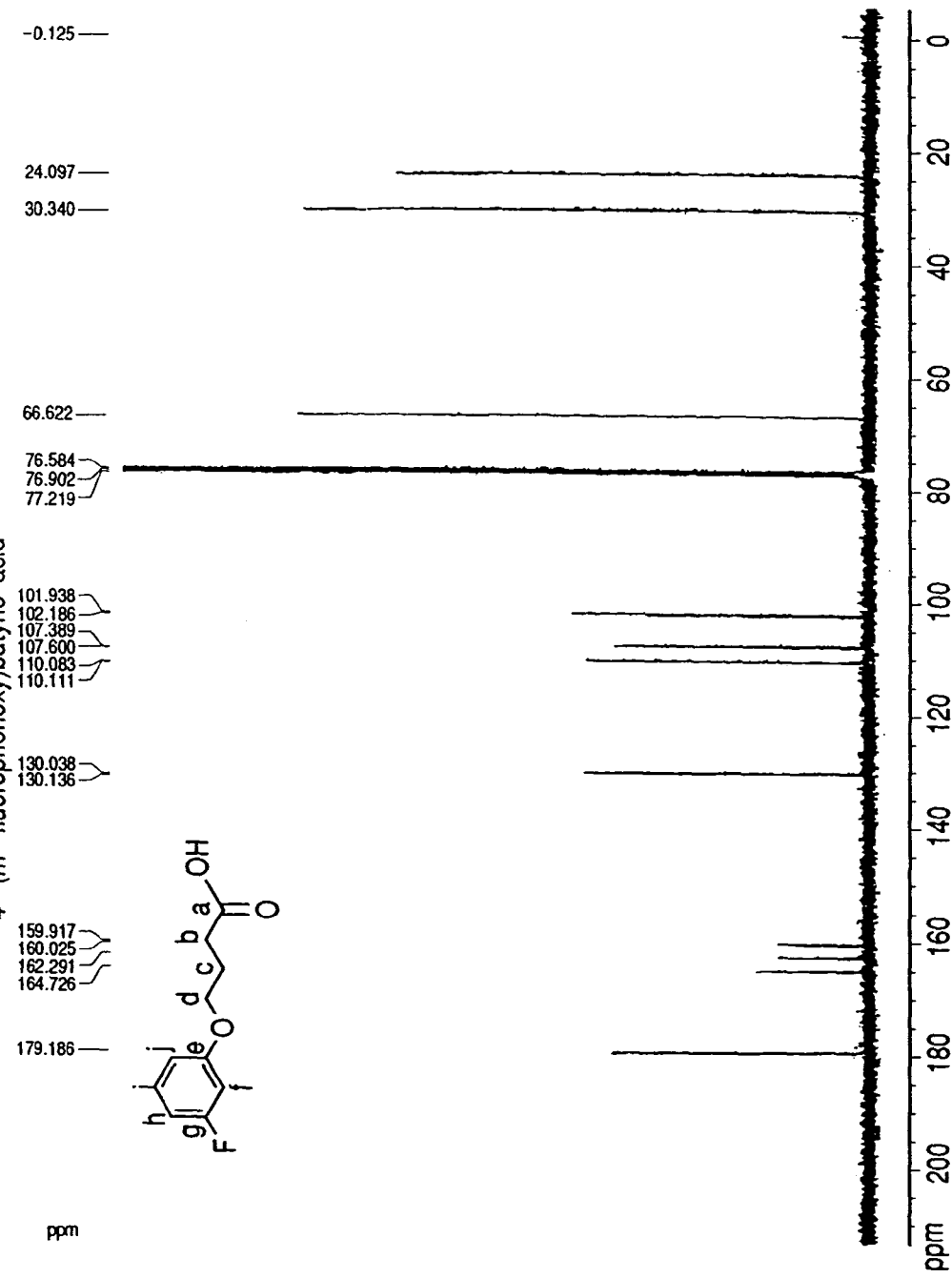
FIG. 21 is a chart which shows the $^{13}$C-NMR spectrum of 4-(3-fluorophenoxy)butyric acid.

<Measuring Apparatus>
  FT-NMR: Bruker DPX400
<Measuring Condition>
  Resonance frequency: $^1$H 400 MHZ
  $^{13}$C 100 MHZ
  Measuring nuclide: $^1$H and $^{13}$C
  Solvent used: $CDCl_3$
  Reference: Capillary sealed $TMS/CDCl_3$
  Measuring temperature: room temperature
  $^1$H-NMR spectrum and $^{13}$C-NMR spectrum are shown in FIG. 20 and FIG. 21, respectively. In Table 53 and Table 54, results of analyses (assignments) of respective signals of NMR spectra, which are shown in FIG. 20 and FIG. 21, are shown. According to the result of analysis (assignment), the obtained compound is confirmed to be the objective compound 4-(3-fluorophenoxy) butyric acid.

Example 48

Cells of *Pseudomonas cichorii* YN2; FERM BP-7375 were inoculated in 10 mL of M9 medium containing D-glucose 0.5% and shake cultured at 30° C. at 125 strokes/min for 72 hours. Then 2 mL of the culture was transferred into 200 ml of M9 medium containing D-glucose 0.5% and mFPxBA 0.1% and shake cultured at 125 strokes/min. After 45 hours, the cells were recovered by centrifugation, and re-suspended in 200 ml of M9 medium containing D-glucose 0.5% and mFPxBA 0.1% but not containing inorganic nitrogen source $NH_4Cl$, and further shake cultured at 30° C. at 125 strokes/min. After 47 hours, cells were recovered by centrifugation, washed once with cold methanol and lyophilized.

The lyophilized pellet was suspended in chloroform 20 mL, and stirred at 60° C. for 20 hours to extract PHA. The extract was filtered using membrane filter, pore size 0.45 μm, concentrated using rotary evaporator, precipitated the concentrate with cold methanol, and recovered the precipitate to obtain PHA by vacuum drying.

Figure 22:
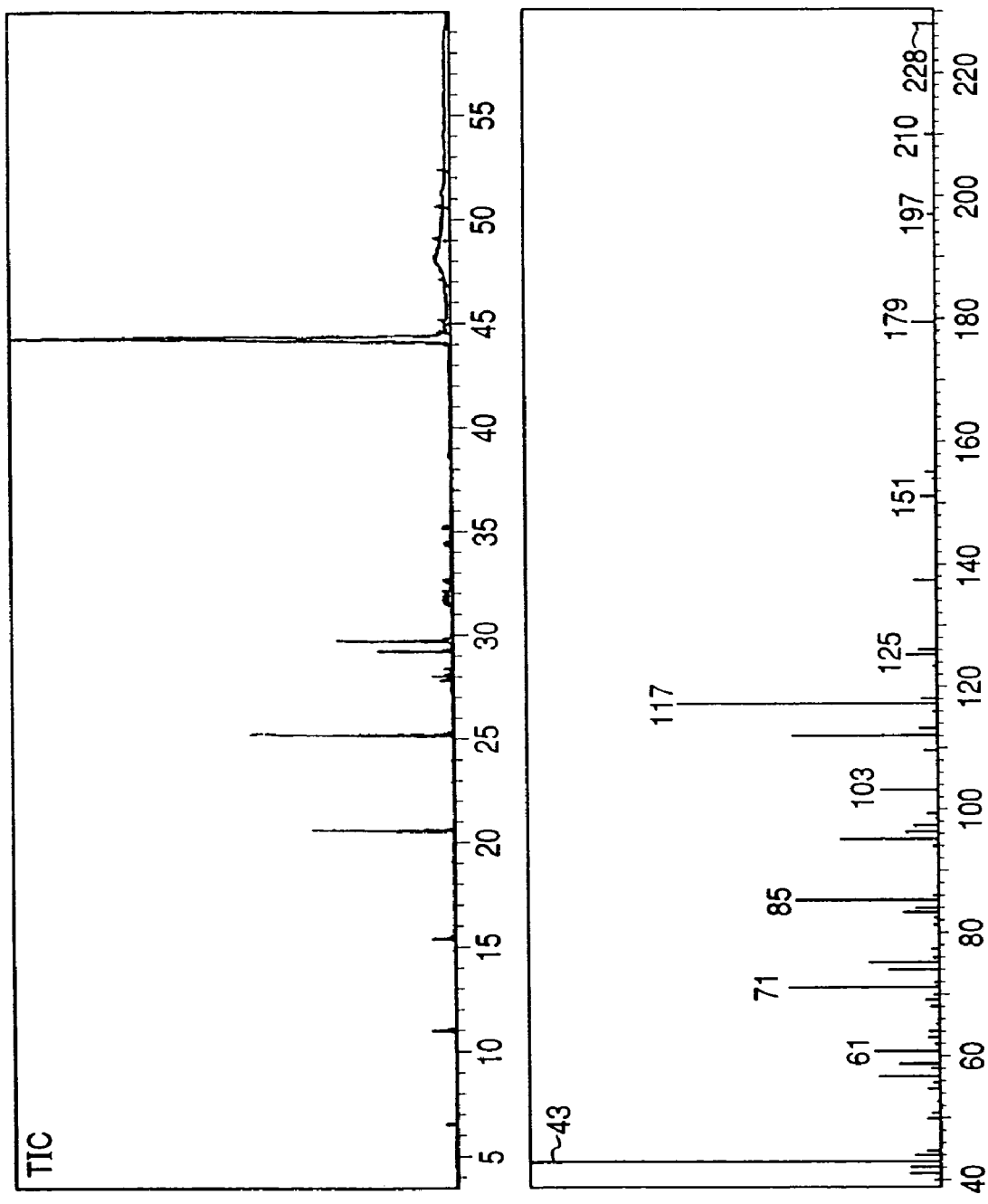
FIG. 22 are charts which show the GC-MS spectrum data measured after methanolysis of PHA recovered from the cultured microbial cells of strain YN2 in Example 47.

The thus obtained PHA was subjected to methanolysis, and the product was analyzed using gas-chromatography mass spectrograph (GC-MS, Shimadzu QP-5050, EI method) to identify methyl esterified PHA monomer units. In FIG. 22, measured GC-MS spectrum data is shown. Upper part of FIG. 22 indicates GC spectrum, and the lower part indicates MS spectrum corresponding to main peaks on the above GC spectrum. As a result, the thus obtained PHA is the PHA, which contains 3-hydroxy-4-(3-fluorophenoxy) butyric acid (3HmFPxB) as a major monomer unit as well as small amount of 6 types of monomer units, and the compound can be illustrated as the following chemical structure (48).

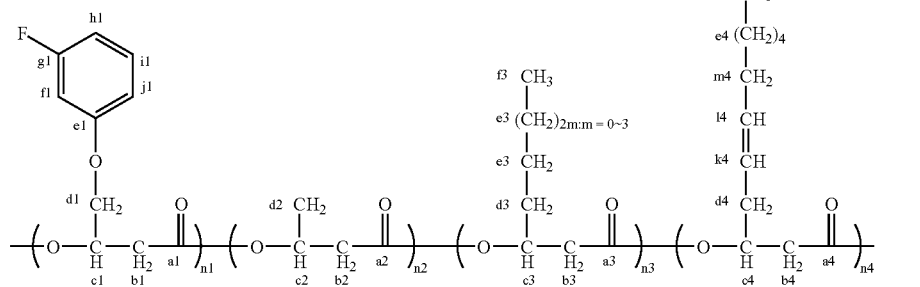

Molecular weight of PHA was measured by using gel-permeation chromatography (GPC: Toso HLC-8020; Column: Polymer Laboratory PLgel MIX ED-C, 5 μm; Solvent: chloroform: Molecular weight: reduced value for polystyrene).

In Table 55, result of identification, average molecular weight, and weight obtained and yield of the lyophilized pellet and the recovered polymer are shown. The thus obtained PHA is the PHA, which contains 3-hydroxy-4-(3-fluorophenoxy) butyric acid (3HmFPxB) as a monomer unit. The extracted PHA mainly consists of 3HmFPxB unit as a main component, and is considered to be a mixture containing more than one of compounds selected from the group consisting of 3-hydroxybutyric acid, 3-hydroxyhexanoic acid, 3-hydroxyoctanoic acid, 3-hydroxydecanoic acid, 3-hydroxydodecanoic acid and 3-hydroxydodecenoic acid, as a monomer unit. The evaluated average molecular weight is: number average molecular weight Mn=34500 and weight-average molecular weight Mw=75200.

Figure 23:
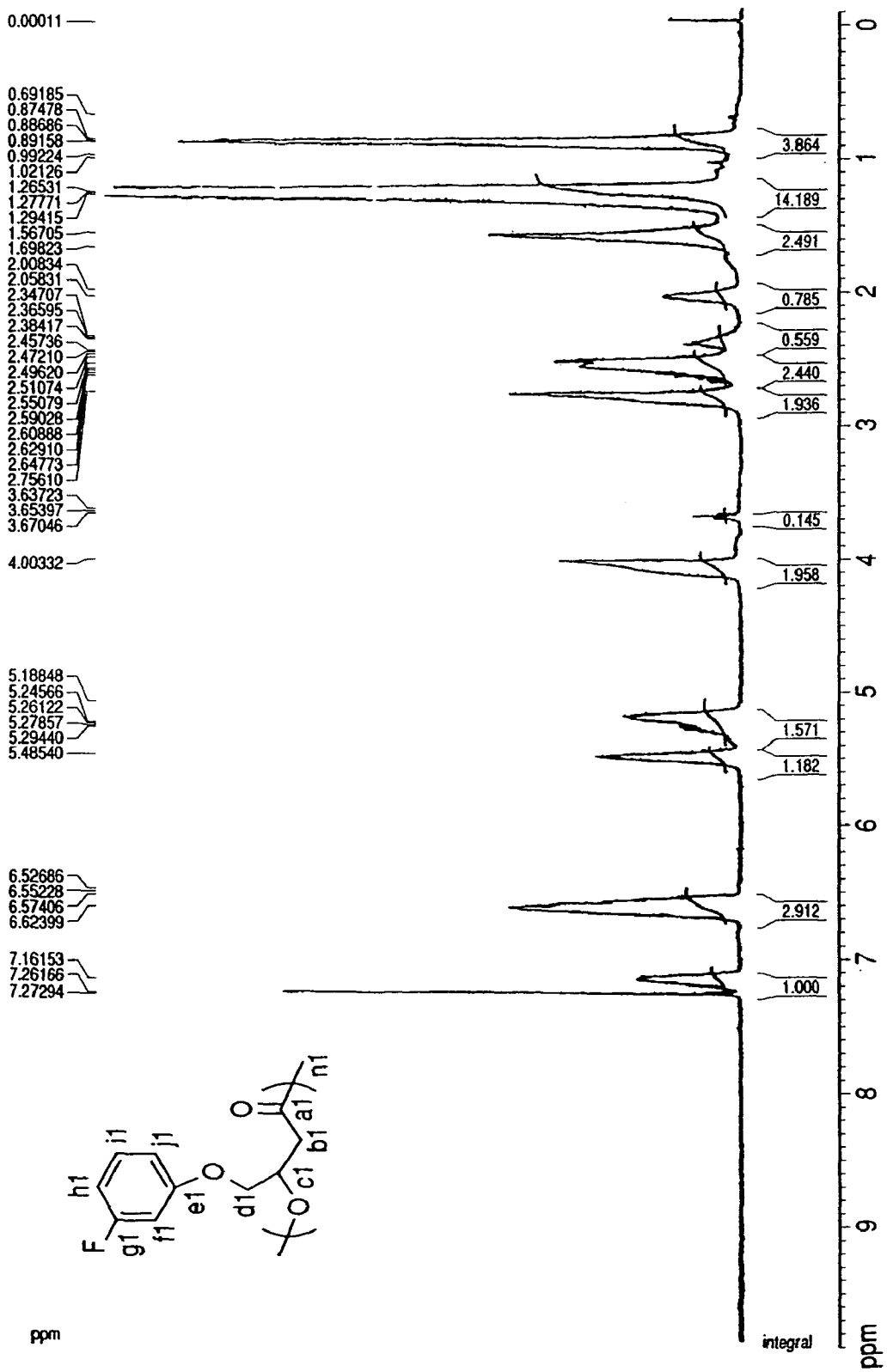
FIG. 23 is a chart which shows the $^1$H-NMR spectrum of PHA recovered from the cultured microbial cells of strain YN2 in Example 47.

NMR analysis of the PHA was performed by the same procedures using same measuring apparatus and measuring conditions as described in example 47. Measured $^1$H-NMR spectrum is shown in FIG. 23. In Table 56, result of analysis (assignment) of major peak signals of NMR spectrum in FIG. 23 is shown. According to the result of analysis (assignment), the obtained compound is confirmed to have 3HmFPxB unit as a major component.

Example 49

Cells of *Pseudomonas cichorii* H45; FERM BP-7374 were inoculated in 10 mL of M9 medium containing D-glucose 0.5% and was cultured at 30° C. with shaking at 125 strokes/min for 72 hours. Then 2 mL of the culture was transferred into 200 mL of M9 medium containing D-glucose 0.5% and mFPxBA 0.1% and shake cultured at 30° C. at 125 strokes/min. After 45 hours, the cells were recovered by centrifugation, and were re-suspended in 200 mL of M9 medium containing D-glucose 0.5% and mFPxBA 0.1% but not containing inorganic nitrogen source (NH$_4$Cl), then further shake cultured at 30° C. in 125 strokes/min. After 47 hours, cells were recovered by centrifugation, washed once with cold methanol and lyophilized.

The lyophilized pellet was suspended in chloroform 20 mL, and stirred at 60° C. for 20 hours to extract PHA. The extract was filtered using membrane filter, pore size 0.45 μm, concentrated using rotary evaporator, precipitated the concentrate with cold methanol, and recovered the precipitate to obtain PHA by vacuum drying.

The thus obtained PHA was subjected to methanolysis, and the product was analyzed using gas-chromatography mass spectrograph (GC-MS, Shimadzu QP-5050, EI method) to identify methyl esterified PHA monomer units. In Table 57, result of identification, and weight obtained and yield of the lyophilized pellet and the recovered polymer are shown. The thus obtained PHA is the PHA, which contains 3HmFPxB as a monomer unit. The extracted PHA mainly consists of 3HmFPxB unit as a main component, and is considered to be a mixture containing more than one of compounds selected from the group consisting of 3-hydroxybutyric acid, 3-hydroxyhexanoic acid, 3-hydroxyoctanoic acid, 3-hydroxydecanoic acid, and 3-hydroxydodecanoic acid, as a monomer unit.

Example 50

*Pseudomonas cichorii* H45 was inoculated in 200 ml of M9 medium containing D-glucose 0.5% and mFPxBA 0.1% and was cultured at 30° C. with shaking at 125 strokes/min. After 96 hours, cultured cells were recovered by centrifugation, and re-suspended in M9 medium containing D-glucose 0.5% and mFPxBA 0.1% but not containing the inorganic nitrogen source NH$_4$Cl, then further shake cultured at 30° C., 125 strokes/min. After 64 hours, cells were recovered by centrifugation, washed once with cold methanol and lyophilized.

The lyophilized pellet was suspended in chloroform 20 mL, and stirred at 60° C. for 20 hours to extract PHA. The extract was filtered using membrane filter, pore size 0.45 μm, concentrated using rotary evaporator, precipitated the concentrate with cold methanol, and recovered the precipitate to obtain PHA by vacuum drying.

The thus obtained PHA was subjected to methanolysis, and the product was analyzed using gas-chromatography mass spectrograph (GC-MS, Shimadzu QP-5050, EI method) to identify methyl esterified PHA monomer units. In Table 58, result of identification, and weight obtained and yield of the lyophilized pellet and the recovered polymer are shown. The thus obtained PHA is the PHA containing 3HmFPxB as a major monomer unit.

Example 51

*Pseudomonas cichorii* YN2 was inoculated in 200 mL of M9 medium containing polypeptone 0.5% and mFPxBA 0.1% and was cultured at 30° C. with shaking at 125 strokes/min. After 24 hours, cultured cells were recovered by centrifugation, and re-suspended in 200 ml of M9 medium containing sodium pyruvate 0.5% and mFPxBA 0.1% but not containing the inorganic nitrogen source NH$_4$Cl, then further shake cultured at 30° C., 125 strokes/min. After 24 hours, bacterial cells were recovered by centrifugation, washed once with cold methanol and lyophilized.

The lyophilized pellet was suspended in chloroform 20 mL, and stirred at 60° C. for 20 hours to extract PHA. The extract was filtered using membrane filter, pore size 0.45 μm, concentrated using rotary evaporator, precipitated the concentrate with cold methanol, and recovered the precipitate to obtain PHA by vacuum drying.

The thus obtained PHA was subjected to methanolysis, and the product was analyzed using gas-chromatography mass spectrograph (GC-MS, Shimadzu QP-5050, EI method) to identify methyl esterified PHA monomer units. In Table 59, result of identification, and weight obtained and yield of the lyophilized pellet and the recovered polymer are shown. The thus obtained PHA is the PHA containing 3HmFPxB as a major monomer unit.

Example 52

*Pseudomonas cichorii* H45 was inoculated in 200 mL of M9 medium containing polypeptone 0.5% and mFPxBA 0.1% and was cultured at 30° C. with shaking at 125 strokes/min. After 24 hours, cultured cells were recovered by centrifugation, and were re-suspended in 200 mL of M9 medium containing sodium pyruvate 0.5% and mFPxBA 0.1% but not containing inorganic nitrogen source NH$_4$Cl, then further shake cultured at 30° C., 125 strokes/min. After 24 hours, the cells were recovered by centrifugation, washed once with cold methanol and lyophilized.

The lyophilized pellet was suspended in chloroform 20 mL, and stirred at 60° C. for 20 hours to extract PHA. The extract was filtered using membrane filter, pore size 0.45 µm, concentrated using rotary evaporator, precipitated the concentrate with cold methanol, and recovered the precipitate to obtain PHA by vacuum drying.

The thus obtained PHA was subjected to methanolysis, and the product was analyzed using gas-chromatography mass spectrograph (GC-MS, Shimadzu QP-5050, EI method) to identify methyl esterified PHA monomer units. In Table 60, result of identification, and weight obtained and yield of the lyophilized pellet and the recovered polymer are shown. The thus obtained PHA is the PHA containing 3HmFPxB as a major monomer unit.

Example 53

Production of PHA Containing HFPxV Unit by Strain YN2 (One Step Culture Using Polypeptone)

The strain YN2 was inoculated in 200 mL of M9 medium containing polypeptone (Wako Pure Chemicals Co.) 0.5% and 5-(4-fluorophenoxy) valeric acid (FPxVA) 0.1% and was cultured at 30° C. with shaking at 125 strokes/min. After 27 hours, cells were recovered by centrifugation, washed once with cold methanol, lyophilized and were weighed.

The lyophilized pellet was suspended in chloroform 100 mL, and stirred at 60° C. for 20 hours to extract polymer. The extract was filtered using membrane filter, pore size 0.45 µm, concentrated using rotary evaporator, precipitated the concentrate with cold methanol, and recovered the precipitate to obtain the polymer by vacuum drying, then weighed as such.

Molecular weight of the obtained polymer was measured by means of gel-permeation chromatography (GPC: Toso, HLC-8020; Column: Polymer Laboratory, PL-gel, MIXED-C 5 µm; Solvent: chloroform; Molecular weight: reduced value for polystyrene).

Figure 24:
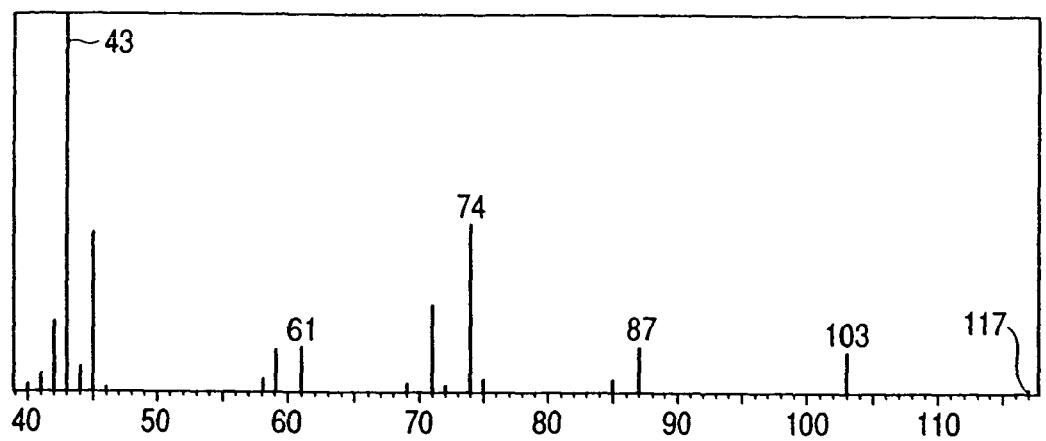
FIG. 24 is a chart which shows the mass spectrum of methyl 3-hydroxybutyrate obtained from the GC-MS measurement in Example 53.
Figure 25:
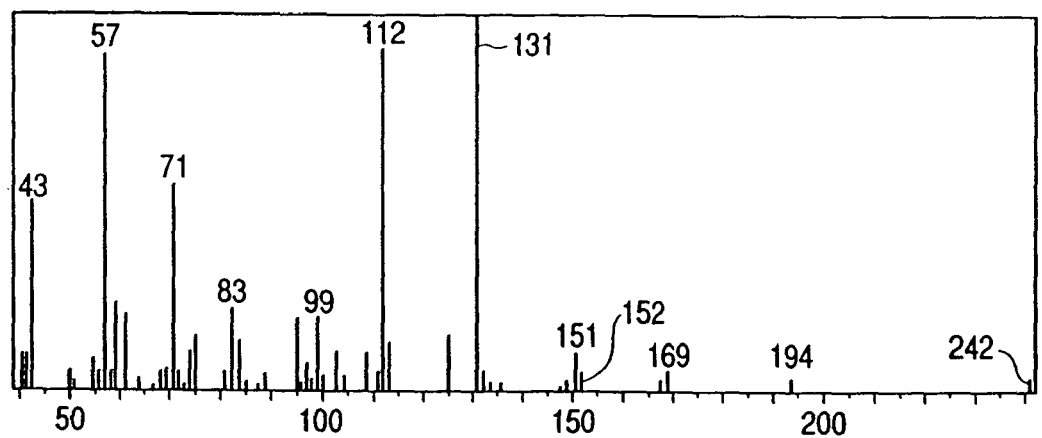
FIG. 25 is a chart which shows the mass spectrum of methyl 3-hydroxy-5-(4-fluorophenoxy)valerate obtained from the GC-MS measurement in Example 53.

Unit composition of the obtained polymer was analyzed by the following manner. The polymer sample 5 mg was poured into the 25 mL round-neck flask, and chloroform 2 mL and 2 mL of methanol containing sulfuric acid (3%, v/v). The mixture was refluxed at 100° C. for 3.5 hours, further added water thereto for separation. The organic layer was analyzed by means of gas-chromatography mass spectrograph (GC-MS, Shimadzu QP-5050, Column: DB-WAX-ETR (J & W Inc.), EI method) to identify methyl esterified PHA monomer unit. Yields of bacterial cells and polymer, molecular weight and analytical result of the monomer unit are shown in Table 61. Ratio of monomer unit was calculated by area ratio of GC-MS total ion chromatogram (TIC). Mass spectra obtained by GC-MS of 3-hydroxybutyric acid methyl ester and 3-hydroxy-5-(4-fluorophenoxy) valeric acid methyl ester are shown in FIG. 24 and FIG. 25.

Result indicates that PHA copolymer containing 3-hydroxy-5-(4-fluorophenoxy) valeric acid unit can be produced by the strain YN2 with a substrate 5-(4-fluorophenoxy) valeric acid.

Example 54

Production of PHA Containing HFPV Unit by Strain YN2 (One Step Culture Using Polypeptone)

The strain YN2 was inoculated in 200 mL of M9 medium containing polypeptone (Wako Pure Chemicals Co.) 0.5% and 5-(4-fluorophenyl) valeric acid (FPVA) 0.1% and was cultured at 30° C. with shaking at 125 strokes/min. After 27 hours, the cells were recovered by centrifugation, washed once with cold methanol, lyophilized and weighed.

The lyophilized pellet was suspended in chloroform 100 mL, and stirred at 60° C. for 20 hours to extract polymer. The extract was filtered using membrane filter, pore size 0.45 µm, concentrated using rotary evaporator, precipitated the concentrate with cold methanol, and recovered the precipitate to obtain the polymer by vacuum drying, then weighed as such.

Molecular weight of the obtained polymer was measured by means of gel-permeation chromatography (GPC: Toso, HLC-8020; Column: Polymer Laboratory, PL-gel, MIXED-C 5 µm; Solvent: chloroform; Molecular weight: reduced value for polystyrene).

Figure 26:
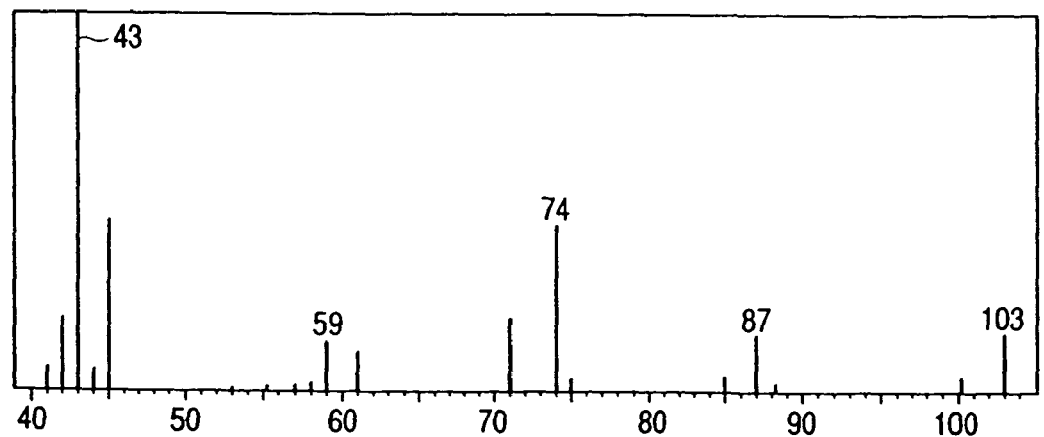
FIG. 26 is a chart which shows the mass spectrum of methyl 3-hydroxybutyrate obtained from the GC-MS measurement in Example 54.
Figure 27:
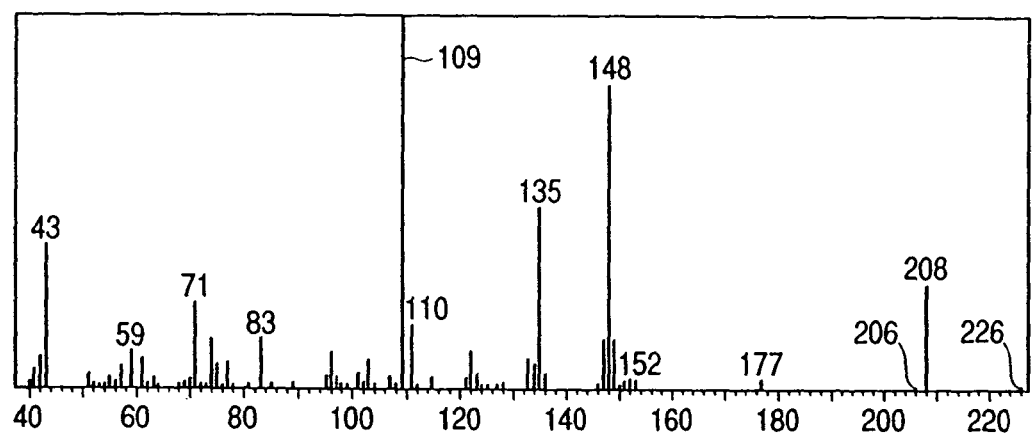
FIG. 27 is a chart which shows the mass spectrum of methyl 3-hydroxy-5-(4-fluorophenyl)valerate obtained from the GC-MS measurement in Example 54.

Unit composition of the obtained polymer was analyzed by the following manner. The polymer sample 5 mg was poured into the 25 mL round-neck flask, and chloroform 2 mL and 2 mL of methanol containing sulfuric acid (3%, v/v). The mixture was refluxed at 100° C. for 3.5 hours, further added water thereto for separation. The organic layer was analyzed by means of gas-chromatography mass spectrograph (GC-MS, Shimadzu QP-5050, Column: DB-WAX-ETR (J & W Inc.), EI method) to identify methyl esterified PHA monomer unit. Yields of bacterial cells and polymer, molecular weight and analytical result of the monomer unit are shown in Table 62. Ratio of monomer unit was calculated by area ratio of GC-MS total ion chromatogram (TIC). Mass spectra obtained by GC-MS of 3-hydroxybutyric acid methyl ester and 3-hydroxy-5-(4-fluorophenyl) valeric acid methyl ester are shown in FIG. 26 and FIG. 27.

Result indicates that PHA copolymer containing 3-hydroxy-5-(4-fluorophenyl) valeric acid unit can be produced by the strain YN2 with a substrate 5-(4-fluorophenyl) valeric acid.

Example 55

Production of PHA Containing HFPxV Unit by Strain YN2 (Two Step Culture Using Glucose)

The strain YN2 was inoculated in 200 mL of M9 medium containing glucose 0.5% and 5-(4-fluorophenoxy) valeric acid (FPxVA) 0.1% and was cultured at 30° C. with shaking at 125 strokes/min. After 24 hours, the cultured cells were recovered by centrifugation, and were re-suspended in 200 mL of M9 medium containing glucose 0.5% and FPxBA 0.1% but not containing nitrogen source ($NH_4Cl$), then further shake cultured at 30° C., 125 strokes/min. After 62 hours, the cells were recovered by centrifugation, washed once with cold methanol and lyophilized.

The lyophilized pellet was suspended in chloroform 100 mL, and stirred at 60° C. for 20 hours to extract polymer. The extract was filtered using membrane filter, pore size 0.45 µm, concentrated using rotary evaporator, precipitated the concentrate with cold methanol, and recovered the precipitate to obtain PHA by vacuum drying.

Molecular weight of the obtained polymer was measured by means of gel-permeation chromatography (GPC: Toso, HLC-8020; Column: Polymer Laboratory, PL-gel, MIXED-C 5 µm; Solvent: chloroform; Molecular weight: reduced value for polystyrene).

Figure 28:
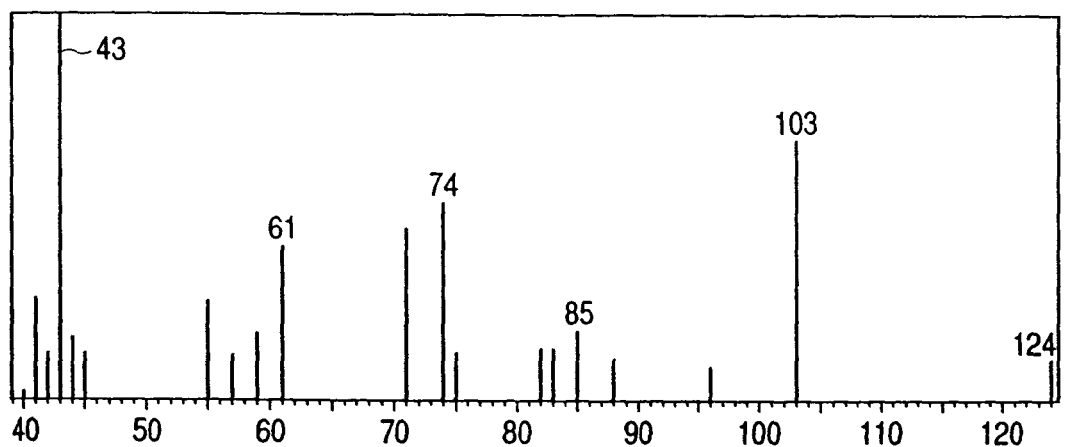
FIG. 28 is a chart which shows the mass spectrum of methyl 3-hydroxyoctanoate obtained from the GC-MS measurement in Example 55.
Figure 29:
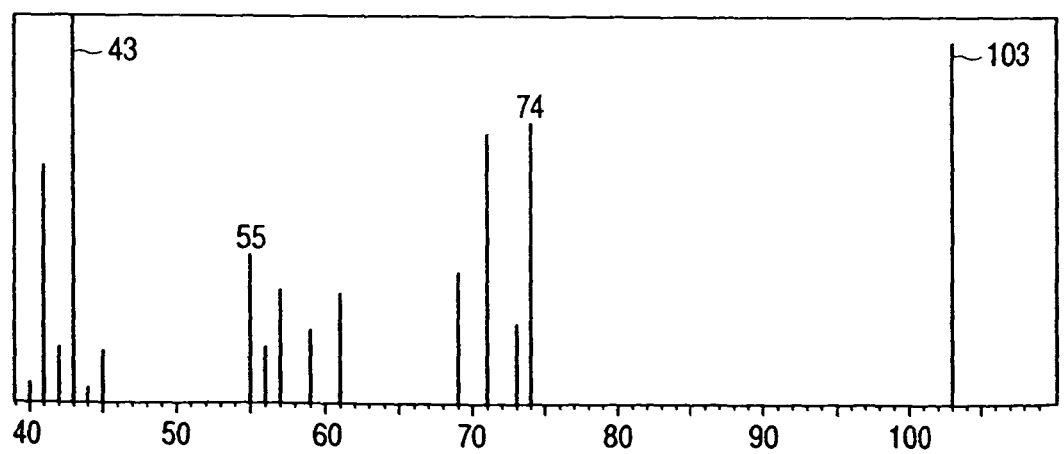
FIG. 29 is a chart which shows the mass spectrum of methyl 3-hydroxydecanoate obtained from the GC-MS measurement in Example 55.
Figure 30:
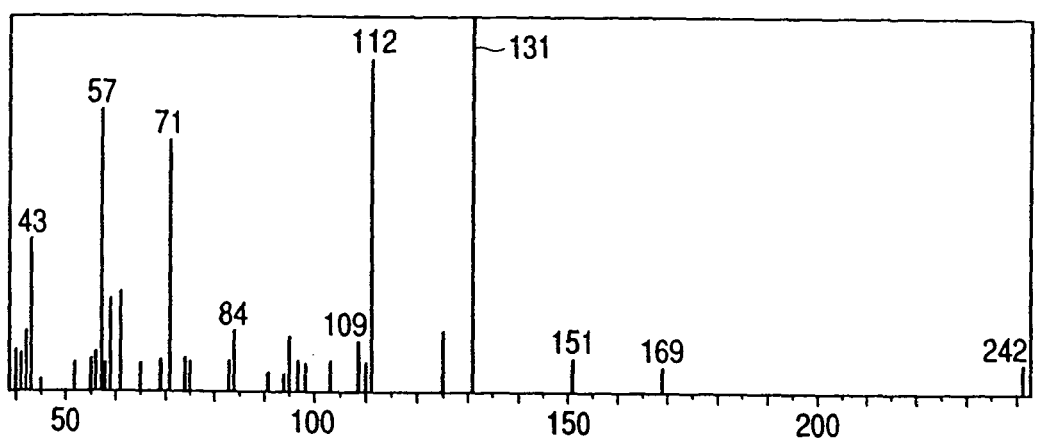
FIG. 30 is a chart which shows the mass spectrum of methyl 3-hydroxy-5-(4-fluorophenoxy)valerate (3HFPxV) obtained from the GC-MS measurement in Example 55.

Unit composition of the obtained polymer was analyzed by the following manner. The polymer sample 5 mg was poured into the 25 mL round-neck flask, and chloroform 2 mL and 2 mL of methanol containing sulfuric acid (3%, v/v). The mixture was refluxed at 100° C. for 3.5 hours, further added water thereto for separation. The organic layer was analyzed by means of gas-chromatography mass spectrograph (GC-MS, Shimadzu QP-5050, Column: DB-WAX-ETR (J & W Inc.), EI method) to identify methyl esterified PHA monomer unit. Yields of bacterial cells and polymer, and analytical result of the monomer unit are shown in Table 63. Mass spectra obtained by GC-MS of 3-hydroxyoctanoic acid methyl ester, 3-hydroxydecanoic acid methyl ester and 3-hydroxy-5-(4-fluorophenoxy) valeric acid (3HFPxV) methyl ester obtained by GC-MS measurement are shown in FIG. 28 to FIG. 30.

Result indicates that PHA copolymer containing 3-hydroxy-5-(4-fluorophenoxy) valeric acid (3HFPxV) unit can be produced by the strain YN2 with a substrate 5-(4-fluorophenoxy) valeric acid.

Example 56

Production of PHA Containing HFPV Unit by Strain YN2 (Two Step Culture Using Glucose)

The strain YN2 was inoculated in 200 mL of M9 medium containing glucose 0.5% and 5-(4-fluorophenyl) valeric acid (FPVA) 0.1% and was cultured at 30° C. with shaking at 125 strokes/min. After 24 hours, the cultured cells were recovered by centrifugation, and were re-suspended in 200 mL of M9 medium containing glucose 0.5% and FPxVA 0.1% but not containing the nitrogen source ($NH_4Cl$), then further shake cultured at 30° C. in 125 strokes/min. After 62 hours, the cells were recovered by centrifugation, washed once with cold methanol and lyophilized.

The lyophilized pellet was suspended in chloroform 100 mL, and stirred at 60° C. for 20 hours to extract polymer. The extract was filtered using membrane filter, pore size 0.45 µm, concentrated using rotary evaporator, precipitated the concentrate with cold methanol, and recovered the precipitate to obtain PHA by vacuum drying.

Molecular weight of the obtained polymer was measured by means of gel-permeation chromatography (GPC: Toso, HLC-8020; Column: Polymer Laboratory, PL-gel, MIXED-C 5 µm; Solvent: chloroform; Molecular weight: reduced value for polystyrene).

Figure 31:
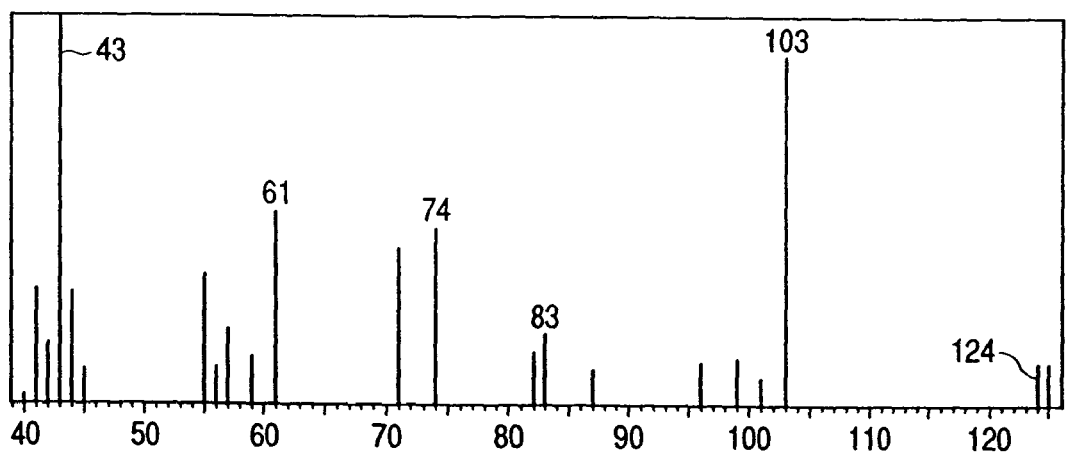
FIG. 31 is a chart which shows the mass spectrum of methyl 3-hydroxyoctanoate obtained from the GC-MS measurement in Example 56.
Figure 32:
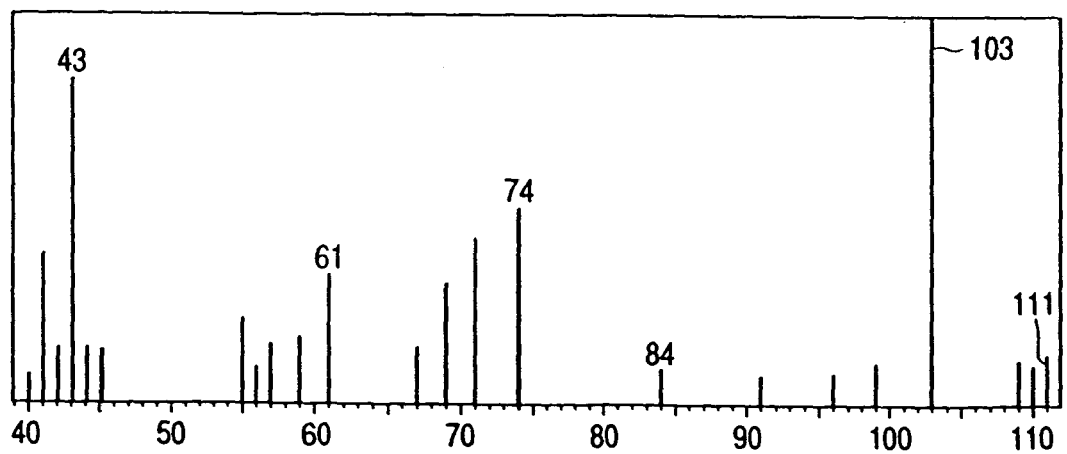
FIG. 32 is a chart which shows the mass spectrum of methyl 3-hydroxydecanoate obtained from the GC-MS measurement in Example 56.
Figure 33:
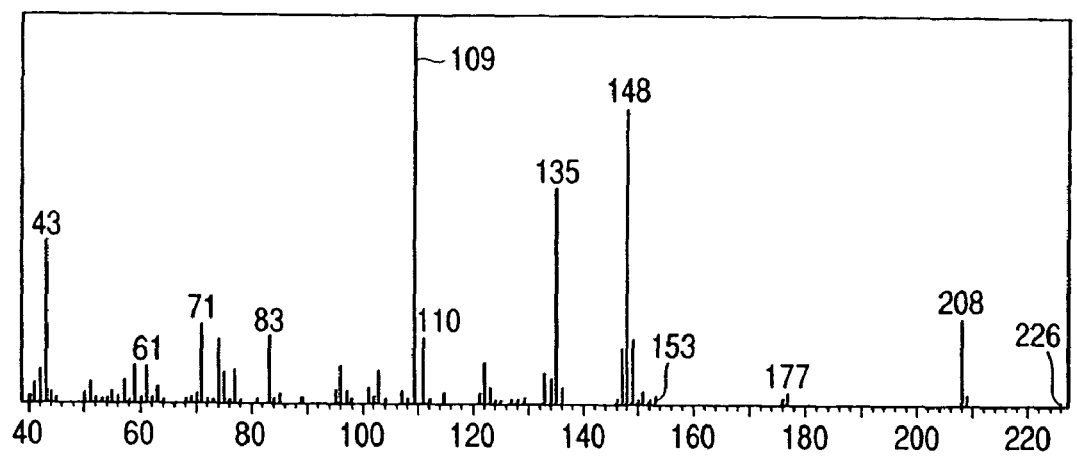
FIG. 33 is a chart which shows the mass spectrum of methyl 3-hydroxy-5-(4-fluorophenyl)valerate (3HFPV) obtained from the GC-MS measurement in Example 56.
Figure 34:
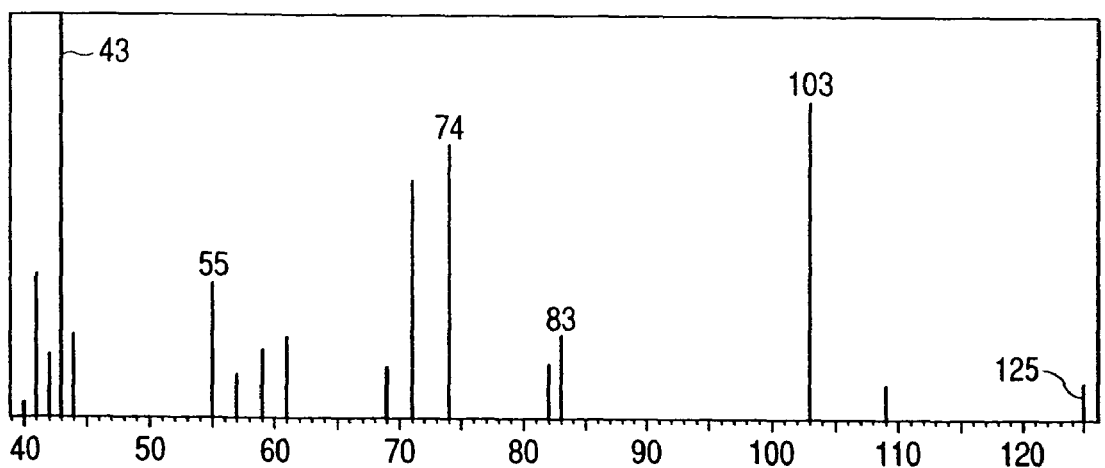
FIG. 34 is a chart which shows the mass spectrum of methyl 3-hydroxyoctanoate obtained from the GC-MS measurement in Example 57.
Figure 35:
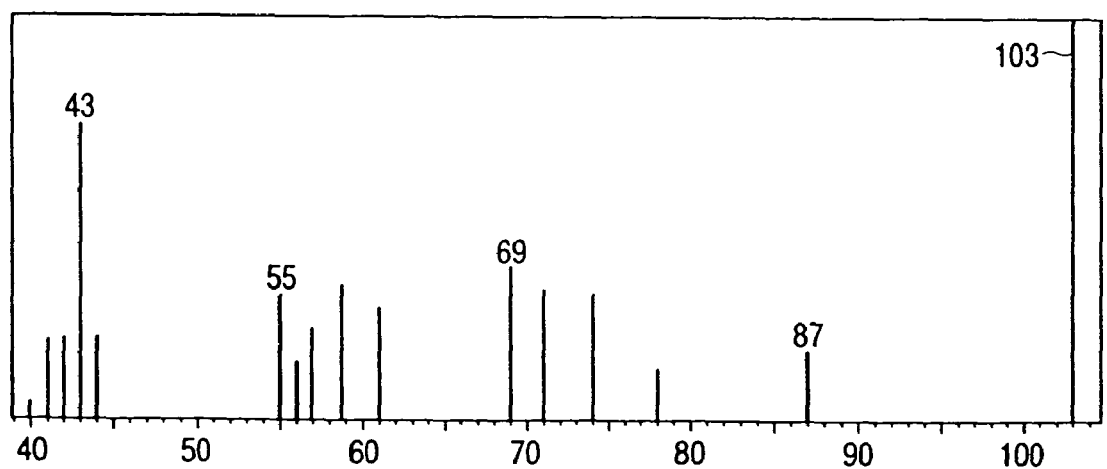
FIG. 35 is a chart which shows the mass spectrum of methyl 3-hydroxydecanoate obtained from the GC-MS measurement in Example 57.
Figure 36:
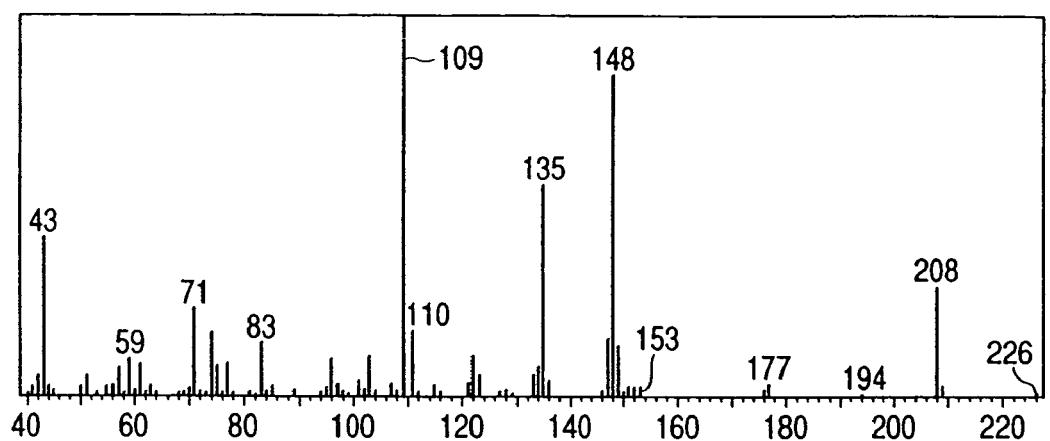
FIG. 36 is a chart which shows the mass spectrum of methyl 3-hydroxy-5-(4-fluorophenyl)valerate (3HFPV) obtained from the GC-MS measurement in Example 57.
Figure 37:
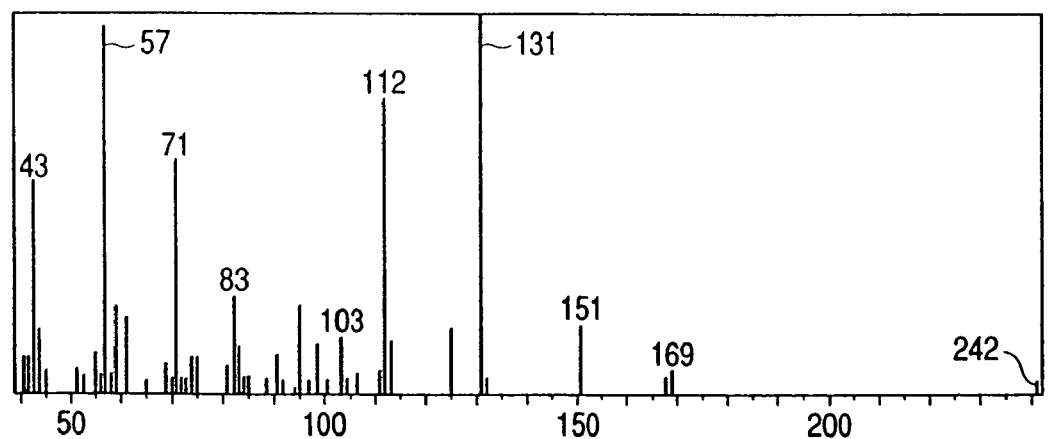
FIG. 37 is a chart which shows the mass spectrum of methyl 3-hydroxy-5-(4-fluorophenoxy)valerate (3HFPxV) obtained from the GC-MS measurement in Example 57.
Figure 38:
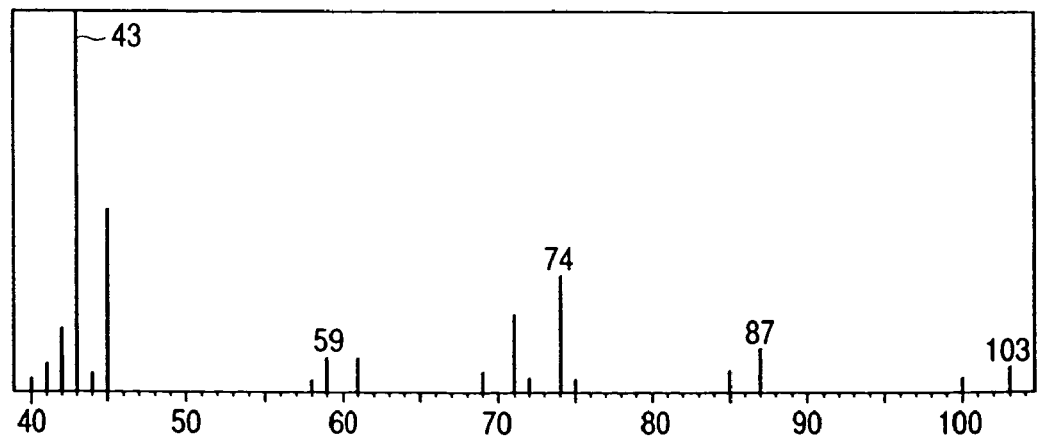
FIG. 38 is a chart which shows the mass spectrum of methyl 3-hydroxybutyrate obtained from the GC-MS measurement in Example 58.
Figure 39:
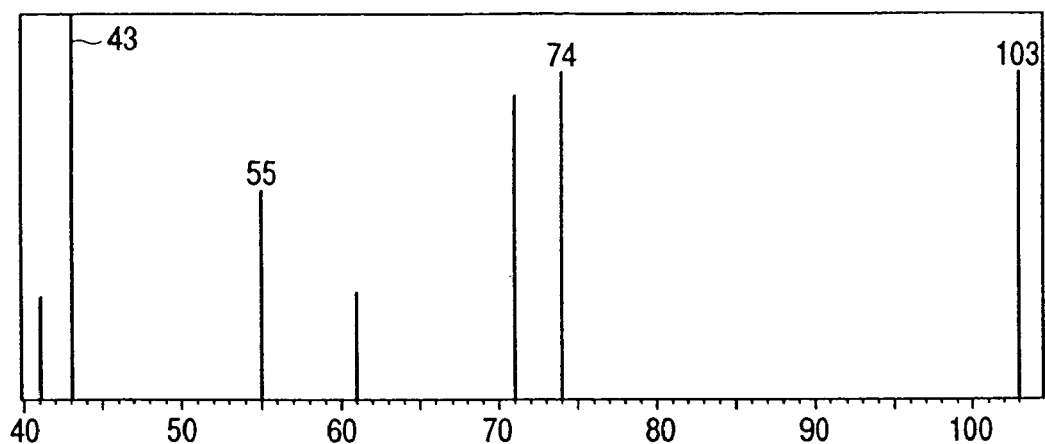
FIG. 39 is a chart which shows the mass spectrum of methyl 3-hydroxyoctanoate obtained from the GC-MS measurement in Example 58.
Figure 40:
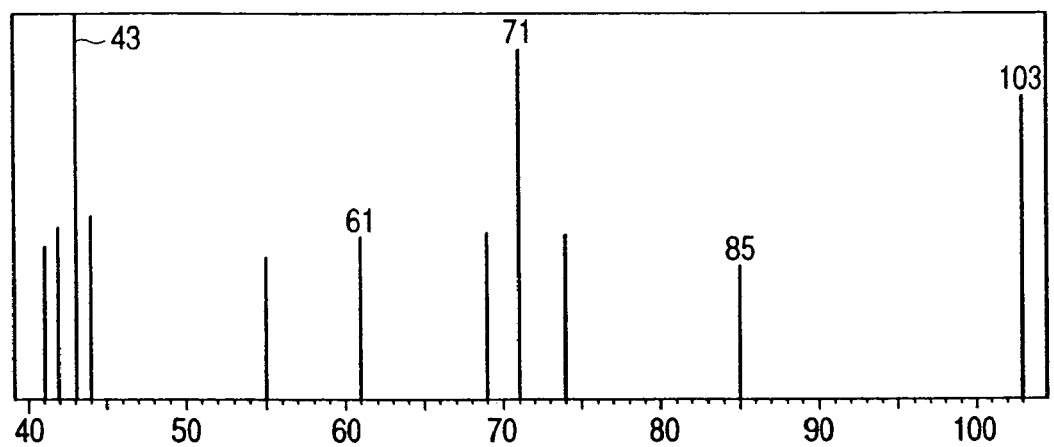
FIG. 40 is a chart which shows the mass spectrum of methyl 3-hydroxydecanoate obtained from the GC-MS measurement in Example 58.
Figure 41:
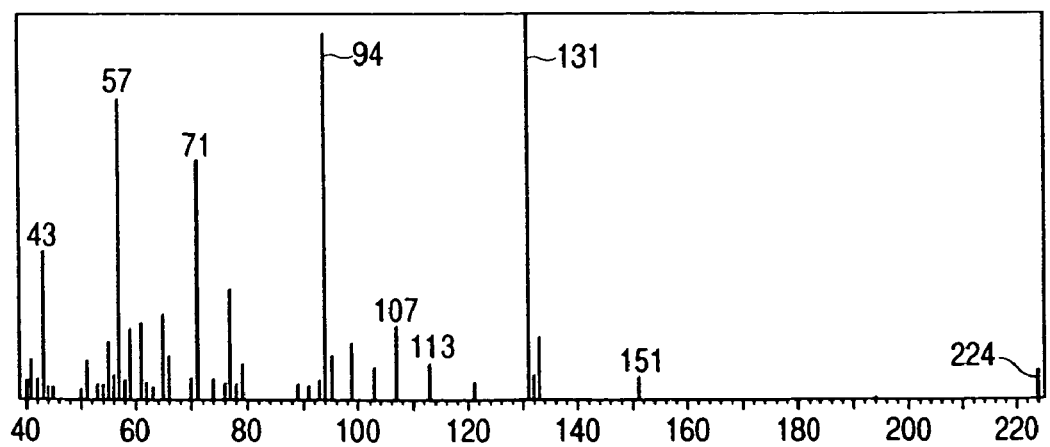
FIG. 41 is a chart which shows the mass spectrum of methyl 3-hydroxy-5-phenoxyvalerate (3HPxV) obtained from the CG-MS measurement in Example 58.
Figure 42:
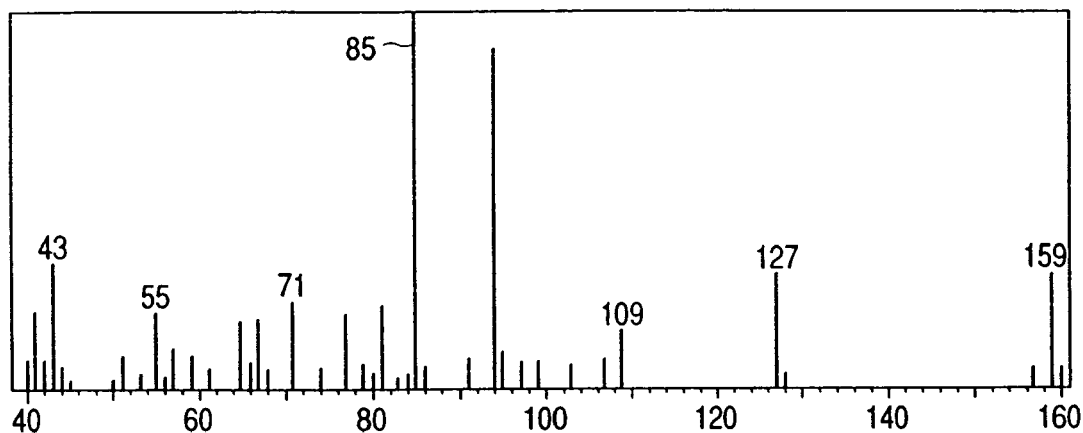
FIG. 42 is a chart which shows the mass spectrum of methyl 3-hydroxy-7-phenoxyheptanoate (3HPxHp) obtained from the GC-MS measurement in Example 58.
Figure 43:
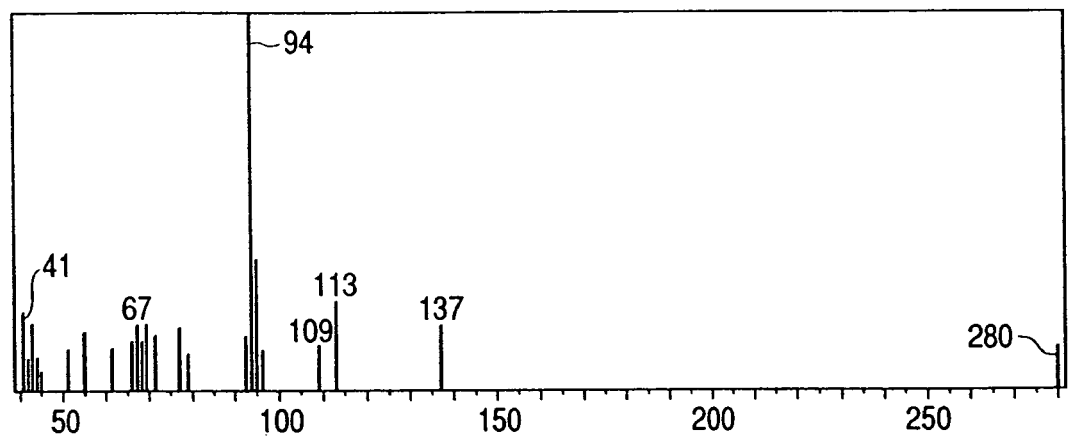
FIG. 43 is a chart which shows the mass spectrum of methyl 3-hydroxy-9-phenoxynonanoate (3HPxN) obtained from the GC-MS measurement in Example 58.
Figure 44:
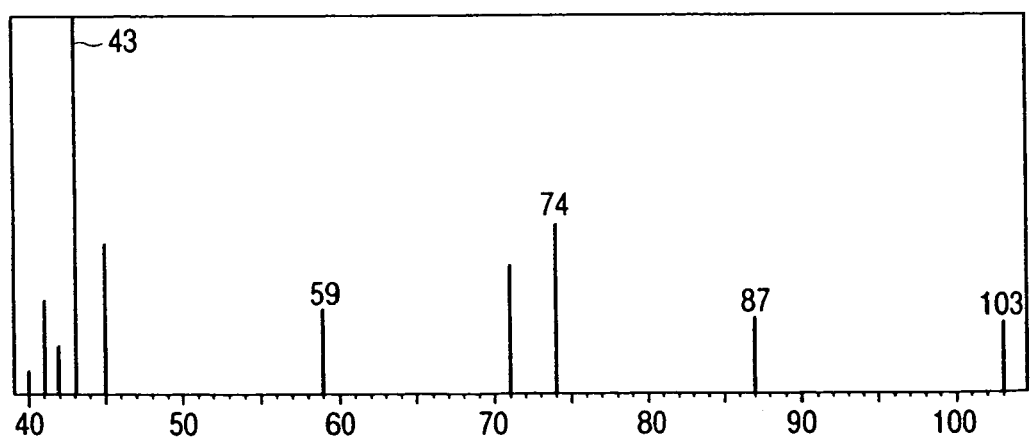
FIG. 44 is a chart which shows the mass spectrum of methyl 3-hydroxybutyrate obtained from the GC-MS measurement in Example 59.
Figure 45:
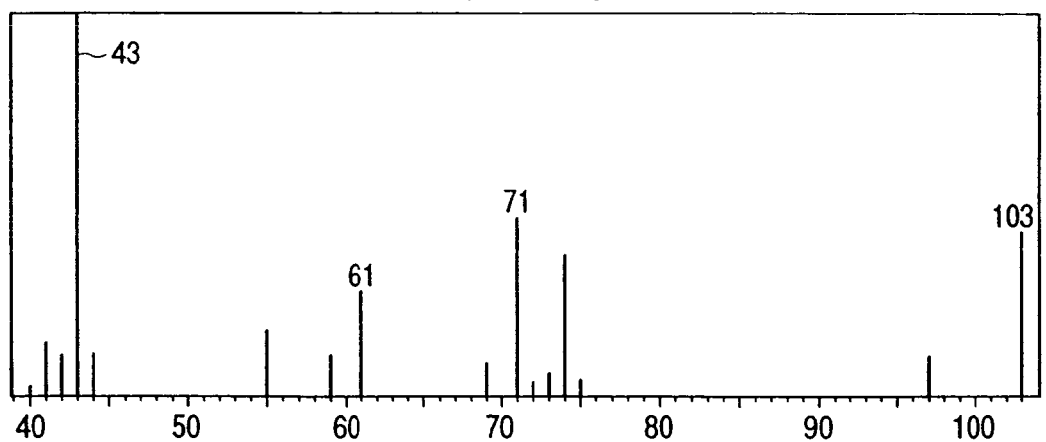
FIG. 45 is a chart which shows the mass spectrum of methyl 3-hydroxyhexanoate obtained from the GC-MS measurement in Example 59.
Figure 46:
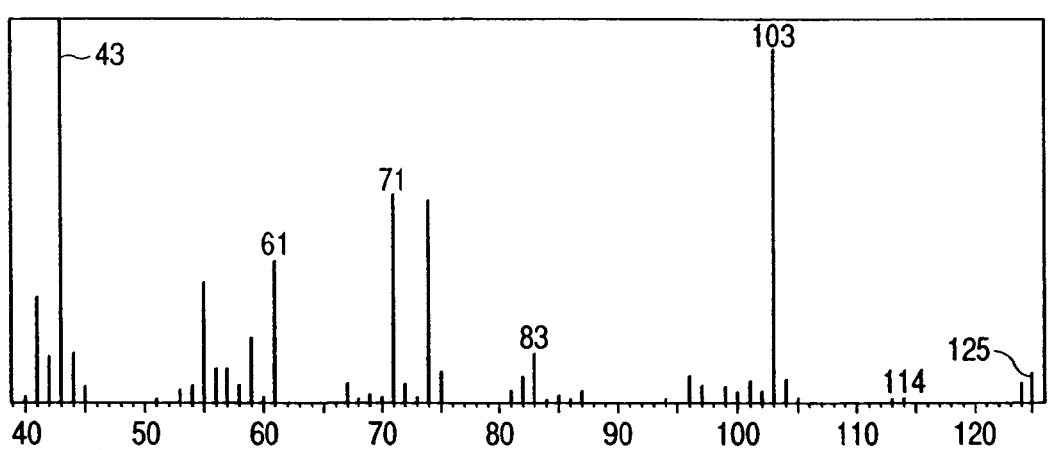
FIG. 46 is a chart which shows the mass spectrum of methyl 3-hydroxyoctanoate obtained from the GC-MS measurement in Example 59.
Figure 47:
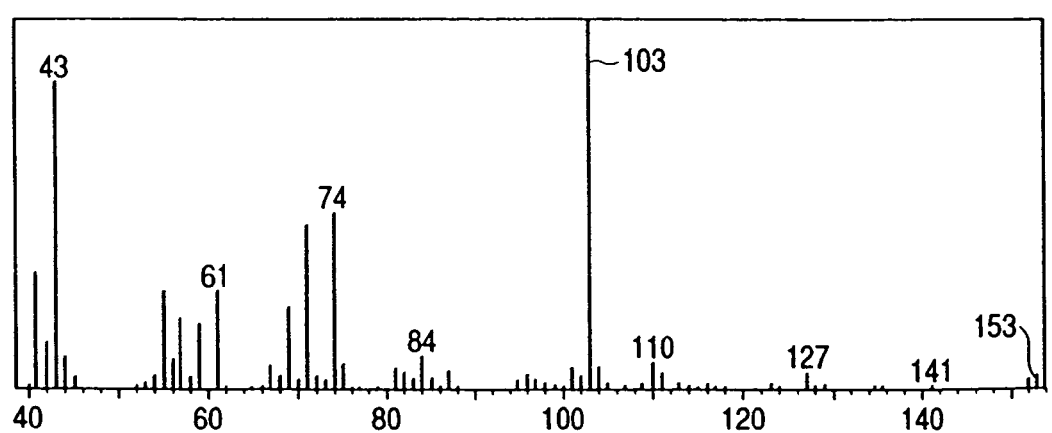
FIG. 47 is a chart which shows the mass spectrum of methyl 3-hydroxydecanoate obtained from the GC-MS measurement in Example 59.
Figure 48:
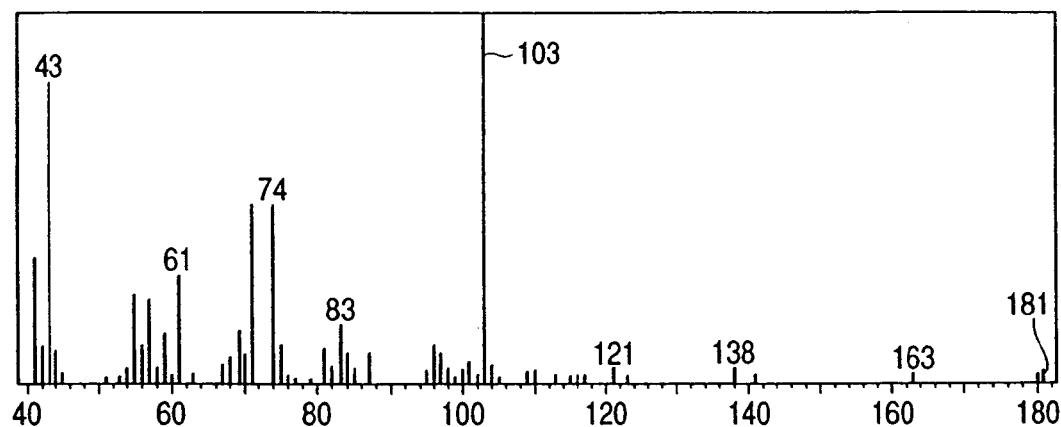
FIG. 48 is a chart which shows the mass spectrum of methyl 3-hydroxydodecanoate obtained from the GC-MS measurement in Example 59.
Figure 49:
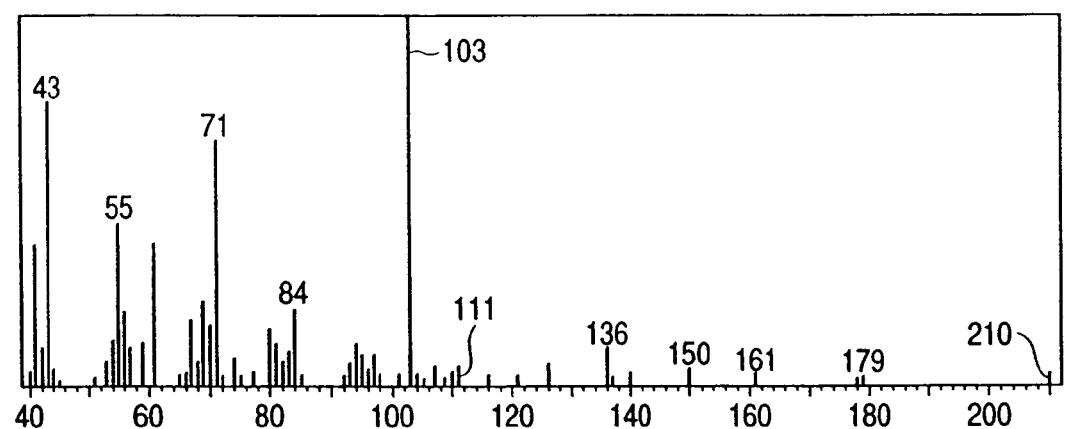
FIG. 49 is a chart which shows the mass spectrum of methyl 3-hydroxydodecenoate obtained from the GC-MS measurement in Example 59.
Figure 50:
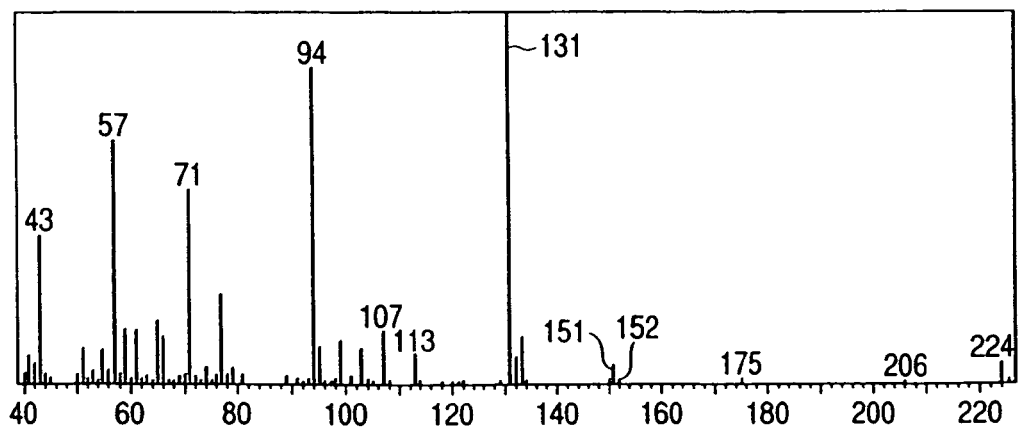
FIG. 50 is a chart which shows the mass spectrum of methyl 3-hydroxy-5-phenoxyvalerate (3HPxV) obtained from the GC-MS measurement in Example 59.
Figure 51:
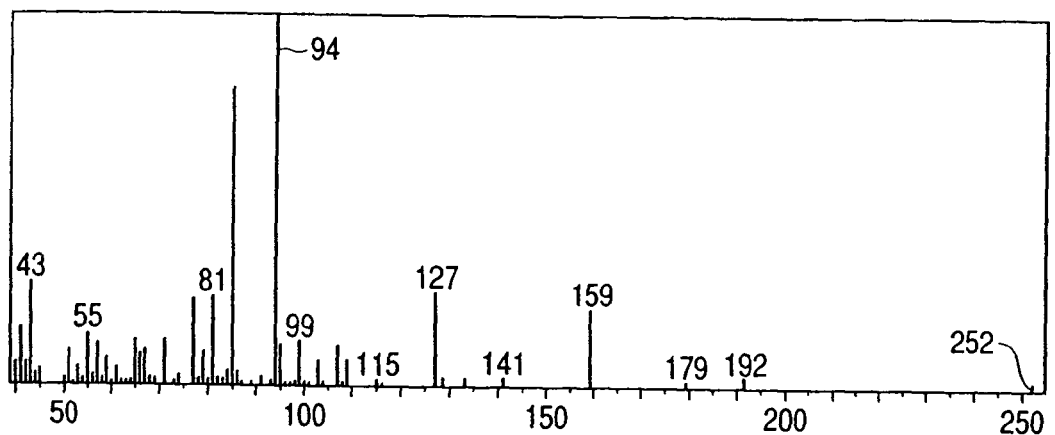
FIG. 51 is a chart which shows the mass spectrum of methyl 3-hydroxy-7-phenoxyheptanoate (3HPxHp) obtained from the GC-MS measurement in Example 59.
Figure 52:
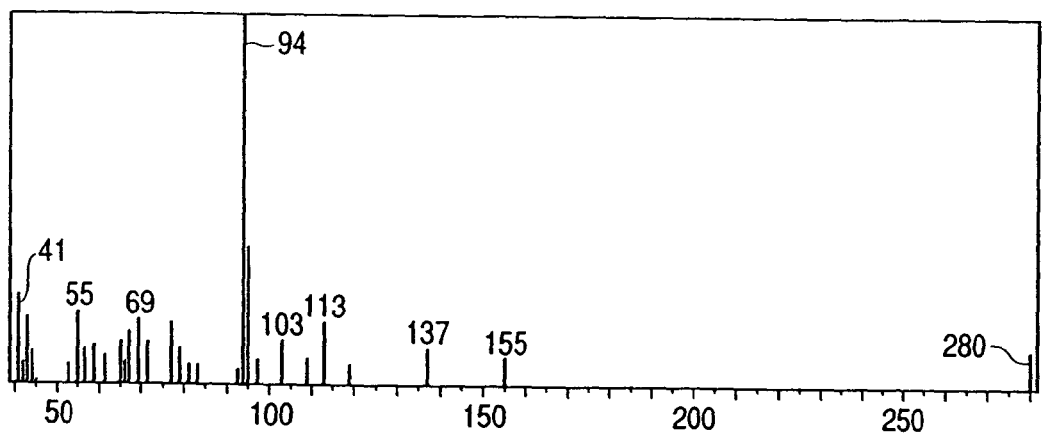
FIG. 52 is a chart which shows the mass spectrum of methyl 3-hydroxy-9-phenoxynonanoate (3HPxN) obtained from the GC-MS measurement in Example 59.
Figure 53:
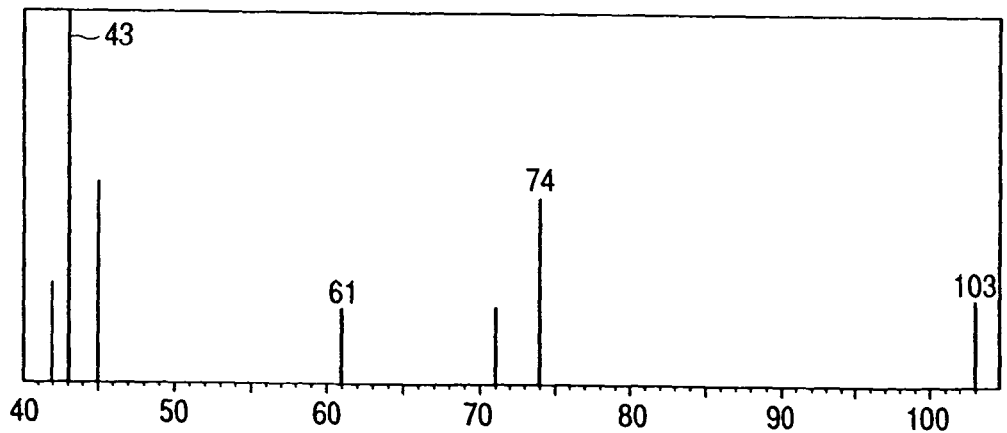
FIG. 53 is a chart which shows the mass spectrum of methyl 3-hydroxybutyrate obtained from the GC-MS measurement in Example 60.
Figure 54:
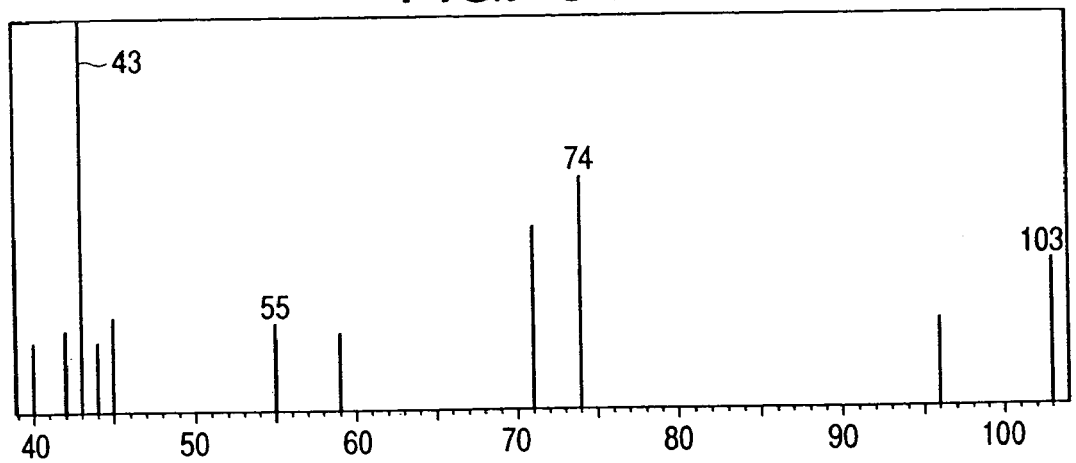
FIG. 54 is a chart which shows the mass spectrum of methyl 3-hydroxy-hexanoate obtained from the GC-MS measurement in Example 60.
Figure 55:
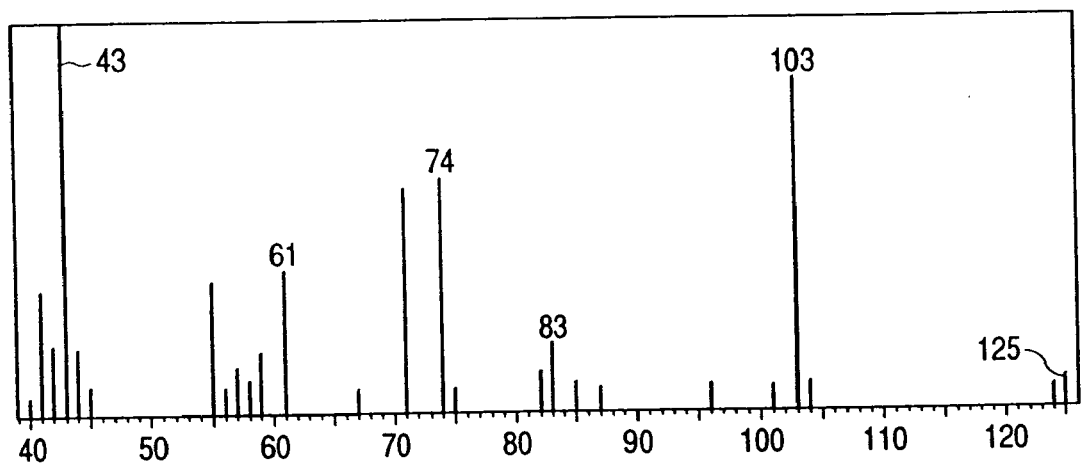
FIG. 55 is a chart which shows the mass spectrum of methyl 3-hydroxyoctanoate obtained from the GC-MS measurement in Example 60.
Figure 56:
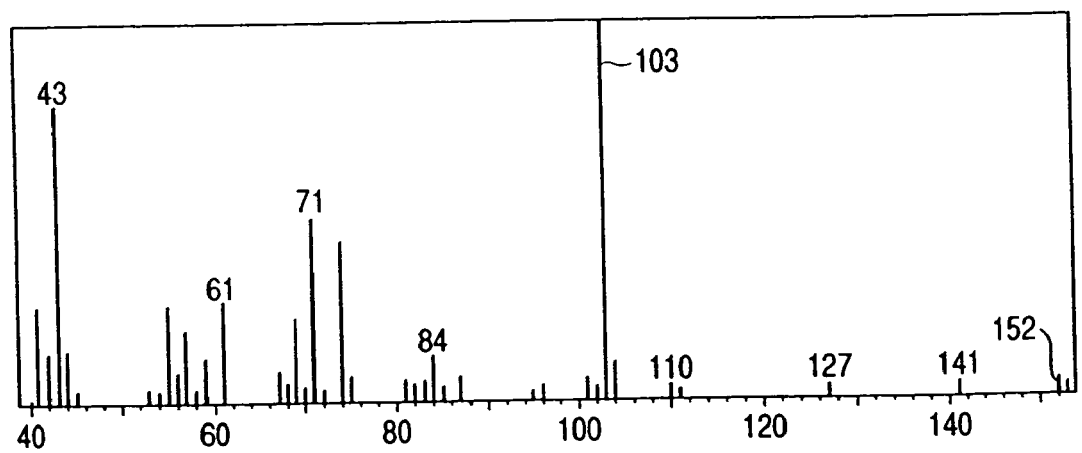
FIG. 56 is a chart which shows the mass spectrum of methyl 3-hydroxydecanoate obtained from the GC-MS measurement in Example 60.
Figure 57:
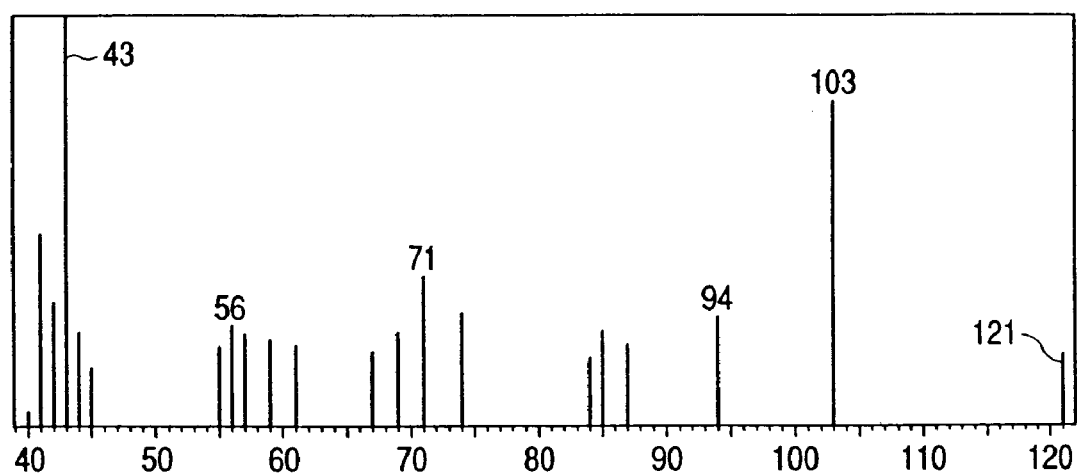
FIG. 57 is a chart which shows the mass spectrum of methyl 3-hydroxydodecanoate obtained from the GC-MS measurement in Example 60.
Figure 58:
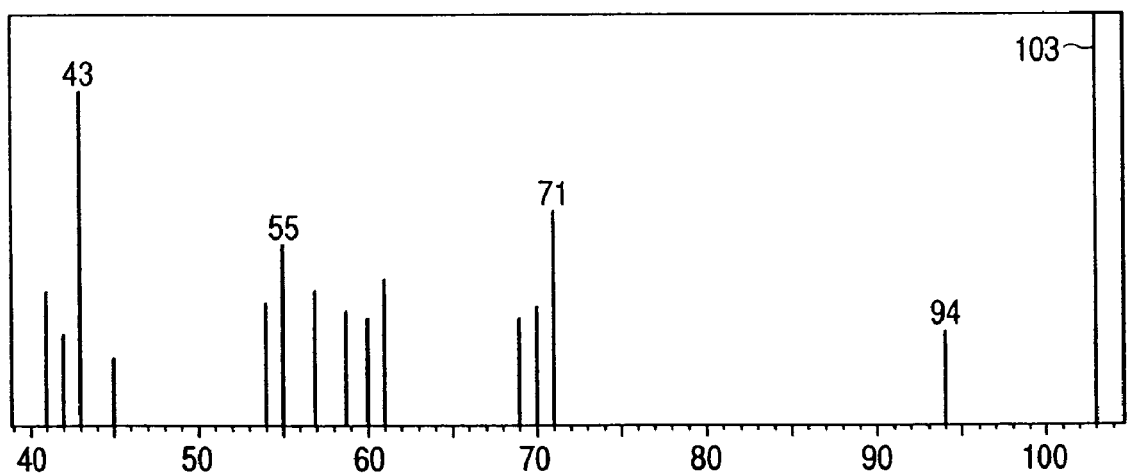
FIG. 58 is a chart which shows the mass spectrum of methyl 3-hydroxydodecenoate obtained from the GC-MS measurement in Example 60.
Figure 59:
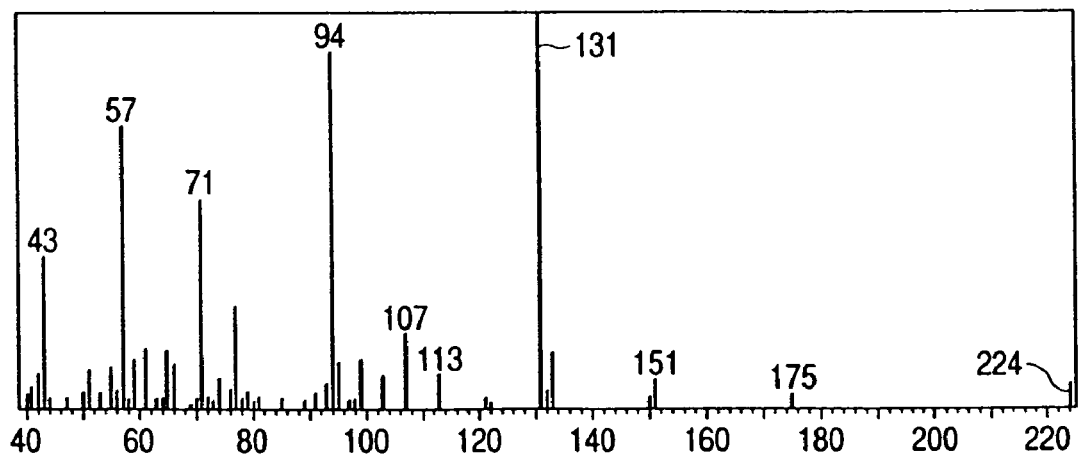
FIG. 59 is a chart which shows the mass spectrum of methyl 3-hydroxy-5-phenoxyvalerate (3HPxV) obtained from the GC-MS measurement in Example 60.
Figure 60:
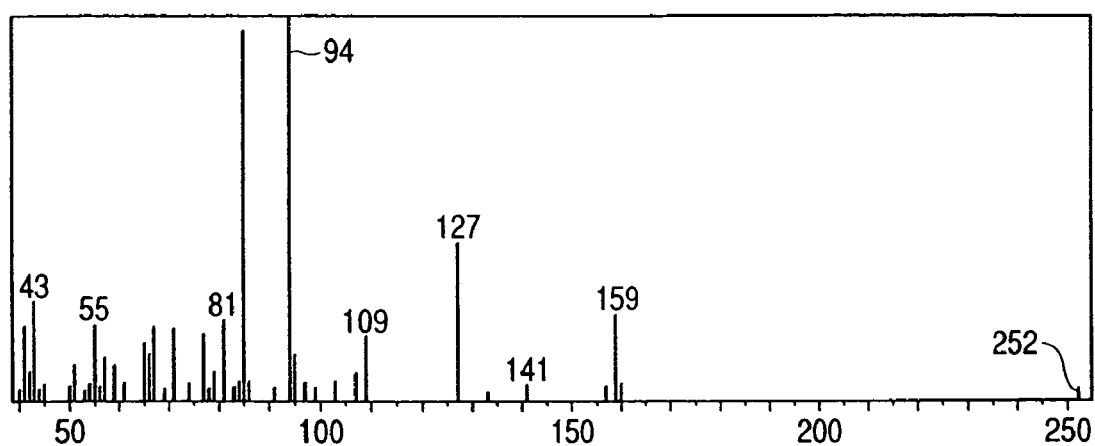
FIG. 60 is a chart which shows the mass spectrum of methyl 3-hydroxy-7-phenoxyheptanoate (3HPxHp) obtained from the GC-MS measurement in Example 60.
Figure 61:
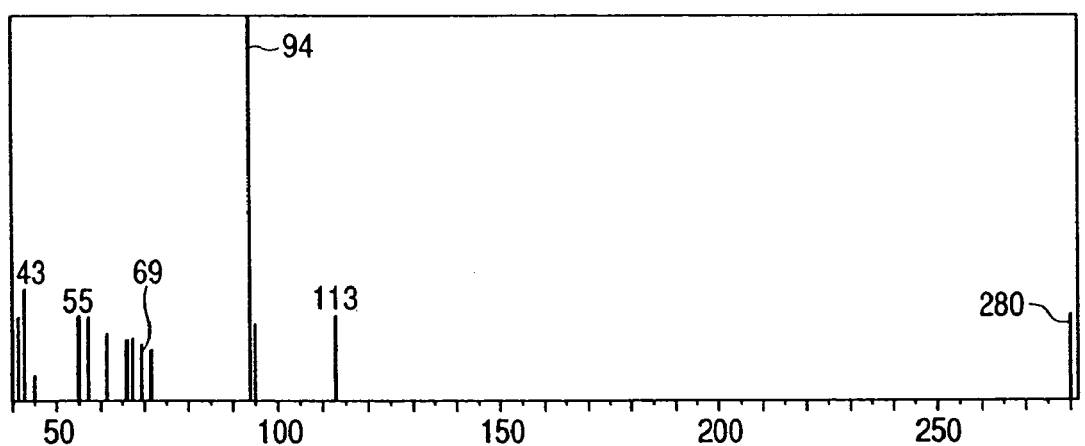
FIG. 61 is a chart which shows the mass spectrum of methyl 3-hydroxy-9-phenoxynonanoate (3HPxN) obtained from the GC-MS measurement in Example 60.
Figure 62:
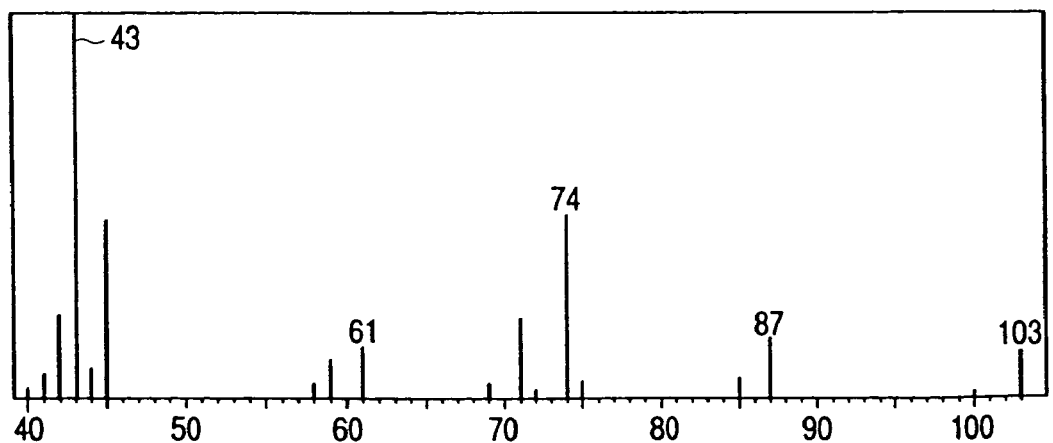
FIG. 62 is a chart which shows the mass spectrum of methyl 3-hydroxybutyrate obtained from the GC-MS measurement in Example 61.
Figure 63:
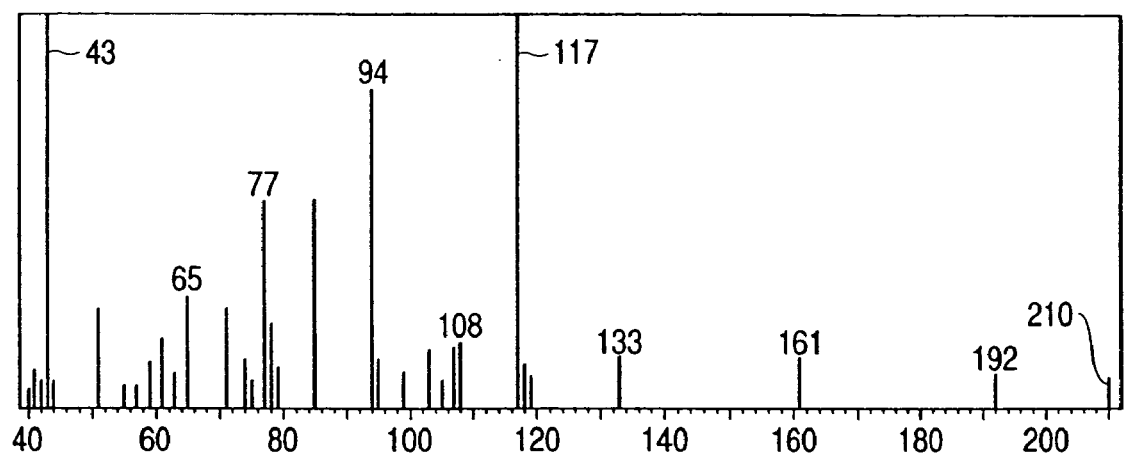
FIG. 63 is a chart which shows the mass spectrum of methyl 3-hydroxy-4-phenoxybutyrate (3HPxB) obtained from the GC-MS measurement in Example 61.
Figure 64:
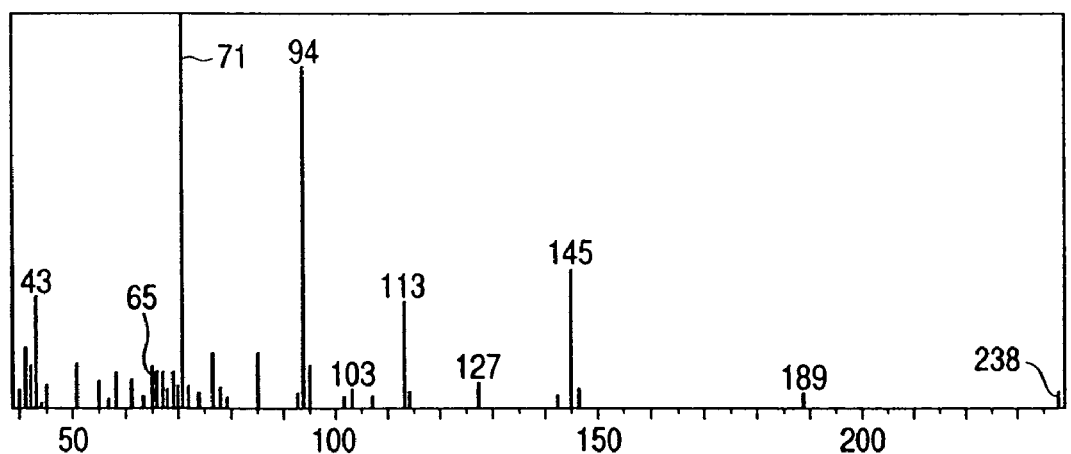
FIG. 64 is a chart which shows the mass spectrum of methyl 3-hydroxy-6-phenoxyhexanoate (3HPxHx) obtained from the GC-MS measurement in Example 61.
Figure 65:
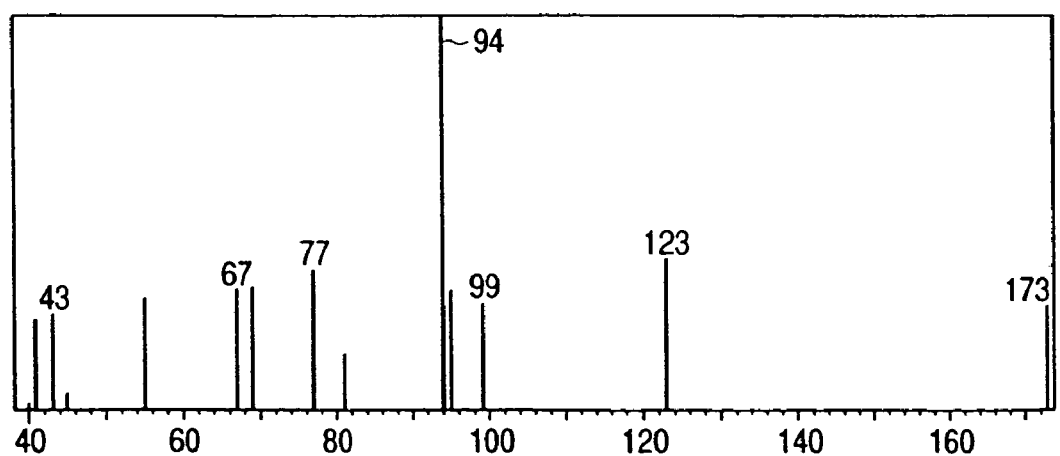
FIG. 65 is a chart which shows the mass spectrum of methyl 3-hydroxy-8-phenoxyoctanoate (3HPxO) obtained from the GC-MS measurement in Example 61.
Figure 66:
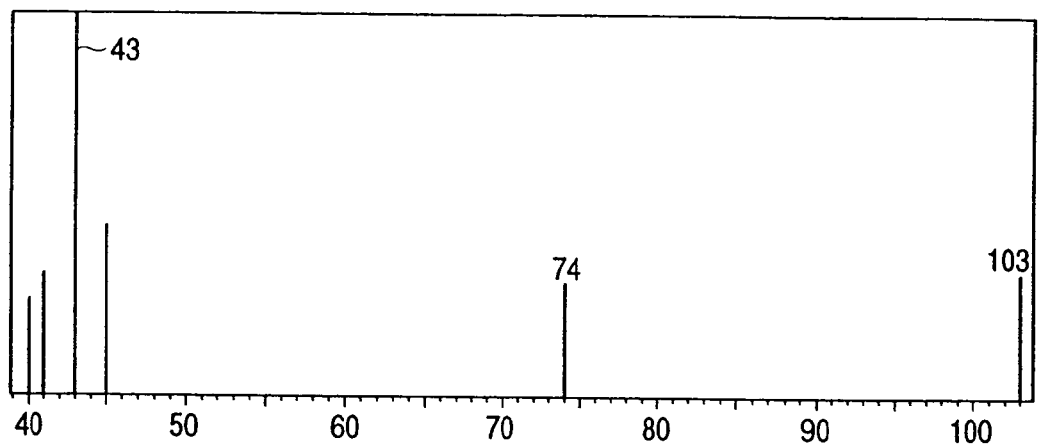
FIG. 66 is a chart which shows the mass spectrum of methyl 3-hydroxybutyrate obtained from the GC-MS measurement in Example 62.
Figure 67:
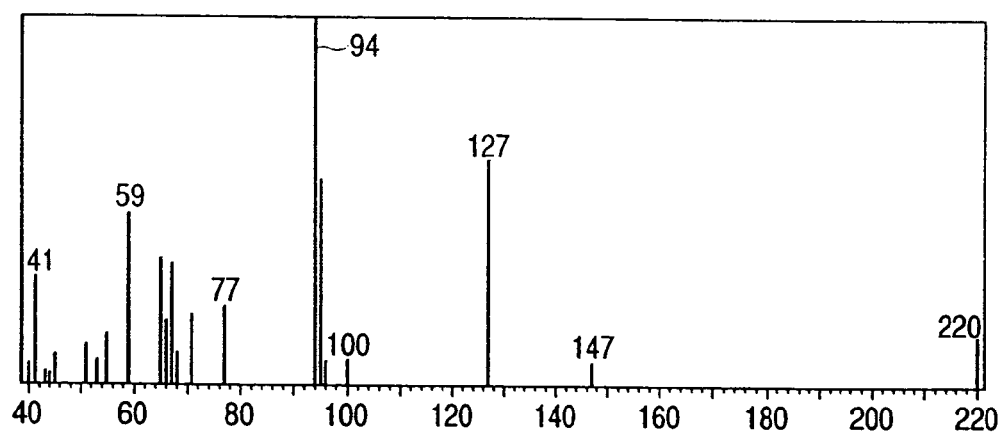
FIG. 67 is a chart which shows the mass spectrum of methyl 3-hydroxy-4-phenoxybutyrate (3HPxB) obtained from the GC-MS measurement in Example 62.
Figure 68:
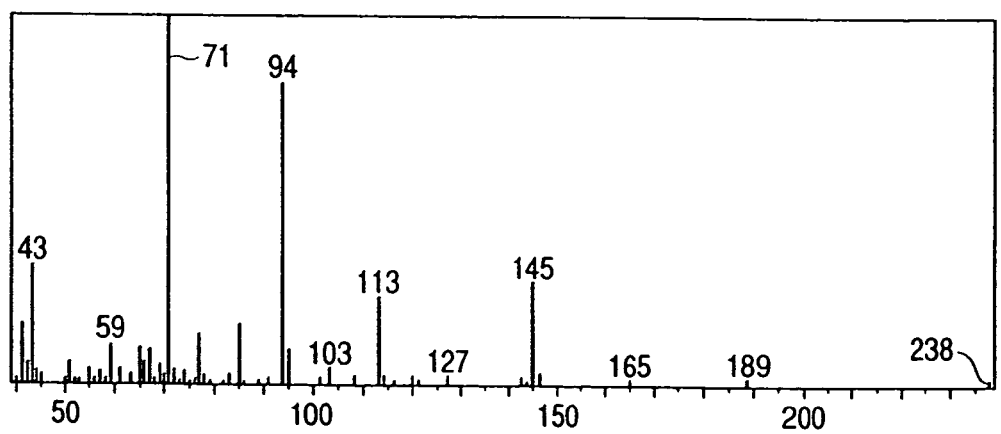
FIG. 68 is a chart which shows the mass spectrum of methyl 3-hydroxy-6-phenoxyhexanoate (3HPxHx) obtained from the GC-MS measurement in Example 62.
Figure 69:
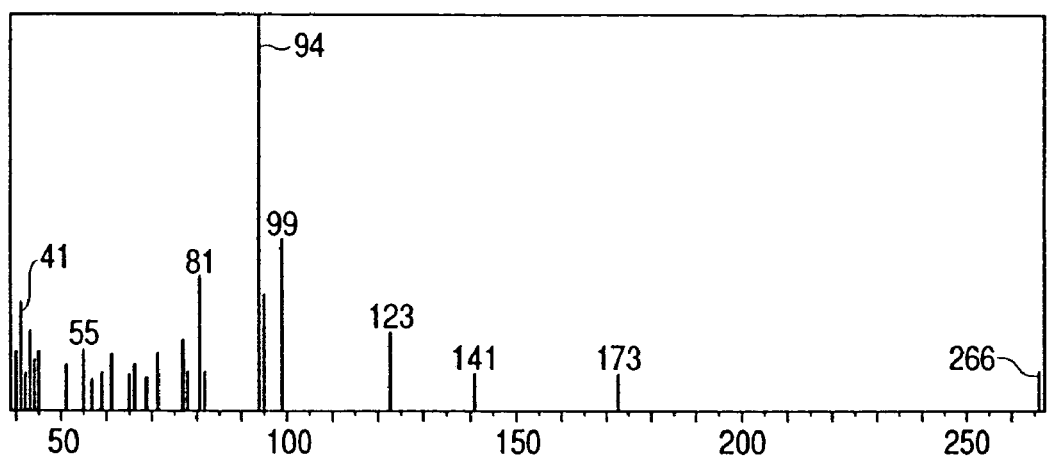
FIG. 69 is a chart which shows the mass spectrum of methyl 3-hydroxy-8-phenoxyoctanoate (3HPxO) obtained from the GC-MS measurement in Example 62.
Figure 70:
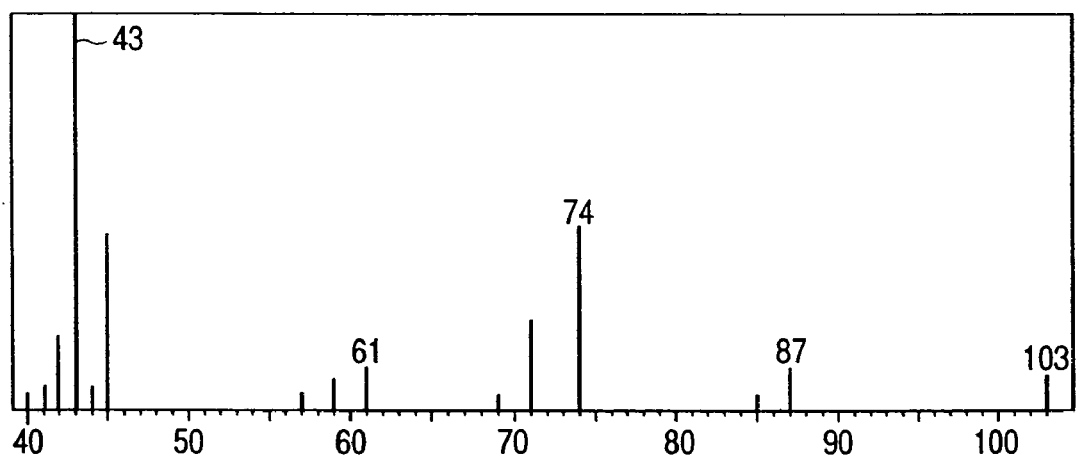
FIG. 70 is a chart which shows the mass spectrum of methyl 3-hydroxybutyrate obtained from the GC-MS measurement in Example 63.
Figure 71:
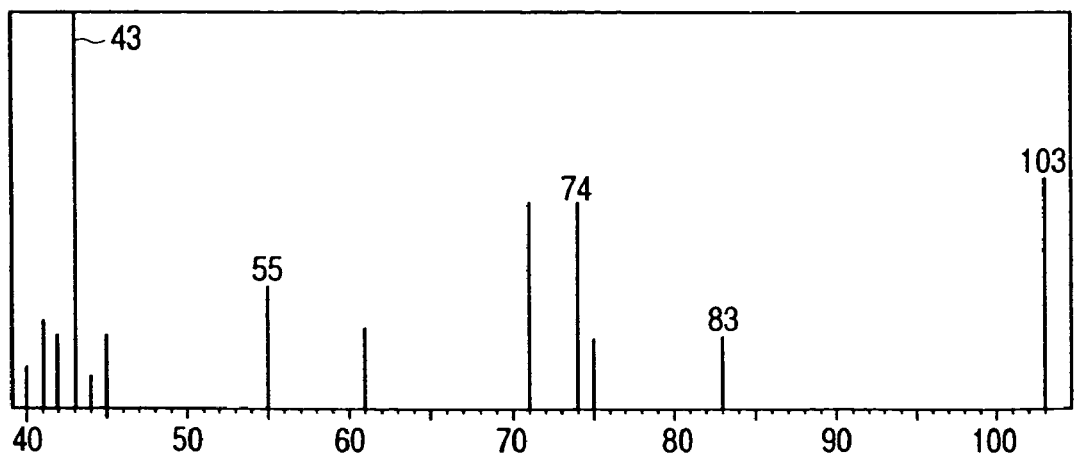
FIG. 71 is a chart which shows the mass spectrum of methyl 3-hydroxy-octanoate obtained from the GC-MS measurement in Example 63.
Figure 72:
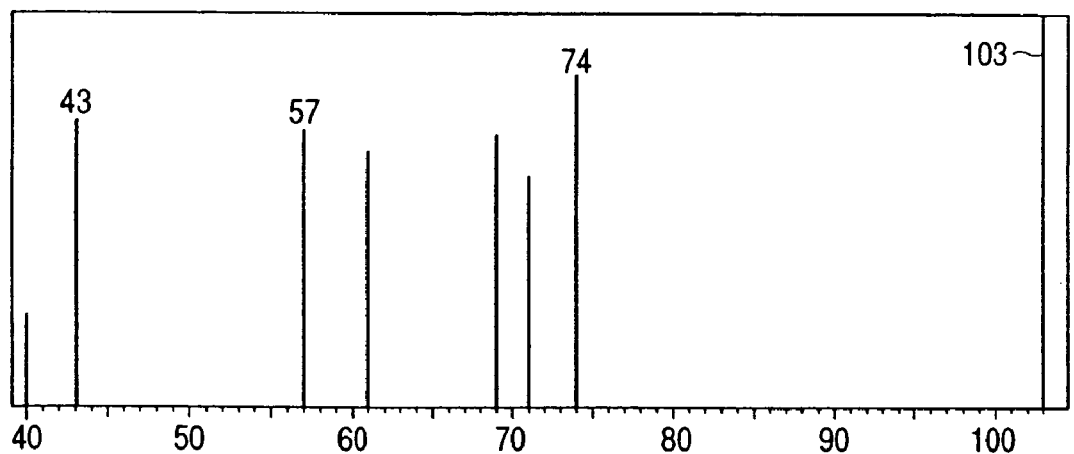
FIG. 72 is a chart which shows the mass spectrum of methyl 3-hydroxydecanoate obtained from the GC-MS measurement in Example 63.
Figure 73:
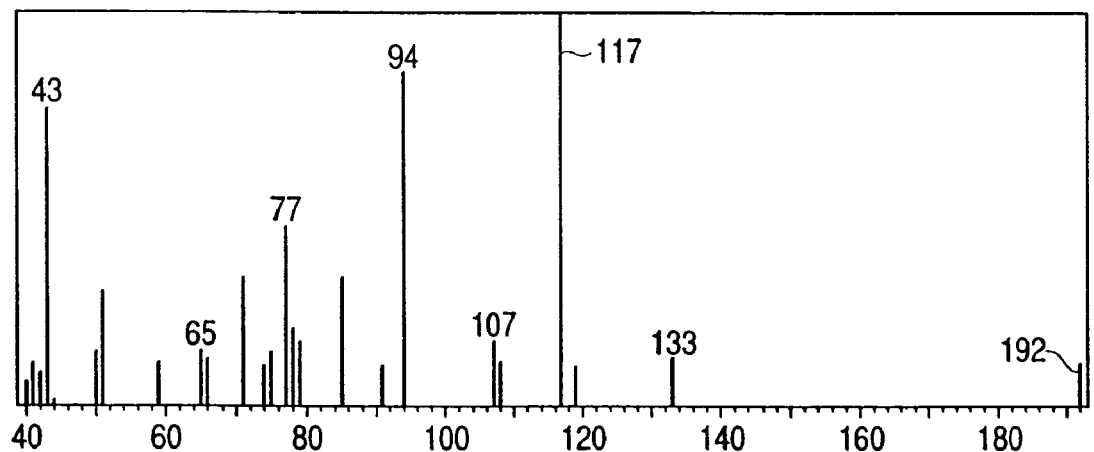
FIG. 73 is a chart which shows the mass spectrum of methyl 3-hydroxy-4-phenoxybutyrate (3HPxB) obtained from the GC-MS measurement in Example 63.
Figure 74:
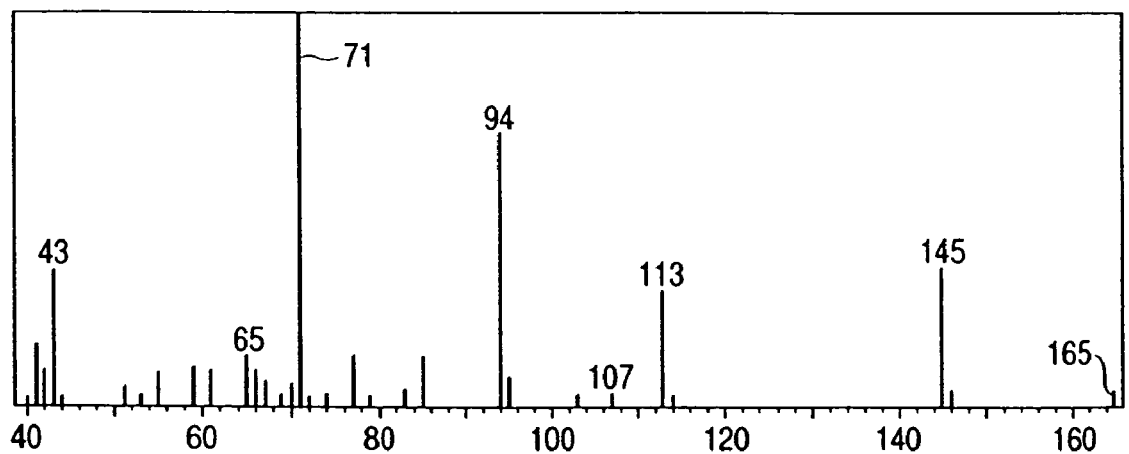
FIG. 74 is a chart which shows the mass spectrum of methyl 3-hydroxy-6-phenoxyhexanoate (3HPxHx) obtained from the GC-MS measurement in Example 63.
Figure 75:
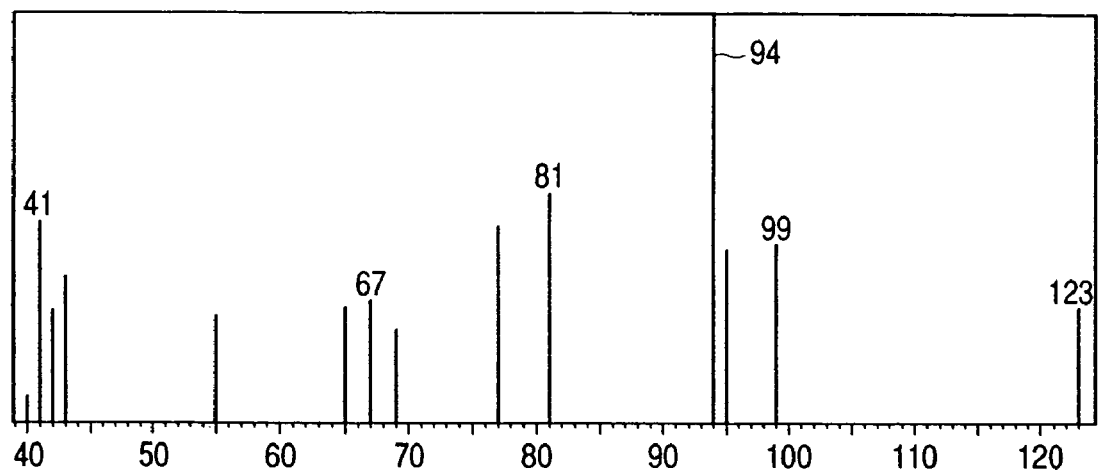
FIG. 75 is a chart which shows the mass spectrum of methyl 3-hydroxy-8-phenoxyoctanoate (3HPxO) obtained from the GC-MS measurement in Example 63.
Figure 76:
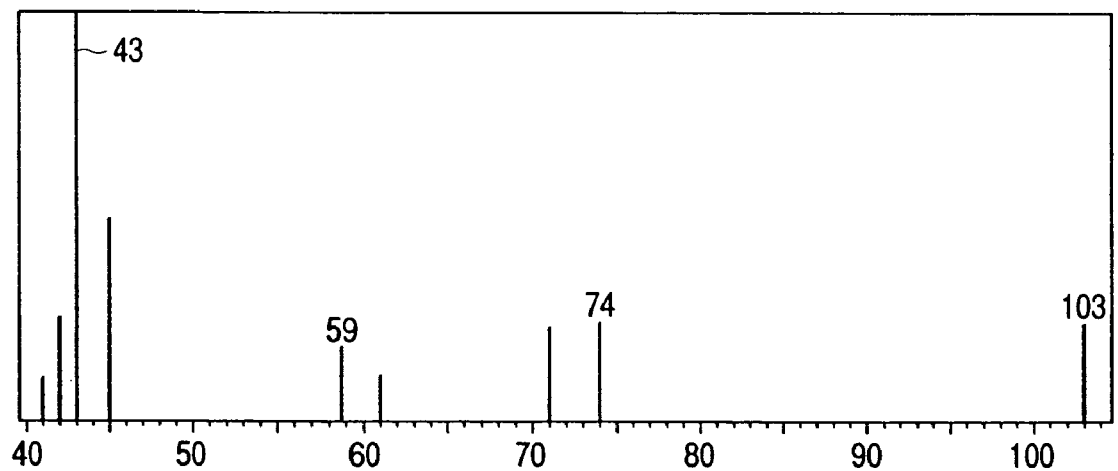
FIG. 76 is a chart which shows the mass spectrum of methyl 3-hydroxybutyrate obtained from the GC-MS measurement in Example 64.
Figure 77:
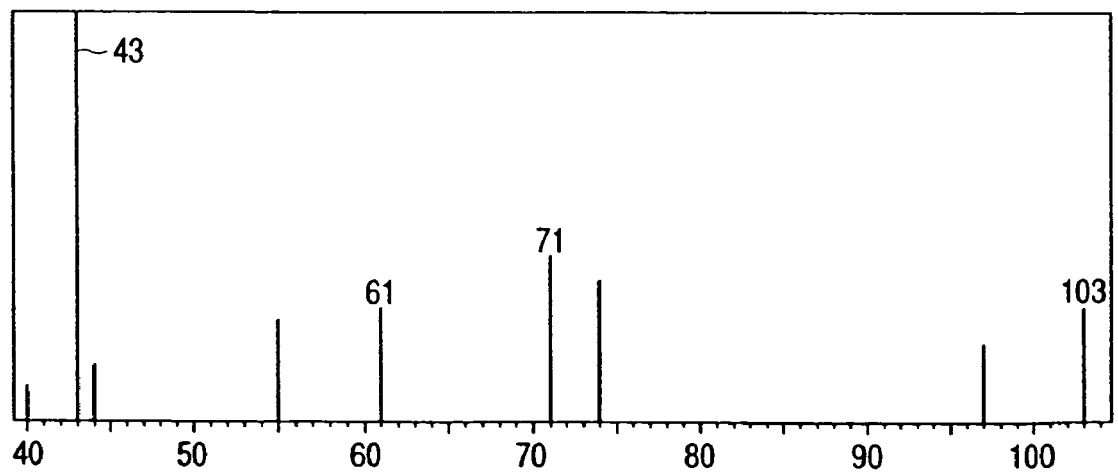
FIG. 77 is a chart which shows the mass spectrum of methyl 3-hydroxyhexanoate obtained from the GC-MS measurement in Example 64.
Figure 78:
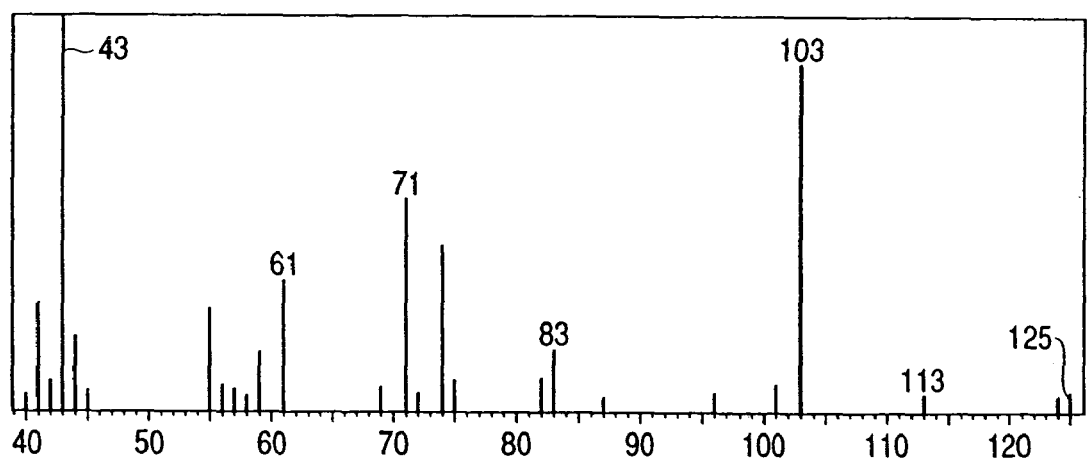
FIG. 78 is a chart which shows the mass spectrum of methyl 3-hydroxyoctanoate obtained from the GC-MS measurement in Example 64.
Figure 79:
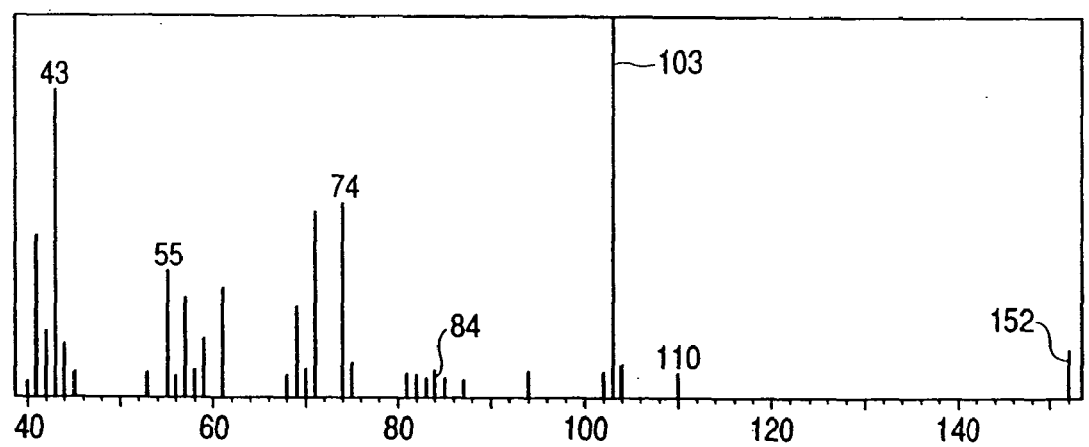
FIG. 79 is a chart which shows the mass spectrum of methyl 3-hydroxydecanoate obtained from the GC-MS measurement in Example 64.
Figure 80:
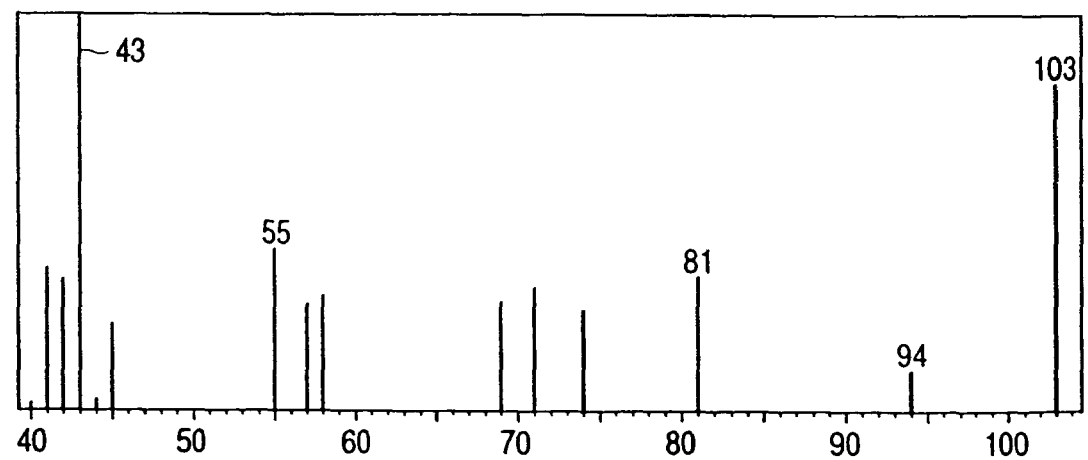
FIG. 80 is a chart which shows the mass spectrum of methyl 3-hydroxydodecanoate obtained from the GC-MS measurement in Example 64.
Figure 81:
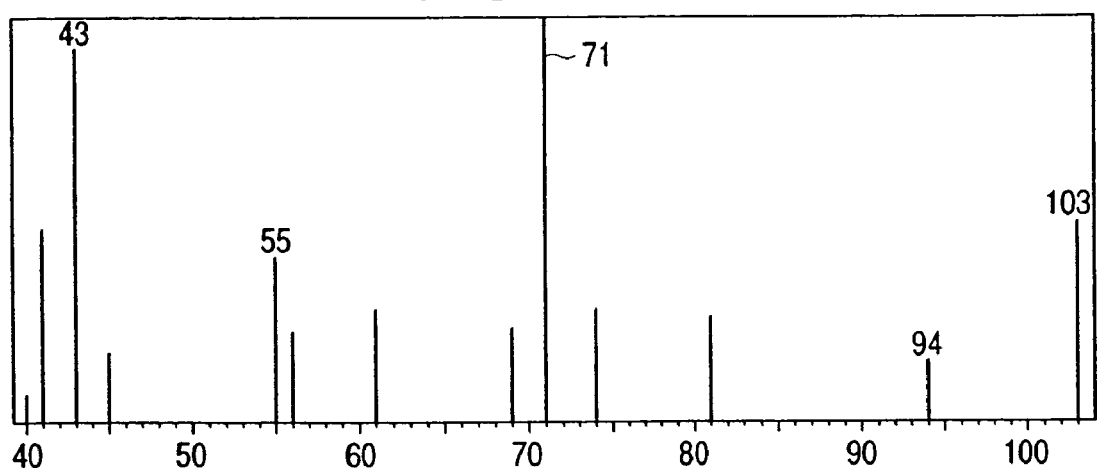
FIG. 81 is a chart which shows the mass spectrum of methyl 3-hydroxydodecenoate obtained from the GC-MS measurement in Example 64.
Figure 82:
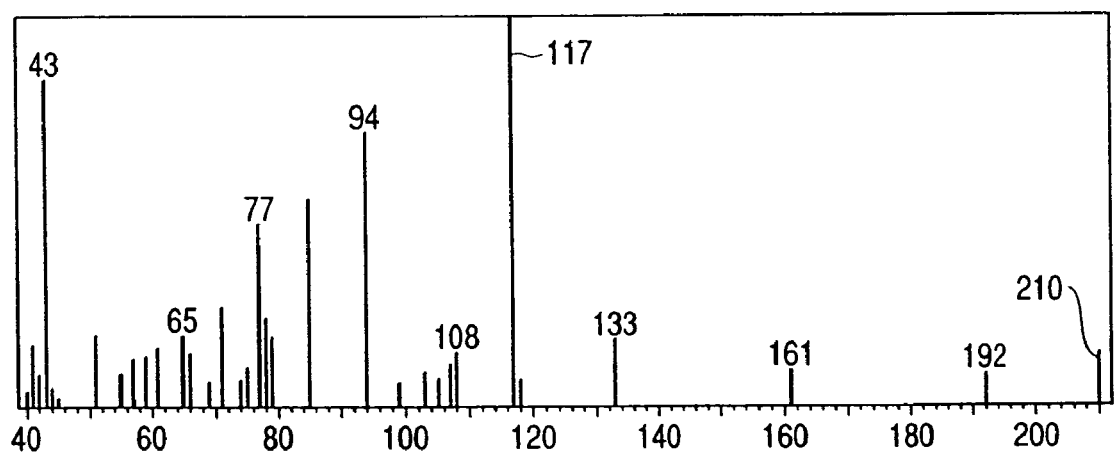
FIG. 82 is a chart which shows the mass spectrum of methyl 3-hydroxy-4-phenoxybutyrate (3HPxB) obtained from the GC-MS measurement in Example 64.
Figure 83:
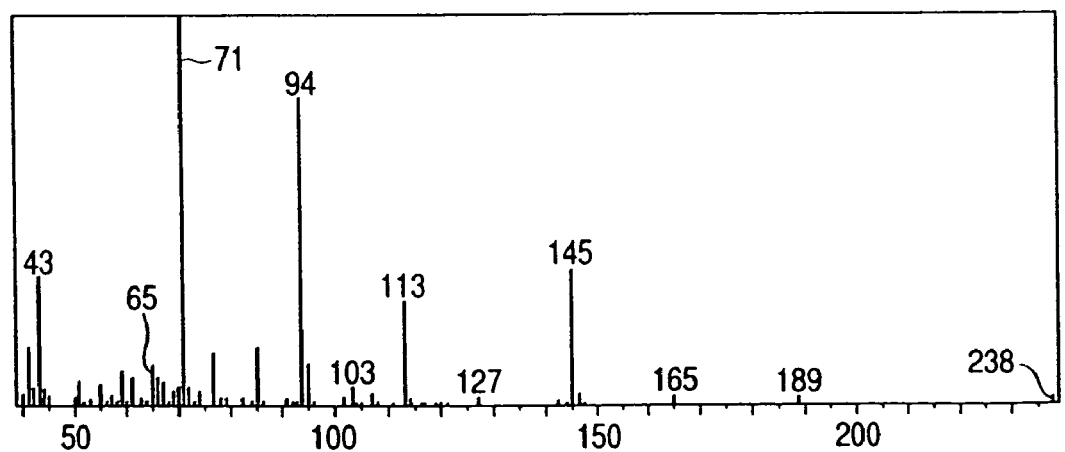
FIG. 83 is a chart which shows the mass spectrum of methyl 3-hydroxy-6-phenoxyhexanoate (3HPxHx) obtained from the GC-MS measurement in Example 64.
Figure 84:
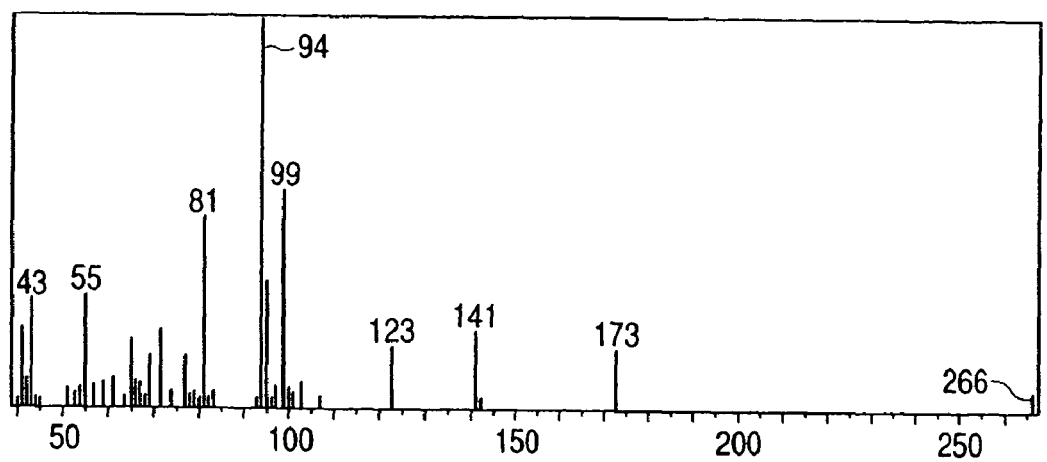
FIG. 84 is a chart which shows the mass spectrum of methyl 3-hydroxy-8-phenoxyoctanoate (3HPxO) obtained from the GC-MS measurement in Example 64.
Figure 85:
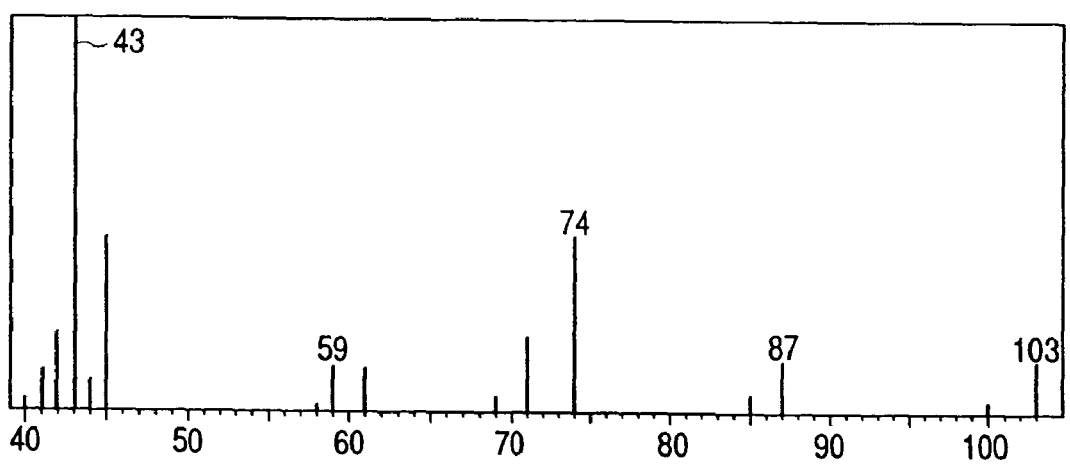
FIG. 85 is a chart which shows the mass spectrum of methyl 3-hydroxybutyrate obtained from the GC-MS measurement in Example 65.
Figure 86:
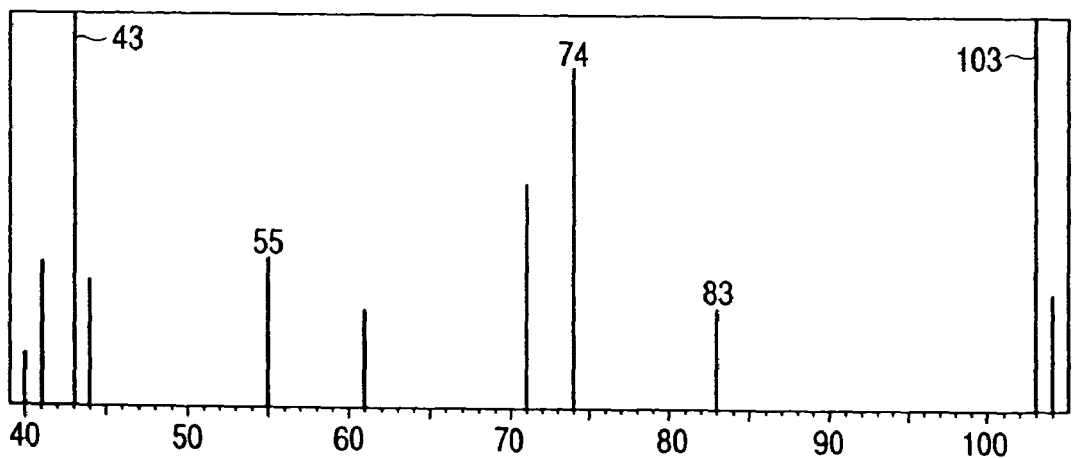
FIG. 86 is a chart which shows the mass spectrum of methyl 3-hydroxyoctanoate obtained from the GC-MS measurement in Example 65.
Figure 87:
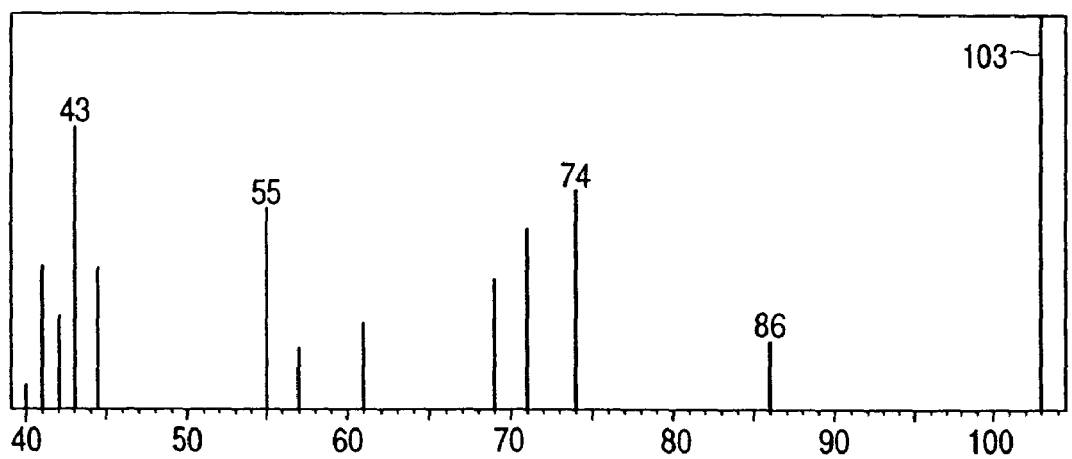
FIG. 87 is a chart which shows the mass spectrum of methyl 3-hydroxydecanoate obtained from the GC-MS measurement in Example 65.
Figure 88:
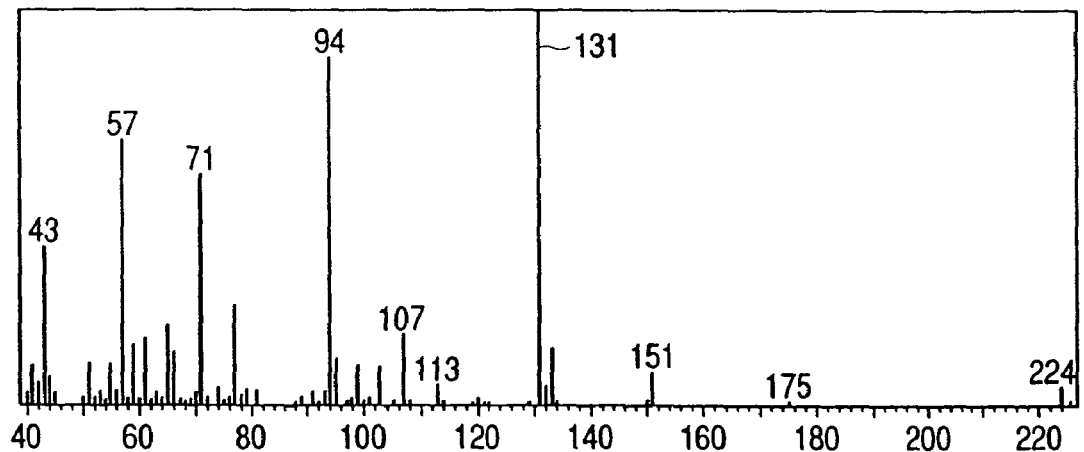
FIG. 88 is a chart which shows the mass spectrum of methyl 3-hydroxy-5-phenoxyvalerate (3HPxV) obtained from the GC-MS measurement in Example 65.
Figure 89:
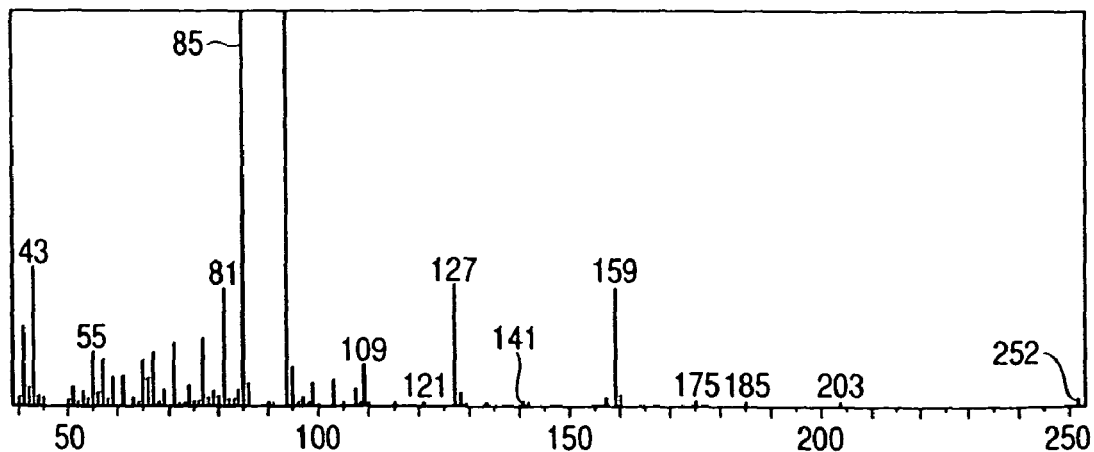
FIG. 89 is a chart which shows the mass spectrum of methyl 3-hydroxy-7-phenoxyheptanoate (3HPxHp) obtained from the GC-MS measurement in Example 65.

Unit composition of the obtained polymer was analyzed by the following manner. The polymer sample 5 mg was poured into the 25 mL round-neck flask, and chloroform 2 mL and 2 mL of methanol containing sulfuric acid (3%, v/v). The mixture was refluxed at 100° C. for 3.5 hours, further added water thereto for separation. The organic layer was analyzed by means of gas-chromatography mass spectrograph (GC-MS, Shimadzu QP-5050, Column: DB-WAX-ETR (J & W Inc.), EI method) to identify methyl esterified PHA monomer unit. Yields of bacterial cells and polymer, and analytical result of the monomer unit are shown in Table 64. Mass spectra obtained by GC-MS of 3-hydroxyoctanoic acid methyl ester, 3-hydroxydecanoic acid methyl ester and 3-hydroxy-5-(4-fluorophenyl) valeric acid (3HFPV) methyl ester obtained by GC-MS measurement are shown in FIG. 31 to FIG. 33.

Result indicates that PHA copolymer containing 3-hydroxy-5-(4-fluorophenyl) valeric acid (3HFPV) unit can be produced by the strain YN2 with a substrate 5-(4-fluorophenyl) valeric acid.

Example 57

Production of PHA Containing HFPV Unit and HFPxV Unit by Strain YN2 (Two Step Culture Using Glucose)

Two M9 media containing glucose 0.5% and 5-(4-fluorophenyl) valeric acid (FPVA) 0.1%, and containing glucose 0.5% and 5-(4-fluorophenoxy) valeric acid (FPxVA) 0.1% were prepared respectively. Cells of strain YN2 were inoculated in 200 mL of each M9 medium, and cultured at 30° C. with shaking at 125 strokes/min. After 94 hours, the cultured cells were recovered by centrifugation, and the cells of these two cultures were re-suspended together in 200 mL of M9 medium containing glucose 0.5%, FPVA 0.1% and FPxVA 0.1% but not containing nitrogen source ($NH_4Cl$), then further shake cultured at 30° C., 125 strokes/min. After 24 hours, the cells were recovered by centrifugation, washed once with cold methanol and lyophilized.

The lyophilized pellet was suspended in chloroform 100 mL, and stirred at 60° C. for 20 hours to extract PHA. The extract was filtered using membrane filter, pore size 0.45 µm, concentrated using rotary evaporator, precipitated the concentrate with cold methanol, and recovered the precipitate to obtain PHA by vacuum drying.

Molecular weight of the obtained polymer was measured by means of gel-permeation chromatography (GPC: Toso, HLC-8020; Column: Polymer Laboratory, PL-gel, MIXED-C 5 µm; Solvent: chloroform; Molecular weight: reduced value for polystyrene).

Unit composition of the obtained polymer was analyzed by the following manner. The polymer sample 5 mg was poured into the 25 mL round-neck flask, and chloroform 2 mL and 2 mL of methanol containing sulfuric acid (3%, v/v). The mixture was refluxed at 100° C. for 3.5 hours, further added water thereto for separation. The organic layer was analyzed by means of gas-chromatography mass spectrograph (GC-MS, Shimadzu QP-5050, Column: DB-WAX-ETR (J & W Inc.), EI method) to identify methyl esterified PHA monomer unit. Yields of bacterial cells and polymer, and analytical result of the monomer unit are shown in Table 65. Mass spectra obtained by GC-MS of 3-hydroxyoctanoic acid methyl ester, 3-hydroxydecanoic acid methyl ester, 3-hydroxy-5-(4-fluorophenyl) valeric acid (3HFPV) methyl ester and 3-hydroxy-5-(4-fluorophenoxy) valeric acid (3HFPxV) methyl ester obtained by GC-MS measurement are shown in FIG. 34 to FIG. 37.

Results indicate that PHA copolymer containing 3-hydroxy-5-(4-fluorophenyl) valeric acid (3HFPV) unit and 3-hydroxy-5-(4-fluorophenoxy) valeric acid (3HFPxV) unit can be produced by the strain YN2 with a substrate 5-(4-fluorophenyl) valeric acid and 5-(4-fluorophenoxy) valeric acid.

Example 58

Production of PHA Containing HPxN Unit, HPxHp Unit and HPxV Unit by Strain YN2 (One Step Culture Using Polypeptone)

The strain YN2 was inoculated in 200 mL of M9 medium containing polypeptone (Wako Pure Chemicals Co.) 0.5% and 11-phenoxyundecanoic acid (PxUDA) 0.1% and was cultured at 30° C. with shaking 125 strokes/min. After 64 hours, the cells were recovered by centrifugation, washed once with cold methanol, lyophilized and weighed.

The lyophilized pellet was suspended in acetone 100 mL, and stirred at room temperature (23° C.) for 72 hours to extract polymer. The extract was filtered using membrane filter, pore size 0.45 µm, concentrated using rotary evaporator, precipitated the concentrate with cold methanol, and recovered the precipitate to obtain the polymer by vacuum drying, then weighed as such.

Molecular weight of the obtained polymer was measured by means of gel-permeation chromatography (GPC: Toso, HLC-8020; Column: Polymer Laboratory, PL-gel, MIXED-C 5 µm; Solvent: chloroform; Molecular weight: reduced value for polystyrene).

Unit composition of the obtained polymer was analyzed by the following manner. The polymer sample 5 mg was poured into the 25 mL round-neck flask, and chloroform 2 mL and 2 mL of methanol containing sulfuric acid (3%, v/v). The mixture was refluxed at 100° C. for 3.5 hours, further added water thereto for separation. The organic layer was analyzed by means of gas-chromatography mass spectrograph (GC-MS, Shimadzu QP-5050, Column: DB-WAX-ETR (J & W Inc.), EI method) to identify methyl esterified PHA monomer unit. Yields of bacterial cells and polymer, and analytical result of the monomer unit are shown in Table 66. Mass spectra obtained by GC-MS of 3-hydroxybutyric acid methyl ester, 3-hydroxyoctanoic acid methyl ester, 3-hydroxydecanoic acid methyl ester, 3-hydroxy-5-phenoxyvaleric acid (3HPxV) methyl ester, 3-hydroxy-7-phenoxyheptanoic acid (3HPxHp) methyl ester and 3-hydroxy-9-phenoxynonanoic acid (3HPxN) methyl ester are shown in FIG. 38 to FIG. 43.

Result indicates that PHA copolymer containing three units of 3-hydroxy-5-phenoxy valeric acid (3HPxV), 3-hydroxy-7-phenoxyheptanoic acid (3HPxHp) and 3-hydroxy-9-phenoxynonanoic acid (3HPxN) can be produced by strain YN2 with a substrate 11-phenoxyundecanoic acid.

Example 59

Production of PHA Containing HPxN Unit, HPxHp Unit and HPxV Unit by Strain YN2 (Two Steps Culture Using Glucose)

The strain YN2 was inoculated in 200 mL of M9 medium containing glucose 0.5% and 11-phenoxyundecanoic acid (PxUDA) 0.1% and was cultured at 30° C. with shaking at 125 strokes/min. After 64 hours, the cultured cells were recovered by centrifugation, and were re-suspended in woo mL of M9 medium 200 mL containing glucose 0.5% and PxUDA 0.1% but not containing nitrogen source (NH$_4$Cl), then further shake cultured at 30° C., 125 strokes/min. After 24 hours, the cells were recovered by centrifugation, washed once with cold methanol, lyophilized and weighed.

The lyophilized pellet was suspended in chloroform 100 mL, and stirred at 60° C. for 24 hours to extract polymer. The extract was filtered using membrane filter, pore size 0.45 µm, concentrated using rotary evaporator, precipitated the concentrate with cold methanol, and recovered the precipitate to obtain the polymer by vacuum drying, then weighed as such.

Molecular weight of the obtained polymer was measured by means of gel-permeation chromatography (GPC: Toso, HLC-8020; Column: Polymer Laboratory, PL-gel, MIXED-C 5 µm; Solvent: chloroform; Molecular weight: reduced value for polystyrene).

Unit composition of the obtained polymer was analyzed by the following manner. The polymer sample 5 mg was poured into the 25 mL round-neck flask, and chloroform 2 mL and 2 mL of methanol containing sulfuric acid (3%, v/v). The mixture was refluxed at 100° C. for 3.5 hours, further added water thereto for separation. The organic layer was analyzed by means of gas-chromatography mass spectrograph (GC-MS, Shimadzu QP-5050, Column: DB-WAX-ETR (J & W Inc.), EI method) to identify methyl esterified PHA monomer unit. Yields of bacterial cells and polymer, and analytical result of the monomer unit are shown in Table 67. Mass spectra obtained by GC-MS of 3-hydroxybutyric acid methyl ester, 3-hydroxyhexanoic acid methyl ester, 3-hydroxyoctanoic acid methyl ester, 3-hydroxydecanoic acid methyl ester, 3-hydroxydodecanoic acid methyl ester, 3-hydroxydodecenoic acid methyl ester, 3-hydroxy-5-phenoxyvaleric acid (3HPxV) methyl ester, 3-hydroxy-7-phenoxyheptanoic acid (3HPxHp) methyl ester and 3-hydroxy-9-phenoxynonanoic acid (3HPxN) methyl ester are shown in FIG. 44 to FIG. 52.

Result indicates that PHA copolymer containing three units of 3-hydroxy-5-phenoxyvaleric acid (3HPxV), 3-hydroxy-7-phenoxyheptanoic acid (3HPxHp) and 3-hydroxy-9-phenoxynonanoic acid (3HPxN) can be produced by the strain YN2 with a substrate 11-phenoxyundecanoic acid.

Example 60

Production of PHA Containing HPxN Unit, HPxHp Unit and HPxV Unit by Strain H45 (Two Steps Culture Using Glucose)

Strain H45 was inoculated in 200 mL of M9 medium containing glucose 0.5% and 11-phenoxyundecanoic acid (PxUDA) 0.1% and was cultured at 30° C. with shaking at 125 strokes/min. After 64 hours, the cultured cells were recovered by centrifugation, and were re-suspended in 200 mL of M9 medium containing glucose 0.5% and PxUDA 0.1% but not containing nitrogen source (NH$_4$Cl), then further shake cultured at 30° C., 125 strokes/min. After 24 hours, the cells were recovered by centrifugation, washed once with cold methanol, lyophilized and weighed.

The lyophilized pellet was suspended in chloroform 100 mL, and stirred at 60° C. for 24 hours to extract polymer. The extract was filtered using membrane filter, pore-size 0.45 µm, concentrated using rotary evaporator, precipitated the concentrate with cold methanol, and recovered the precipitate to obtain the polymer by vacuum drying, then weighed as such.

Molecular weight of the obtained polymer was measured by means of gel-permeation chromatography (GPC: Toso, HLC-8020; Column: Polymer Laboratory, PL-gel, MIXED-C 5 µm; Solvent: chloroform; Molecular weight: reduced value for polystyrene).

Unit composition of the obtained polymer was analyzed by the following manner. The polymer sample 5 mg was poured into the 25 mL round-neck flask, and chloroform 2 mL and 2 mL of methanol containing sulfuric acid (3%, v/v). The mixture was refluxed at 100° C. for 3.5 hours, further added water thereto for separation. The organic layer was analyzed by means of gas-chromatography mass spectrograph (GC-MS, Shimadzu QP-5050, Column: DB-WAX-ETR (J & W Inc.), EI method) to identify methyl esterified PHA monomer unit. Yields of bacterial cells and polymer, and analytical result of the monomer unit are shown in Table 68. Mass spectra obtained by GC-MS of 3-hydroxybutyric acid methyl ester, 3-hydroxyhexanoic acid methyl ester, 3-hydroxyoctanoic acid methyl ester, 3-hydroxydecanoic acid methyl ester, 3-hydroxydodecanoic acid methyl ester, 3-hydroxydodecenoic acid methyl ester, 3-hydroxy-5-phenoxyvaleric acid (3HPxV) methyl ester, 3-hydroxy-7-phenoxyheptanoic acid (3HPxHp) methyl ester and 3-hydroxy-9-phenoxynonanoic acid (3HPxN) methyl ester are shown in FIG. 53 to FIG. 61.

Result indicates that PHA copolymer containing three units of 3-hydroxy-5-phenoxyvaleric acid (3HPxV), 3-hydroxy-7-phenoxyheptanoic acid (3HPxHp) and 3-hydroxy-9-phenoxynonanoic acid (3HPxN) can be produced by the strain H45 with a substrate 11-phenoxyundecanoic acid.

Example 61

Production of PHA Containing HPxO Unit, HPxHx Unit and HPxB Unit by Strain YN2 (One Step Culture Using Polypeptone)

The strain YN2 was inoculated in 200 mL of M9 medium containing polypeptone (Wako Pure Chemicals Co.) 0.5% and 8-phenoxyoctanoic acid (PxOA) 0.1% and was shake cultured at 30° C. in 125 strokes/min. After 24 hours, the cells were recovered by centrifugation, washed once with cold methanol, lyophilized and weighed.

The lyophilized pellet was suspended in chloroform 100 mL, and stirred at 60° C. for 24 hours to extract polymer. The extract was filtered using membrane filter, pore size 0.45 μm, concentrated using rotary evaporator, precipitated the concentrate with cold methanol, and recovered the precipitate to obtain the polymer by vacuum drying, then weighed as such.

Molecular weight of the obtained polymer was measured by means of gel-permeation chromatography (GPC: Toso, HLC-8020; Column: Polymer Laboratory, PL-gel, MIXED-C 5 μm; Solvent: chloroform; Molecular weight: reduced value for polystyrene).

Unit composition of the obtained polymer was analyzed by the following manner. The polymer sample 5 mg was poured into the 25 mL round-neck flask, and chloroform 2 mL and 2 mL of methanol containing sulfuric acid (3%, v/v). The mixture was refluxed at 100° C. for 3.5 hours, further added water thereto for separation. The organic layer was analyzed by means of gas-chromatography mass spectrograph (GC-MS, Shimadzu QP-5050, Column: DB-WAX-ETR (J & W Inc.), EI method) to identify methyl esterified PHA monomer unit. Yields of bacterial cells and polymer, and analytical result of the monomer unit are shown in Table 69. Mass spectra obtained by GC-MS of 3-hydroxybutyric acid methyl ester, 3-hydroxy-4-phenoxybutyric acid (3HPxB) methyl ester, 3-hydroxy-6-phenoxyhexanoic acid (3HPxHx) methyl ester and 3-hydroxy-8-phenoxyoctanoic acid (3HPxO) methyl ester are shown in FIG. 62 to FIG. 65.

Result indicates that PHA copolymer containing three units of 3-hydroxy-4-phenoxybutyric acid (3HPxB), 3-hydroxy-6-phenoxyhexanoic acid (3HPxHx) and 3-hydroxy-8-phenoxyoctanoic acid (3HPxO) can be produced by the strain YN2 with a substrate 8-phenoxyoctanoic acid.

Example 62

Production of PHA Containing HPxO Unit, HPxHx Unit and HPxB Unit by Strain H45 (One Step Culture Using Polypeptone)

The strain H45 was inoculated in 200 mL of M9 medium containing polypeptone (Wako Pure Chemicals Co.) 0.5% and 8-phenoxyoctanoic acid (PxOA) 0.1% and was shake cultured at 30° C. in 125 strokes/min. After 24 hours, the cells were recovered by centrifugation, washed once with cold methanol, lyophilized and weighed.

The lyophilized pellet was suspended in chloroform 100 mL, and stirred at 60° C. for 24 hours to extract polymer. The extract was filtered using membrane filter, pore size 0.45 μm, concentrated using rotary evaporator, precipitated the concentrate with cold methanol, and recovered the precipitate to obtain the polymer by vacuum drying, then weighed as such.

Molecular weight of the obtained polymer was measured by means of gel-permeation chromatography (GPC: Toso, HLC-8020; Column: Polymer Laboratory, PL-gel, MIXED-C 5 μm; Solvent: chloroform; Molecular weight: reduced value for polystyrene).

Unit composition of the obtained polymer was analyzed by the following manner. The polymer sample 5 mg was poured into the 25 mL round-neck flask, and chloroform 2 mL and 2 mL of methanol containing sulfuric acid (3%, v/v). The mixture was refluxed at 100° C. for 3.5 hours, further added water thereto for separation. The organic layer was analyzed by means of gas-chromatography mass spectrograph (GC-MS, Shimadzu QP-5050, Column: DB-WAX-ETR (J & W Inc.), EI method) to identify methyl esterified PHA monomer unit. Yields of bacterial cells and polymer, and analytical result of the monomer unit are shown in Table 70. Mass spectra obtained by GC-MS of 3-hydroxybutyric acid methyl ester, 3-hydroxy-4-phenoxybutyric acid (3HPxB) methyl ester, 3-hydroxy-6-phenoxyhexanoic acid (3HPxHx) methyl ester and 3-hydroxy-8-phenoxyoctanoic acid (3HPxO) methyl ester are shown in FIG. 66 to FIG. 69.

Result indicates that PHA copolymer containing three units of 3-hydroxy-4-phenoxybutyric acid (3HPxB), 3-hydroxy-6-phenoxyhexanoic acid (3HPxHx) and 3-hydroxy-8-phenoxyoctanoic acid (3HPxO) can be produced by the strain H45 with a substrate 8-phenoxyoctanoic acid.

Example 63

Production of PHA Containing HPxO Unit, HPxHx Unit and HPxB Unit by Strain YN2 (Two Steps Culture Using Glucose)

The strain YN2 was inoculated in 200 mL of M9 medium containing glucose 0.5% and 8-phenoxyoctanoic acid (PxOA) 0.1% and was cultured at 30° C. with shaking at 125 strokes/min. After 48 hours, the cultured cells were recovered by centrifugation, and were re-suspended in 200 mL of M9 medium containing glucose 0.5% and PxOA 0.1% but not containing nitrogen source (NH$_4$Cl), then further shake cultured at 30° C. in 125 strokes/min. After 24 hours, bacterial cells were recovered by centrifugation, washed once with cold methanol, lyophilized and were weighed.

The lyophilized pellet was suspended in chloroform 100 mL, and stirred at 60° C. for 24 hours to extract polymer. The extract was filtered using membrane filter, pore size 0.45 μm, concentrated using rotary evaporator, precipitated the concentrate with cold methanol, and recovered the precipitate to obtain the polymer by vacuum drying, then weighed as such.

Molecular weight of the obtained polymer was measured by means of gel-permeation chromatography (GPC: Toso, HLC-8020; Column: Polymer Laboratory, PL-gel, MIXED-C 5 μm; Solvent: chloroform; Molecular weight: reduced value for polystyrene).

Unit composition of the obtained polymer was analyzed by the following manner. The polymer sample 5 mg was poured into the 25 mL round-neck flask, and chloroform 2 mL and 2 mL of methanol containing sulfuric acid (3%, v/v). The mixture was refluxed at 100° C. for 3.5 hours, further added water thereto for separation. The organic layer was analyzed by means of gas-chromatography mass spectrograph (GC-MS, Shimadzu QP-5050, Column: DB-WAX-ETR (J & W Inc.), EI method) to identify methyl esterified PHA monomer unit. Yields of bacterial cells and polymer, and analytical result of the monomer unit are shown in Table 71. Mass spectra obtained by GC-MS measurement of 3-hydroxybutyric acid methyl ester, 3-hydroxyoctanoic acid methyl ester, 3-hydroxydecanoic acid methyl ester, 3-hydroxy-4-phenoxybutyric acid (3HPxB) methyl ester, 3-hydroxy-6-phenoxyhexanoic acid (3HPxHx) methyl ester and 3-hydroxy-8-phenoxyoctanoic acid (3HPxO) methyl ester are shown in FIG. 70 to FIG. 75.

Result indicates that PHA copolymer containing three units of 3-hydroxy-4-phenoxybutyric acid (3HPxB), 3-hydroxy-6-phenoxyhexanoic acid (3HPxHx) and 3-hydroxy-8-phenoxyoctanoic acid (3HPxO) can be produced by the strain YN2 with a substrate 8-phenoxyoctanoic acid.

Example 64

Production of PHA Containing HPxO Unit, HPxHx Unit and HPxB Unit by Strain H45 (Two Steps Culture Using Glucose)

The strain H45 was inoculated in 200 mL of M9 medium containing glucose 0.5% and 8-phenoxyoctanoic acid (PxOA) 0.1% and cultured at 30° C. with shaking at 125 strokes/min. After 48 hours, cultured bacterial cells were recovered by centrifugation, and were re-suspended in 200 mL of M9 medium containing glucose 0.5% and PxOA 0.1% but not containing nitrogen source ($NH_4Cl$), then further shake cultured at 30° C., 125 strokes/min. After 24 hours, the cells were recovered by centrifugation, washed once with cold methanol, lyophilized and weighed.

The lyophilized pellet was suspended in chloroform 100 mL, and stirred at 60° C. for 24 hours to extract polymer. The extract was filtered using membrane filter, pore size 0.45 μm, concentrated using rotary evaporator, precipitated the concentrate with cold methanol, and recovered the precipitate to obtain the polymer by vacuum drying, then weighed as such.

Molecular weight of the obtained polymer was measured by means of gel-permeation chromatography (GPC: Toso, HLC-8020; Column: Polymer Laboratory, PL-gel, MIXED-C 5 μm; Solvent: chloroform; Molecular weight: reduced value for polystyrene).

Unit composition of the obtained polymer was analyzed by the following manner. The polymer sample 5 mg was poured into the 25 mL round-neck flask, and chloroform 2 mL and 2 mL of methanol containing sulfuric acid (3%, v/v). The mixture was refluxed at 100° C. for 3.5 hours, further added water thereto for separation. The organic layer was analyzed by means of gas-chromatography mass spectrograph (GC-MS, Shimadzu QP-5050, Column: DB-WAX-ETR (J & W Inc.), EI method) to identify methyl esterified PHA monomer unit. Yields of bacterial cells and polymer, and analytical result of the monomer unit are shown in Table 72. Mass spectra obtained by GC-MS measurement of 3-hydroxybutyric acid methyl ester, 3-hydroxyhexanoic acid methyl ester, 3-hydroxyoctanoic acid methyl ester, 3-hydroxydecanoic acid methyl ester, 3-hydroxydodecanoic acid methyl ester, 3-hydroxydodecenoic acid methyl ester, 3-hydroxy-4-phenoxybutyric acid (3HPxB) methyl ester, 3-hydroxy-6-phenoxyhexanoic acid (3HPxHx) methyl ester and 3-hydroxy-8-phenoxyoctanoic acid (3HPxO) methyl ester are shown in FIG. 76 to FIG. 84.

Result indicates that PHA copolymer containing three units of 3-hydroxy-4-phenoxybutyric acid (3HPxB), 3-hydroxy-6-phenoxyhexanoic acid (3HPxHx) and 3-hydroxy-8-phenoxyoctanoic acid (3HPxO) can be produced by the strain H45 with a substrate 8-phenoxyoctanoic acid.

Example 65

Production of PHA Containing HPxHp Unit and HPxV Unit by Strain YN2 (One Step Culture Using Polypeptone)

The strain YN2 was inoculated in 200 mL of M9 medium containing polypeptone (Wako Pure Chemicals Co.) 0.5% and 7-phenoxyheptanoic acid (PxHpA) 0.1% and was cultured at 30° C. with shaking at 125 strokes/min. After 64 hours, the cells were recovered by centrifugation, washed once with cold methanol, lyophilized and weighed.

The lyophilized pellet was suspended in chloroform 100 mL, and stirred at 60° C. for 24 hours to extract polymer. The extract was filtered using membrane filter, pore size 0.45 μm, concentrated using rotary evaporator, precipitated the concentrate with cold methanol, and recovered the precipitate to obtain the polymer by vacuum drying, then weighed as such.

Molecular weight of the obtained polymer was measured by means of gel-permeation chromatography (GPC: Toso, HLC-8020; Column: Polymer Laboratory, PL-gel, MIXED-C 5 μm; Solvent: chloroform; Molecular weight: reduced value for polystyrene).

Unit composition of the obtained polymer was analyzed by the following manner. The polymer sample 5 mg was poured into the 25 mL round-neck flask, and chloroform 2 mL and 2 mL of methanol containing sulfuric acid (3%, v/v). The mixture was refluxed at 100° C. for 3.5 hours, further added water thereto for separation. The organic layer was analyzed by means of gas-chromatography mass spectrograph (GC-MS, Shimadzu QP-5050, Column: DB-WAX-ETR (J & W Inc.), EI method) to identify methyl esterified PHA monomer unit. Yields of bacterial cells and polymer, and analytical result of the monomer unit are shown in Table 73. Mass spectra obtained by GC-MS of 3-hydroxybutyric acid methyl ester, 3-hydroxyoctanoic acid methyl ester, 3-hydroxydecanoic acid methyl ester, 3-hydroxy-5-phenoxyvaleric acid (3HPxV) methyl ester and 3-hydroxy-7-phenoxyheptanoic acid (3HPxHp) methyl ester are shown in FIG. 85 to FIG. 89.

Result indicates that PHA copolymer containing two units of 3-hydroxy-5-phenoxyvaleric acid (3HPxV) and 3-hydroxy-7-phenoxyheptanoic acid (3HPxHp) can be produced by strain YN2 with a substrate 7-phenoxyheptanoic acid.

Example 66

Production of PHA Containing HPxHp Unit and HPxV Unit by Using Strain H45 (Polypeptone, One-Step Culture)

Strain H45 was inoculated in 200 mL of M9 medium containing 0.5% polypeptone (Wako Jun-Yaku Kogyo available) and 0.1% 7-phenoxyheptanoic acid (PxHpA) and cultured with shaking at 125 strokes/min at 30° C. After 64 hr, the cells were collected by centrifugation, washed once with cold methanol, lyophilized and weighed.

This lyophilized pellet was suspended in 100 mL of chloroform and stirred at 60° C. for 24 hr to extract the polymer. After filtered through a 0.45 µm pore-size membrane filter, the extract was concentrated by using a rotary evaporator and the concentrated solution was re-precipitated in cold methanol, and the precipitate was collected, vacuum-dried and weight as the polymer.

The molecular weight of the obtained polymer was measured by using gel permeation chromatography (GPC: Toso/HLC-8020; column: Polymer Laboratory/PL gel/MIXED-C/5 µm; solvent: chloroform; polystyrene reduced molecular weight).

Figure 90:
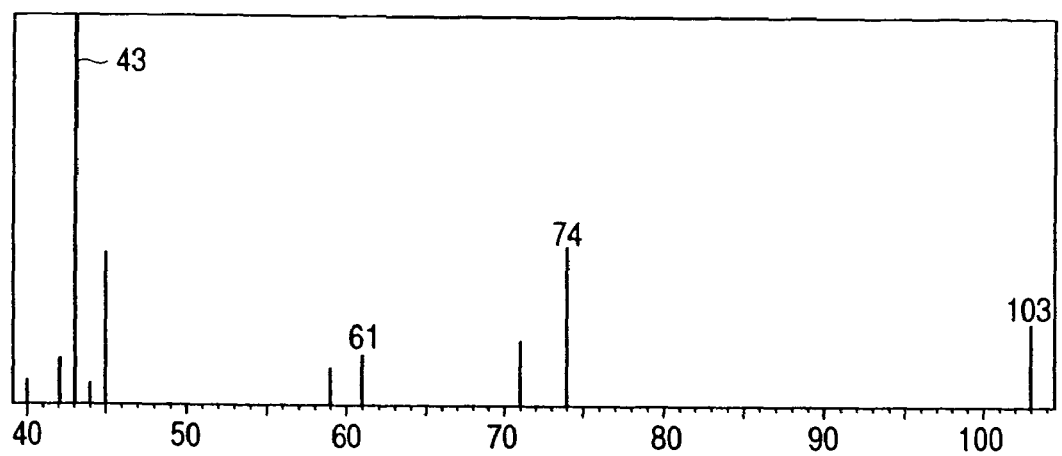
FIG. 90 is a chart which shows the mass spectrum of methyl 3-hydroxybutyrate obtained from the GC-MS measurement in Example 66.
Figure 91:
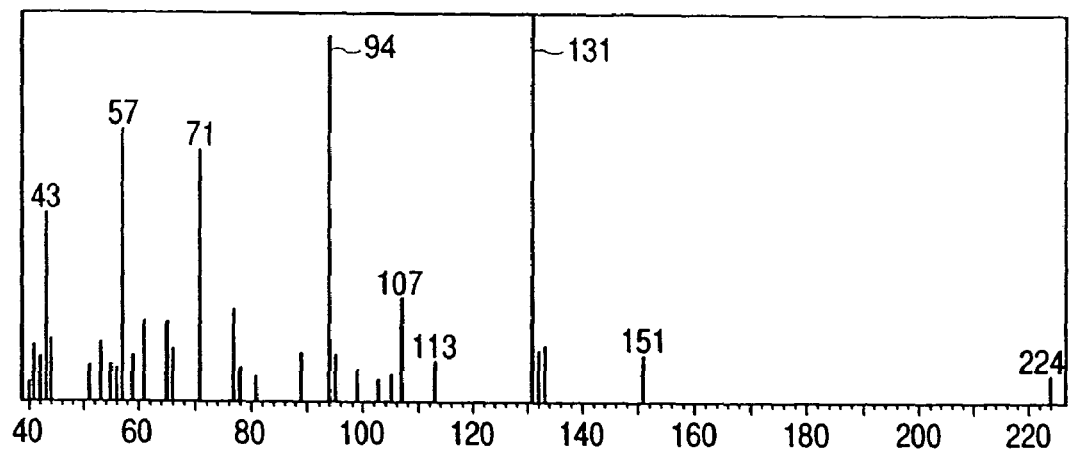
FIG. 91 is a chart which shows the mass spectrum of methyl 3-hydroxy-5-phenoxyvalerate (3HPxV) obtained from the GC-MS measurement in Example 66.
Figure 92:
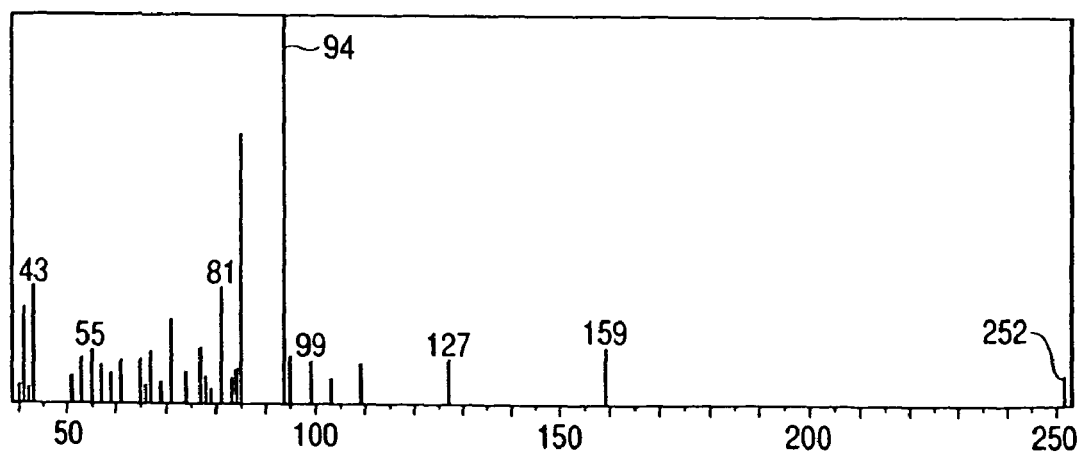
FIG. 92 is a chart which shows the mass spectrum of methyl 3-hydroxy-7-phenoxyheptanoate (3HPxHp) obtained from the GC-MS measurement in Example 66.
Figure 93:
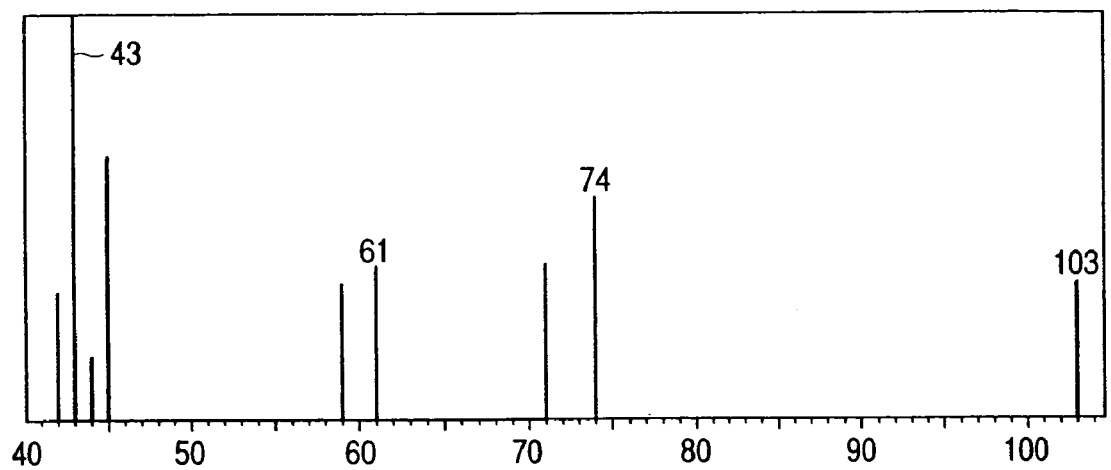
FIG. 93 is a chart which shows the mass spectrum of methyl 3-hydroxybutyrate obtained from the GC-MS measurement in Example 67.
Figure 94:
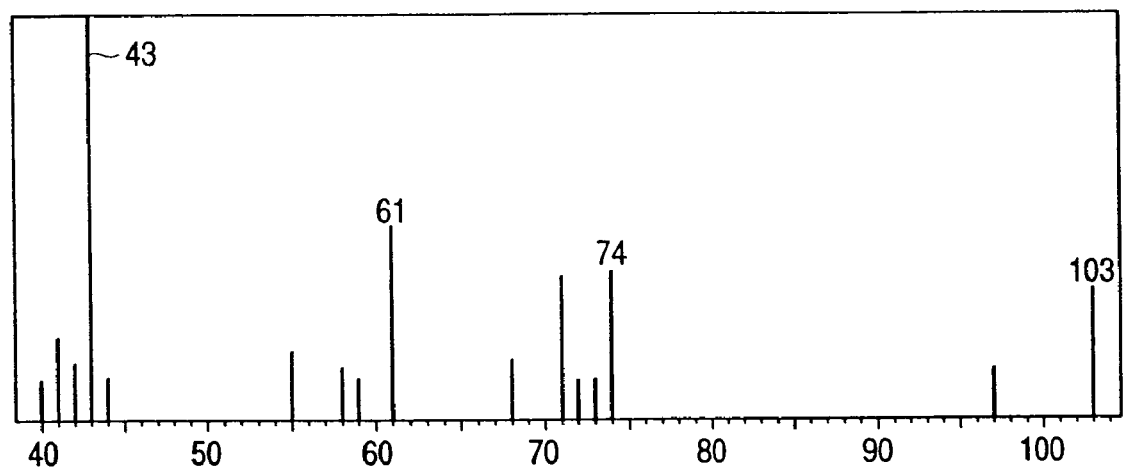
FIG. 94 is a chart which shows the mass spectrum of methyl 3-hydroxyhexanoate obtained from the GC-MS measurement in Example 67.
Figure 95:
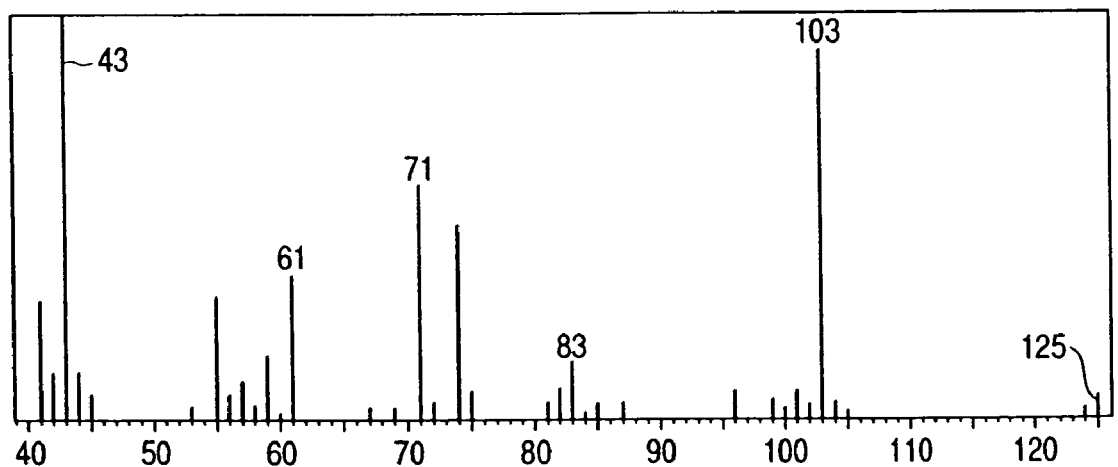
FIG. 95 is a chart which shows the mass spectrum of methyl 3-hydroxyoctanoate obtained from the GC-MS measurement in Example 67.
Figure 96:
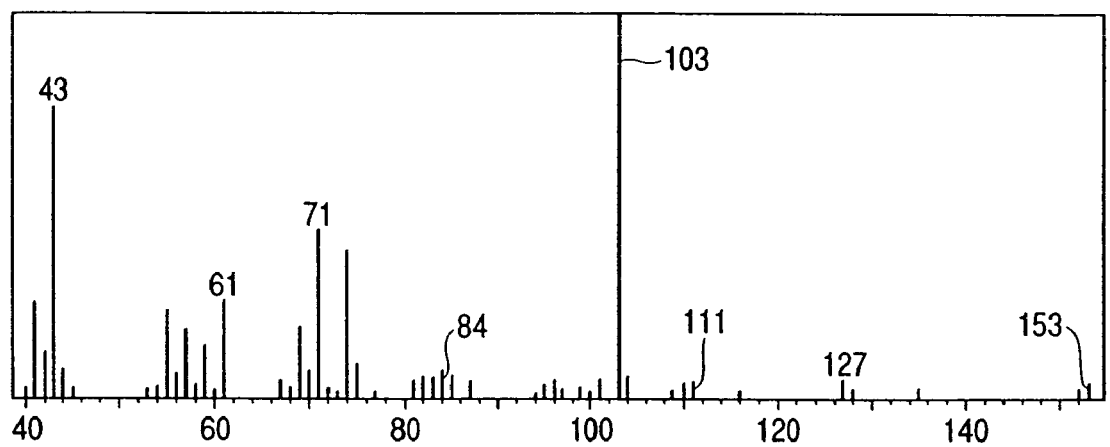
FIG. 96 is a chart which shows the mass spectrum of methyl 3-hydroxydecanoate obtained from the GC-MS measurement in Example 67.
Figure 97:
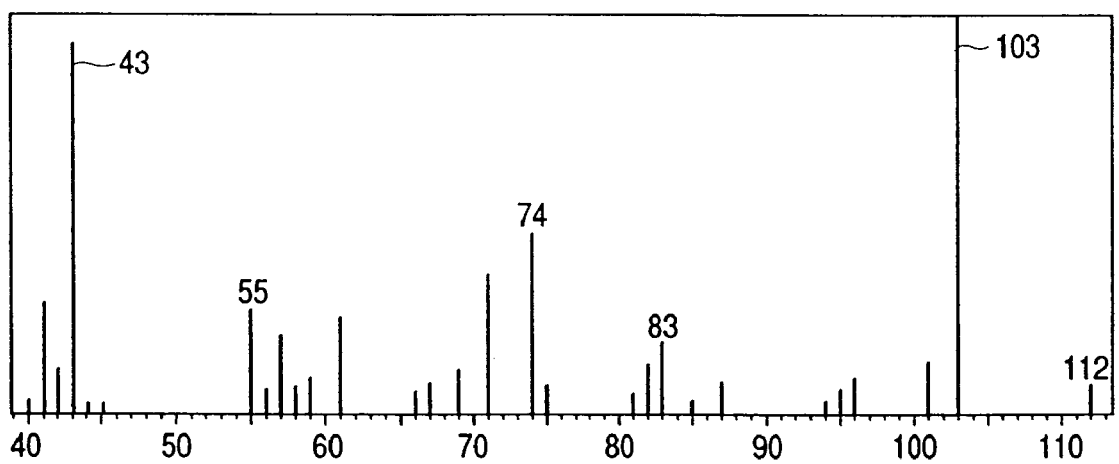
FIG. 97 is a chart which shows the mass spectrum of methyl 3-hydroxydodecanoate obtained from the GC-MS measurement in Example 67.
Figure 98:
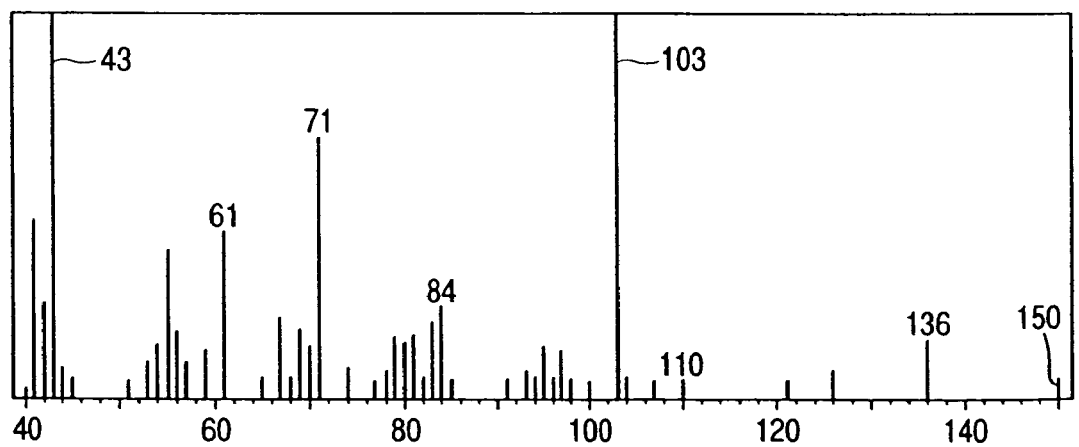
FIG. 98 is a chart which shows the mass spectrum of methyl 3-hydroxydodecenoate obtained from the GC-MS measurement in Example 67.
Figure 99:
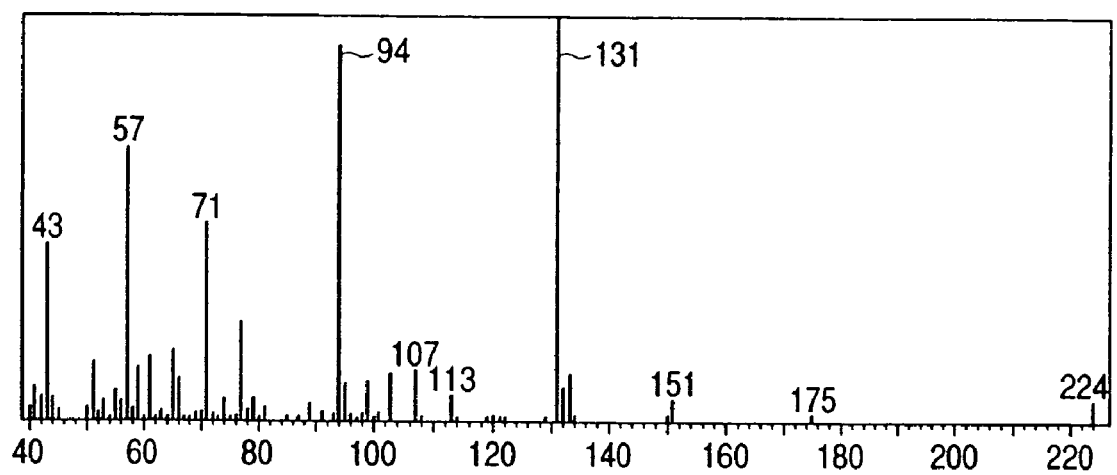
FIG. 99 is a chart which shows the mass spectrum of methyl 3-hydroxy-5-phenoxyvalerate (3HPxV) obtained from the GC-MS measurement in Example 67.
Figure 100:
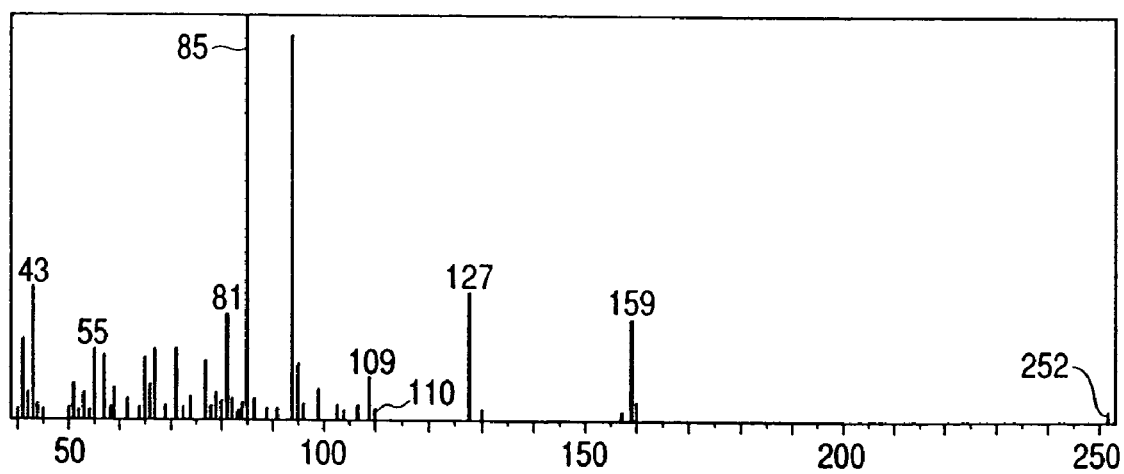
FIG. 100 is a chart which shows the mass spectrum of methyl 3-hydroxy-7-phenoxyheptanoate (3HPxHp) obtained from the GC-MS measurement in Example 67.
Figure 101:
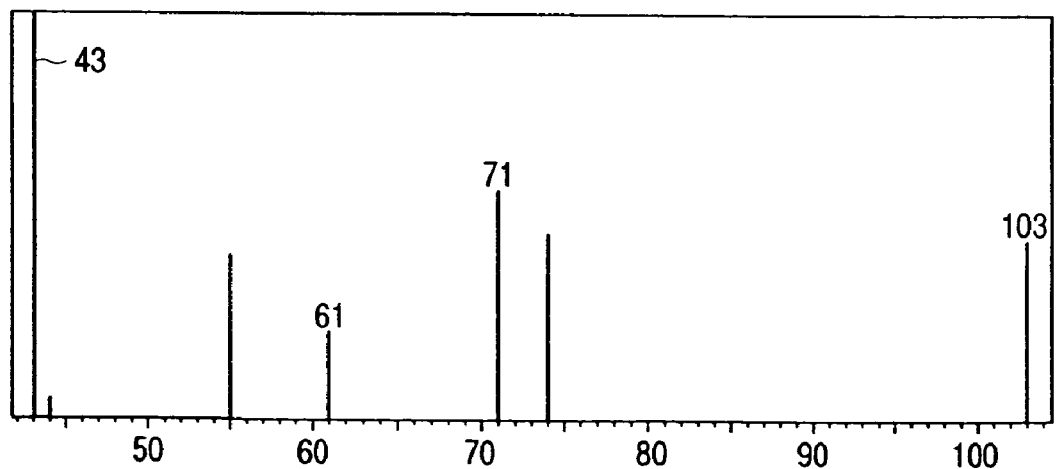
FIG. 101 is a chart which shows the mass spectrum of methyl 3-hydroxyhexanoate obtained from the GC-MS measurement in Example 68.
Figure 102:
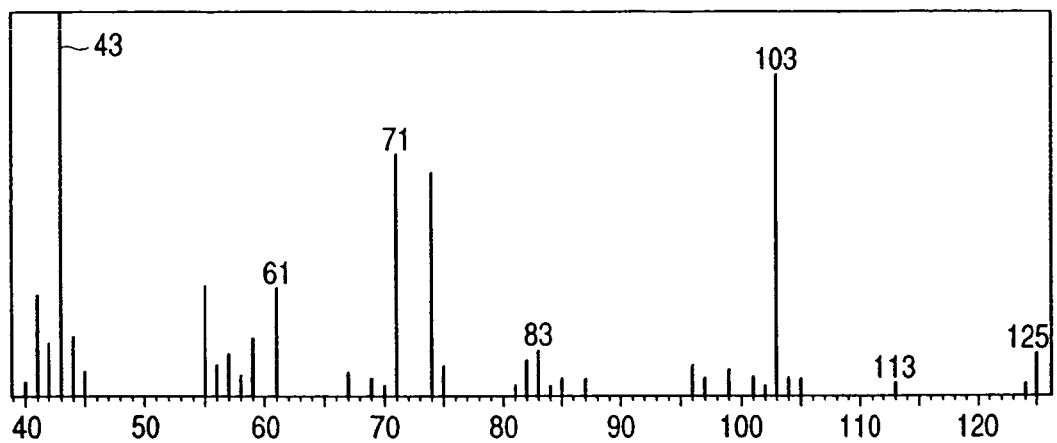
FIG. 102 is a chart which shows the mass spectrum of methyl 3-hydroxyoctanoate obtained from the GC-MS measurement in Example 68.
Figure 103:
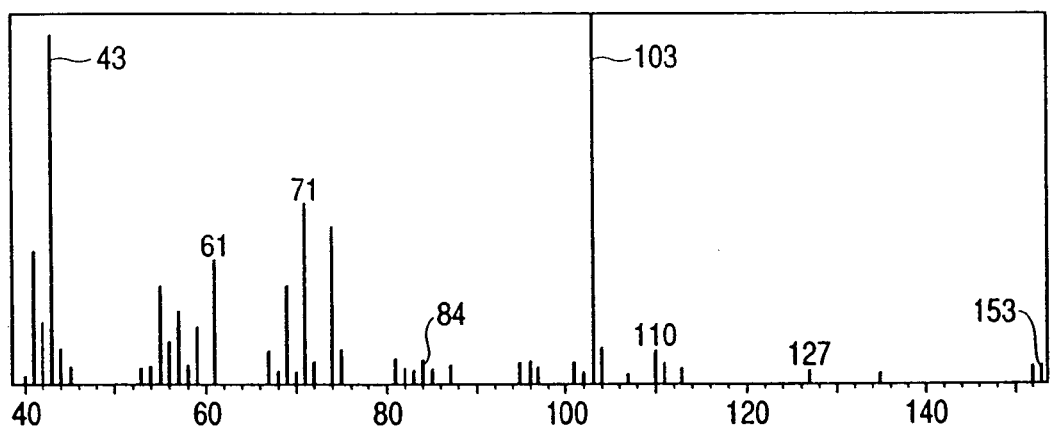
FIG. 103 is a chart which shows the mass spectrum of methyl 3-hydroxydecanoate obtained from the GC-MS measurement in Example 68.
Figure 104:
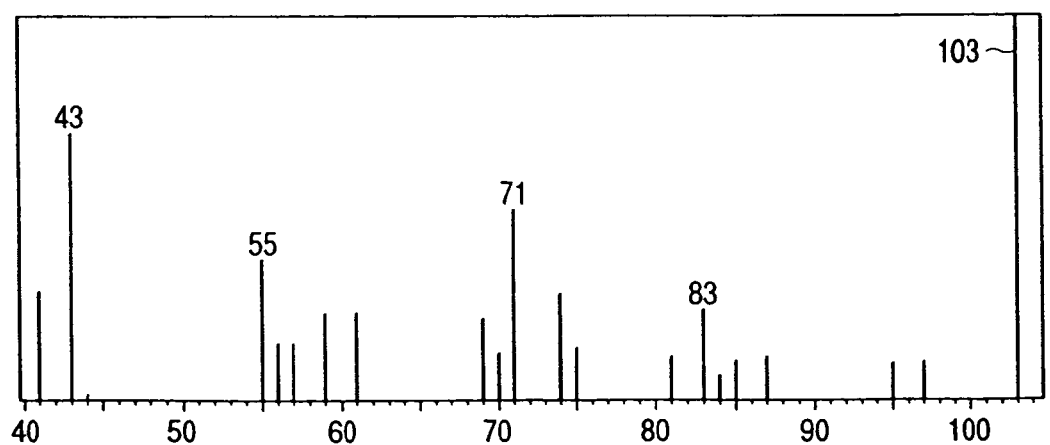
FIG. 104 is a chart which shows the mass spectrum of methyl 3-hydroxydodecanoate obtained from the GC-MS measurement in Example 68.
Figure 105:
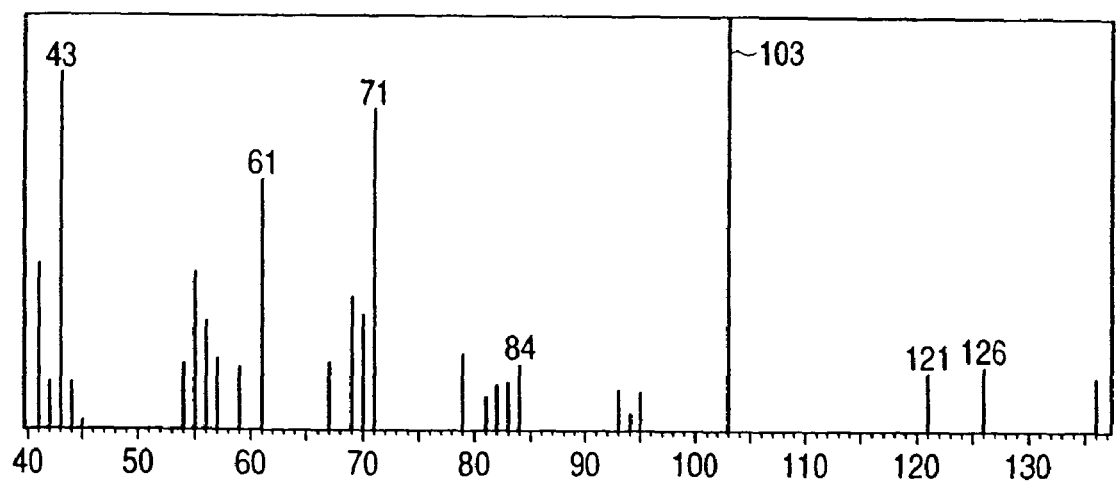
FIG. 105 is a chart which shows the mass spectrum of methyl 3-hydroxydodecenoate obtained from the GC-MS measurement in Example 68.
Figure 106:
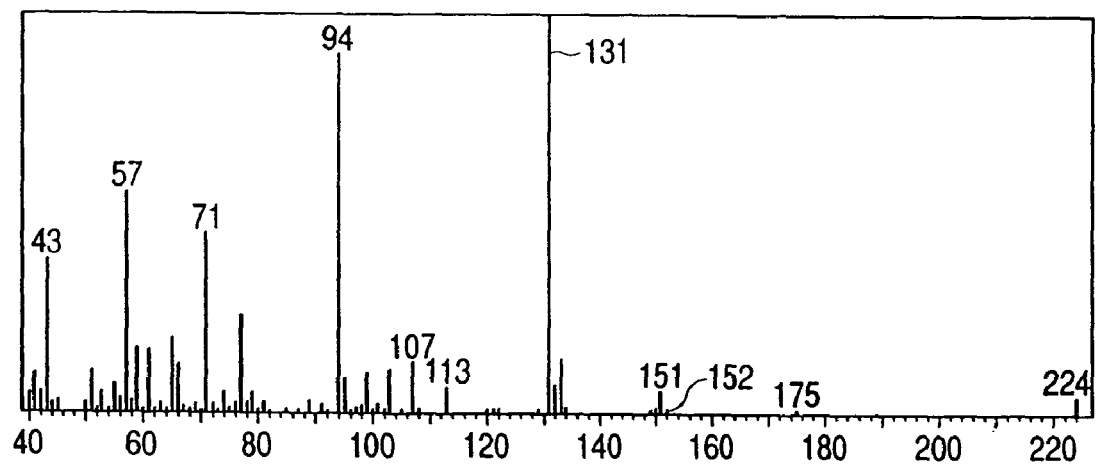
FIG. 106 is a chart which shows the mass spectrum of methyl 3-hydroxy-5-phenoxyvalerate (3HPxV) obtained from the GC-MS measurement in Example 68.
Figure 107:
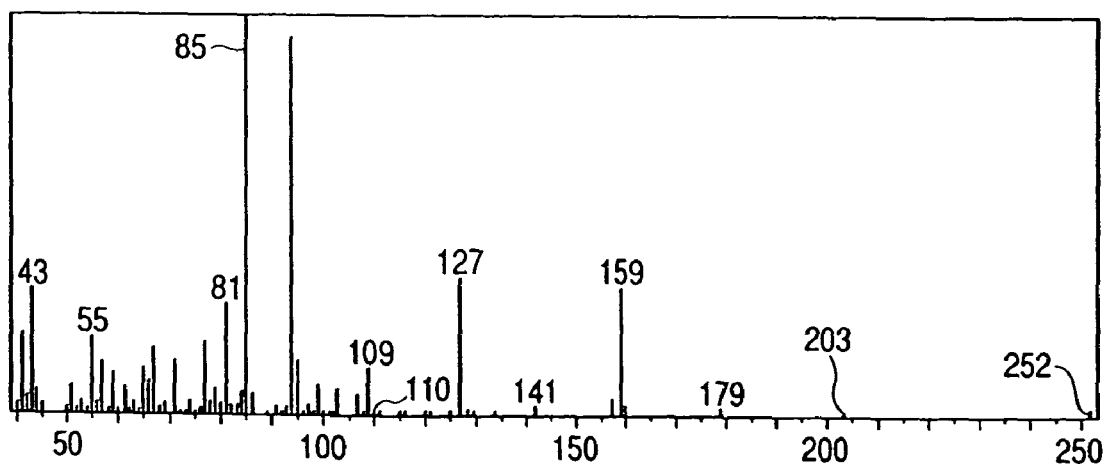
FIG. 107 is a chart which shows the mass spectrum of methyl 3-hydroxy-7-phenoxyheptanoate (3HPxHp) obtained from the GC-MS measurement in Example 68.
Figure 108:
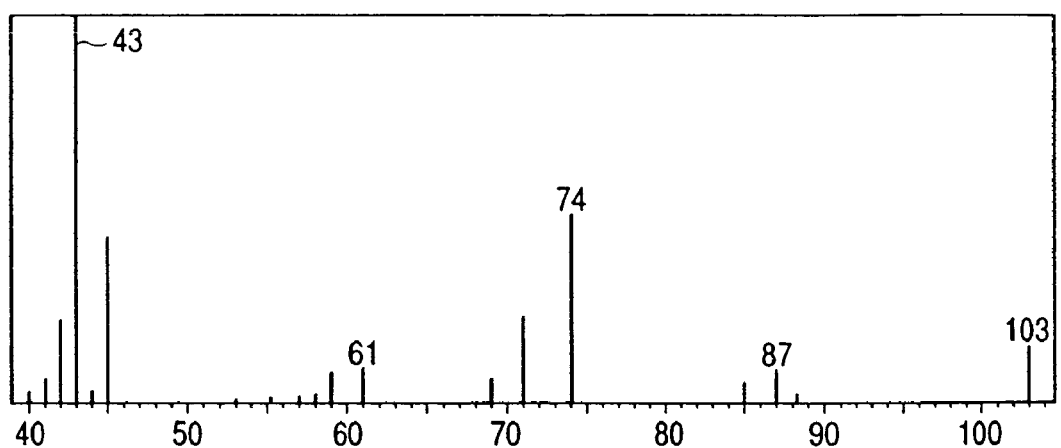
FIG. 108 is a chart which shows the mass spectrum of methyl 3-hydroxybutyrate obtained from the GC-MS measurement in Example 69.
Figure 109:
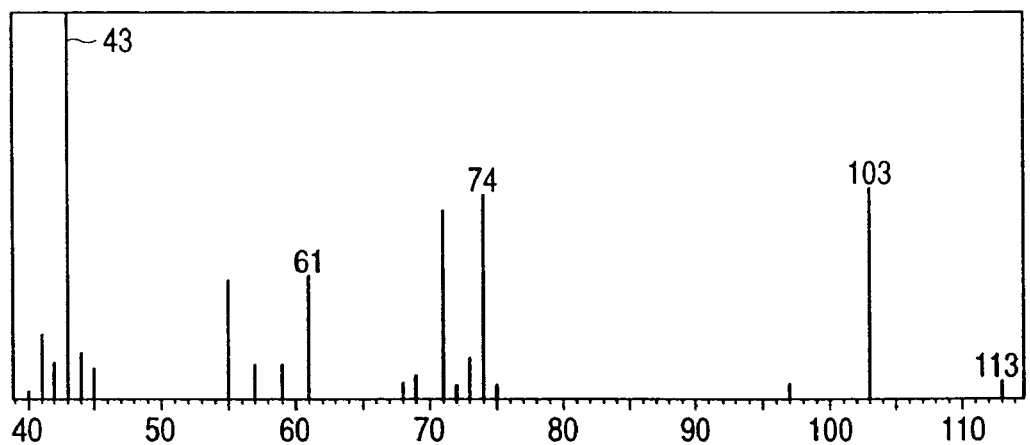
FIG. 109 is a chart which shows the mass spectrum of methyl 3-hydroxyhexanoate obtained from the GC-MS measurement in Example 69.
Figure 110:
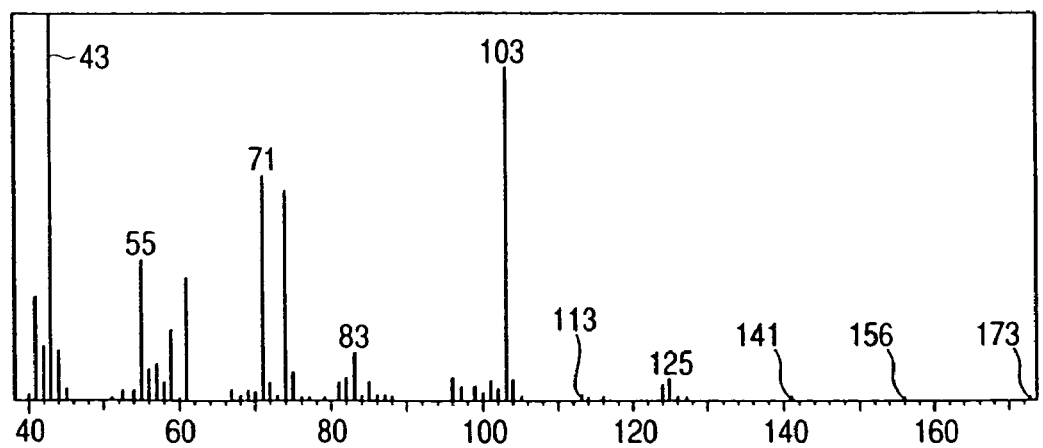
FIG. 110 is a chart which shows the mass spectrum of methyl 3-hydroxyoctanoate obtained from the GC-MS measurement in Example 69.
Figure 111:
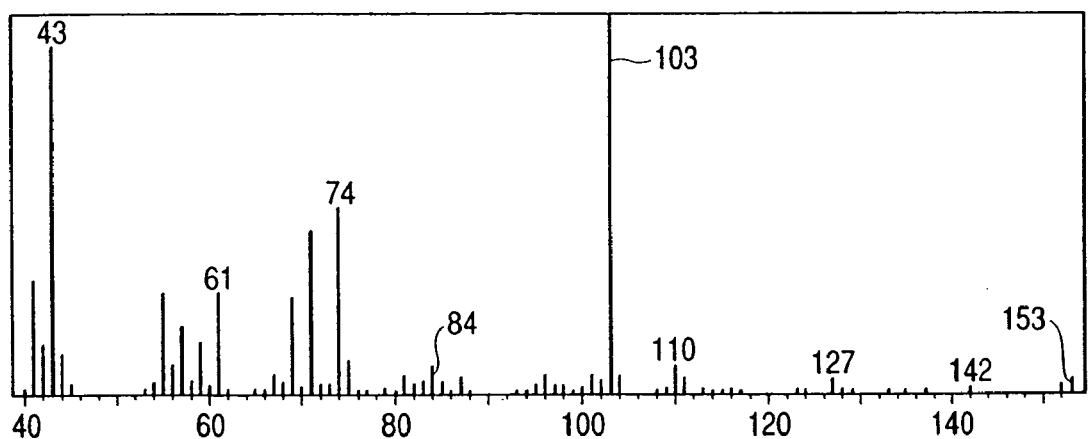
FIG. 111 is a chart which shows the mass spectrum of methyl 3-hydroxydecanoate obtained from the GC-MS measurement in Example 69.
Figure 112:
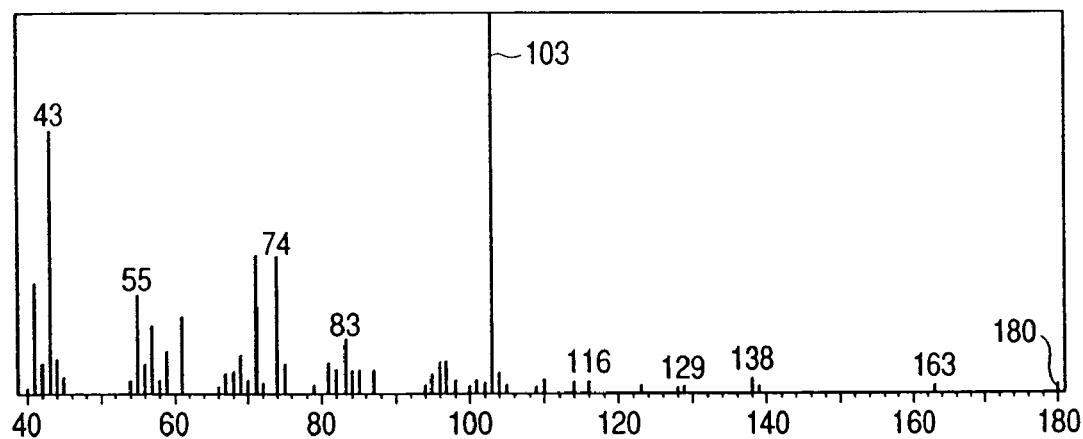
FIG. 112 is a chart which shows the mass spectrum of methyl 3-hydroxydodecanoate obtained from the GC-MS measurement in Example 69.
Figure 113:
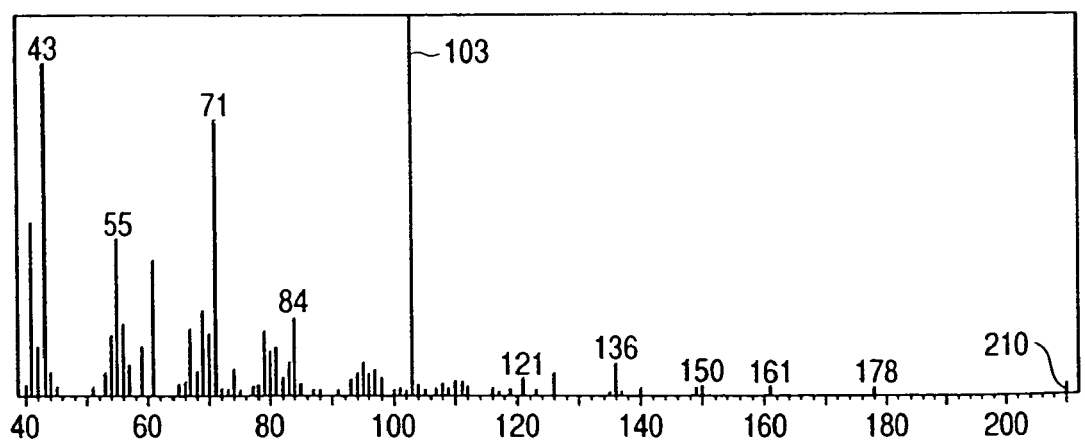
FIG. 113 is a chart which shows the mass spectrum of methyl 3-hydroxydodecenoate obtained from the GC-MS measurement in Example 69.
Figure 114:
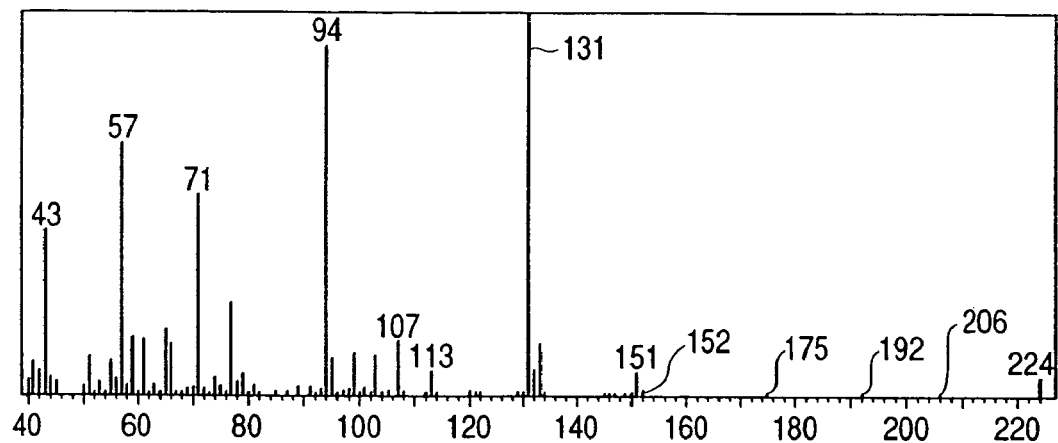
FIG. 114 is a chart which shows the mass spectrum of methyl 3-hydroxy-5-phenoxyvalerate (3HPxV) obtained from the GC-MS measurement in Example 69.
Figure 115:
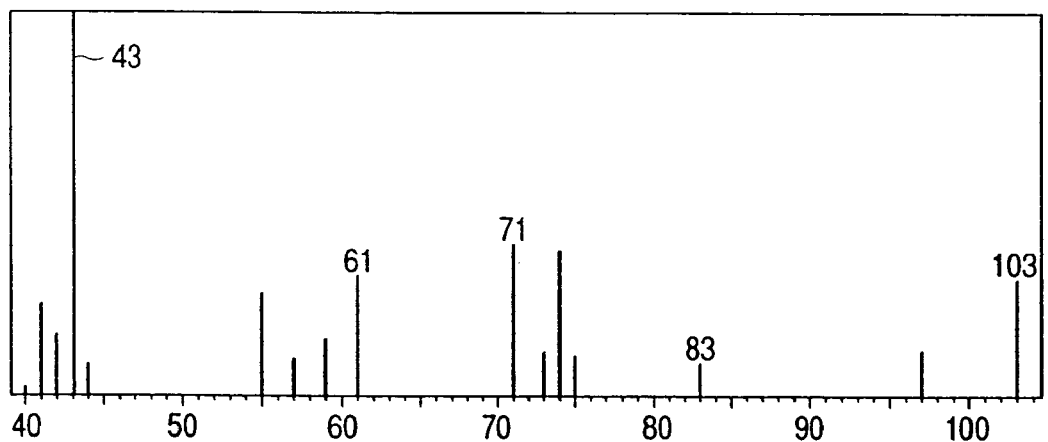
FIG. 115 is a chart which shows the mass spectrum of methyl 3-hydroxyhexanoate obtained from the GC-MS measurement in Example 70.
Figure 116:
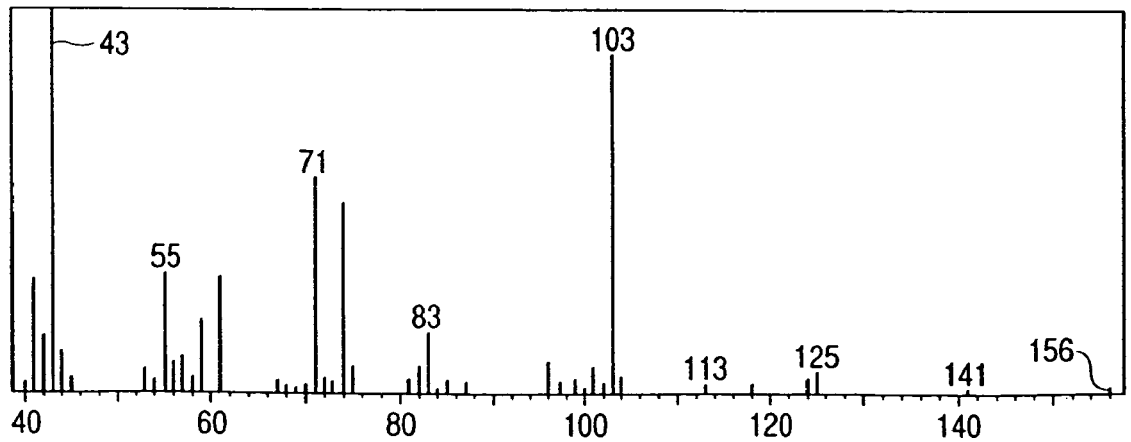
FIG. 116 is a chart which shows the mass spectrum of methyl 3-hydroxyoctanoate obtained from the GC-MS measurement in Example 70.
Figure 117:
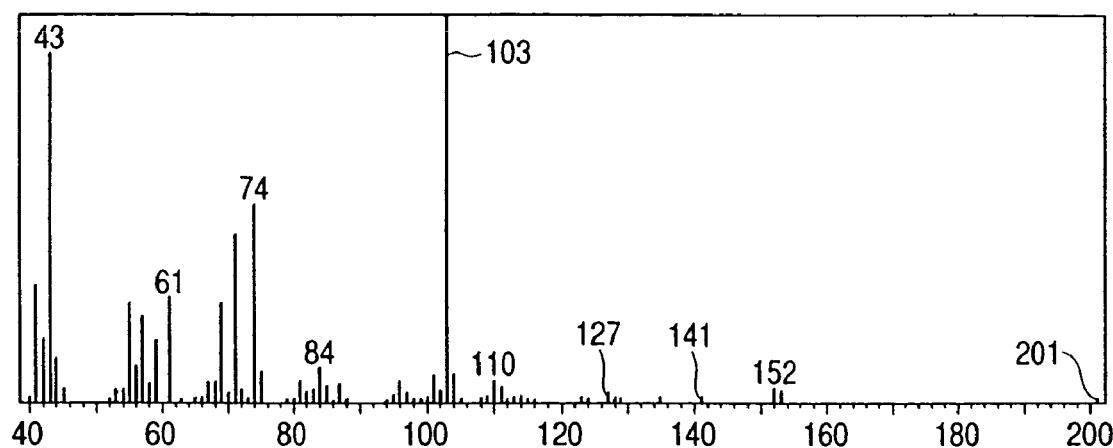
FIG. 117 is a chart which shows the mass spectrum of methyl 3-hydroxydecanoate obtained from the GC-MS measurement in Example 70.
Figure 118:
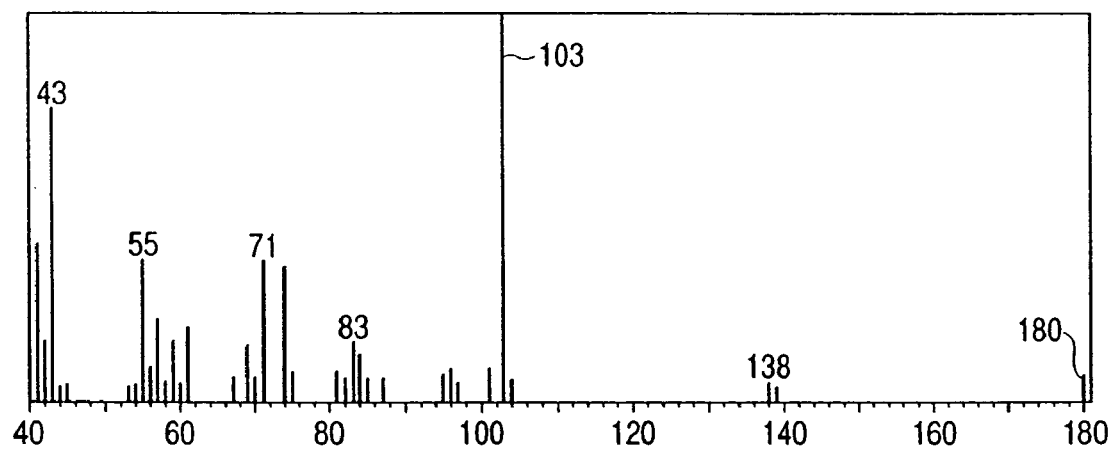
FIG. 118 is a chart which shows the mass spectrum of methyl 3-hydroxydodecanoate obtained from the GC-MS measurement in Example 70.
Figure 119:
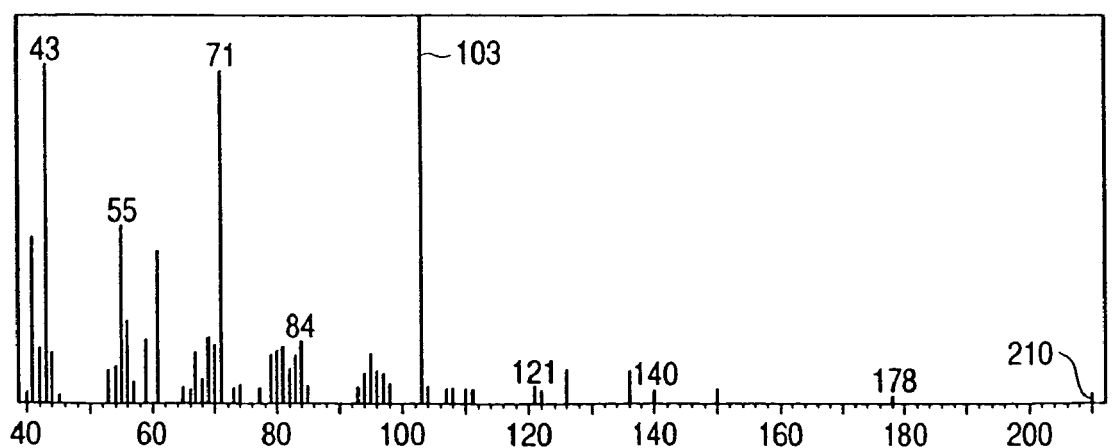
FIG. 119 is a chart which shows the mass spectrum of methyl 3-hydroxydodecenoate obtained from the GC-MS measurement in Example 70.
Figure 120:
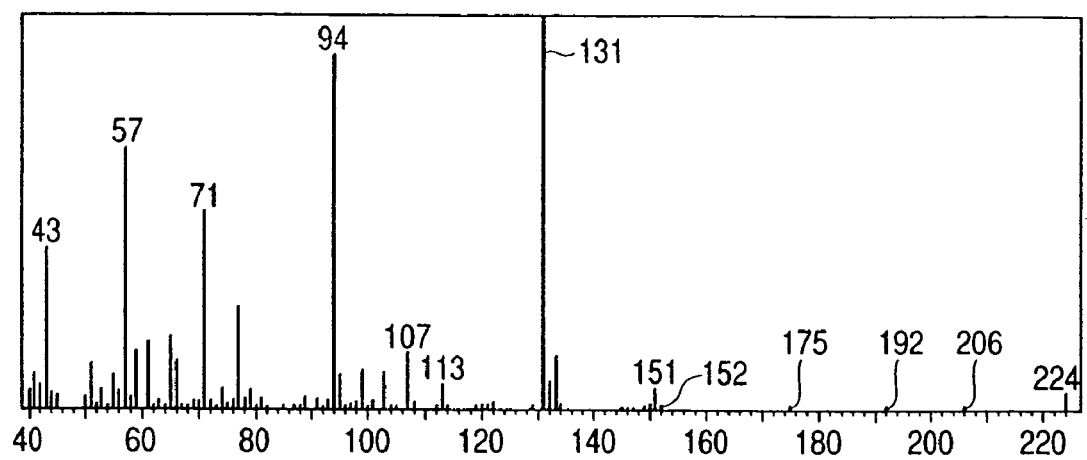

The unit composition of the obtained polymer was analyzed as follows: To 5 mg of a polymer sample put in a 25 mL volume round bottom flask, 2 mL of chloroform and 2 mL of methanol containing 3% (v/v) sulfuric acid was added, the mixture was subjected to 100° C. and 3.5 hr reflux and separated with a further addition of water, then the organic layer was analyzed by a gas chromatograph-mass spectrometer (GC-MS, Shimadzu QP-5050; column: DB-WAXETR (J & W Co. available); EI method) to identify a methyl esterified substance of the PHA monomer unit. Table 74 shows the yield of the cells and polymers and the analyzed result of the monomer unit. Besides, FIGS. 90 to 92 show the mass spectra, obtained by the GC-MS measurement of 3-hydroxybutyrate methyl ester, 3-hydroxy-5-phenoxyvalerate (3HPxV) methyl ester and 3-hydroxy-7-phenoxyheptanoate (3HPxHp) methyl ester, respectively.

From this result, it was revealed that PHA copolymer containing two units of 3-hydroxy-5-phenoxyvaleric acid (3HPxV) and 3-hydroxy-7-phenoxyheptanoic acid (3HPxHp) could be produced using strain H45 and 7-phenoxyheptanoic acid as the substrate.

Example 67

Production of PHA Containing HPxHp Unit and HPxV Unit by Using Strain YN2 (Glucose, Two-Step Culture)

Strain YN2 was inoculated in 200 mL of M9 culture medium containing 0.5% glucose and 0.1% 7-phenoxyheptanoic acid (PxHpA) and cultured with 125 strokes/min of shaking at 30° C. After 64 hr, the cells were collected by centrifugation, re-suspended into 200 mL of M9 culture medium containing 0.5% glucose and 0.1% PxHpA and no nitrogen source ($NH_4Cl$) and further cultured with 125 strokes/min of shaking at 30° C. After 24 hr, the cells were collected by centrifugation, washed once with cold methanol, lyophilized and weighed.

This lyophilized pellet was suspended in 100 mL of chloroform and stirred at 60° C. for 24 hr to extract polymer. After filtered through a 0.45 µm pore-size membrane filter, the extract was concentrated by using a rotary evaporator and the concentrated solution was re-precipitated in cold methanol, and the precipitate was collected and vacuum-dried to obtain a polymer, then this polymer was weighed.

The molecular weight of the obtained polymer was measured by using gel permeation chromatography (GPC: Toso/HLC-8020; column: Polymer Laboratory/PL gel/MIXED-C/5 µm; solvent: chloroform; polystyrene reduced molecular weight).

The unit composition of the obtained polymer was analyzed as follows: To 5 mg of a polymer sample put in a 25 mL volume round bottom flask, 2 mL of chloroform and 2 mL of methanol containing 3% (v/v) sulfuric acid was added, the mixture was subjected to 100° C. and 3.5 hr reflux and separated with a further addition of water, then the organic layer was analyzed on a gas chromatograph-mass spectrometer (GC-MS, Shimadzu QP-5050; column: DB-WAXETR (J & W Co. available); EI method) to identify the methyl esterified substance of the PHA monomer unit. Table 75 shows the yield of the cells and polymer and the analyzed result of the monomer unit. Besides, FIGS. 93 to 100 show the mass spectra, obtained by the GC-MS measurement of 3-hydroxybutyrate methyl ester, 3-hydroxyhexanoate methyl ester, 3-hydroxyoctanoate methyl ester, 3-hydroxydecanoate methyl ester, 3-hydroxydodecanoate methyl ester, 3-hydroxydodecenoate methyl ester, 3-hydroxy-5-phenoxyvalerate (3HPxV) methyl ester and 3-hydroxy-7-phenoxyheptanoate (3HPxHp) methyl ester, respectively.

From this result, it was revealed that PHA copolymer containing two units of 3-hydroxy-5-phenoxyvaleric acid (3HPxV) and 3-hydroxy-7-phenoxyheptanoic acid (3HPxHp) could be produced using strain YN2 and 7-phenoxyheptanoic acid as the substrate.

Example 68

Production of PHA Containing HPxHp Unit and HPxV Unit by Using Strain H45 (Glucose, Two-Step Culture)

Strain H45 was inoculated in 200 mL of M9 culture medium containing 0.5% glucose and 0.1% 7-phenoxyheptanoic acid (PxHpA) and cultured with 125 strokes/min of shaking at 30° C. After 64 hr, the cells were collected by centrifugation, re-suspended into 200 mL of M9 culture medium containing 0.5% glucose and 0.1% PxHpA and no nitrogen source ($NH_4Cl$) and further cultured with 125 strokes/min of shaking at 30° C. After 24 hr, the cells were collected by centrifugation, washed once with cold methanol, lyophilized and weighed.

This lyophilized pellet was suspended in 100 mL of chloroform and stirred at 60° C., for 24 hr to extract polymer. After filtered through a 0.45 µm pore-size membrane filter, the extract was concentrated using a rotary evaporator and the concentrated solution was re-precipitated in cold methanol, and the precipitate was collected and vacuum-dried to obtain a polymer, then this polymer was weighed.

The molecular weight of the obtained polymer was measured by using gel permeation chromatography (GPC: Toso/HLC-8020; column: Polymer Laboratory/PL gel/MIXED-C/5 µm; solvent: chloroform; polystyrene reduced molecular weight).

The unit composition of the obtained polymer was analyzed as follows: To 5 mg of a polymer sample put in a 25 mL volume round bottom flask, 2 mL of chloroform and 2 mL of methanol containing 3% (v/v) sulfuric acid was added, the mixture was subjected to 100° C. and 3.5 hr reflux and separated with a further addition of water, then the organic layer was analyzed on a gas chromatograph-mass spectrometer (GC-MS, Shimadzu QP-5050; column: DB-WAXETR (J & W Co. available); EI method) to identify a methyl esterified substance of the PHA monomer unit. Table 76 shows the yield of the cells and polymer and the analyzed result of the monomer unit. Besides, FIGS. 101 to 107 show the mass spectra, obtained by the GC-MS measurement of 3-hydroxyhexanoate methyl ester, 3-hydroxyoctanoate methyl ester, 3-hydroxydecanoate methyl ester, 3-hydroxydodecanoate methyl ester, 3-hydroxydodecenoate methyl ester, 3-hydroxy-5-phenoxyvalerate (3HPxV) methyl ester and 3-hydroxy-7-phenoxyheptanoate (3HPxHp) methyl ester, respectively.

From this result, it was revealed that PHA copolymer containing two units of 3-hydroxy-5-phenoxyvaleric acid (3HPxV) and 3-hydroxy-7-phenoxyheptanoic acid (3HPxHp) could be produced using strain H45 with 7-phenoxyheptanoic acid as the substrate.

Example 69

Production of PHA Containing PHPxV Unit by Using Strain YN2 (Sodium Malate Two-Step Culture)

Strain YN2 was inoculated in 200 mL of M9 culture medium containing 0.5% sodium malate and 0.1% 5-phenoxyvaleric acid (PxVA) and cultured with 125 strokes/min of shaking at 30° C. After 60 hr, the cells were collected by centrifugation, re-suspended into 200 mL of M9 culture medium containing 0.5% sodium malate and 0.1% PxVA and no nitrogen source (NH$_4$Cl) and further cultured with 125 strokes/min of shaking at 30° C. After 24 hr, the cells were collected by centrifugation, washed once with cold methanol, lyophilized and weighed.

This lyophilized pellet was suspended in 100 mL of chloroform and stirred at 60° C. for 24 hr to extract polymer. After filtered through a 0.45 μm pore-size membrane filter, the extract was concentrated by using a rotary evaporator and the concentrated solution was re-precipitated in cold methanol, further the precipitate alone was collected and vacuum-dried to obtain a polymer, then this polymer was weighed.

The molecular weight of the obtained polymer was measured by using gel permeation chromatography (GPC: Toso/HLC-8020; column: Polymer Laboratory/PL gel/MIXED-C/5 μm; solvent: chloroform; polystyrene reduced molecular weight).

The unit composition of the obtained polymer was analyzed as follows: To 5 mg of a polymer sample put in a 25 mL volume round bottom flask, 2 mL of chloroform and 2 mL of methanol containing 3% (v/v) sulfuric acid was added, the mixture was subjected to 100° C. and 3.5 hr reflux and separated with a further addition of water, then the organic layer was analyzed on a gas chromatograph-mass spectrometer (GC-MS, Shimadzu QP-5050; column: DB-WAXETR (J & W Co. available); EI method) to identify a methyl esterified substance of the PHA monomer unit. Table 77 shows the yield of the cells and polymer and the analyzed result of the monomer unit. Besides, FIGS. 108 to 114 show the mass spectra, obtained by the GC-MS measurement, of 3-hydroxybutyrate methyl ester, 3-hydroxyhexanoate methyl ester, 3-hydroxyoctanoate methyl ester, 3-hydroxydecanoate methyl ester, 3-hydroxydodecanoate methyl ester, 3-hydroxydodecenoate methyl ester and 3-hydroxy-5-phenoxyvalerate (3HPxV) methyl ester, respectively.

From this result, it was revealed that PHA copolymer containing 3-hydroxy-5-phenoxyvaleric acid (3HPxV) unit could be produced using strain YN2 with 5-phenoxyvaleric acid as the substrate.

Example 70

Production of PHA Containing HPxV Unit by Using Strain H45 (Sodium Malate Two-Step Culture)

Strain H45 was inoculated in 200 mL of M9 culture containing 0.5% sodium malate and 0.1% 5-phenoxyvaleric acid (PxVA) and cultured with 125 strokes/min of shaking at 30° C. After 60 hr, the cells were collected by centrifugation, re-suspended into 200 mL of M9 culture medium containing 0.5% sodium maleate and 0.1% PxVA and no nitrogen source (NH$_4$Cl) and further cultured with 125 strokes/min of shaking at 30° C. After 24 hr, the cells were collected by centrifugation, washed once with cold methanol, lyophilized and weighed.

This lyophilized pellet was suspended in 100 mL of chloroform and stirred at 60° C. for 24 hr to extract polymer. After filtered through a 0.45 μm pore-size membrane filter, the extract was concentrated using a rotary evaporator and the concentrated solution was re-precipitated in cold methanol, and the precipitate was collected and vacuum-dried to obtain a polymer, then this polymer was weighed.

The molecular weight of the obtained polymer was measured by using gel permeation chromatography (GPC: Toso/HLC-8020; column: Polymer Laboratory/PL gel/MIXED-C/5 μm; solvent: chloroform; polystyrene reduced molecular weight).

The unit composition of the obtained polymer was analyzed as follows: To 5 mg of a polymer sample put in a 25 mL volume round bottom flask, 2 mL of chloroform and 2 mL of methanol containing 3% (v/v) sulfuric acid was added, the mixture was subjected to 100° C. and 3.5 hr reflux and separated with a further addition of water, then the organic layer was analyzed on a gas chromatograph-mass spectrometer (GC-MS, Shimadzu QP-5050; column: DB-WAXETR (J & W Co. available); EI method) to identify a methyl esterified substance of the PHA monomer unit. Table 78 shows the yield of the cells and polymer and the analyzed result of the monomer unit. Besides, FIGS. 115 to 120 show the mass spectra, obtained by the GC-MS measurement, of 3-hydroxyhexanoate methyl ester, 3-hydroxyoctanoate methyl ester, 3-hydroxydecanoate methyl ester, 3-hydroxydodecanoate methyl ester, 3-hydroxydodecenoate methyl ester and 3-hydroxy-5-phenoxyvalerate (3HPxV) methyl ester, respectively.

From this result, it was revealed that PHA copolymer containing 3-hydroxy-5-phenoxyvaleric acid (3HPxV) unit could be produced using strain H45 with 5-phenoxyvaleric acid as the substrate.

Example 71

Production of PHA Containing HPV Unit by Using Strain YN2 (Fructose Two-Step Culture)

Strain YN2 was inoculated in 200 mL of M9 culture medium containing 0.5% fructose and 0.1% 5-phenylvaleric acid (PVA) and cultured with 125 strokes/min of shaking at 30° C. After 120 hr, the cells were collected by centrifugation, re-suspended into 200 mL of M9 culture medium containing 0.5% fructose and 0.1% PxVA and no nitrogen source (NH$_4$Cl) and further cultured with 125 strokes/min of shaking at 30° C. After 50 hr, the cells were collected by centrifugation, washed once with cold methanol, lyophilized and weighed.

This lyophilized pellet was suspended in 100 mL of chloroform and stirred at 60° C. for 24 hr to extract polymer. After filtered through a 0.45 μm pore-size membrane filter, the extract was concentrated by using a rotary evaporator and the concentrated solution was re-precipitated in cold methanol, further the precipitate alone was collected and vacuum-dried to obtain a polymer, then this polymer was weighed.

The molecular weight of the obtained polymer was measured using gel permeation chromatography (GPC: Toso/HLC-8020; column: Polymer Laboratory/PL gel/MIXED-C/5 µm; solvent: chloroform; polystyrene reduced molecular weight).

Figure 121:
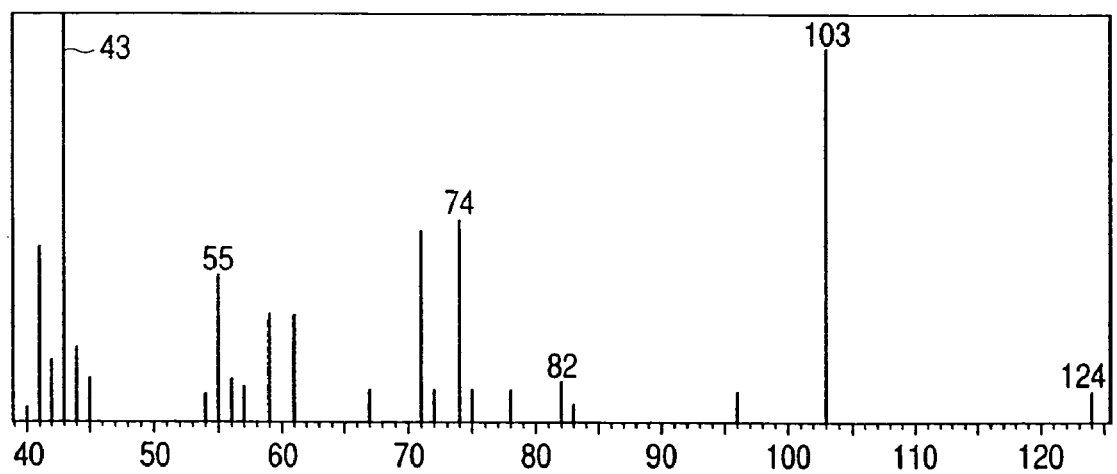
Figure 122:
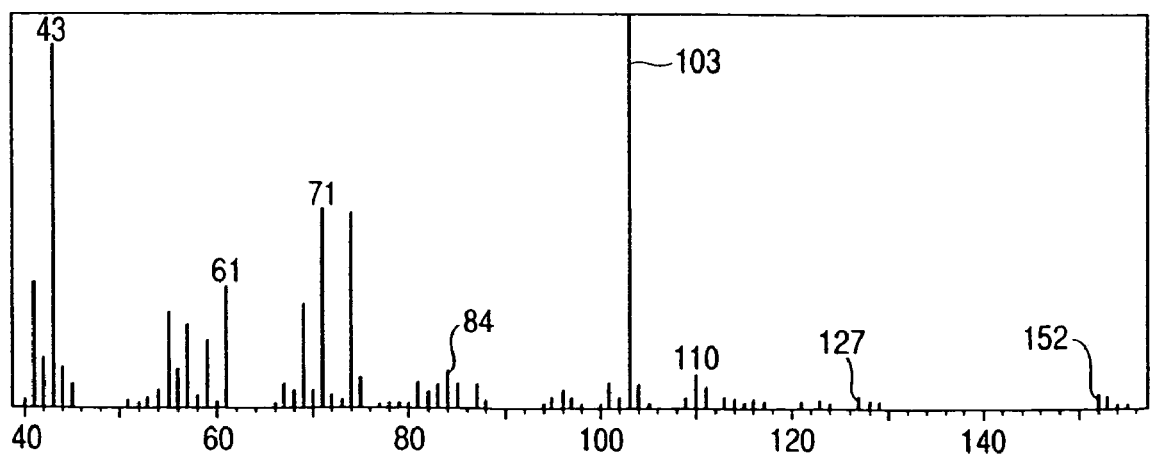
Figure 123:
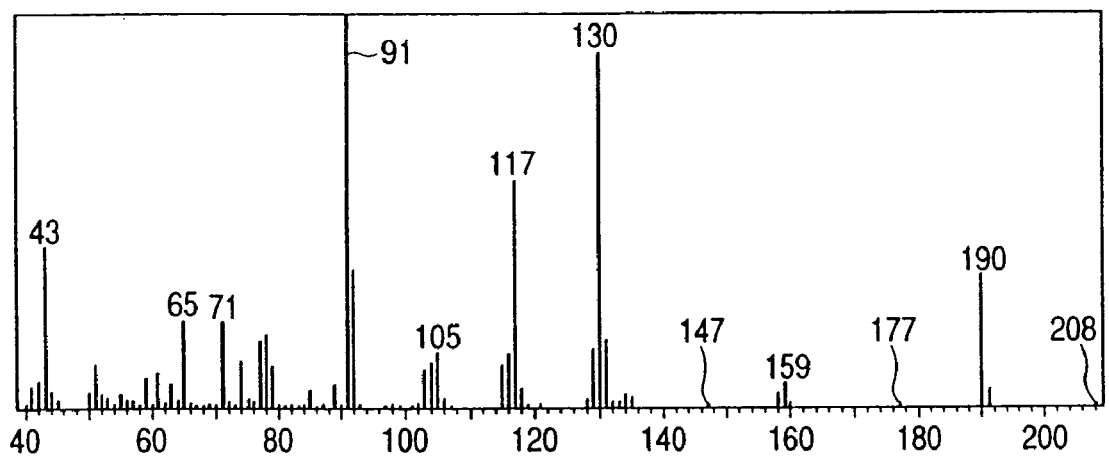

The unit composition of the obtained polymer was analyzed as follows: To 5 mg of a polymer sample put in a 25 mL volume round bottom flask, 2 mL of chloroform and 2 mL of methanol containing 3% (v/v) sulfuric acid was added, the mixture was subjected to 100° C. and 3.5 hr reflux and separated with a further addition of water, then the organic layer was analyzed on a gas chromatograph-mass spectrometer (GC-MS, Shimadzu QP-5050; column: DB-WAXETR (J & W Co. available); EI method) to identify a methyl esterified substance of the PHA monomer unit. Table 79 shows the yield of the cells and polymer and the analyzed result of the monomer unit. Besides, FIGS. 121 to 123 show the mass spectra, obtained by the GC-MS measurement of 3-hydroxyoctanoate methyl ester, 3-hydroxydecanoate methyl ester and 3-hydroxy-5-phenylvalerate (3HPV) methyl ester, respectively.

From this result, it was revealed that a PHA copolymer containing 3-hydroxy-5-phenylvaleric acid (3HPV) unit could be produced using strain YN2 with 5-phenylvaleric acid as the substrate.

Example 72

Production of PHA Containing HPV Unit by Using Strain YN2 (Mannose Two-Step Culture)

Strain YN2 was inoculated in 200 mL of M9 culture medium containing 0.5% mannose and 0.1% 5-phenylvaleric acid (PVA) and cultured with 125 strokes/min of shaking at 30° C. After 43 hr, the cells were collected by centrifugation, re-suspended into 200 mL of M9 culture medium containing 0.5% mannose and 0.1% PxVA and no nitrogen source ($NH_4Cl$) and further cultured with 125 strokes/min of shaking at 30° C. After 91 hr, the cells were collected by centrifugation, washed once with cold methanol, lyophilized and weighed.

This lyophilized pellet was suspended in 100 mL of chloroform and stirred at 60° C. for 24 hr to extract polymer. After filtered through a 0.45 µm pore-size membrane filter, the extract was concentrated using a rotary evaporator and the concentrated solution was re-precipitated in cold methanol, and the precipitate was collected and vacuum-dried to obtain a polymer, then this polymer was weighed.

The molecular weight of the obtained polymer was measured by using gel permeation chromatography (GPC: Toso/HLC-8020; column: Polymer Laboratory/PL gel/MIXED-C/5 µm; solvent: chloroform; polystyrene seduced molecular weight).

Figure 124:
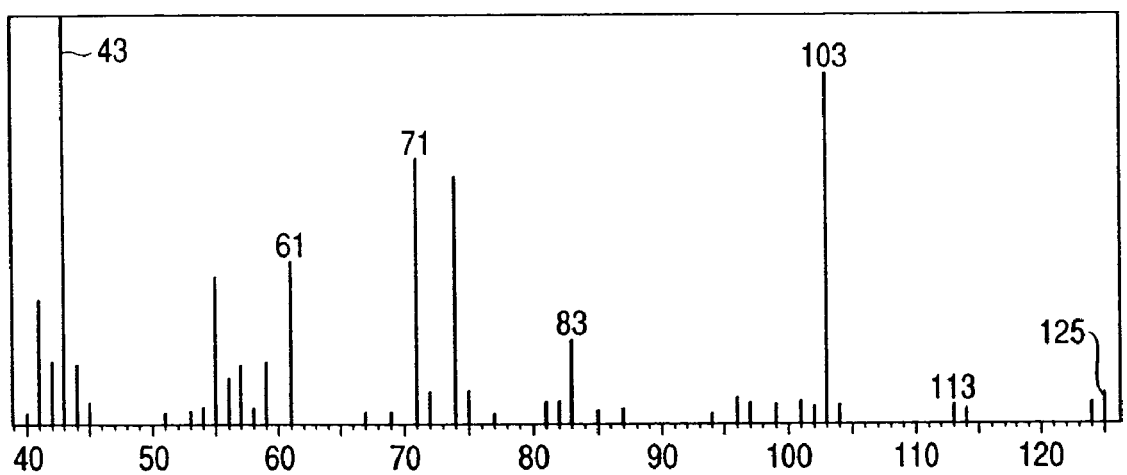
Figure 125:
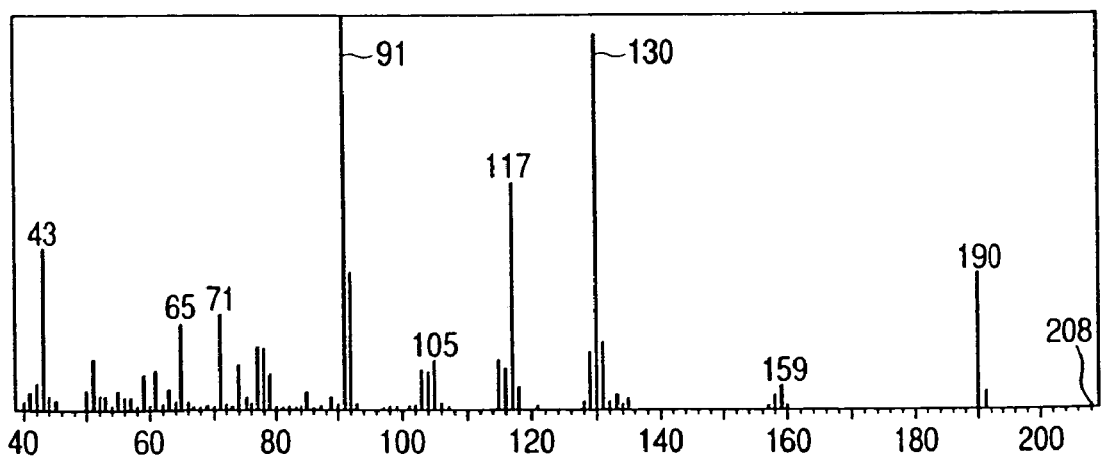
Figure 126:
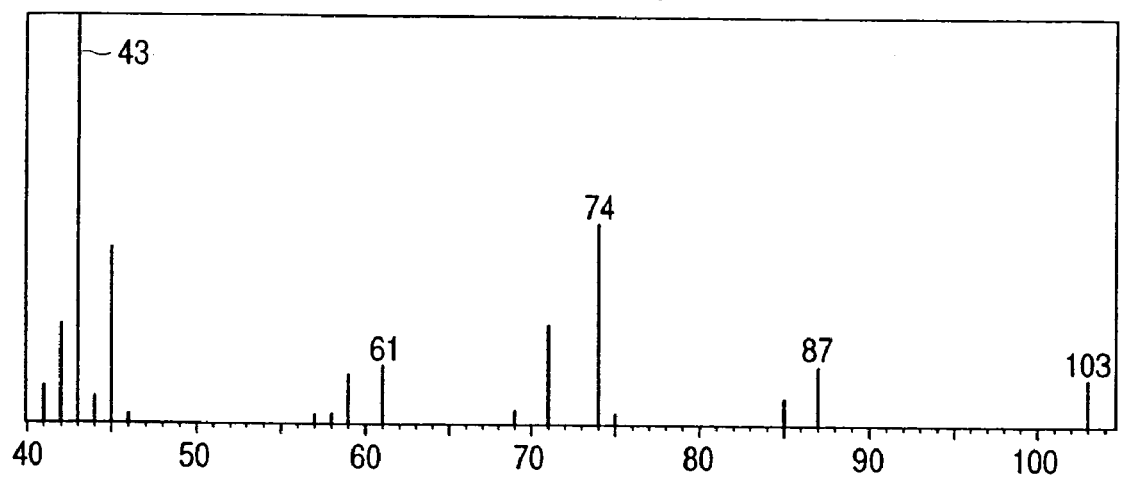
Figure 127:
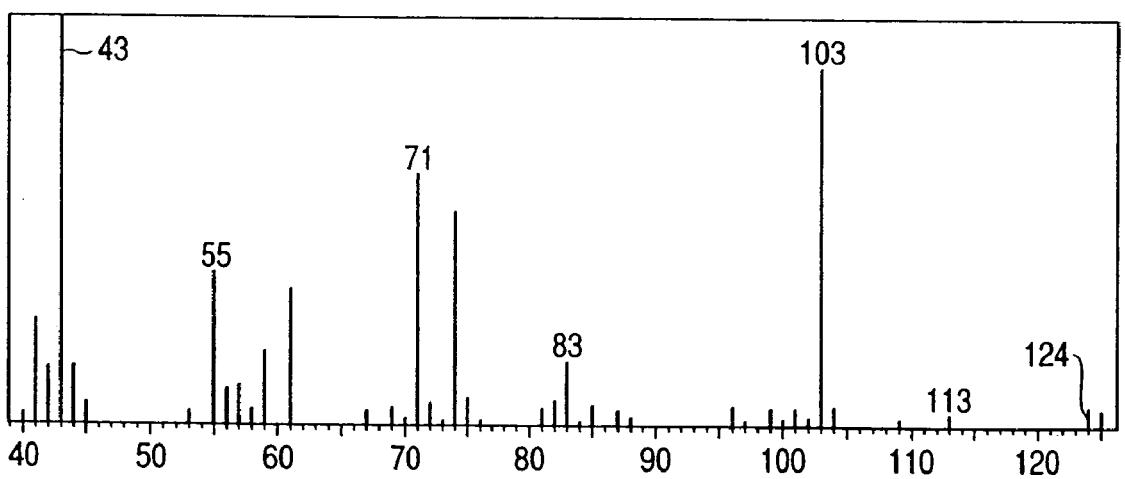
Figure 128:
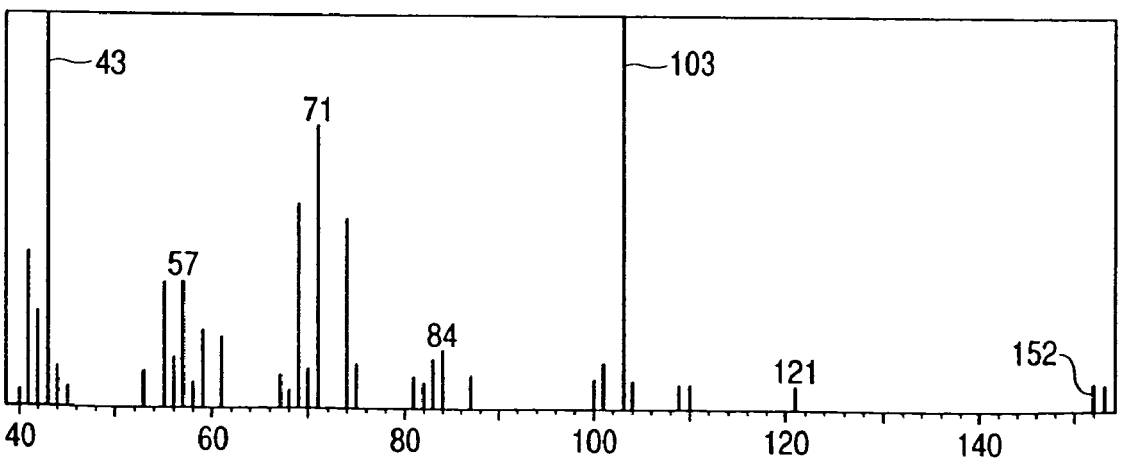
Figure 129:
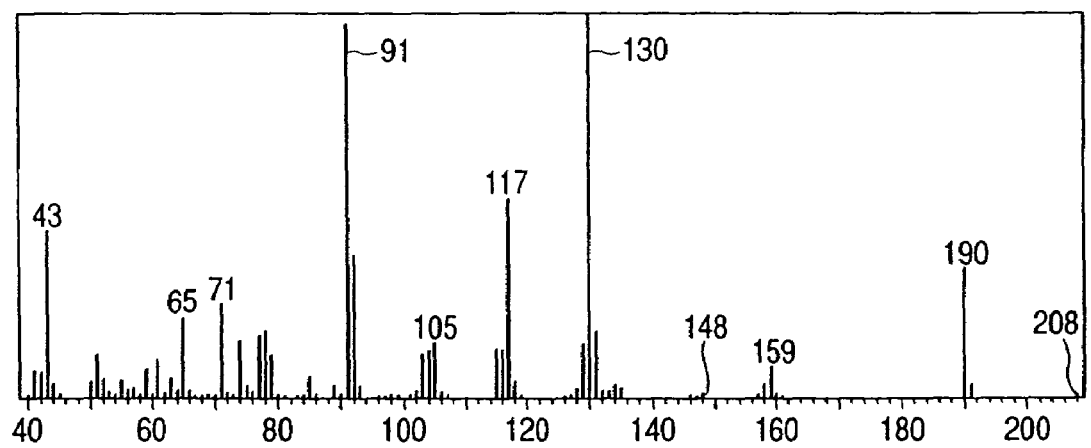

The unit composition of the obtained polymer was analyzed as follows: To 5 mg of a polymer sample put in a 25 mL volume round bottom flask, 2 mL of chloroform and 2 mL of methanol containing 3% (v/v) sulfuric acid was added, the mixture was subjected to 100° C. and 3.5 hr reflux and separated with a further addition of water, then the organic layer was analyzed on a gas chromatograph-mass spectrometer (GC-MS, Shimadzu QP-5050; column: DB-WAXETR (J & W Co. available); EI method) to identify a methyl esterified substance of the PHA monomer unit. Table 80 shows the yield of the cells and polymer and the analyzed result of the monomer unit. Besides, FIGS. 124 and 125 show the mass spectra, obtained by the GC-MS measurement, of 3-hydroxyoctanoate methyl ester and 3-hydroxy-5-phenylvalerate (3HPV) methyl ester, respectively.

From this result, it was revealed that PHA copolymer containing 3-hydroxy-5-phenylvaleric acid (3HPV) unit could be produced using strain YN2 with 5-phenylvaleric acid as the substrate.

Example 73

Production of PHA Containing HPV Unit by Using Strain YN2 (Sodium Lactate Two-Step Culture)

Strain YN2 was inoculated in 200 mL of M9 culture medium containing 0.5% sodium lactate and 0.1% 5-phenylvaleric acid (PVA) and cultured with 125 strokes/min of shaking at 30° C. After 46 hr, the cells were collected by centrifugation, re-suspended into 200 mL of M9 culture containing 0.5% sodium lactate and 0.1% PxVA and no nitrogen source ($NH_4Cl$) and further cultured with 125 strokes/min of shaking at 30° C. After 28 hr, the cells were collected by centrifugation, washed once with cold methanol, lyophilized and weighed.

This lyophilized pellet was suspended in 100 mL of chloroform and stirred at 60° C. for 24 hr to extract polymer. After filtered-through a 0.45 µm pore-size membrane filter, the extract was concentrated by using a rotary evaporator and the concentrated solution was re-precipitated in cold methanol, and the precipitate was collected and vacuum-dried to obtain a polymer, then this polymer was weighed.

The molecular weight of the obtained polymer was measured using gel permeation chromatography (GPC: Toso/HLC-8020; column: Polymer Laboratory/PL gel/MIXED-C/5 µm; solvent: chloroform; polystyrene reduced molecular weight).

The unit composition of the obtained polymer was analyzed as follows: To 5 mg of a polymer sample put in a 25 mL volume round bottom flask, 2 mL of chloroform and 2 mL of methanol containing 3% (v/v) sulfuric acid was added, the mixture was subjected to 100° C. and 3.5 hr reflux and separated with a further addition of water, then the organic layer was analyzed on a gas chromatograph-mass spectrometer (GC-MS, Shimadzu QP-5050; column: DB-WAXETR (J & W Co. available); EI method) to identify a methyl esterified substance of the PHA monomer unit. Table 81 shows the yield of the cells and polymer and the analyzed result of the monomer unit. Besides, FIGS. 126 to 129 show the mass spectra, obtained by the GC-MS measurement, of 3-hydroxybutyrate methyl ester, 3-hydroxyoctanoate methyl ester, 3-hydroxydecanoate methyl ester and 3-hydroxy-5-phenylvalerate (3HPV) methyl ester, respectively.

From this result, it was revealed that PHA copolymer containing 3-hydroxy-5-phenylvaleric acid (3HPV) unit could be produced using strain YN2 with 5-phenylvaleric acid as the substrate.

Example 74

Production of PHA Containing HPxB Unit by Using Strain YN2 (Disodium Malate Two-Step Culture)

*Pseudomonas cichorii* strain YN2 was inoculated in 200 mL of 5 types of M9 culture media each containing 0.1% 4-phenoxy-n-butyric acid (PxBA) and one of 0.5% of disodium malate semihydrate, L-sodium glutamate monohydrate, D(+)-glucose and n-nonanoic acid and polypeptone (Nihon Seiyaku) respectively, and cultured with 125 strokes/ min of shaking at 30° C. After 48 hr, the cells were collected by centrifugation, washed once with cold methanol and vacuum-dried.

These five pellets were suspended in 20 mL of chloroform separately and stirred at 60° C. for 20 hr to extract PHA. After filtered through a 0.45 μm pore-size membrane filter, each extract was concentrated using a rotary evaporator and the concentrated solution was re-precipitated in cold methanol, and each precipitate was collected and vacuum-dried to obtain PHA. After subjected to methanolysis in accordance with the usual way, the obtained PHAs were analyzed using a gas chromatograph-mass spectrometer (GC-MS, Shimadzu QP-5050; EI method) to identify the methyl esterified substance of the PHA monomer unit. As a result, in case of culturing with disodium malate as the growth carbon source, as shown in Table 82, PHA having a high proportion of 3-hydroxy-4-phenoxy-n-butyric acid (3HPxB) unit, a desired monomer unit derived from 4-phenoxy-n-butyric acid, was obtained at a high yield. Furthermore, Table 83 shows the yield of the cells and polymer and the composition of the polymer in the case of culture using disodium malate.

Example 75

Production of PHA Containing HPxB Unit by Using Strain YN2 (Disodium Malate Two-Step Culture: Mass Culture)

*Pseudomonas cichorii* strain YN2 was inoculated in 200 mL of M9 culture medium containing 0.5% yeast extract (Oriental Yeast Industries), and cultured with 125 strokes/min of shaking at 30° C. as a seed culture. In a 10 L jar fermenter containing 5 L of M9 medium containing 0.5% of disodium malate semihydrate and 0.1% 4-phenoxy-n-butyric acid, 50 mL of seed cells was inoculated and shake cultured at 30° C. with 80 stroke/min under aeration of 2.5 L/min. After 39 hr, the cells were collected by centrifugation. This pellet was suspended in 120 mL of an approx. 1.7% sodium hypochlorite solution and shaken at 4° C. for 2 hr to extract PHA. PHA was collected by centrifugation and dried to obtain 56 mg of PHA per liter culture medium.

After subjected to methanolysis in accordance with the usual way, the obtained PHA was analyzed using a gas chromatograph-mass spectrometer (GC-MS, Shimadzu QP-5050; EI method.) to identify a methyl esterified substance of the PHA monomer unit. As a result, the composition ratio (GC-MS, peak area ratio) of 3-hydroxy-4-phenoxy-n-butyric acid unit, a desired monomer unit derived from 4-phenoxy-n-butyric acid, was 99.7%.

TABLE 1

| Carbon Source (alkanoate) | Weight of dry cell (mg/L) | Weight of dry polymer (mg/L) | Yield (%) |
|---|---|---|---|
| 6-phenoxyhexanoic acid | 950 | 100 | 10.5 |
| 8-phenoxyoctanoic acid | 820 | 90 | 11 |
| 11-phenoxyundecanoic acid | 150 | 15 | 10 |

TABLE 2

| NA:CHBA | CDW | PDW | Yield | Unit |
|---|---|---|---|---|
| 5:5 | 756.0 | 89.1 | 11.8 | NA, CHBA |
| 1:9 | 132.8 | 19.3 | 14.5 | NA, CHBA |

CDW: Cell (Dry Weight)
PDW: Polymer (Dry Weight)
Yield: PDW/CDW (%)

TABLE 3

| Chemical Shift/ppm | type | Assignment |
|---|---|---|
| 1.67 | m | c, d |
| 2.39 | t | b |
| 2.62 | t | e |
| 6.97 | t | h, j |
| 7.12 | t | g, k |
| 10.7 | broad | COOH |

TABLE 4

| *P. cichorii* strain H45 | |
|---|---|
| Cell (Dry weight) | 750 mg/L |
| Polymer (Dry weight) | 400 mg/L |
| Polymer (Dry weight)/Cell (Dry weight) | 53% |
| Monomer Unit Composition (area ratio) | |
| 3-hydroxybutyric acid | 0% |
| 3-hydroxyvaleric acid | 0% |
| 3-hydroxyhexanoic acid | 0% |
| 3-hydroxyheptanoic acid | 13% |
| 3-hydroxyoctanoic acid | 3% |
| 3-hydroxynonanoic acid | 37% |
| 3-hydroxydecanoic acid | 0% |
| 3-hydroxy-5-(4-fluorophenyl)valeric acid | 47% |

TABLE 5

| *P. cichorii* strain YN2 | |
|---|---|
| Cell (Dry weight) | 850 mg/L |
| Polymer (Dry weight) | 420 mg/L |
| Polymer (Dry weight)/Cell (Dry weight) | 49% |
| Monomer Unit Composition (area ratio) | |
| 3-hydroxybutyric acid | 1% |
| 3-hydroxyvaleric acid | 1% |
| 3-hydroxyhexanoic acid | 0% |
| 3-hydroxyheptanoic acid | 15% |
| 3-hydroxyoctanoic acid | 2% |
| 3-hydroxynonanoic acid | 68% |
| 3-hydroxydecanoic acid | 0% |
| 3-hydroxy-5-(4-fluorophenyl)valeric acid | 13% |

TABLE 6

| *P. putida* P 91 strain | |
|---|---|
| Cell (Dry weight) | 670 mg/L |
| Polymer (Dry weight) | 51 mg/L |
| Polymer (Dry weight)/Cell (Dry weight) | 8% |
| Monomer Unit Composition (area ratio) | |
| 3-hydroxybutyric acid | 0% |
| 3-hydroxyvaleric acid | 1% |
| 3-hydroxyhexanoic acid | 0% |
| 3-hydroxyheptanoic acid | 11% |
| 3-hydroxyoctanoic acid | 2% |

TABLE 6-continued

*P. putida* P 91 strain

| | |
|---|---|
| 3-hydroxynonanoic acid | 34% |
| 3-hydroxydecanoic acid | 0% |
| 3-hydroxy-5-(4-fluorophenyl)valeric acid | 52% |

TABLE 7

*P. jessenii* strain P161

| | |
|---|---|
| Cell (Dry weight) | 1200 mg/L |
| Polymer (Dry weight) | 640 mg/L |
| Polymer (Dry weight)/Cell (Dry weight) | 53% |
| Monomer Unit Composition (area ratio) | |
| 3-hydroxybutyric acid | 1% |
| 3-hydroxyvaleric acid | 1% |
| 3-hydroxyhexanoic acid | 0% |
| 3-hydroxyheptanoic acid | 17% |
| 3-hydroxyoctanoic acid | 3% |
| 3-hydroxynonanoic acid | 45% |
| 3-hydroxydecanoic acid | 0% |
| 3-hydroxy-5-(4-fluorophenyl)valeric acid | 33% |

TABLE 8

Purified PHA

Monomer Unit Composition (area ratio)

| | |
|---|---|
| 3-hydroxybutyric acid | 0% |
| 3-hydroxyvaleric acid | 0% |
| 3-hydroxyhexanoic acid | 0% |
| 3-hydroxyheptanoic acid | 0% |
| 3-hydroxyoctanoic acid | 0% |
| 3-hydroxynonanoic acid | 0% |
| 3-hydroxydecanoic acid | 0% |
| 3-hydroxy-5-(4-fluorophenyl)valeric acid | 100% |

TABLE 9

(Results of $^1$H spectrometry)
Resonance frequency: 400 MHz

| δ (ppm) | Assignment |
|---|---|
| 0.9 to 1.7 | broad peak → impurity |
| 1.8 to 1.9 | m: 2H, —CH$_2$ → d |
| 2.4 to 2.6 | m: 4H, —CH$_2$ × 2 → b, e |
| 5.2 to 5.3 | m: 1H, —OCH → c |
| 6.9 to 7.0 | t: 2H, proton at the ortho position of the F group → h, j |
| 7.1 | t: 2H, proton at the para position of the F group → g, k |
| 7.3 | s: solvent (CDCl$_3$) | m: multiplet,
t: triplet,
s: singlet

TABLE 10

(Results of $^{13}$C spectrometry)
Resonance frequency: 100 MHz

| δ (ppm) | Assignment |
|---|---|
| 31.0 | —CH$_2$ → d |
| 35.9 | —CH$_2$ → e |
| 39.4 | —CH$_2$ → b |
| 70.5 | —CH → c |

TABLE 10-continued (Results of $^{13}$C spectrometry)
Resonance frequency: 100 MHz

| δ (ppm) | Assignment |
|---|---|
| 77.1 to 77.7 | Solvent (CDCl$_3$) |
| 115.5, 115.7 | —CH at the ortho position of the F group → h, j |
| 130.0 | —CH at the meta position of the F group → g, k |
| 136.8 | C at the para position of the F group → f |
| 160.5, 163.0 | —C at the F substituent position → i |
| 169.6 | carbonyl group —C=O → a |

TABLE 11

(Results of $^1$H-NMR spectrum identification (see FIG. 4))

| Chemical Shift/ppm | Integral/H | type | Identification |
|---|---|---|---|
| 1.85 | 4 | m | c, d |
| 2.46 | 2 | t | b |
| 3.95 | 2 | t | e |
| 6.83 | 2 | m | h, j |
| 6.97 | 2 | t | g, k |
| 10.15 | | broad | OH | m: multiple,
t: triplet,
d: doublet

TABLE 12

(Various microorganisms and the yields of produced PHA)

| | CDW(mg/L) | PDW(mg/L) | PDW/CDW(%) |
|---|---|---|---|
| strain P91 (Example 8) | 650 | 50 | 7.7 |
| strain YN2 1 (Example 9) | 1250 | 755 | 60.4 |
| strain P161 (Example 10) | 1150 | 680 | 59.1 |
| strain H45 (Example 11) | 1150 | 600 | 52.2 |
| strain YN2 2 (Example 12) | 500 | 240 | 48.0 |

TABLE 13

(Molecular weight of PHA produced by each microorganism)

| | Mn (×10$^4$) | Mw (×10$^5$) | Mw/Mn |
|---|---|---|---|
| strain P91 (Example 8) | 5.1 | 1.0 | 2.0 |
| strain YN2 1 (Example 9) | 8.8 | 2.4 | 2.7 |
| strain P161 (Example 10) | 6.8 | 1.8 | 2.7 |
| strain H45 (Example 11) | 8.8 | 2.2 | 2.5 |
| strain YN2 2 (Example 12) | 5.7 | 1.4 | 2.5 |

TABLE 14

| Dried cell (mg/L) | Dried polymer (mg/L) | Yield (polymer/cell, %) |
|---|---|---|
| 850 | 110 | 12.9 |

TABLE 15

| | |
|---|---|
| 3-hydroxyvaleric acid | 1.4% |
| 3-hydroxyheptanoic acid | 29.3% |
| 3-hydroxyoctanoic acid | 3.2% |
| 3-hydroxynonanoic acid | 64.6% |
| 3-hydroxy-5-(4-trifluomethylphenyl)valeric acid | 1.5% |

TABLE 16

| Dried cell (mg/L) | Dried polymer (mg/L) | Yield (polymer/cell, %) |
|---|---|---|
| 720 | 29 | 4.0 |

TABLE 17

| | |
|---|---|
| 3-hydroxyvaleric acid | 0.6% |
| 3-hydroxyheptanoic acid | 21.5% |
| 3-hydroxyoctanoic acid | 4.0% |
| 3-hydroxynonanoic acid | 70.5% |
| 3-hydroxydecanoic acid | 1.1% |
| 3-hydroxy-5-(4-trifluomethylphenyl)valeric acid | 2.3% |

TABLE 18

| Carbon Source for growth | D-glucose | n-nonanoic acid |
|---|---|---|
| Cell (Dry Weight) (mg/L) | 1300 | 1000 |
| Polymer (Dry Weight) (mg/L) | 945 | 570 |
| Polymer (Dry Weight)/Cell (Dry Weight) | 73% | 57% |
| Monomer Unit Composition (area ratio) | | |
| 3-hydroxybutyric acid | 0% | 1% |
| 3-hydroxyvaleric acid | 0% | 1% |
| 3-hydroxyhexanoic acid | 0% | 0% |
| 3-hydroxyheptanoic acid | 0% | 14% |
| 3-hydroxyoctanoic acid | 1% | 2% |
| 3-hydroxynonanoic acid | 0% | 70% |
| 3-hydroxydecanoic acid | 2% | 0% |
| 3-hydroxyundecanoic acid | 0% | 0% |
| 3-hydroxydodecanoic acid | 0% | 0% |
| 3-hydroxy-5-phenylvaleric acid | 97% | 12% |

TABLE 19

| Carbon Source for growth | D-glucose | n-nonanoic acid |
|---|---|---|
| Cell (Dry Weight) (mg/L) | 750 | 800 |
| Polymer (Dry Weight) (mg/L) | 400 | 385 |
| Polymer (Dry Weight)/Cell (Dry Weight) | 53% | 48% |
| Monomer Unit Composition (area ratio) | | |
| 3-hydroxybutyric acid | 0% | 0% |
| 3-hydroxyvaleric acid | 0% | 0% |
| 3-hydroxyhexanoic acid | 0% | 0% |
| 3-hydroxyheptanoic acid | 0% | 14% |
| 3-hydroxyoctanoic acid | 0% | 0% |
| 3-hydroxynonanoic acid | 0% | 76% |
| 3-hydroxydecanoic acid | 0% | 0% |
| 3-hydroxyundecanoic acid | 0% | 0% |
| 3-hydroxydodecanoic acid | 0% | 0% |
| 3-hydroxy-5-phenylvaleric acid | 100% | 10% |

TABLE 20

| Carbon Source for growth | D-mannose | D-fructose |
|---|---|---|
| Cell (Dry Weight) (mg/L) | 780 | 760 |
| Polymer (Dry Weight) (mg/L) | 452 | 418 |
| Polymer (Dry Weight)/Cell (Dry Weight) | 58% | 55% |
| Monomer Unit Composition (area ratio) | | |
| 3-hydroxybutyric acid | 0% | 0% |
| 3-hydroxyvaleric acid | 0% | 0% |
| 3-hydroxyhexanoic acid | 0% | 0% |
| 3-hydroxyheptanoic acid | 0% | 0% |
| 3-hydroxyoctanoic acid | 2% | 1% |
| 3-hydroxynonanoic acid | 0% | 0% |
| 3-hydroxydecanoic acid | 0% | 1% |
| 3-hydroxyundecanoic acid | 0% | 0% |
| 3-hydroxydodecanoic acid | 0% | 0% |
| 3-hydroxy-5-phenylvaleric acid | 98% | 98% |

TABLE 21

| Carbon Source for growth | D-glucose | n-nonanoic acid |
|---|---|---|
| Cell (Dry Weight) (mg/L) | 1150 | 1180 |
| Polymer (Dry Weight) (mg/L) | 830 | 752 |
| Polymer (Dry Weight)/Cell (Dry Weight) | 72% | 64% |
| Monomer Unit Composition (area ratio) | | |
| 3-hydroxybutyric acid | 0% | 2% |
| 3-hydroxyvaleric acid | 0% | 1% |
| 3-hydroxyhexanoic acid | 0% | 0% |
| 3-hydroxyheptanoic acid | 0% | 17% |
| 3-hydroxyoctanoic acid | 1% | 3% |
| 3-hydroxynonanoic acid | 0% | 44% |
| 3-hydroxydecanoic acid | 3% | 0% |
| 3-hydroxyundecanoic acid | 0% | 0% |
| 3-hydroxydodecanoic acid | 0% | 0% |
| 3-hydroxy-5-phenylvaleric acid | 96% | 33% |

TABLE 22

| Carbon Source for growth | D-glucose | n-nonanoic acid |
|---|---|---|
| Cell (Dry Weight) (mg/L) | 1250 | 920 |
| Polymer (Dry Weight) (mg/L) | 900 | 543 |
| Polymer (Dry Weight)/Cell (Dry Weight) | 72% | 59% |
| Monomer Unit Composition (area ratio) | | |
| 3-hydroxybutyric acid | 0% | 0% |
| 3-hydroxyvaleric acid | 0% | 0% |
| 3-hydroxyhexanoic acid | 0% | 0% |
| 3-hydroxyheptanoic acid | 0% | 11% |
| 3-hydroxyoctanoic acid | 1% | 0% |
| 3-hydroxynonanoic acid | 0% | 80% |
| 3-hydroxydecanoic acid | 2% | 0% |

TABLE 22-continued

| Carbon Source for growth | D-glucose | n-nonanoic acid |
|---|---|---|
| 3-hydroxyundecanoic acid | 0% | 0% |
| 3-hydroxydodecanoic acid | 0% | 0% |
| 3-hydroxy-5-(4-fluorophenyl)valeric acid | 97% | 9% |

TABLE 23

| Carbon Source for growth | D-glucose | n-nonanoic acid |
|---|---|---|
| Cell (Dry Weight) (mg/L) | 1100 | 900 |
| Polymer (Dry Weight) (mg/L) | 143 | 119 |
| Polymer (Dry Weight)/Cell (Dry Weight) | 13% | 13% |
| Monomer Unit Composition (area ratio) | | |
| 3-hydroxybutyric acid | 2% | 2% |
| 3-hydroxyvaleric acid | 0% | 1% |
| 3-hydroxyhexanoic acid | 1% | 0% |
| 3-hydroxyheptanoic acid | 0% | 18% |
| 3-hydroxyoctanoic acid | 1% | 3% |
| 3-hydroxynonanoic acid | 0% | 48% |
| 3-hydroxydecanoic acid | 0% | 0% |
| 3-hydroxyundecanoic acid | 0% | 0% |
| 3-hydroxydodecanoic acid | 0% | 0% |
| 3-hydroxy-6-phenylhexanoic acid | 96% | 28% |

TABLE 24

| Carbon Source for growth | D-glucose | n-nonanoic acid |
|---|---|---|
| Cell (Dry Weight) (mg/L) | 685 | 440 |
| Polymer (Dry Weight) (mg/L) | 137 | 263 |
| Polymer (Dry Weight)/Cell (Dry Weight) | 20% | 60% |
| Monomer Unit Composition (area ratio) | | |
| 3-hydroxybutyric acid | 0% | 0% |
| 3-hydroxyvaleric acid | 0% | 1% |
| 3-hydroxyhexanoic acid | 0% | 1% |
| 3-hydroxyheptanoic acid | 0% | 30% |
| 3-hydroxyoctanoic acid | 3% | 4% |
| 3-hydroxynonanoic acid | 0% | 62% |
| 3-hydroxydecanoic acid | 4% | 1% |
| 3-hydroxyundecanoic acid | 0% | 0% |
| 3-hydroxydodecanoic acid | 1% | 1% |
| 3-hydroxy-4-phenoxybutyric acid | 92% | 0% |

TABLE 25

| Carbon Source for growth | D-glucose | n-nonanoic acid |
|---|---|---|
| Cell (Dry Weight) (mg/L) | 450 | 340 |
| Polymer (Dry Weight) (mg/L) | 18 | 216 |
| Polymer (Dry Weight)/Cell (Dry Weight) | 4% | 64% |
| Monomer Unit Composition (area ratio) | | |
| 3-hydroxybutyric acid | 0% | 0% |
| 3-hydroxyvaleric acid | 0% | 1% |
| 3-hydroxyhexanoic acid | 1% | 0% |
| 3-hydroxyheptanoic acid | 0% | 28% |
| 3-hydroxyoctanoic acid | 5% | 4% |
| 3-hydroxynonanoic acid | 0% | 67% |
| 3-hydroxydecanoic acid | 5% | 0% |
| 3-hydroxyundecanoic acid | 0% | 0% |
| 3-hydroxydodecanoic acid | 1% | 0% |
| 3-hydroxy-4-phenoxybutyric acid | 88% | 0% |

TABLE 26

| Carbon Source for growth | D-glucose | n-nonanoic acid |
|---|---|---|
| Cell (Dry Weight) (mg/L) | 600 | 400 |
| Polymer (Dry Weight) (mg/L) | 51 | 144 |
| Polymer (Dry Weight)/Cell (Dry Weight) | 9% | 36% |
| Monomer Unit Composition (area ratio) | | |
| 3-hydroxybutyric acid | 3% | 0% |
| 3-hydroxyvaleric acid | 0% | 1% |
| 3-hydroxyhexanoic acid | 1% | 1% |
| 3-hydroxyheptanoic acid | 0% | 26% |
| 3-hydroxyoctanoic acid | 9% | 5% |
| 3-hydroxynonanoic acid | 0% | 63% |
| 3-hydroxydecanoic acid | 11% | 2% |
| 3-hydroxyundecanoic acid | 0% | 0% |
| 3-hydroxydodecanoic acid | 0% | 0% |
| 3-hydroxy-4-phenoxybutyric acid | 76% | 2% |

TABLE 27

| Carbon Source for growth | D-glucose | n-nonanoic acid |
|---|---|---|
| Cell (Dry Weight) (mg/L) | 1150 | 900 |
| Polymer (Dry Weight) (mg/L) | 590 | 420 |
| Polymer (Dry Weight)/Cell (Dry Weight) | 51% | 47% |
| Monomer Unit Composition (area ratio) | | |
| 3-hydroxybutyric acid | 1% | 0% |
| 3-hydroxyvaleric acid | 0% | 0% |
| 3-hydroxyhexanoic acid | 0% | 0% |
| 3-hydroxyheptanoic acid | 0% | 13% |
| 3-hydroxyoctanoic acid | 0% | 5% |
| 3-hydroxynonanoic acid | 0% | 69% |
| 3-hydroxydecanoic acid | 10% | 0% |
| 3-hydroxyundecanoic acid | 0% | 0% |
| 3-hydroxydodecanoic acid | 0% | 0% |
| 3-hydroxy-5-phenylvaleric acid | 89% | 13% |

TABLE 28

| | CDW (mg/L) | PDW (mg/L) | Yield (%) |
|---|---|---|---|
| (1) YE | 1225 | 488 | 39.8 |
| (2) BE | 600 | 185 | 30.8 |
| (3) CA | 950 | 445 | 46.8 |
| (4) PP | 1200 | 755 | 62.9 |

CDW: Cell (Dry Weight) (mg/L)
PDW: Polymer (Dry Weight) (mg/L)
Yield: PDW/CDW (%)

TABLE 29

| | CDW (mg/L) | PDW (mg/L) | Yield (%) |
|---|---|---|---|
| (1) YE | 1100 | 225 | 20.5 |
| (2) PP | 1200 | 850 | 70.8 |

CDW: Cell (Dry Weight) (mg/L)
PDW: Polymer (Dry Weight) (mg/L)
Yield: PDW/CDW (%)

TABLE 30

| | CDW (mg/L) | PDW (mg/L) | Yield (%) |
|---|---|---|---|
| (1) YE | 1050 | 205 | 19.5 |
| (2) PP | 1000 | 345 | 34.5 |

CDW: Cell (Dry Weight) (mg/L)
PDW: Polymer (Dry Weight) (mg/L)
Yield: PDW/CDW (%)

TABLE 31

| | CDW (mg/L) | PDW (mg/L) | Yield (%) |
|---|---|---|---|
| (1) YE | 750 | 220 | 29.3 |
| (2) SG | 700 | 260 | 37.1 |
| (3) CA | 900 | 340 | 37.7 |
| (4) PP | 1100 | 450 | 40.9 |

CDW: Cell (Dry Weight) (mg/L)
PDW: Polymer (Dry Weight) (mg/L)
Yield: PDW/CDW (%)

TABLE 32

| | CDW (mg/L) | PDW (mg/L) | Yield (%) |
|---|---|---|---|
| (1) YE | 950 | 325 | 34.2 |
| (2) SG | 750 | 240 | 32.0 |
| (3) BE | 450 | 130 | 28.9 |
| (4) PP | 1000 | 450 | 45.0 |

CDW: Cell (Dry Weight) (mg/L)
PDW: Polymer (Dry Weight) (mg/L)
Yield: PDW/CDW (%)

TABLE 33

Identification results of the $^1$H-NMR spectral patterns (cf. FIG. 14)

| Chemical shift (ppm) | Identification |
|---|---|
| 2.80 | b1 |
| 4.24 | d1 |
| 5.50 | c1 |
| 7.00 | f1, j1 |
| 8.20 | g1, l1 |

TABLE 34

| | |
|---|---|
| Cell (Dry Weight) | 280 mg/L |
| Polymer (Dry Weight) | 30 mg/L |
| Polymer (Dry Weight)/Cell (Dry Weight) | 10.7% |
| Ratio of monomer unit determined by NMR (mole ratio) | |
| 3HNO$_2$PxB contained in PHA | 3.3 mol % |
| Fatty acid-derived monomer unit composition (peak area ratio) | |
| 3-hydroxybutyric acid | 9.3% |
| 3-hydroxyhexanoic acid | 2.0% |
| 3-hydroxyoctanoic acid | 12.2% |
| 3-hydroxydecanoic acid | 47.9% |
| 3-hydroxydodecanoic acid | 15.7% |
| 3-hydroxydodecenoic acid | 12.9% |

TABLE 35

| | |
|---|---|
| Cell (Dry Weight) | 250 mg/L |
| Polymer (Dry Weight) | 30 mg/L |
| Polymer (Dry Weight)/Cell (Dry Weight) | 12.0% |
| Ratio of monomer unit determined by NMR (mole ratio) | |
| 3HNO$_2$PxB contained in PHA | 4.3 mol % |
| Fatty acid-derived monomer unit composition (peak area ratio) | |
| 3-hydroxybutyric acid | 1.3% |
| 3-hydroxyhexanoic acid | 0.0% |
| 3-hydroxyoctanoic acid | 12.6% |
| 3-hydroxydecanoic acid | 38.8% |

TABLE 35-continued

| | |
|---|---|
| 3-hydroxydodecanoic acid | 22.7% |
| 3-hydroxydodecenoic acid | 24.6% |

TABLE 36

| | |
|---|---|
| Cell (Dry Weight) | 785 mg/L |
| Polymer (Dry Weight) | 55 mg/L |
| Polymer (Dry Weight)/Cell (Dry Weight) | 7.0% |
| Ratio of monomer unit determined by NMR (mole ratio) | |
| 3HNO$_2$PxB contained in PHA | 3.8 mol % |
| Fatty acid-derived monomer unit composition (peak area ratio) | |
| 3-hydroxybutyric acid | 2.9% |
| 3-hydroxyhexanoic acid | 1.5% |
| 3-hydroxyoctanoic acid | 12.1% |
| 3-hydroxydecanoic acid | 40.0% |
| 3-hydroxydodecanoic acid | 14.7% |
| 3-hydroxydodecenoic acid | 28.8% |

TABLE 37

Identification results of $^1$H-NMR spectral patterns (cf. FIG. 15)

| Chemical shift (ppm) | Identification |
|---|---|
| 2.79 | b1 |
| 4.18 | d1 |
| 5.51 | c1 |
| 6.98 | f1, j1 |
| 7.58 | g1, l1 |

TABLE 38

PHA production by *Pseudomonas cichorii* YN2

| | |
|---|---|
| Cell (Dry Weight) | 900 mg/L |
| Polymer (Dry Weight) | 180 mg/L |
| Polymer (Dry Weight)/Cell (Dry Weight) | 20.0% |
| Ratio of monomer unit determined by NMR (mole ratio) | |
| 3HCNPxBA contained in PHA | 4.1 mol % |
| Fatty acid-derived monomer unit composition (peak area ratio) | |
| 3-hydroxybutyric acid | 9.3% |
| 3-hydroxyhexanoic acid | 2.0% |
| 3-hydroxyoctanoic acid | 12.2% |
| 3-hydroxydecanoic acid | 47.9% |
| 3-hydroxydodecanoic acid | 15.7% |
| 3-hydroxydodecenoic acid | 12.9% |

TABLE 39

PHA production by *Pseudomonas cichorii* H45

| | |
|---|---|
| Cell (Dry Weight) | 775 mg/L |
| Polymer (Dry Weight) | 150 mg/L |
| Polymer (Dry Weight)/Cell (Dry Weight) | 19.4% |
| Ratio of monomer unit determined by NMR (mole ratio) | |
| 3HCNPxBA contained in PHA | 3.2 mol % |
| Fatty acid-derived monomer unit composition (peak area ratio) | |
| 3-hydroxybutyric acid | 70.5% |
| 3-hydroxyhexanoic acid | 1.0% |
| 3-hydroxyoctanoic acid | 10.3% |
| 3-hydroxydecanoic acid | 13.4% |
| 3-hydroxydodecanoic acid | 2.3% |
| 3-hydroxydodecenoic acid | 2.6% |

TABLE 40

PHA production by *Pseudomonas cichorii* YN2

| | |
|---|---|
| Cell (Dry Weight) | 930 mg/L |
| Polymer (Dry Weight) | 200 mg/L |
| Polymer (Dry Weight)/Cell (Dry Weight) | 21.5% |
| Ratio of monomer unit determined by NMR (mole ratio) | |
| 3HCNPxBA contained in PHA | 4.5 mol % |
| Fatty acid-derived monomer unit composition (peak area ratio) | |
| 3-hydroxybutyric acid | 12.5% |
| 3-hydroxyhexanoic acid | 2.0% |
| 3-hydroxyoctanoic acid | 12.2% |
| 3-hydroxydecanoic acid | 47.3% |
| 3-hydroxydodecanoic acid | 15.2% |
| 3-hydroxydodecenoic acid | 10.8% |

TABLE 41

PHA production by *Pseudomonas cichorii* H45

| | |
|---|---|
| Cell (Dry Weight) | 750 mg/L |
| Polymer (Dry Weight) | 135 mg/L |
| Polymer (Dry Weight)/Cell (Dry Weight) | 18.0% |
| Ratio of monomer unit determined by NMR (mole ratio) | |
| 3HCNPxBA contained in PHA | 4.4 mol % |
| Fatty acid-derived monomer unit composition (peak area ratio) | |
| 3-hydroxybutyric acid | 25.0% |
| 3-hydroxyhexanoic acid | 2.1% |
| 3-hydroxyoctanoic acid | 21.4% |
| 3-hydroxydecanoic acid | 37.3% |
| 3-hydroxydodecanoic acid | 6.0% |
| 3-hydroxydodecenoic acid | 8.2% |

TABLE 42

PHA production by *Pseudomonas cichorii* YN2

| | |
|---|---|
| Cell (Dry Weight) | 1030 mg/L |
| Polymer (Dry Weight) | 130 mg/L |
| Polymer (Dry Weight)/Cell (Dry Weight) | 12.6% |
| Ratio of monomer unit determined by NMR (mole ratio) | |
| 3HCNPxBA contained in PHA | 7.2 mol % |
| Fatty acid-derived monomer unit composition (peak area ratio) | |
| 3-hydroxybutyric acid | 7.3% |
| 3-hydroxyhexanoic acid | 1.9% |
| 3-hydroxyoctanoic acid | 14.3% |
| 3-hydroxydecanoic acid | 48.2% |
| 3-hydroxydodecanoic acid | 12.8% |
| 3-hydroxydodecenoic acid | 15.5% |

TABLE 43

PHA production by *Pseudomonas cichorii* H45

| | |
|---|---|
| Cell (Dry Weight) | 695 mg/L |
| Polymer (Dry Weight) | 55 mg/L |
| Polymer (Dry Weight)/Cell (Dry Weight) | 7.9% |
| Ratio of monomer unit determined by NMR (mole ratio) | |
| 3HCNPxBA contained in PHA | 2.6 mol % |
| Fatty acid-derived monomer unit composition (peak area ratio) | |
| 3-hydroxybutyric acid | 2.3% |
| 3-hydroxyhexanoic acid | 1.7% |
| 3-hydroxyoctanoic acid | 19.5% |
| 3-hydroxydecanoic acid | 52.1% |
| 3-hydroxydodecanoic acid | 10.3% |
| 3-hydroxydodecenoic acid | 14.1% |

TABLE 44

Figure 16:
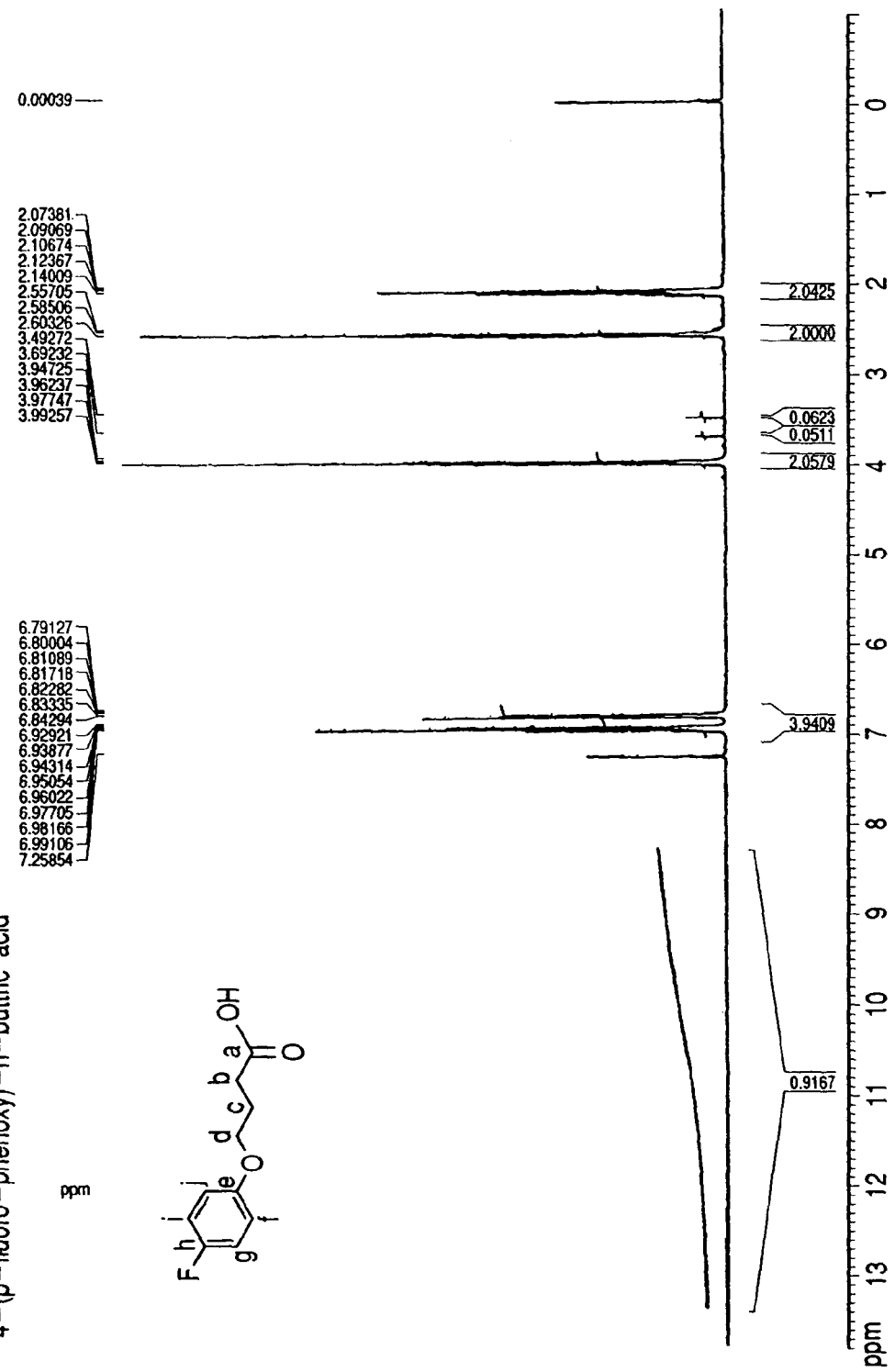
FIG. 16 is a chart which shows the $^1$H-NMR spectrum of 4-(4-fluorophenoxy)butyric acid.

$^1$H-NMR Spectrum (cf. FIG. 16)

| Chemical shift (ppm) | Integral value | type | Identification |
|---|---|---|---|
| 2.11 | 2H | quint | $CH_2$ c |
| 2.59 | 2H | t | $CH_2$ b |
| 3.97 | 2H | t | $CH_2$ d |
| 6.82 | 2H | m | g, i |
| 6.95 | 2H | m | f, j |
| 8.00 to 13.00 | 1H | br | OH |

TABLE 45

Figure 17:
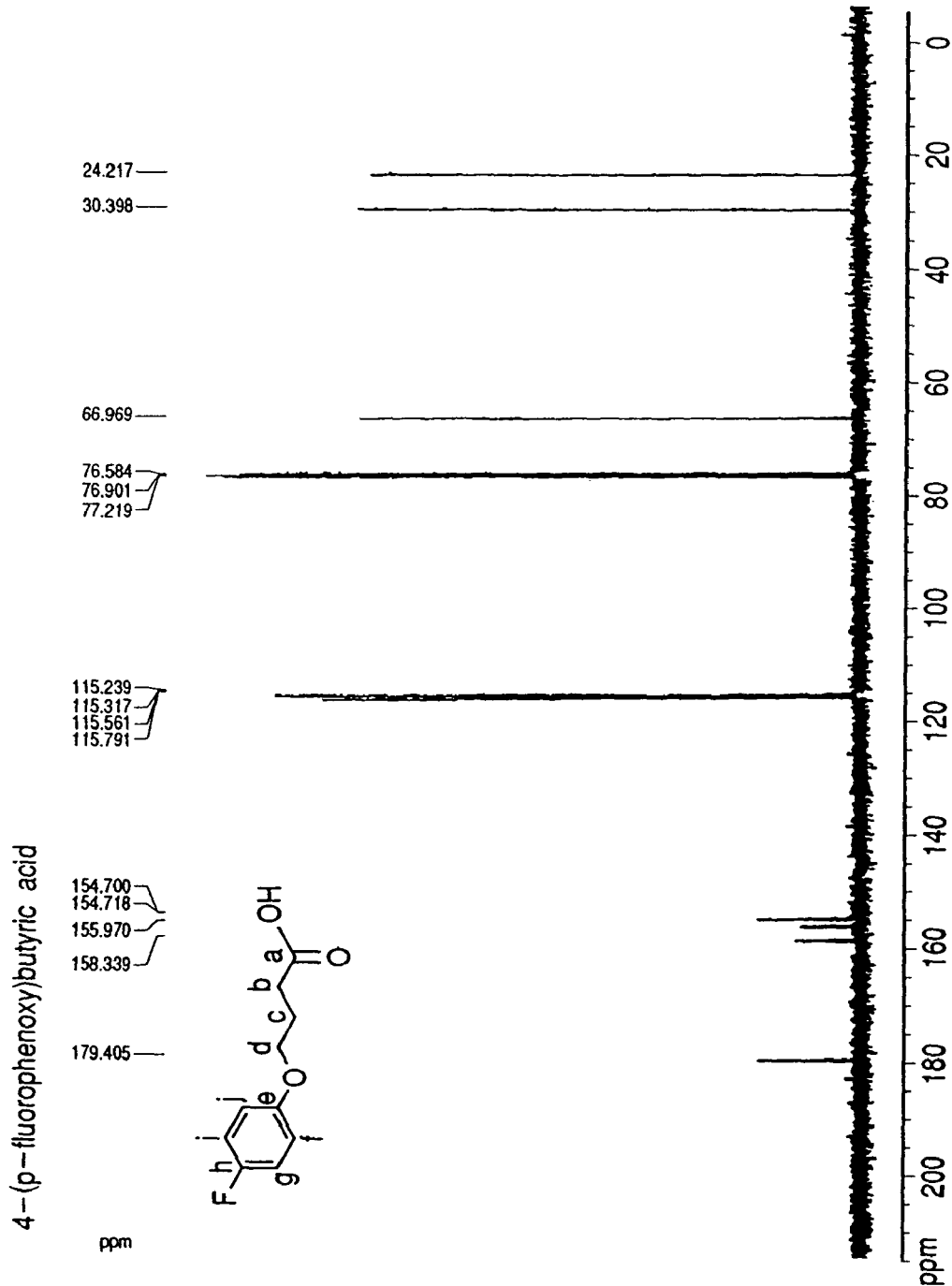
FIG. 17 is a chart which shows the $^{13}$C-NMR spectrum of 4-(4-fluorophenoxy)butyric acid.

$^{13}$C-NMR Spectrum (cf. FIG. 17)

| Chemical shift (ppm) | type | Identification |
|---|---|---|
| 24.21 | s | $CH_2$ c |
| 30.39 | s | $CH_2$ b |
| 66.96 | s | $CH_2$ d |
| 115.23 & 115.31 | d | f, j or g, i |
| 115.56 & 115.79 | d | f, j or g, i |
| 154.70 & 154.71 | d | e |
| 155.97 & 158.33 | d | h |
| 179.40 | s | C=O a |

TABLE 46

PHA production containing 3HpFPxB unit by strain YN2

| | |
|---|---|
| Cell (Dry Weight) | 885 mg/L |
| Polymer (Dry Weight) | 220 mg/L |
| Polymer (Dry Weight)/Cell (Dry Weight) | 24.9% |
| Polymer Molecular Weight | Mn = 42,400 |
| | Mw = 90,600 |
| Monomer Unit Composition (area ratio) | |
| 3-hydroxybutyric acid | 1.8% |
| 3-hydroxyhexanoic acid | 1.0% |
| 3-hydroxyoctanoic acid | 5.4% |
| 3-hydroxydecanoic acid | 10.4% |
| 3-hydroxydodecanoic acid | 2.9% |
| 3-hydroxydodecenoic acid | 5.9% |
| 3-hydroxy-4-(4-fluorophenoxy)butyric acid | 72.6% |

TABLE 47

$^1$H-NMR Spectrum (cf. FIG. 19)

| Chemical shift (ppm) | Identification |
|---|---|
| 2.76 | 2H, $CH_2$ b1 |
| 3.95 to 4.06 | 2H, $CH_2$ d1 |
| 5.46 | 1H, CH c1 |
| 6.71 to 6.90 | 4H, —$C_6H_4$— f1, g1, i1, j1 |

TABLE 48

Production of PHA containing 3HpFPxB unit by culturing strain H45

| | |
|---|---|
| Cell (dry weight) | 640 mg/L |
| Polymer (dry weight) | 90 mg/L |
| Polymer (dry weight)/Cell (dry weight) | 14.0% |
| Monomer Unit Composition (area ratio) | |
| 3-hydroxybutyric acid | 4.6% |
| 3-hydroxyhexanoic acid | 2.0% |

TABLE 48-continued

Production of PHA containing 3HpFPxB unit by culturing strain H45

| | |
|---|---|
| 3-hydroxyoctanoic acid | 15.2% |
| 3-hydroxydecanoic acid | 19.8% |
| 3-hydroxydodecanoic acid | 4.0% |
| 3-hydroxydodecenoic acid | 7.4% |
| 3-hydroxy-4-(4-fluorophenoxy)butyric acid | 47.0% |

TABLE 49

Production of PHA containing 3HpFPxB unit by culturing strain YN2

| | |
|---|---|
| Cell (dry weight) | 780 mg/L |
| Polymer (dry weight) | 200 mg/L |
| Polymer (dry weight)/Cell (dry weight) | 25.6% |
| Monomer Unit Composition (area ratio) | |
| 3-hydroxybutyric acid | 0.3% |
| 3-hydroxyhexanoic acid | 0.8% |
| 3-hydroxyoctanoic acid | 3.9% |
| 3-hydroxydecanoic acid | 6.7% |
| 3-hydroxydodecanoic acid | 2.1% |
| 3-hydroxydodecenoic acid | 3.7% |
| 3-hydroxy-4-(4-fluorophenoxy)butyric acid | 82.5% |

TABLE 50

Production of PHA containing 3HpFPxB unit by culturing strain H45

| | |
|---|---|
| Cell (dry weight) | 590 mg/L |
| Polymer (dry weight) | 45 mg/L |
| Polymer (dry weight)/Cell (dry weight) | 7.6% |
| Monomer Unit Composition (area ratio) | |
| 3-hydroxybutyric acid | 0.2% |
| 3-hydroxyhexanoic acid | 1.9% |
| 3-hydroxyoctanoic acid | 11.9% |
| 3-hydroxydecanoic acid | 12.1% |
| 3-hydroxydodecanoic acid | 2.2% |
| 3-hydroxydodecenoic acid | 5.0% |
| 3-hydroxy-4-(4-fluorophenoxy)butyric acid | 66.7% |

TABLE 51

Production of PHA containing 3HpFPxB unit by culturing strain YN2

| | |
|---|---|
| Cell (dry weight) | 960 mg/L |
| Polymer (dry weight) | 155 mg/L |
| Polymer (dry weight)/Cell (dry weight) | 16.1% |
| Monomer Unit Composition (area ratio) | |
| 3-hydroxybutyric acid | 0.5% |
| 3-hydroxyhexanoic acid | 1.0% |
| 3-hydroxyoctanoic acid | 8.9% |
| 3-hydroxydecanoic acid | 23.4% |
| 3-hydroxydodecanoic acid | 7.0% |
| 3-hydroxydodecenoic acid | 14.2% |
| 3-hydroxy-4-(4-fluorophenoxy)butyric acid | 45.0% |

TABLE 52

Production of PHA containing 3HpFPxB unit by culturing strain H45

| | |
|---|---|
| Cell (dry weight) | 545 mg/L |
| Polymer (dry weight) | 30 mg/L |
| Polymer (dry weight)/Cell (dry weight) | 5.5% |

TABLE 52-continued

Production of PHA containing 3HpFPxB unit by culturing strain H45

Monomer Unit Composition (area ratio)

| | |
|---|---|
| 3-hydroxybutyric acid | 2.3% |
| 3-hydroxyhexanoic acid | 1.6% |
| 3-hydroxyoctanoic acid | 15.6% |
| 3-hydroxydecanoic acid | 36.9% |
| 3-hydroxydodecanoic acid | 8.7% |
| 3-hydroxydodecenoic acid | 12.9% |
| 3-hydroxy-4-(4-fluorophenoxy)butyric acid | 22.0% |

TABLE 53

$^1$H-NMR Spectrum (cf. FIG. 20)

| Chemical shift (ppm) | Integral value | type | Identification |
|---|---|---|---|
| 2.11 | 2H | d, quint | $CH_2$ c |
| 2.59 | 2H | t | $CH_2$ b |
| 3.97 | 2H | t | $CH_2$ d |
| 6.62 | 3H | m | h, i, j |
| 7.21 | 1H | m | f |
| 10.62 | 1H | br | OH |

TABLE 54

$^{13}$C-NMR Spectrum (cf. FIG. 21)

| Chemical shift (ppm) | type | Identification |
|---|---|---|
| 24.1 | s | $CK_2$ c |
| 30.34 | s | $CH_2$ b |
| 66.62 | s | $CH_2$ d |
| 101.23 & 102.19 | d | f |
| 107.39 & 107.60 | d | h |
| 110.08 & 110.11 | d | j |
| 130.04 & 130.14 | d | i |
| 159.92 & 160.03 | d | e |
| 162.29 & 164.73 | d | g |
| 179.19 | s | C=O a |

TABLE 55

PHA production containing 3HmFPxB unit by strain YN2

| | |
|---|---|
| Cell (Dry Weight) | 745 mg/L |
| Polymer (Dry Weight) | 80 mg/L |
| Polymer (Dry Weight)/Cell (Dry Weight) | 10.7% |
| Polymer Molecular Weight | Mn = 34,500 |
| | Mw = 75,200 |
| Monomer Unit Composition (area ratio) | |
| 3-hydroxybutyric acid | 1.2% |
| 3-hydroxyhexanoic acid | 1.0% |
| 3-hydroxyoctanoic acid | 6.5% |
| 3-hydroxydecanoic acid | 9.5% |
| 3-hydroxydodecanoic acid | 3.5% |
| 3-hydroxydodecenoic acid | 5.9% |
| 3-hydroxy-4-(3-fluorophenoxy)butyric acid | 72.5% |

TABLE 56

¹H-NMR Spectrum (cf. FIG. 23)

| Chemical shift (ppm) | Identification |
| --- | --- |
| 2.75 | 2H, $CH_2$ b1 |
| 4.00 | 2H, $CH_2$ d1 |
| 5.48 | 1H, CH c1 |
| 6.52 to 6.62 | 3H, h1, i1, j1 |
| 7.26 | 3H, f1 |

TABLE 57

PHA production containing 3HmFPxB unit by strain H45

| | |
| --- | --- |
| Cell (Dry Weight) | 630 mg/L |
| Polymer (Dry Weight) | 45 mg/L |
| Polymer (Dry Weight)/Cell (Dry Weight) | 7.1% |
| Monomer Unit Composition (area ratio) | |
| 3-hydroxybutyric acid | 3.7% |
| 3-hydroxyhexanoic acid | 2.2% |
| 3-hydroxyoctanoic acid | 21.0% |
| 3-hydroxydecanoic acid | 29.2% |
| 3-hydroxydodecanoic acid | 8.2% |
| 3-hydroxydodecenoic acid | 10.1% |
| 3-hydroxy-4-(3-fluorophenoxy)butyric acid | 25.6% |

TABLE 58

PHA production containing 3HmFPxB unit by strain H45

| | |
| --- | --- |
| Cell (Dry Weight) | 515 mg/L |
| Polymer (Dry Weight) | 40 mg/L |
| Polymer (Dry Weight)/Cell (Dry Weight) | 7.8% |
| Monomer Unit Composition (area ratio) | |
| 3-hydroxybutyric acid | 3.0% |
| 3-hydroxyhexanoic acid | 2.0% |
| 3-hydroxyoctanoic acid | 16.8% |
| 3-hydroxydecanoic acid | 16.8% |
| 3-hydroxydodecanoic acid | 4.7% |
| 3-hydroxydodecenoic acid | 7.4% |
| 3-hydroxy-4-(3-fluorophenoxy)butyric acid | 49.3% |

TABLE 59

PHA production containing 3HmFPxB unit by strain YN2

| | |
| --- | --- |
| Cell (Dry Weight) | 900 mg/L |
| Polymer (Dry Weight) | 90 mg/L |
| Polymer (Dry Weight)/Cell (Dry Weight) | 10.0% |
| Monomer Unit Composition (area ratio) | |
| 3-hydroxybutyric acid | 20.1% |
| 3-hydroxyhexanoic acid | 1.5% |
| 3-hydroxyoctanoic acid | 9.8% |
| 3-hydroxydecanoic acid | 15.5% |
| 3-hydroxydodecanoic acid | 5.5% |
| 3-hydroxydodecenoic acid | 9.7% |
| 3-hydroxy-4-(3-fluorophenoxy)butyric acid | 37.9% |

TABLE 60

PHA production containing 3HmFPxB unit by strain H45

| | |
| --- | --- |
| Cell (Dry Weight) | 565 mg/L |
| Polymer (Dry Weight) | 25 mg/L |
| Polymer (Dry Weight)/Cell (Dry Weight) | 4.4% |

TABLE 60-continued

PHA production containing 3HmFPxB unit by strain H45

| Monomer Unit Composition (area ratio) | |
| --- | --- |
| 3-hydroxybutyric acid | 4.2% |
| 3-hydroxyhexanoic acid | 1.9% |
| 3-hydroxyoctanoic acid | 17.8% |
| 3-hydroxydecanoic acid | 38.0% |
| 3-hydroxydodecanoic acid | 9.5% |
| 3-hydroxydodecenoic acid | 13.8% |
| 3-hydroxy-4-(3-fluorophenoxy)butyric acid | 14.8% |

TABLE 61

| | |
| --- | --- |
| Cell (Dry Weight) (mg/L) | 665 |
| Polymer (Dry Weight) (mg/L) | 105 |
| Number Average Molecular Weight (Mn) × $10^4$ | 1.6 |
| Weight Average Molecular Weight (Mw) × $10^4$ | 3.7 |
| 3-hydroxybutyric acid (%) | 75.2 |
| 3-hydroxy-5-(4-fluorophenoxy)valeric acid (%) | 24.8 |

TABLE 62

| | |
| --- | --- |
| Cell (Dry Weight) (mg/L) | 1120 |
| Polymer (Dry Weight) (mg/L) | 625 |
| Number Average Molecular Weight (Mn) × $10^4$ | 4.8 |
| Weight Average Molecular Weight (Mw) × $10^4$ | 9.9 |
| 3-hydroxybutyric acid (%) | 17.4 |
| 3-hydroxy-5-(4-fluorophenyl)valeric acid (%) | 82.6 |

TABLE 63

| | |
| --- | --- |
| Cell (Dry Weight) (mg/L) | 835 |
| Polymer (Dry Weight) (mg/L) | 395 |
| Number Average Molecular Weight (Mn) × $10^4$ | 5.2 |
| Weight Average Molecular Weight (Mw) × $10^4$ | 14.9 |
| 3-hydroxyoctanoic acid (%) | 10.6 |
| 3-hydroxydecanoic acid (%) | 9.5 |
| 3-hydroxy-5-(4-fluorophenoxy)valeric acid (%) | 79.9 |

TABLE 64

| | |
| --- | --- |
| Cell (Dry Weight) (mg/L) | 1450 |
| Polymer (Dry Weight) (mg/L) | 1010 |
| Number Average Molecular Weight (Mn) × $10^4$ | 6.0 |
| Weight Average Molecular Weight (Mw) × $10^4$ | 14.8 |
| 3-hydroxyoctanoic acid (%) | 2.8 |
| 3-hydroxydecanoic acid (%) | 2.7 |
| 3-hydroxy-5-(4-fluorophenoxy)valeric acid (%) | 94.5 |

TABLE 65

| | |
| --- | --- |
| Cell (Dry Weight) (mg/L) | 1605 |
| Polymer (Dry Weight) (mg/L) | 760 |
| Number Average Molecular Weight (Mn) × $10^4$ | 4.6 |
| Weight Average Molecular Weight (Mw) × $10^4$ | 12.6 |
| 3-hydroxyoctanoic acid (%) | 0.5 |
| 3-hydroxydecanoic acid (%) | 0.4 |
| 3-hydroxy-5-(4-fluorophenyl)valeric acid (%) | 90.0 |
| 3-hydroxy-5-(4-fluorophenoxy)valeric acid (%) | 9.1 |

TABLE 66

| | |
| --- | --- |
| Cell (Dry Weight) (mg/L) | 1200 |
| Polymer (Dry Weight) (mg/L) | 500 |

TABLE 66-continued

| | |
|---|---|
| Number Average Molecular Weight (Mn) × $10^4$ | 2.2 |
| Weight Average Molecular Weight (Mw) × $10^4$ | 4.9 |
| 3-hydroxybutyric acid (%) | 3.4 |
| 3-hydroxyoctanoic acid (%) | 0.3 |
| 3-hydroxydecanoic acid (%) | 0.5 |
| 3-hydroxy-5-phenoxyvaleric acid (%) | 34.1 |
| 3-hydroxy-7-phenoxyheptanoic (%) | 51.1 |
| 3-hydroxy-9-phenoxynonanoic acid (%) | 10.6 |

TABLE 67

| | |
|---|---|
| Cell (Dry Weight) (mg/L) | 1305 |
| Polymer (Dry Weight) (mg/L) | 765 |
| Number Average Molecular Weight (Mn) × $10^4$ | 5.0 |
| Weight Average Molecular Weight (Mw) × $10^4$ | 11.6 |
| 3-hydroxybutyric acid (%) | 0.1 |
| 3-hydroxyhexanoic acid (%) | 0.3 |
| 3-hydroxyoctanoic acid (%) | 3.0 |
| 3-hydroxydecanoic acid (%) | 5.2 |
| 3-hydroxydodecanoic acid (%) | 1.6 |
| 3-hydroxydodecenoic acid (%) | 2.0 |
| 3-hydroxy-5-phenoxyvaleric acid (%) | 40.7 |
| 3-hydroxy-7-phenoxyheptanoic (%) | 40.4 |
| 3-hydroxy-9-phenoxynonanoic acid (%) | 6.7 |

TABLE 68

| | |
|---|---|
| Cell (Dry Weight) (mg/L) | 1085 |
| Polymer (Dry Weight) (mg/L) | 585 |
| Number Average Molecular Weight (Mn) × $10^4$ | 4.0 |
| Weight Average Molecular Weight (Mw) × $10^4$ | 8.9 |
| 3-hydroxybutyric acid (%) | 0.4 |
| 3-hydroxyhexanoic acid (%) | 0.3 |
| 3-hydroxyoctanoic acid (%) | 3.2 |
| 3-hydroxydecanoic acid (%) | 5.1 |
| 3-hydroxydodecanoic acid (%) | 1.1 |
| 3-hydroxydodecenoic acid (%) | 0.9 |
| 3-hydroxy-5-phenoxyvaleric acid (%) | 43.0 |
| 3-hydroxy-7-phenoxyheptanoic (%) | 43.9 |
| 3-hydroxy-9-phenoxynonanoic acid (%) | 2.1 |

TABLE 69

| | |
|---|---|
| Cell (Dry Weight) (mg/L) | 1100 |
| Polymer (Dry Weight) (mg/L) | 440 |
| Number Average Molecular Weight (Mn) × $10^4$ | 4.0 |
| Weight Average Molecular Weight (Mw) × $10^4$ | 7.4 |
| 3-hydroxybutyric acid (%) | 16.4 |
| 3-hydroxy-4-phenoxybutyric acid (%) | 13.4 |
| 3-hydroxy-6-phenoxyhexanoic acid (%) | 67.9 |
| 3-hydroxy-8-phenoxyoctanoic acid (%) | 2.3 |

TABLE 70

| | |
|---|---|
| Cell (Dry Weight) (mg/L) | 860 |
| Polymer (Dry Weight) (mg/L) | 190 |
| Number Average Molecular Weight (Mn) × $10^4$ | 3.4 |
| Weight Average Molecular Weight (Mw) × $10^4$ | 6.8 |
| 3-hydroxybutyric acid (%) | 0.2 |
| 3-hydroxy-4-phenoxybutyric acid (%) | 5.1 |
| 3-hydroxy-6-phenoxyhexanoic acid (%) | 82.9 |
| 3-hydroxy-8-phenoxyoctanoic acid (%) | 11.8 |

TABLE 71

| | |
|---|---|
| Cell (Dry Weight) (mg/L) | 1405 |
| Polymer (Dry Weight) (mg/L) | 700 |
| Number Average Molecular Weight (Mn) × $10^4$ | 4.9 |
| Weight Average Molecular Weight (Mw) × $10^4$ | 10.7 |
| 3-hydroxybutyric acid (%) | 4.8 |
| 3-hydroxyoctanoic acid (%) | 1.2 |
| 3-hydroxydecanoic acid (%) | 0.5 |
| 3-hydroxy-4-phenoxybutyric acid (%) | 7.8 |
| 3-hydroxy-6-phenoxyhexanoic acid (%) | 74.8 |
| 3-hydroxy-8-phenoxyoctanoic acid (%) | 10.9 |

TABLE 72

| | |
|---|---|
| Cell (Dry Weight) (mg/L) | 1255 |
| Polymer (Dry Weight) (mg/L) | 560 |
| Number Average Molecular Weight (Mn) × $10^4$ | 4.8 |
| Weight Average Molecular Weight (Mw) × $10^4$ | 9.7 |
| 3-hydroxybutyric acid (%) | 0.2 |
| 3-hydroxyhexanoic acid (%) | 0.1 |
| 3-hydroxyoctanoic acid (%) | 0.9 |
| 3-hydroxydecanoic acid (%) | 0.9 |
| 3-hydroxydodecanoic acid (%) | 0.1 |
| 3-hydroxydodecenoic acid (%) | 0.2 |
| 3-hydroxy-4-phenoxybutyric acid (%) | 2.5 |
| 3-hydroxy-6-phenoxyhexanoic acid (%) | 82.8 |
| 3-hydroxy-8-phenoxyoctanoic acid (%) | 12.3 |

TABLE 73

| | |
|---|---|
| Cell (Dry Weight) (mg/L) | 995 |
| Polymer (Dry Weight) (mg/L) | 505 |
| Number Average Molecular Weight (Mn) × $10^4$ | 4.6 |
| Weight Average Molecular Weight (Mw) × $10^4$ | 9.2 |
| 3-hydroxybutyric acid (%) | 1.4 |
| 3-hydroxyoctanoic acid (%) | 0.1 |
| 3-hydroxydecanoic acid (%) | 0.2 |
| 3-hydroxy-5-phenoxyvaleric acid (%) | 29.7 |
| 3-hydroxy-7-phenoxyheptanoic acid (%) | 68.6 |

TABLE 74

| | |
|---|---|
| Cell (Dry Weight) (mg/L) | 815 |
| Polymer (Dry Weight) (mg/L) | 270 |
| Number Average Molecular Weight (Mn) × $10^4$ | 3.3 |
| Weight Average Molecular Weight (Mw) × $10^4$ | 6.4 |
| 3-hydroxybutyric acid (%) | 1.2 |
| 3-hydroxy-5-phenoxyvaleric acid (%) | 26.7 |
| 3-hydroxy-7-phenoxyheptanoic acid (%) | 72.1 |

TABLE 75

| | |
|---|---|
| Cell (Dry Weight) (mg/L) | 1520 |
| Polymer (Dry Weight) (mg/L) | 860 |
| Number Average Molecular Weight (Mn) × $10^4$ | 6.1 |
| Weight Average Molecular Weight (Mw) × $10^4$ | 13.0 |
| 3-hydroxybutyric acid (%) | 0.1 |
| 3-hydroxyhexanoic acid (%) | 0.4 |
| 3-hydroxyoctanoic acid (%) | 3.5 |
| 3-hydroxydecanoic acid (%) | 4.1 |
| 3-hydroxydodecanoic acid (%) | 1.1 |
| 3-hydroxydodecenoic acid (%) | 3.1 |
| 3-hydroxy-5-phenoxyvaleric acid (%) | 55.0 |
| 3-hydroxy-7-phenoxyheptanoic acid (%) | 32.7 |

TABLE 76

| | |
|---|---|
| Cell (Dry Weight) (mg/L) | 1305 |
| Polymer (Dry Weight) (mg/L) | 685 |
| Number Average Molecular Weight (Mn) × $10^4$ | 4.1 |
| Weight Average Molecular Weight (Mw) × $10^4$ | 8.8 |
| 3-hydroxyhexanoic acid (%) | 0.1 |
| 3-hydroxyoctanoic acid (%) | 1.3 |
| 3-hydroxydecanoic acid (%) | 1.8 |
| 3-hydroxydodecanoic acid (%) | 0.4 |
| 3-hydroxydodecenoic acid (%) | 0.6 |
| 3-hydroxy-5-phenoxyvaleric acid (%) | 36.1 |
| 3-hydroxy-7-phenoxyheptanoic acid (%) | 59.7 |

TABLE 77

| | |
|---|---|
| Cell (Dry Weight) (mg/L) | 890 |
| Polymer (Dry Weight) (mg/L) | 420 |
| Number Average Molecular Weight (Mn) × $10^4$ | 9.7 |
| Weight Average Molecular Weight (Mw) × $10^4$ | 29.7 |
| 3-hydroxybutyric acid (%) | 0.2 |
| 3-hydroxyhexanoic acid (%) | 0.3 |
| 3-hydroxyoctanoic acid (%) | 2.4 |
| 3-hydroxydecanoic acid (%) | 3.3 |
| 3-hydroxydodecanoic acid (%) | 0.7 |
| 3-hydroxydodecenoic acid (%) | 1.5 |
| 3-hydroxy-5-phenoxyvaleric acid (%) | 91.6 |

TABLE 78

| | |
|---|---|
| Cell (Dry Weight) (mg/L) | 910 |
| Polymer (Dry Weight) (mg/L) | 390 |
| Number Average Molecular Weight (Mn) × $10^4$ | 9.1 |
| Weight Average Molecular Weight (Mw) × $10^4$ | 21.4 |
| 3-hydroxyhexanoic acid (%) | 0.2 |
| 3-hydroxyoctanoic acid (%) | 2.2 |
| 3-hydroxydecanoic acid (%) | 4.9 |
| 3-hydroxydodecanoic acid (%) | 0.8 |
| 3-hydroxydodecenoic acid (%) | 1.5 |
| 3-hydroxy-5-phenoxyvaleric acid (%) | 90.4 |

TABLE 79

| | |
|---|---|
| Cell (Dry Weight) (mg/L) | 1400 |
| Polymer (Dry Weight) (mg/L) | 935 |
| Number Average Molecular Weight (Mn) × $10^4$ | 6.2 |
| Weight Average Molecular Weight (Mw) × $10^4$ | 14.0 |
| 3-hydroxyoctanoic acid (%) | 0.6 |
| 3-hydroxydecanoic acid (%) | 0.7 |
| 3-hydroxy-5-phenylvaleric acid (%) | 98.7 |

TABLE 80

| | |
|---|---|
| Cell (Dry Weight) (mg/L) | 1350 |
| Polymer (Dry Weight) (mg/L) | 955 |
| Number Average Molecular Weight (Mn) × $10^4$ | 6.1 |
| Weight Average Molecular Weight (Mw) × $10^4$ | 13.8 |
| 3-hydroxyoctanoic acid (%) | 1.9 |
| 3-hydroxy-5-phenylvaleric acid (%) | 98.1 |

TABLE 81

| | |
|---|---|
| Cell (Dry Weight) (mg/L) | 2050 |
| Polymer (Dry Weight) (mg/L) | 1310 |
| Number Average Molecular Weight (Mn) × $10^4$ | 6.3 |
| Weight Average Molecular Weight (Mw) × $10^4$ | 13.9 |
| 3-hydroxybutyric acid (%) | 7.5 |
| 3-hydroxyoctanoic acid (%) | 0.8 |
| 3-hydroxydecanoic acid (%) | 0.8 |
| 3-hydroxy-5-phenylvaleric acid (%) | 90.6 |

TABLE 82

Production of Polyhydroxyalkanoate by Using strain YN2

| | Polymer Yield (mg/L) | 3-hydroxy-4-phenoxy-n-butyric acid unit ratio |
|---|---|---|
| Disodium malate | 20 | 96.6% |
| Sodium L-glutamate | 13 | 8.9% |
| D(+)-glucose | 8 | 98.4% |
| n-nonanoic acid | 440 | ND |
| Polypeptone | 17 | 43.5% |

*GC-MS, TIC peak area ratio, ND not detected.

TABLE 83

Production of Polyhydroxyalkanoate by Using strain YN2

| | |
|---|---|
| Cell (Dry Weight) (mg/L) | 290 |
| Polymer (Dry Weight) (mg/L) | 20 |
| Monomer Unit Composition (peak area ratio) | |
| 3-hydroxybutyric acid | 0.1% |
| 3-hydroxyhexanoic acid | 0.2% |
| 3-hydroxyoctanoic acid | 1.1% |
| 3-hydroxynonanoic acid | 0.1% |
| 3-hydroxydecanoic acid | 0.9% |
| 3-hydroxydodecanoic acid | 0.2% |
| 3-hydroxydodecenoic acid | 0.5% |
| 3-hydroxy-4-phenoxy-n-butyric acid | 96.9% |

What is claimed is:

1. A biologically pure culture of *Pseudomonas cichorii* H45, FERM BP-7374.

2. A biologically pure culture of *Pseudomonas cichorii* YN2, FERM BP-7375.

3. A biologically pure culture of *Pseudomonas putida* P91, FERM BP-7373.

4. A biologically pure culture of *Pseudomonas jessenii* P161, FERM BP-7376.

* * * * *

UNITED STATES PATENT AND TRADEMARK OFFICE
CERTIFICATE OF CORRECTION

PATENT NO.        : 7,169,598 B2
APPLICATION NO.   : 10/649646
DATED             : January 30, 2007
INVENTOR(S)       : Honma et al.

It is certified that error appears in the above-identified patent and that said Letters Patent is hereby corrected as shown below:

ON THE TITLE PAGE, ITEM [56]:
OTHER PUBLICATIONS, After Kim, et al, (second occurrence):
"pp. 3432-3235." should read -- pp. 3432-3435. --;
OTHER PUBLICATIONS, "Hulsman, et al.," should read -- Huisman, et al., --; and
(57) ABSTRACT, "—$C_2F_5$." should read -- —$C_2F_5$ --.

IN THE DRAWINGS:
Sheet 13, Fig. 16, "4-(p-fluoro-phenoxy)-n-buttric acid" should read
-- 4-(p-fluoro-phenoxy)-n-butyric acid --.

COLUMN 1:
Line 18, "plastics etc." should read -- plastics, etc., --; and
Line 33, "processes etd.," should read -- processes, etc., --.

COLUMN 5:
Line 64, "unknown)" should read -- unknown). --.

COLUMN 6:
Line 3, "coexist" should read -- coexisting --;
Line 22, "an" should read -- one --; and
Line 61, "interferes intra-molecular" should read -- interferes with intra-molecular --.

COLUMN 19:
Line 31, "is no" should read -- are no --.

COLUMN 21:
Line 22, "a ortho" should read -- an ortho --; and
Line 25, "is no" should read -- are no --.

Signed and Sealed this
Twenty-second Day of March, 2011

David J. Kappos
*Director of the United States Patent and Trademark Office*

COLUMN 22:
Line 14, "kinds" should read -- kind --;
Line 32, "a ortho" should read -- an ortho--; and
Line 35, "is no" should read -- are no --.

COLUMN 23:
Line 28, "kinds" should read -- kind --;
Line 34, "secondary"" should read -- "secondary" --;
Line 46, "a ortho" should read -- an ortho --; and
Line 49, "is no" should read -- are no --.

COLUMN 24:
Line 40, "kinds" should read -- kind --;
Line 58, "a ortho" should read -- an ortho --; and
Line 61, "is no" should read -- are no --.

COLUMN 26:
Line 4, "a ortho" should read -- an ortho --; and
Line 7, "is no" should read -- are no --.

COLUMN 35:
Line 43, "comprise" should be deleted.

COLUMN 48:
Line 30, "is essentially" should read -- are essentially --.

COLUMN 49:
Line 13, "form" should read -- from --; and
Line 27, "cycles" should read -- cycle --.

COLUMN 53:
Line 5, "is" should read -- are --.

COLUMN 54:
Line 11, "oleovorance" should read -- oleovorans --;
Line 15, "report" should read -- reports --; and
Line 19, "oleovorance" should read -- oleovorans --.

COLUMN 60:
Line 6, "cial" should read -- cially --.

COLUMN 62:
Line 46, "resumed" should read -- returned --; and
Line 62, "was" should read -- were --.

COLUMN 64:
Line 30, "dried" should read -- dry --.

COLUMN 65:
Line 9, "reprecipitated, vacuum-dried" should read -- reprecipitated, and vacuum-dried --.

COLUMN 67:
Line 6, "performed" should read -- performed. --.

COLUMN 71:
Line 60, "was" should read -- were --.

COLUMN 75:
In Chemical Formula (45), "d2 $CH_2$" should read -- d2 $CH_3$ --.

COLUMN 77:
Line 42, "done methanolysis" should read -- done by methanolysis --; and
Line 54, "Polypeptone" should read -- polypeptone --.

COLUMN 78:
Line 26, "was" should read -- were --.

COLUMN 79:
In Chemical Formula (46), "d2 $CH_2$" should read -- d2 $CH_3$ --; and
Line 29, "solvent; (chloroform," should read -- solvent: chloroform, --.

COLUMN 81:
Line 55, "Sodium" should read -- sodium --.

COLUMN 82:
Line 20, "opening" should read -- openings --.

COLUMN 83:
Line 6, "result" should read -- results --; and
In Chemical Formula (47), "d2 $CH_2$" should read -- d2 $CH_3$ --.

COLUMN 84:
Line 4, "solvent;" should read -- solvent: --.

COLUMN 86:
Line 24, "spectrograph" should read -- spectrography --.

CERTIFICATE OF CORRECTION (continued)

COLUMN 87:
Line 5, "and" should read -- was added and --;
Line 15, "spectrograph:" should read -- spectrography: --;
Line 17, "subsequent ester" should read -- subsequent to ester --; and
In Chemical Formula (48), "d2 CH$_2$" should read -- d2 CH$_3$ --.

COLUMN 89:
Line 4, "chloroform:" should read -- chloroform; --.

COLUMN 93:
Line 57, "result" should read -- results --.

COLUMN 95:
Line 47, "in woo" should read -- in 200 --; and
Line 48, "200 mL" should be deleted.

COLUMN 105:
Line 52, "seduced" should read -- reduced --.

COLUMN 106:
Line 24, "filtered - through" should read -- filtered through --.

COLUMN 111:
Table 15, "(4-trifluomethylphenyl)" should read -- (4-trifluoromethylphenyl) --; and
Table 17, "(4-trifluomethylphenyl)" should read -- (4-trifluoromethylphenyl) --.

SEQUENCE LISTING

<160> NUMBER OF SEQ ID NOS: 1

<210> SEQ ID NO 1
<211> LENGTH: 1501
<212> TYPE: DNA
<213> ORGANISM: Pseudomonas jessenii 161 strain

<400> SEQUENCE: 1

```
tgaacgctgg cggcaggcct aacacatgca agtcgagcgg atgacgggag cttgctcctg     60
aattcagcgg cggacgggtg agtaatgcct aggaatctgc ctggtagtgg gggacaacgt    120
ctcgaaaggg acgctaatac cgcatacgtc ctacgggaga aagcagggga ccttcgggcc    180
ttgcgctatc agatgagcct aggtcggatt agctagttgg tgaggtaatg gctcaccaag    240
gcgacgatcc gtaactggtc tgagaggatg atcagtcaca ctggaactga gacacggtcc    300
agactcctac gggaggcagc agtggggaat attggacaat gggcgaaagc ctgatccagc    360
catgccgcgt gtgtgaagaa ggtcttcgga ttgtaaagca ctttaagttg ggaggaaggg    420
cattaaccta atacgttagt gttttgacgt taccgacaga ataagcaccg gctaactctg    480
tgccagcagc cgcggtaata cagagggtgc aagcgttaat cggaattact gggcgtaaag    540
cgcgcgtagg tggtttgtta agttggatgt gaaagccccg ggctcaacct gggaactgca    600
ttcaaaactg acaagctaga gtatggtaga gggtggtgga atttcctgtg tagcggtgaa    660
atgcgtagat ataggaagga acaccagtgg cgaaggcgac cacctggact gatactgaca    720
ctgaggtgcg aaagcgtggg gagcaaacag gattagatac cctggtagtc cacgccgtaa    780
acgatgtcaa ctagccgttg ggagccttga gctcttagtg gcgcagctaa cgcattaagt    840
tgaccgcctg gggagtacgg ccgcaaggtt aaaactcaaa tgaattgacg ggggcccgca    900
caagcggtgg agcatgtggt ttaattcgaa gcaacgcgaa gaaccttacc aggccttgac    960
atccaatgaa ctttccagag atggatgggt gccttcggga acattgagac aggtgctgca   1020
tggctgtcgt cagctcgtgt cgtgagatgt tgggttaagt cccgtaacga gcgcaaccct   1080
tgtccttagt taccagcacg taatggtggg cactctaagg agactgccgg tgacaaaccg   1140
gaggaaggtg gggatgacgt caagtcatca tggcccttac ggcctgggct acacacgtgc   1200
tacaatggtc ggtacagagg gttgccaagc cgcgaggtgg agctaatccc acaaaaccga   1260
tcgtagtccg gatcgcagtc tgcaactcga ctgcgtgaag tcggaatcgc tagtaatcgc   1320
gaatcagaat gtcgcggtga atacgttccc gggccttgta cacaccgccc gtcacaccat   1380
gggagtgggt tgcaccagaa gtagctagtc taaccttcgg gaggacggtt accacggtgt   1440
gattcatgac tggggtgaag tcgtaccaag gtagccgtag gggaacctgc ggctggatca   1500
c                                                                  1501
```